US007816406B2

(12) United States Patent
Whitten et al.

(10) Patent No.: US 7,816,406 B2
(45) Date of Patent: Oct. 19, 2010

(54) QUINOLONE ANALOGS

(75) Inventors: Jeffrey P. Whitten, Santee, CA (US); Fabrice Pierre, La Jolla, CA (US); Collin Regan, San Diego, CA (US); Michael Schwaebe, San Diego, CA (US); Johnny Y. Nagasawa, San Diego, CA (US); Peter Chua, San Diego, CA (US)

(73) Assignee: Cylene Pharmaceuticals, Inc., San Diego, CA (US)

( * ) Notice: Subject to any disclaimer, the term of this patent is extended or adjusted under 35 U.S.C. 154(b) by 779 days.

(21) Appl. No.: 11/228,636

(22) Filed: Sep. 16, 2005

(65) Prior Publication Data

US 2006/0074089 A1 Apr. 6, 2006

Related U.S. Application Data

(63) Continuation-in-part of application No. 11/149,007, filed on Jun. 9, 2005, now Pat. No. 7,652,134.

(60) Provisional application No. 60/611,030, filed on Sep. 17, 2004, provisional application No. 60/688,986, filed on Jun. 9, 2005, provisional application No. 60/368,603, filed on Dec. 22, 2004, provisional application No. 60/688,796, filed on Jun. 9, 2005.

(51) Int. Cl.
*C07D 471/22* (2006.01)
*A61K 31/437* (2006.01)
*A61K 31/4365* (2006.01)

(52) U.S. Cl. .................. 514/587; 514/557; 544/99; 544/361; 546/66; 546/75

(58) Field of Classification Search .................. 544/99, 544/361; 546/66, 75; 514/257, 287
See application file for complete search history.

(56) References Cited

U.S. PATENT DOCUMENTS

| | | | |
|---|---|---|---|
| 4,528,285 | A | 7/1985 | Chu |
| 5,646,163 | A | 7/1997 | Demuth et al. |
| 6,645,981 | B2 | 1/2003 | Ledoussal et al. |
| 6,900,224 | B2 | 2/2004 | Ledoussal et al. |
| 6,821,969 | B2 | 11/2004 | Thorarensen |
| 7,141,565 | B1 | 11/2006 | Whitten et al. |
| 2002/0025960 | A1 | 2/2002 | Bundy et al. |
| 2004/0029882 | A1 | 2/2004 | Ledoussal et al. |
| 2005/0203120 | A1 | 9/2005 | Adelman et al. |
| 2005/0215583 | A1 | 9/2005 | Arkin et al. |

FOREIGN PATENT DOCUMENTS

| | | |
|---|---|---|
| EP | 0 058 392 | 8/1982 |
| WO | WO-89/12055 | 12/1989 |
| WO | WO-92/03136 | 3/1992 |
| WO | WO-95/29894 | 11/1995 |
| WO | WO-02/17916 | 3/2002 |
| WO | WO 2004/014893 | 2/2004 |
| WO | WO-2004/091504 | 10/2004 |
| WO | WO-2005/089756 | 9/2005 |
| WO | WO-2005/089757 | 9/2005 |

OTHER PUBLICATIONS

Dorwald F. A. Side Reactions in Organic Synthesis, 2005, Wiley: VCH, Weinheim p. IX of Preface.*
Database CA [Online], database accession No. 1997:692822.
Database CA [Online], database accession No. 1997:522331.
Database CA [Online], database accession No. 1997:70540.
Database CA [Online], database accession No. 1989:632785.
Database CA [Online], database accession No. 1987:18529.
Database CA [Online], database accession No. 1983:575560.
Database Chemcats, accession No. 2003:2367544.
International Search Report for PCT/US2005/033323, mailed on Jul. 4, 2006, 11 pages.
Kim et al., Bioorganic & Medicinal Chemistry Letters (1995) 5(17):1953-1956.
Kim, Journal of Heterocyclic Chemistry (1981) 18(7):1389-1392.
Schroeder et al., Journal of Heterocyclic Chemistry (1988) 25(6):1769-1772.
Wang et al., Tetrahedron Letters (2001) 42(13):2553-2555.
Barn et al., Tetrahedron Letters (1996) 37(18):3213-3216.
European Search Report for EP 05813754.8, mailed Aug. 13, 2008, 6 pages.
Cecchetti et al., Bioorganic & Medicinal Chemistry (1997) 5(7):1339-1344.
Chu et al., J. Med. Chem. (1986) 29:1531-1534.
Chung and Kim, Tetrahedron (1995) 51(46):12549-12562.
Han et al., Trends Pharm. Sci. (2000) 21:136-142.
Kondo et al., J. Med. Chem. (1990) 33:2012-2015.
Satchell and Satchell, Chem. Rev. (1969) 69:251-255.
U.S. Appl. No. 06/604,208, filed by Daniel Tim-Wo Chu in Apr. 1984.
Wentland et al., J. Med. Chem. (1993) 36:1580-1596.

* cited by examiner

*Primary Examiner*—Rita J Desai
(74) *Attorney, Agent, or Firm*—Cooley LLP

(57) ABSTRACT

The present invention provides quinolone analogs which may inhibit cell proliferation and/or induce cell apoptosis. The present invention also provides methods of preparing quinolone analogs, and methods of using the same.

17 Claims, 6 Drawing Sheets

QUINOLONE ANALOGS

CROSS-REFERENCE TO RELATED APPLICATIONS

This application is a continuation-in-part of U.S. patent Ser. No. 11/149,007 filed Jun. 9, 2005, which is incorporated herein by reference in its entirety, and claims the benefit of U.S. provisional patent application Ser. No. 60/611,030 filed Sep. 17, 2004. This application also claims the benefit of U.S. provisional patent application Ser. No. 60/688,986 filed Jun. 9, 2005; Ser. No. 60/638,603 filed Dec. 22, 2004; and Ser. No. 60/688,796 filed Jun. 9, 2005, each of which is incorporated herein by reference in its entirety.

FIELD OF THE INVENTION

The invention relates to quinolone analogs and uses thereof. The invention also relates to methods of preparing quinolone analogs.

BACKGROUND

Evidence suggests quadruplex structures can exist in vivo in specific regions of the genome, including the telomeric ends of chromosomes and oncogene regulatory regions (Han, et al., *Trends Pharm. Sci.* (2000) 21:136-142). Quadruplex structures can form in purine-rich strands of nucleic acids. In duplex nucleic acids, certain purine rich strands are capable of engaging in a slow equilibrium between a typical duplex helix structure and in unwound and non-B-form regions. These unwound and non-B forms can be referred to as "paranemic structures." Some forms are associated with sensitivity to S1 nuclease digestion, which can be referred to as "nuclease hypersensitivity elements" or "NHEs." A quadruplex is one type of paranemic structure and certain NHEs can adopt a quadruplex structure.

SUMMARY OF THE INVENTION

The present invention provides quinolone analogs which may inhibit cell proliferation and/or induce cell apoptosis. The present invention also provides methods of preparing quinolone analogs, and methods of using the same.

In one aspect, the present invention provides compounds having the general formula:

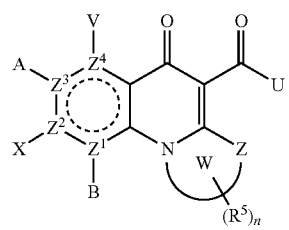

(1)

and pharmaceutically acceptable salts, esters and prodrugs thereof;

wherein B, X, A, or V is absent if $Z^2$, $Z^3$, or $Z^4$, respectively, is N, and independently H, halo, azido, $R^2$, $CH_2R^2$, $SR^2$, $OR^2$ or $NR^1R^2$ if $Z^2$, $Z^3$, or $Z^4$, respectively, is C; or A and V, A and X, or X and B may form a carbocyclic ring, heterocyclic ring, aryl or heteroaryl, each of which may be optionally substituted and/or fused with a cyclic ring;

Z is O, S, $NR^1$, $CH_2$, or C=O;

$Z^1$, $Z^2$, $Z^3$ and $Z^4$ are C or N, provided any two N are non-adjacent;

W together with N and Z forms an optionally substituted 5- or 6-membered ring that is fused to an optionally substituted saturated or unsaturated ring; said saturated or unsaturated ring may contain a heteroatom and is monocyclic or fused with a single or multiple carbocyclic or heterocyclic rings;

U is $R^2$, $OR^2$, $NR^1R^2$, $NR^1$—$(CR^1{}_2)_n$—$NR^3R^4$, or N=$CR^1R^2$, wherein in N=$CR^1R^2R^1$ and $R^2$ together with C may form a ring, provided U is not H, and when U is OH, $OR^2$ or $NH_2$, then at least one of $Z^1$-$Z^4$ is N;

in each $NR^1R^2$, $R^1$ and $R^2$ together with N may form an optionally substituted ring;

in $NR^3R^4$, $R^3$ and $R^4$ together with N may form an optionally substituted ring;

$R^1$ and $R^3$ are independently H or $C_{1-6}$ alkyl;

each $R^2$ is H, or a $C_{1-10}$ alkyl or $C_{2-10}$ alkenyl each optionally substituted with a halogen, one or more non-adjacent heteroatoms, a carbocyclic ring, a heterocyclic ring, an aryl or heteroaryl, wherein each ring is optionally substituted; or $R^2$ is an optionally substituted carbocyclic ring, heterocyclic ring, aryl or heteroaryl;

$R^4$ is H, a $C_{1-10}$ alkyl or $C_{2-10}$ alkenyl optionally containing one or more non-adjacent heteroatoms selected from N, O and S, and optionally substituted with a carbocyclic or heterocyclic ring; or $R^3$ and $R^4$ together with N may form an optionally substituted ring;

each $R^5$ is a substituent at any position on ring W; and is H, $OR^2$, amino, alkoxy, amido, halogen, cyano or an inorganic substituent; or $R^5$ is $C_{1-6}$ alkyl, $C_{2-6}$ alkenyl, $C_{2-6}$ alkynyl, —$CONHR^1$, each optionally substituted by halo, carbonyl or one or more non-adjacent heteroatoms; or two adjacent $R^5$ are linked to obtain a 5-6 membered optionally substituted carbocyclic or heterocyclic ring that may be fused to an additional optionally substituted carbocyclic or heterocyclic ring; and n is 1-6.

In the above formula (1), B may be absent when $Z^1$ is N, or is H or a halogen when $Z^1$ is C.

In the above formula (1), W together with N and Z forms an optionally substituted 5- or 6-membered ring that is fused to an optionally substituted aryl or heteroaryl selected from the group consisting of:

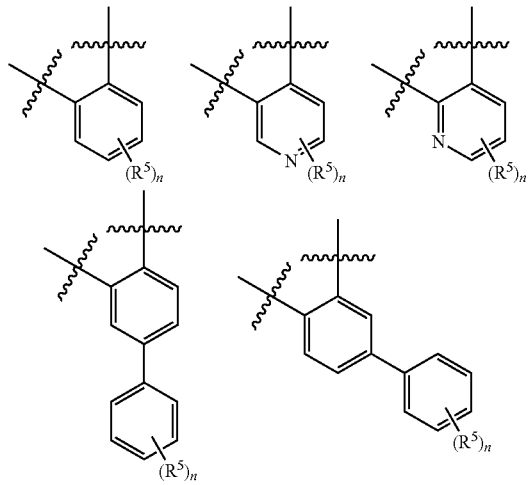

-continued
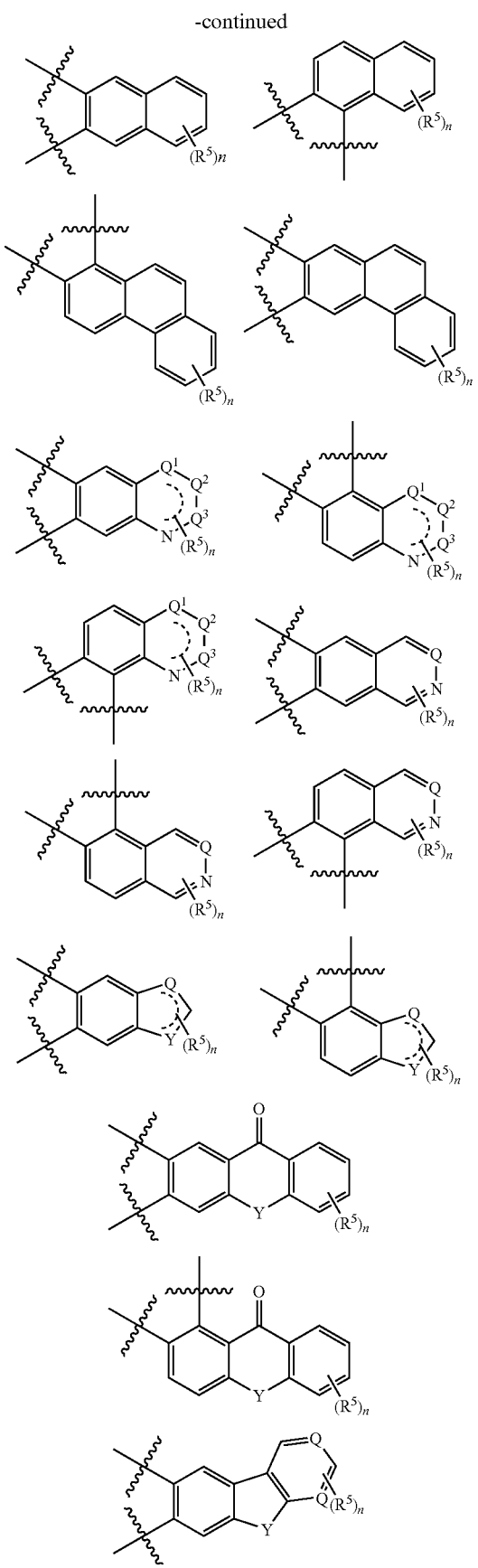
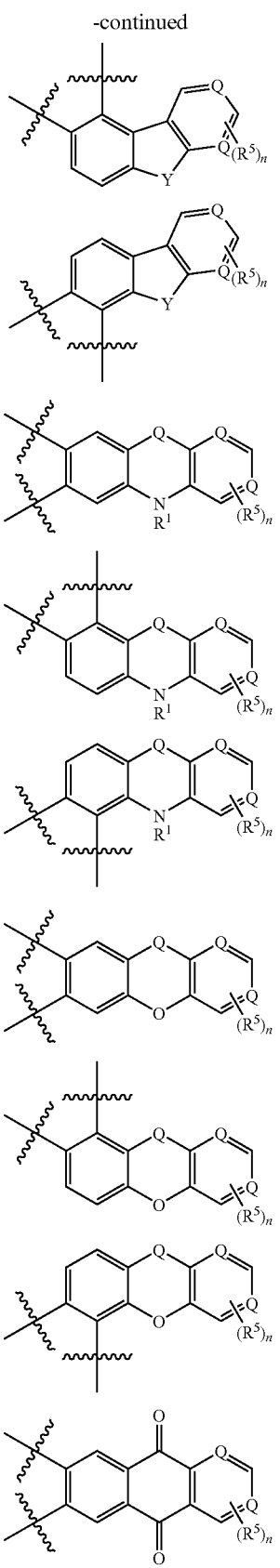

-continued

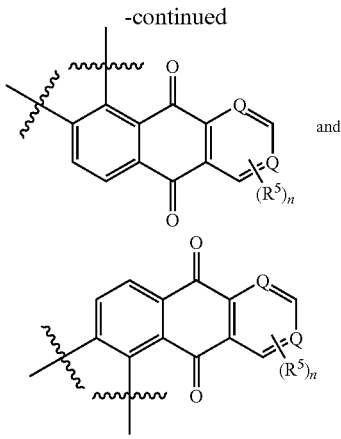

wherein each Q, Q¹, Q², and Q³ is independently CH or N;
Y is independently O, CH, C=O or NR¹;
n and $R^5$ is as defined above.

In other embodiments, W together with N and Z form a group having the formula selected from the group consisting of

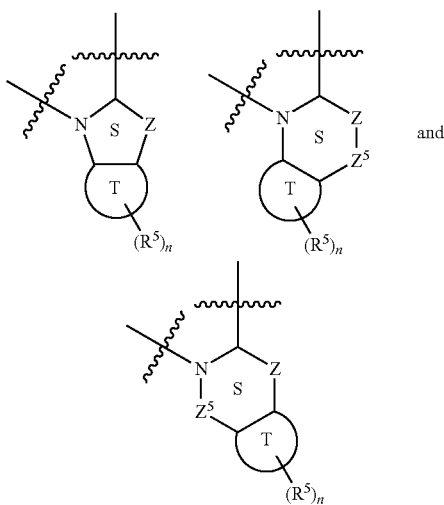

wherein Z is O, S, CR¹, NR¹, or C=O;
each $Z^5$ is CR⁶, NR¹, or C=O, provided Z and $Z^5$ if adjacent are not both NR¹;
each R¹ is H, $C_{1-6}$ alkyl, COR² or $S(O)_pR^2$ wherein p is 1-2;
R⁶ is H, or a substituent known in the art, including but not limited to hydroxyl, alkyl, alkoxy, halo, amino, or amido; and
ring S and ring T may be saturated or unsaturated.

In some embodiments, W together with N and Z forms a 5- or 6-membered ring that is fused to a phenyl. In other embodiments, W together with N and Z forms a 5- or 6-membered ring that is optionally fused to another ring, when U is NR¹R², provided U is not NH₂. In certain embodiments, W together with N and Z forms a 5- or 6-membered ring that is not fused to another ring, when U is NR¹R² (e.g., NH₂).

In yet another embodiment, the compounds of the present invention have the general formula (2A) or (2B):

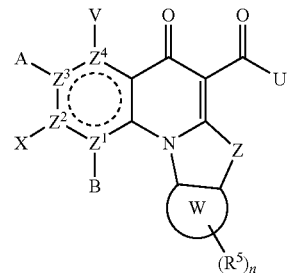

(2A)

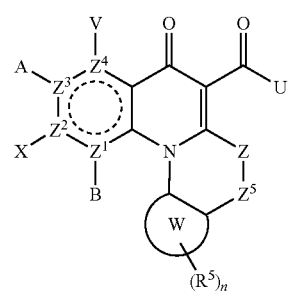

(2B)

wherein A, B, V, X, U, Z, Z¹, Z², Z³, Z⁴ and n are as described above;
$Z^5$ is O, NR¹, CR⁶, or C=O;
R⁶ is H, $C_{1-6}$ alkyl, hydroxyl, alkoxy, halo, amino or amido; and
Z and $Z^5$ may optionally form a double bond.

In the above formula (1), (2A) and (2B), U may be NR¹R², wherein R¹ is H, and R² is a $C_{1-10}$ alkyl optionally substituted with a heteroatom, a $C_{3-6}$ cycloalkyl, aryl or a 5-14 membered heterocyclic ring containing one or more N, O or S. For example, R² may be a $C_{1-10}$ alkyl substituted with an optionally substituted morpholine, thiomorpholine, imidazole, aminodithiadazole, pyrrolidine, piperazine, pyridine or piperidine. In other examples, R¹ and R² together with N form an optionally substituted piperidine, pyrrolidine, piperazine, morpholine, thiomorpholine, imidazole, or aminodithiazole.

In other embodiments, U is NR¹—(CR¹₂)ₙ—NR³R⁴; n is 1-4; and R³ and R⁴ in NR³R⁴ together form an optionally substituted piperidine, pyrrolidine, piperazine, morpholine, thiomorpholine, imidazole, or aminodithiazole. In some examples, U is NH—(CH₂)ₙ—NR³R⁴ wherein R³ and R⁴ together with N form an optionally substituted pyrrolidine, which may be linked to (CH₂)ₙ at any position in the pyrrolidine ring. In one embodiment, R³ and R⁴ together with N form an N-methyl substituted pyrrolidine. In some embodiments, U is 2-(1-methylpyrrolidin-2-yl)ethylamino or (2-pyrrolidin-1-yl)ethanamino.

In the above formula (1), (2A) and (2B), Z may be S or NR¹. In some embodiments, at least one of B, X, or A is halo and Z¹, Z², and Z³ are C. In other embodiments, X and A are not each H when Z² and Z³ are C. In the above formula (1), (2A) and (2B), V may be H. In particular embodiments, U is not OH.

In one embodiment, each of Z¹, Z², Z³ and Z⁴ are C. In another embodiment, three of Z¹, Z², Z³ and Z⁴ is C, and the other is N. For example, Z¹, Z² and Z³ are C, and Z⁴ is N. Alternatively, Z¹, Z² and Z⁴ are C, and Z³ is N. In other examples, Z¹, Z³ and Z⁴ are C and Z² is N. In yet other examples, Z², Z³ and Z⁴ are C, and Z¹ is N.

In another embodiment, two of Z¹, Z², Z³ and Z⁴ are C, and the other two are non-adjacent nitrogens. For example, Z¹ and $Z^3$ may be C, and $Z^2$ and $Z^4$ are N. Alternatively, $Z^1$ and $Z^3$ may be N, and $Z^2$ and $Z^4$ may be C. In other examples, $Z^1$ and $Z^4$ are N, and $Z^2$ and $Z^3$ are C. In particular examples, W together with N and Z forms a 5- or 6-membered ring that is fused to a phenyl.

In some embodiments, each of B, X, A, and V is H and $Z^1$-$Z^4$ are C. In many embodiments, at least one of B, X, A, and V is H and the corresponding adjacent $Z^1$-$Z^4$ atom is C. For example, any two of B, X, A, and V may be H. In one example, V and B may both be H. In other examples, any three of B, X, A, and V are H and the corresponding adjacent $Z^1$-$Z^4$ atom is C.

In certain embodiments, one of B, X, A, and V is a halogen (e.g., fluorine) and the corresponding adjacent $Z^1$-$Z^4$ is C. In other embodiments, two of X, A, and V are halogen or $SR^2$, wherein $R^2$ is a $C_{0-10}$ alkyl or $C_{2-10}$ alkenyl optionally substituted with a heteroatom, a carbocyclic ring, a heterocyclic ring, an aryl or a heteroaryl; and the corresponding adjacent $Z^2$-$Z^4$ is C. For example, each X and A may be a halogen. In other examples, each X and A if present may be $SR^2$, wherein $R^2$ is a $C_{0-10}$ alkyl substituted with phenyl or pyrazine. In yet other examples, V, A and X may be alkynyls, fluorinated alkyls such as $CF_3$, $CH_2CF_3$, perfluorinated alkyls, etc.; cyano, nitro, amides, sulfonyl amides, or carbonyl compounds such as $COR^2$.

In each of the above formulas, U, and X, V, and A if present may independently be $NR^1R^2$, wherein $R^1$ is H, and $R^2$ is a $C_{1-10}$ alkyl optionally substituted with a heteroatom, a $C_{3-6}$ cycloalkyl, aryl or a 5-14 membered heterocyclic ring containing one or more N, O or S. If more than one $NR^1R^2$ moiety is present in a compound within the invention, as when both A and U are $NR^1R^2$ in a compound according to any one of the above formula, each $R^1$ and each $R^2$ is independently selected. In one example, $R^2$ is a $C_{1-10}$ alkyl substituted with an optionally substituted 5-14 membered heterocyclic ring. For example, $R^2$ may be a $C_{1-10}$ alkyl substituted with morpholine, thiomorpholine, imidazole, aminodithiadazole, pyrrolidine, piperazine, pyridine or piperidine. Alternatively, $R^1$ and $R^2$ together with N may form an optionally substituted heterocyclic ring containing one or more N, O or S. For example, $R^1$ and $R^2$ together with N may form piperidine, pyrrolidine, piperazine, morpholine, thiomorpholine, imidazole, or aminodithiazole.

Illustrative examples of optionally substituted heterocyclic rings include but are not limited to tetrahydrofuran, 1,3-dioxolane, 2,3-dihydrofuran, tetrahydropyran, benzofuran, isobenzofuran, 1,3-dihydro-isobenzofuran, isoxazole, 4,5-dihydroisoxazole, piperidine, pyrrolidine, pyrrolidin-2-one, pyrrole, pyridine, pyrimidine, octahydro-pyrrolo[3,4-b]pyridine, piperazine, pyrazine, morpholine, thiomorpholine, imidazole, aminodithiadazole, imidazolidine-2,4-dione, benzimidazole, 1,3-dihydrobenzimidazol-2-one, indole, thiazole, benzothiazole, thiadiazole, thiophene, tetrahydro-thiophene 1,1-dioxide, diazepine, triazole, diazabicyclo[2.2.1]heptane, 2,5-diazabicyclo[2.2.1]heptane, and 2,3,4,4a,9,9a-hexahydro-1H-β-carboline.

In one embodiment, the present invention provides compounds having formula (1), (2A) or (2B), wherein:
  each of A, V and B if present is independently H or halogen (e.g., chloro or fluoro);
  X is —$(R^5)R^1R^2$, wherein $R^5$ is C or N and wherein in each —$(R^5)R^1R^2$, $R^1$ and $R^2$ together may form an optionally substituted aryl or heteroaryl ring;
  Z is NH or N-alkyl (e.g., N—$CH_3$);
  W together with N and Z forms an optionally substituted 5- or 6-membered ring that is fused with an optionally substituted aryl or heteroaryl ring; and
  U is —$R^5R^6$—$(CH_2)_n$—$CHR^2$—$NR^3R^4$, wherein $R^6$ is H or $C_{1-10}$ alkyl and wherein in the —$CHR^2$—$NR^3R^4$ moiety each $R^3$ or $R^4$ together with the C may form an optionally substituted heterocyclic or heteroaryl ring, or wherein in the —$CHR^2$—$NR^3R^4$ moiety each $R^3$ or $R^4$ together with the N may form an optionally substituted carbocyclic, heterocyclic, aryl or heteroaryl ring.

In another embodiment, the present invention provides compounds having formula (1), (2A) or (2B), wherein:
  A if present is H or halogen (e.g., chloro or fluoro);
  X if present is —$(R^5)R^1R^2$, wherein $R^5$ is C or N and wherein in each —$(R^5)R^1R^2$, $R^1$ and $R^2$ together may form an optionally substituted aryl or heteroaryl ring;
  Z is NH or N-alkyl (e.g., N—$CH_3$);
  W together with N and Z forms an optionally substituted 5- or 6-membered ring that is fused with an optionally substituted aryl or heteroaryl ring; and
  U is —$R^5R^6$—$(CH_2)_n$—$CHR^2$—$NR^3R^4$, wherein $R^6$ is H or alkyl and wherein in the —$CHR^2$—$NR^3R^4$ moiety each $R^3$ or $R^4$ together with the C may form an optionally substituted heterocyclic or heteroaryl ring, or wherein in the —$CHR^2$—$NR^3R^4$ moiety each $R^3$ or $R^4$ together with the N may form an optionally substituted carbocyclic, heterocyclic, aryl or heteroaryl ring.

In each of the above formula, each optionally substituted moiety may be substituted with one or more halo, $OR^2$, $NR^1R^2$, carbamate, $C_{1-10}$ alkyl, $C_{2-10}$ alkenyl, each optionally substituted by halo, C=O, aryl or one or more heteroatoms; inorganic substituents, aryl, carbocyclic or a heterocyclic ring. Other substituents include but are not limited to alkynyl, cycloalkyl, fluorinated alkyls such as $CF_3$, $CH_2CF_3$, perfluorinated alkyls, etc.; oxygenated fluorinated alkyls such as $OCF_3$ or $CH_2CF_3$, etc.; cyano, nitro, $COR^2$, $NR^2COR^2$, sulfonyl amides; $NR^2SOOR^2$; $SR^2$, $SOR^2$, $COOR^2$, $CONR^2{}_2$, $OCOR^2$, $OCOOR^2$, $OCONR^2{}_2$, $NRCOOR^2$, $NRCONR^2{}_2$, $NRC(NR)(NR^2{}_2)$, $NR(CO)NR^2{}_2$, and $SOONR^2{}_2$, wherein each $R^2$ is as defined in formula 1.

The present invention also provides pharmaceutical compositions comprising a compound having any one of the above formula, and a pharmaceutically acceptable excipient. In one example, the composition comprises a compound having any one of the above formula, polyethylene glycol, and propylene glycol in a buffer solution.

Furthermore, the present invention relates to methods for reducing cell proliferation and/or inducing cell death, comprising contacting a system with an effective amount of a compound having any one of the above formula, or a pharmaceutical composition thereof and optionally in combination with a chemotherapeutic agent, thereby reducing cell proliferation and/or inducing cell death, such as apoptosis or apoptotic cell death, in said system. The system may be a cell or a tissue. In one embodiment, the system includes a pancreatic cell, such as a cell from a subject or a cultured cell (e.g., in vitro or ex vivo). In particular embodiments, the system includes a pancreatic cancer cell. In one embodiment, the system is a cell line such as PC3, HCT116, HT29, MIA Paca-2, HPAC, Hs700T, Panc10.05, Panc 02.13, PL45, SW 190, Hs 766T, CFPAC-1 and PANC-1.

The present invention also provides methods for ameliorating a cell proliferative disorder, comprising administering to a subject in need thereof an effective amount of a compound having any one of the above formula, or a pharmaceutical composition thereof and optionally in combination with a chemotherapeutic agent, thereby ameliorating said cell-proliferative disorder. For example, cell proliferation may be reduced, and/or cell death, such as apoptosis or apoptotic cell death, may be induced. The cell proliferative disorder may be a tumor or a cancer in a human or animal subject. In a particular embodiment, the cancer is pancreatic cancer, including non-endocrine and endocrine tumors. Illustrative examples of non-endocrine tumors include but are not limited to adenocarcinomas, acinar cell carcinomas, adenosquamous carcinomas, giant cell tumors, intraductal papillary mucinous neoplasms, mucinous cystadenocarcinomas, pancreatoblastomas, serous cystadenomas, solid and pseudopapillary tumors. An endocrine tumor may be an islet cell tumor.

The above methods for reducing cell proliferation and/or inducing cell death may also be practiced in combination with a procedure and/or a chemotherapeutic agent. Examples of procedures that may be used in combination with the methods of the present invention include but are not limited to radiotherapy or surgery. In certain embodiments, the compounds of the present invention are administered in combination with gemcitabine, and used to reduce cell proliferation, induce cell death, and/or ameliorate a cell proliferative disorder.

Furthermore, the present invention provides methods for reducing microbial titers, comprising contacting a system with an effective amount of a compound having any one of the above formula, or a pharmaceutical composition thereof and optionally with an antimicrobial agent, thereby reducing microbial titers. The system may be a cell or a tissue. The present invention also provides methods for ameliorating a microbial infection, comprising administering to a subject in need thereof an effective amount of a compound having any one of the above formula, or a pharmaceutical composition thereof and optionally with an antimicrobial agent, thereby ameliorating said microbial infection. The subject may be human or an animal. The microbial titers may be viral, bacterial or fungal titers.

The present invention also relates to methods for determining interaction selectivity between a compound having any one of the above formula, and nucleic acids capable of forming a quadruplex structure, comprising: a) contacting a compound in the absence of a competitor molecule with three or more nucleic acids capable of forming a quadruplex structure, wherein each nucleic acid is not a telomere nucleic acid; b) measuring a direct interaction between the compound and said three or more nucleic acids; and c) determining interaction selectivity from a comparison of the interaction measurements. In one example, three or more nucleic acids comprise a nucleotide sequence located 5' of an oncogene nucleotide sequence. The oncogene may be MYC, HIF, VEGF, ABL, TGF, PDGFα, MYB, SPARC, HER, VAV, RET, H-RAS, EGF, SRC, BCL-1, BCL-2, DHFR, or HMGA. In determining interaction selectivity, the compound may be separately contacted with each of said three or more nucleic acids in a different vessel. Furthermore, the interaction selectivity may be determined from a comparison of $IC_{50}$ values.

The compounds of the present invention may or may not interact with regions of DNA that can form quadruplexes. In certain embodiments, the compounds of the present invention may bind and/or stabilize a propeller quadruplex. Examples of propeller quadruplexes include but are not limited to H-RAS, RET, BCL-1, DHFR, TGF-β, HIF-1α, VEGF, c-Myc, or PDGFα. In another embodiment, the compound may bind and/or stabilize a chair-eller or a basket quadruplex. For example, the compound may bind and/or stabilize BCL-2.

The present invention also provides methods for inducing cell death, such as apoptotic cell death (apoptosis), comprising administering to a system or a subject in need thereof an effective amount of a compound having any one of the above formula, or a pharmaceutical composition thereof and optionally with a chemotherapeutic agent. The present invention also provides methods for treating or ameliorating a disorder mediated by oncogene overexpression, such as c-Myc overexpression, comprising administering to a system or a subject in need thereof an effective amount of a compound having any of the formula, or a pharmaceutical composition thereof and optionally with a chemotherapeutic agent. The subject may be human or an animal, and system may be a cell or a tissue.

In another aspect, the present invention provides methods for preparing compounds having formula (3)

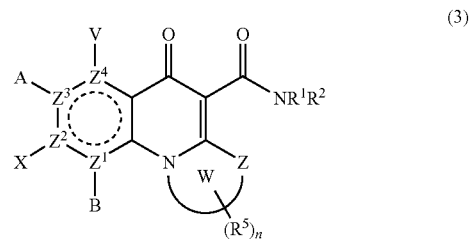

(3)

or formula (4)

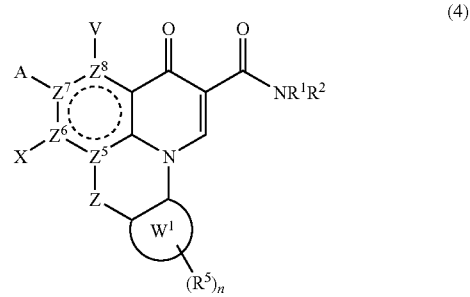

(4)

comprising contacting an ester, $NHR^1R^2$, and a Lewis acid, wherein said ester has formula (5)

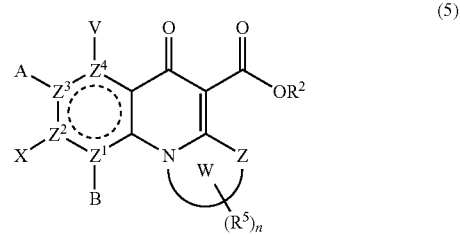

(5)

or formula (6)

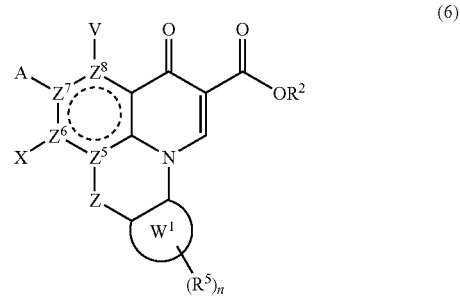

(6)

wherein A, B, V, X, $R^1$, $R^2$, $R^5$, Z, $Z^1$, $Z^2$, $Z^3$, $Z^4$ and n are as described above in formula (1);

W together with N and Z forms an optionally substituted 5- or 6-membered ring that is fused to an optionally substituted aryl or heteroaryl, wherein said aryl or heteroaryl may be monocyclic or fused with a single or multiple ring, and wherein said ring optionally contains a heteroatom;

$W^1$ is an optionally substituted aryl or heteroaryl, which may be monocyclic, or fused with a single or multiple ring and optionally containing a heteroatom;

$Z^5$ is C or N, provided $Z^5$ is C if Z is O, S or $NR^1$, and further provided that Z and $Z^6$ are not N if $Z^5$ is N; and $Z^6$, $Z^7$, and $Z^8$ are independently C or N, provided any two N are non-adjacent.

The present methods for preparing compounds having formula (3) involve amide coupling of an ester with an amine in the presence of a Lewis acid such as aluminum chloride. Suitable Lewis acids may be selected by conducting a test reaction, and observing the amount of reaction product produced, as described hereafter. The present methods do not require hydrolysis of the ester to a carboxylic acid prior to amide coupling. Thus, the present methods are simpler. As shown in Example 29, the present methods also provide higher yields and purity than previous methods involving requiring hydrolysis of the ester to the acid (Example 30).

In one embodiment, the Lewis acid has formula $ML_n$, wherein L is a halogen atom or an organic radical, n is 3-5, and M is a group III elemental atom, a group IV elemental atom, As, Sb, V or Fe.

In the above methods, the contacting step may be performed at room temperature. Alternatively, the ester, amine and Lewis acid may be contacted at cooler or elevated temperatures than room temperature, which may be determined by one skilled in the art.

In one example, the contacting step comprises contacting the ester and amine in an organic solvent to form a solution, and contacting the solution with a Lewis acid. In one example, the organic solvent is methylene chloride. The reaction may also be conducted using other suitable solvents known in the art.

In one embodiment, an excess of amine in relation to the ester may be used. For example, the ratio of the ester to the amine may be 1:2; 1:1.5; or 1:1.25.

In another embodiment, an equimolar amount of Lewis acid to the amine may be used. Alternatively, the amount of Lewis acid used may be more or less than the amine.

The above methods may further comprise isolating a compound having any one of the above formula. The isolated compounds may further be purified using any methods known in the art. For example, the isolated compounds may be purified through column chromatography, recrystallization, or both.

In the above methods, the purity of the isolated compounds may be between 90 and 99%. For example, the isolated compounds may have a purity between 90 and 95%.

In the above methods, the ester may be contacted with $NHR^1R^2$, wherein $R^1$ is a $(CR^3{}_2)_n$ group;

$R^2$ is $NR^3R^4$;

$R^3$ is H or $C_{1-6}$ alkyl;

n is 1-6; and $R^4$ is H or a $C_{1-10}$ alkyl or $C_{2-10}$ alkenyl optionally containing one or more non-adjacent heteroatoms selected from N, O and S, and optionally substituted with a carbocyclic or heterocyclic ring; and wherein in $NR^3R^4$, $R^3$ and $R^4$ may form an optionally substituted ring such as those previously described above.

DEFINITIONS

Figure 1:
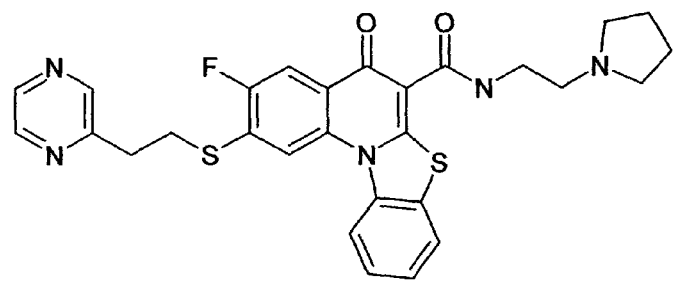
FIGS. 1-10 show the activity of exemplary compounds of the present invention in an HCT-116 colorectal cancer xenograft model.
Figure 1:
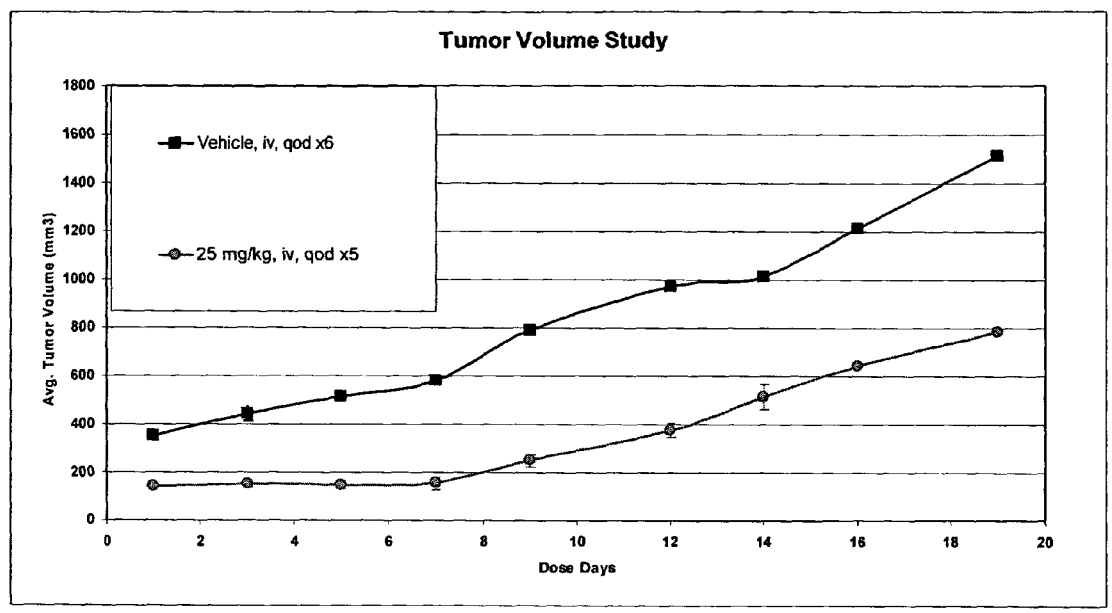
Figure 2:
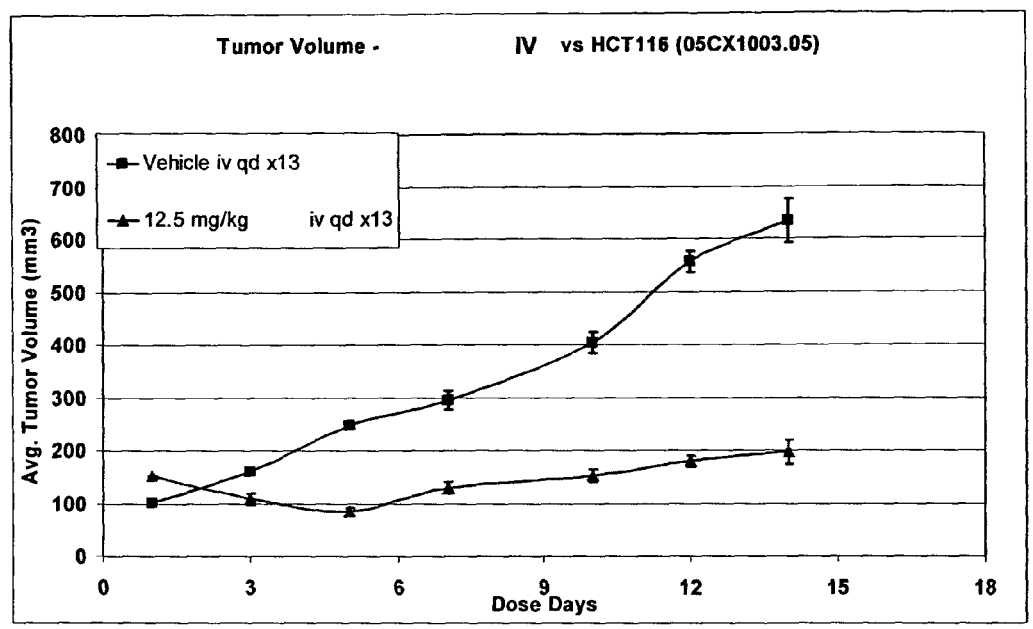
Figure 2:
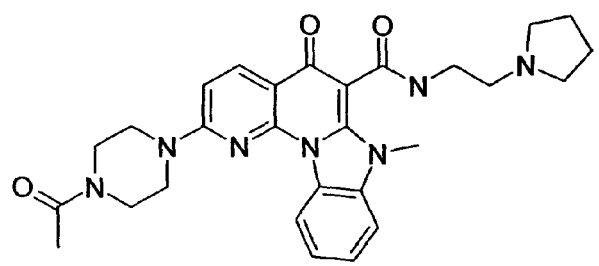

As used herein, the term "alkyl" refers to a carbon-containing compound, and encompasses compounds containing one or more heteroatoms. The term "alkyl" also encompasses alkyls substituted with one or more substituents including but not limited to $OR^1$, amino, amido, halo, =O, aryl, heterocyclic groups, or inorganic substituents.

As used herein, the term "carbocycle" refers to a cyclic compound containing only carbon atoms in the ring, whereas a "heterocycle" refers to a cyclic compound comprising a heteroatom. The carbocyclic and heterocyclic structures encompass compounds having monocyclic, bicyclic or multiple ring systems.

As used herein, the term "aryl" refers to a polyunsaturated, typically aromatic hydrocarbon substituent, whereas a "heteroaryl" or "heteroaromatic" refer to an aromatic ring containing a heteroatom. The aryl and heteroaryl structures encompass compounds having monocyclic, bicyclic or multiple ring systems.

As used herein, the term "heteroatom" refers to any atom that is not carbon or hydrogen, such as nitrogen, oxygen or sulfur.

Illustrative examples of heterocycles include but are not limited to tetrahydrofuran, 1,3-dioxolane, 2,3-dihydrofuran, pyran, tetrahydropyran, benzofuran, isobenzofuran, 1,3-dihydro-isobenzofuran, isoxazole, 4,5-dihydroisoxazole, piperidine, pyrrolidine, pyrrolidin-2-one, pyrrole, pyridine, pyrimidine, octahydro-pyrrolo[3,4-b]pyridine, piperazine, pyrazine, morpholine, thiomorpholine, imidazole, imidazolidine-2,4-dione, 1,3-dihydrobenzimidazol-2-one, indole, thiazole, benzothiazole, thiadiazole, thiophene, tetrahydrothiophene 1,1-dioxide, diazepine, triazole, guanidine, diazabicyclo[2.2.1]heptane, 2,5-diazabicyclo[2.2.1]heptane, 2,3,4,4a,9,9a-hexahydro-1H-β-carboline, oxirane, oxetane, tetrahydropyran, dioxane, lactones, aziridine, azetidine, piperidine, lactams, and may also encompass heteroaryls. Other illustrative examples of heteroaryls include but are not limited to furan, pyrrole, pyridine, pyrimidine, imidazole, benzimidazole and triazole.

As used herein, the term "inorganic substituent" refers to substituents that do not contain carbon or contain carbon bound to elements other than hydrogen (e.g., elemental carbon, carbon monoxide, carbon dioxide, and carbonate). Examples of inorganic substituents include but are not limited to nitro, halogen, sulfonyls, sulfinyls, phosphates, etc.

The terms "treat," "treatment" and "therapeutic effect" as used herein refer to reducing or stopping a cell proliferation rate (e.g., slowing or halting tumor growth) or reducing the number of proliferating cancer cells (e.g., removing part or all of a tumor). These terms also are applicable to reducing a titre of a microorganism in a system (i.e., cell, tissue, or subject) infected with a microorganism, reducing the rate of microbial propagation, reducing the number of symptoms or an effect of a symptom associated with the microbial infection, and/or removing detectable amounts of the microbe from the system. Examples of microorganism include but are not limited to virus, bacterium and fungus.

As used herein, the term "chemotherapeutic agent" refers to a therapeutic agent that may be used for treating or ameliorating a cell proliferative disorder such as tumors or cancer. Examples of chemotherapeutic agents include but are not limited to an antineoplastic agent, an alkylating agent, a plant alkaloid, an antimicrobial agent, a sulfonamide, an antiviral agent, a platinum agent, and other anticancer agents known in the art. Particular examples of chemotherapeutic agents include but are not limited to cisplatin, carboplatin, busulphan, methotrexate, daunorubicin, doxorubicin, cyclophosphamide, mephalan, vincristine, vinblastine, chlorambucil, paclitaxel, gemcitabine, and others known in the art. (See e.g., Goodman & Gilman's, *The Pharmacological Basis of Therapeutics* (9th Ed) (Goodman, et al., eds.) (McGraw-Hill) (1996); and 1999 *Physician's Desk Reference* (1998)).

As used herein, the term "apoptosis" refers to an intrinsic cell self-destruction or suicide program. In response to a triggering stimulus, cells undergo a cascade of events including cell shrinkage, blebbing of cell membranes and chromatic condensation and fragmentation. These events culminate in cell conversion to clusters of membrane-bound particles (apoptotic bodies), which are thereafter engulfed by macrophages.

DESCRIPTION OF THE INVENTION

The present invention relates to quinolone compounds having formula (1), (2A), and (2B), and pharmaceutically acceptable salts, esters, and prodrugs thereof. The present invention also relates to methods for using the compounds described herein, such as in screening and in treatment. The compounds of the present invention may or may not interact with regions of DNA that can form quadruplexes.

The compounds of present invention having formula (1), (2A), and (2B) are reproduced below:

(1)

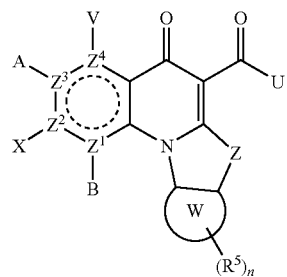

(2A)

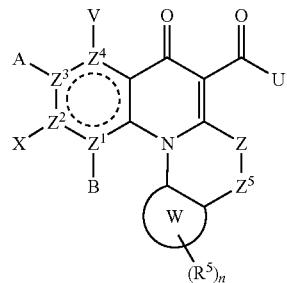

(2B)

wherein A, B, V, X, U, Z, $Z^1$, $Z^2$, $Z^3$, $Z^4$, $X^2$ and n are as described above.

Synthetic procedures for preparing the compounds of the present invention are illustrated in Scheme 1, and in the Examples. Other variations in the synthetic procedures known to those with ordinary skill in the art may also be used to prepare the compounds of the present invention. For example, various protecting groups may be used in the preparation of the intermediate illustrated in Side-Chain 1. (See, e.g., Example 31.)

Scheme 1

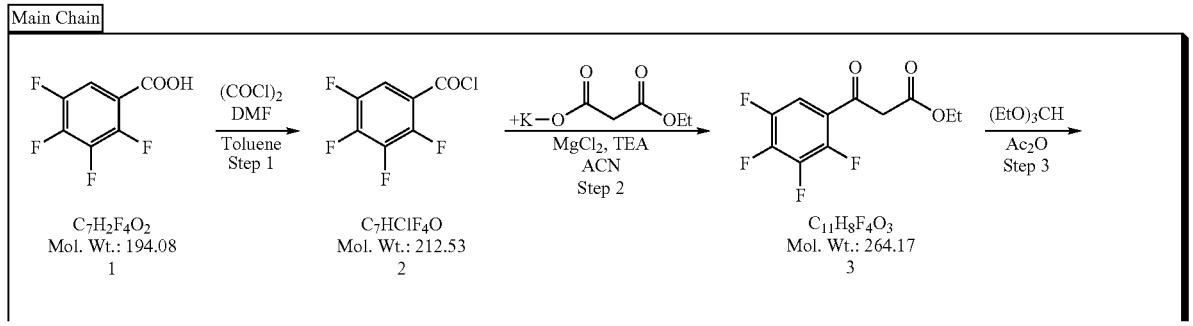

-continued
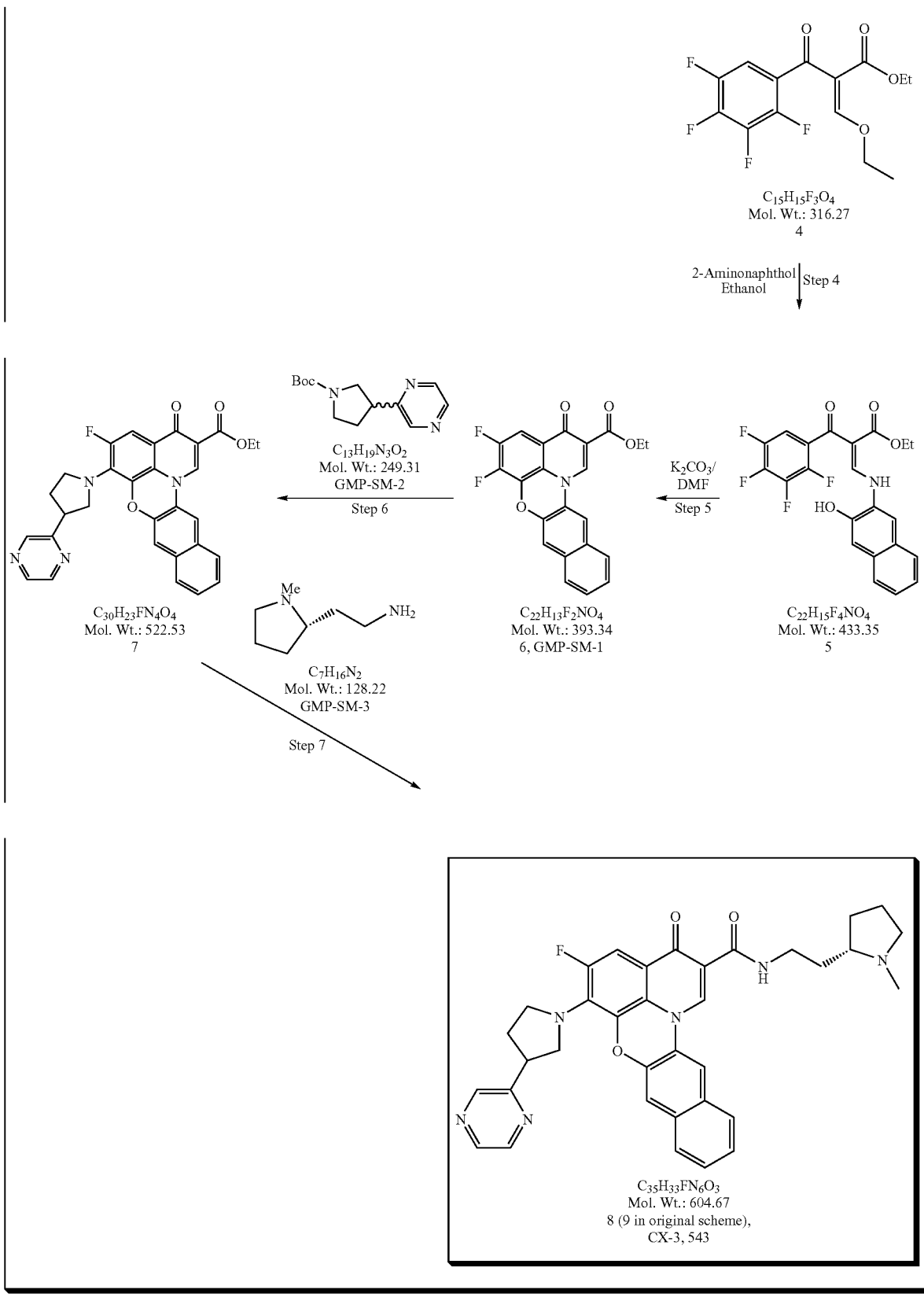

-continued

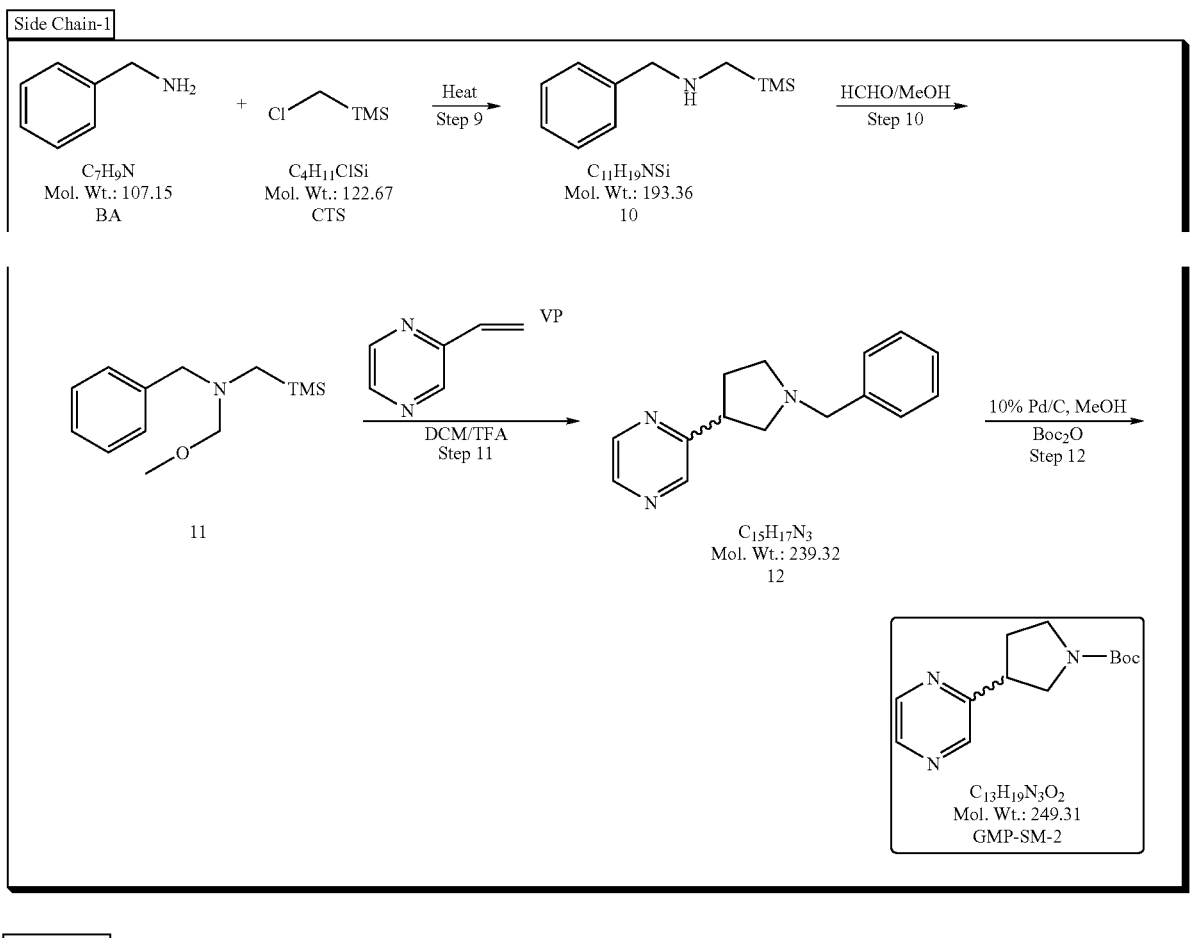

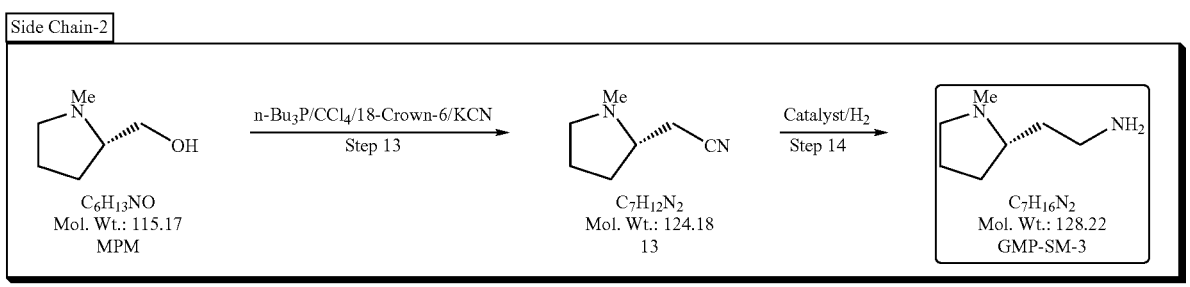

The compounds of the present invention may be chiral. As used herein, a chiral compound is a compound that is different from its mirror image, and has an enantiomer. Furthermore, the compounds may be racemic, or an isolated enantiomer or stereoisomer. Methods of synthesizing chiral compounds and resolving a racemic mixture of enantiomers are well known to those skilled in the art. See, e.g., March, "*Advanced Organic Chemistry,*" John Wiley and Sons, Inc., New York, (1985), which is incorporated herein by reference.

The compounds of the present invention were tested using screening assays such as those described herein. FIGS. 1-10 show the activity of an exemplary compound of the present invention in an HCT-116 colorectal cancer xenograft model. Some compounds did not show activity at a given dosage.

Illustrative examples of compounds having the above formula are shown in Table 1 (A-C), and in the Examples. The present invention also encompasses other compounds having any one formula (1), (2A) and (2B), comprising substituents U, A, X, V, and B independently selected from the substituents exemplified in Table 1 (A-C), and in the Examples. For example, the isopropyl substituent in the last two compounds shown in Table 1A may be replaced with an acetyl substituent, or the N—$CH_3$ in the fused ring may be replaced with an NH group. Furthermore, the fluoro group may be replaced with H. Thus, the present invention is not limited to the specific combination of substituents described in various embodiments below.

TABLE 1A
| MOL STRUCTURE | STOP uM | HCT-116 MTs uM |
| --- | --- | --- |
| 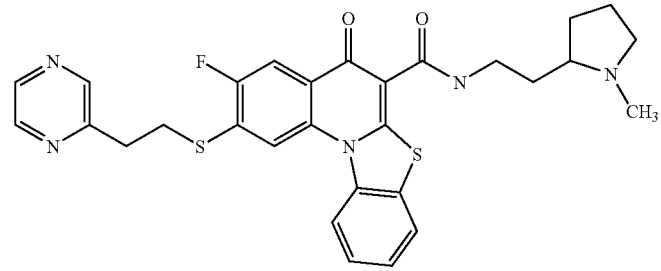 | 7.2 | 1.1 |
| 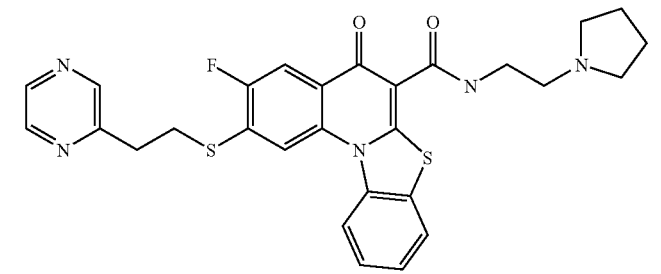 | 5.8 | 0.57 |
| 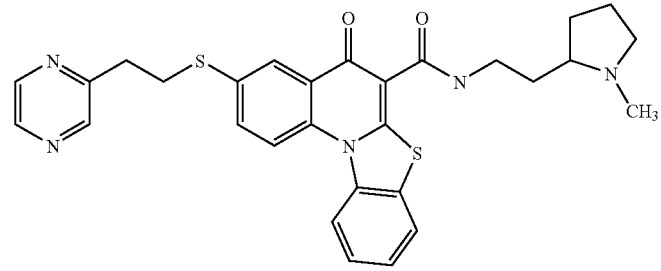 | 10 | 6.1 |
| 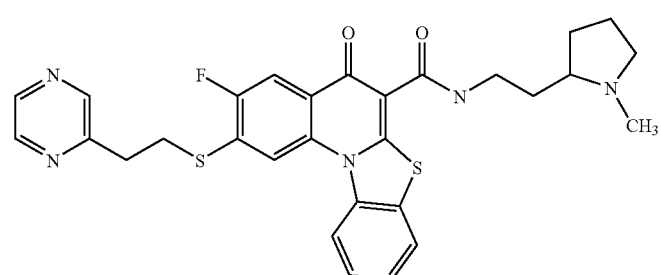 | 9.3 | 5.7 |
| 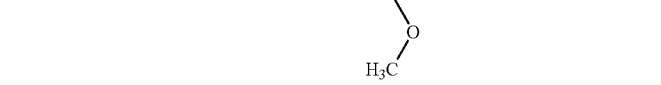 | 1.7 | 3.57 |

TABLE 1A-continued

| MOL STRUCTURE | STOP uM | HCT-116 MTs uM |
| --- | --- | --- |
| | 9 | 0.3 |
| | >15 | |
| | 15 | 2.4 |
| | 11.6 | 3.5 |
| | 1.3 | 3.4 |

TABLE 1A-continued
| MOL STRUCTURE | STOP uM | HCT-116 MTs uM |
| --- | --- | --- |
| 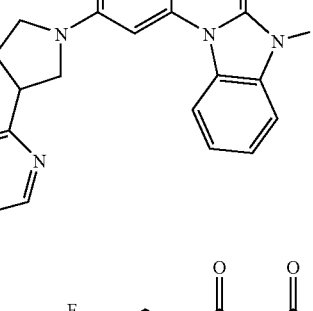 | 10.5 | 0.7 |
| 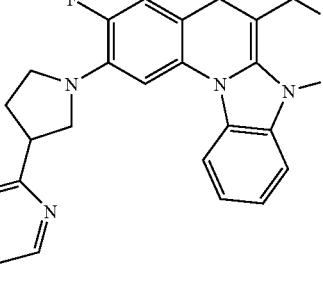 | 8.2 | 0.1 |
| 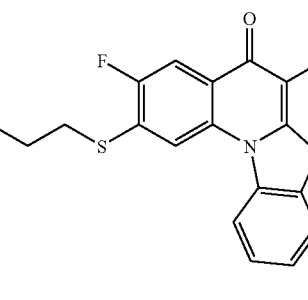 | 15 | 2.3 |
| 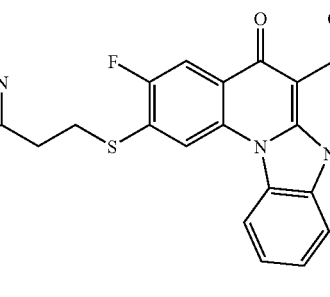 | 15 | 0.3 |
| 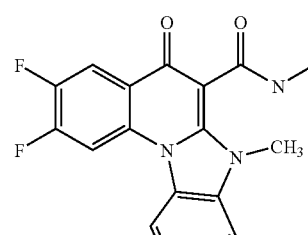 | 15 | 0.3 |

TABLE 1A-continued
| MOL STRUCTURE | STOP uM | HCT-116 MTs uM |
|---|---|---|
| 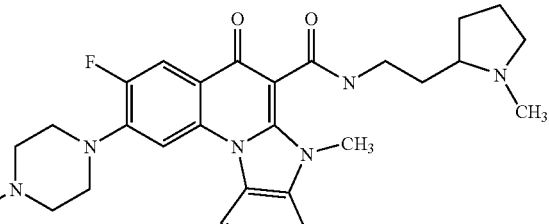 | 15 | 0.3 |
| | >15 | |
TABLE 1B
| MOL STRUCTURE |
|---|
| 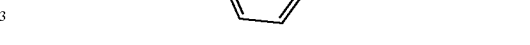 |

TABLE 1B-continued
MOL STRUCTURE
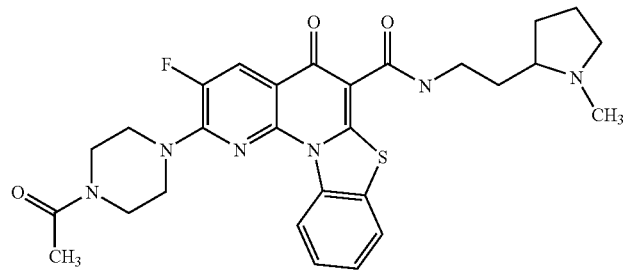
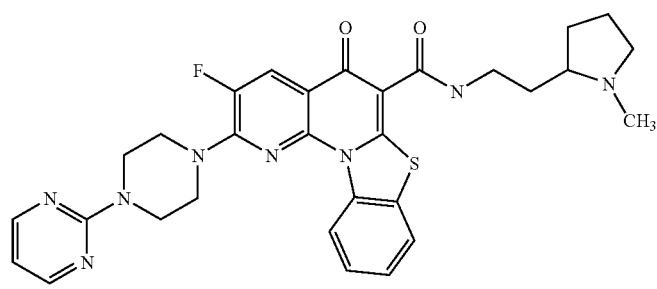
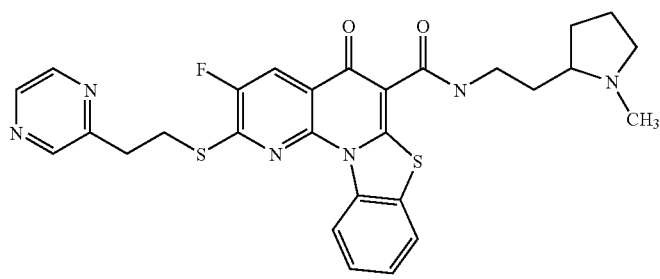
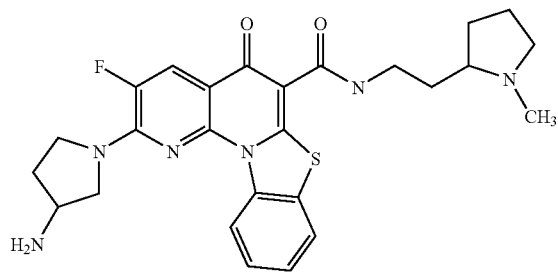
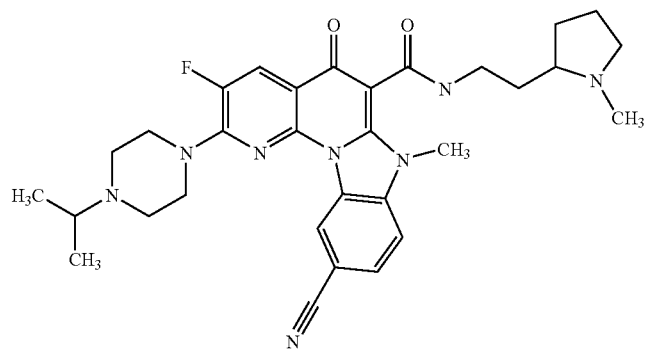

TABLE 1B-continued
| MOL STRUCTURE |
| --- |
| 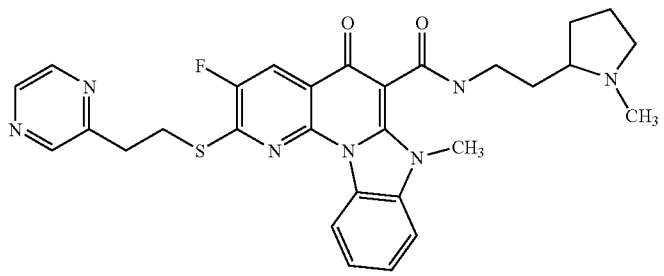 |
| 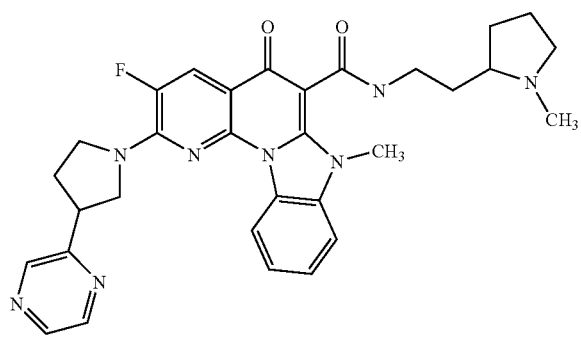 |
| 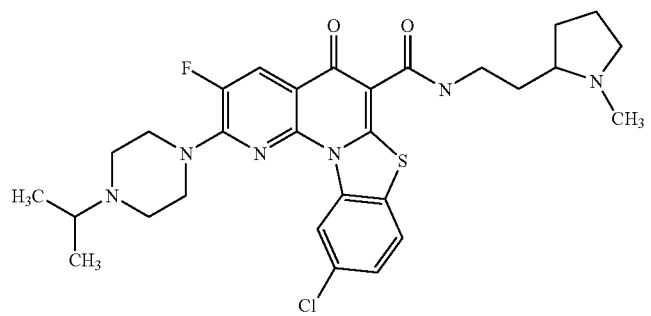 |
| 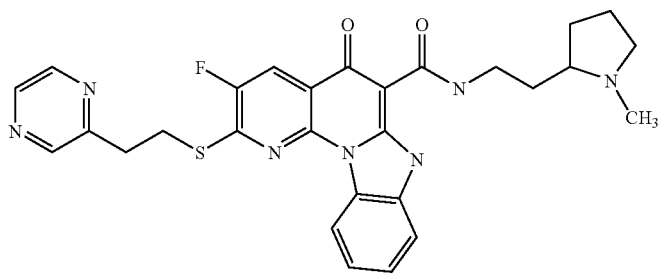 |
| 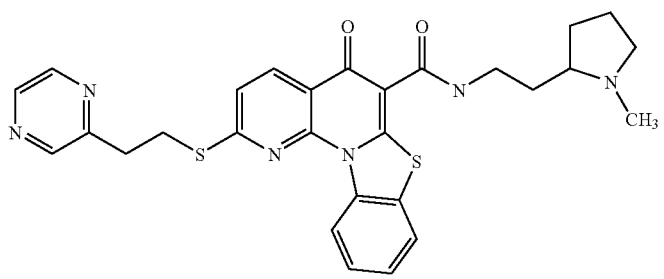 |

TABLE 1B-continued
| MOL STRUCTURE |
| --- |
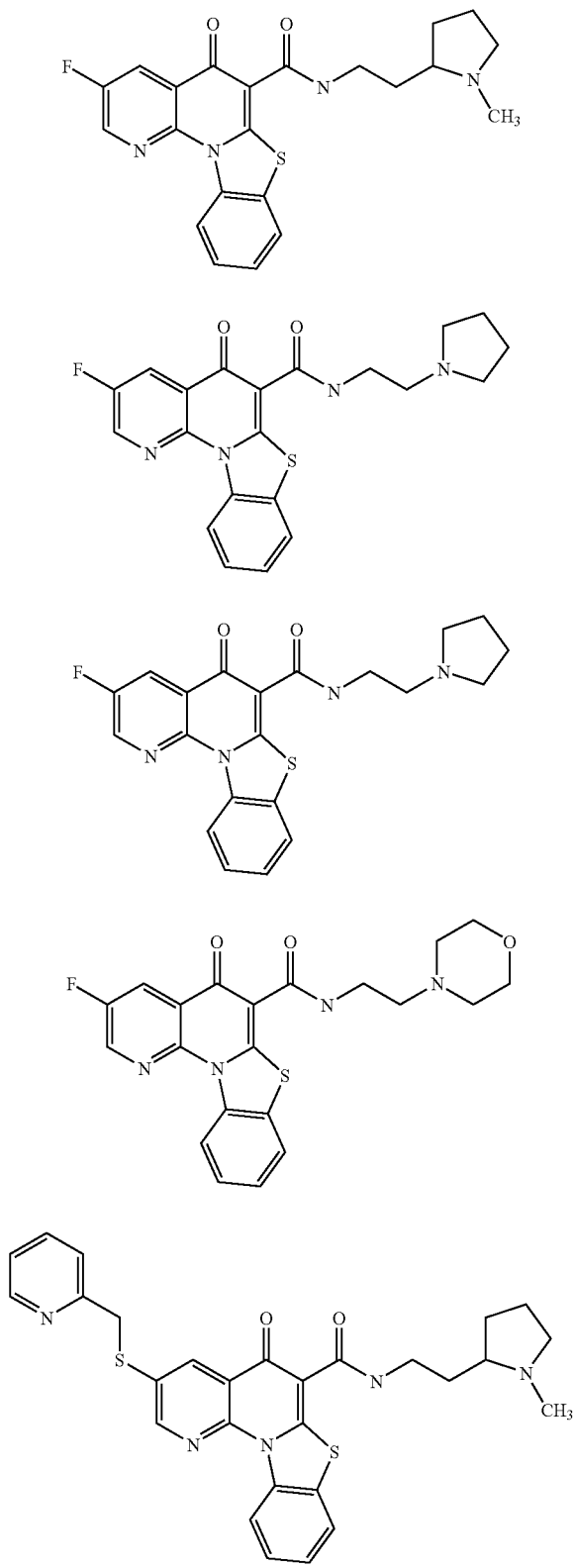

TABLE 1B-continued
MOL STRUCTURE
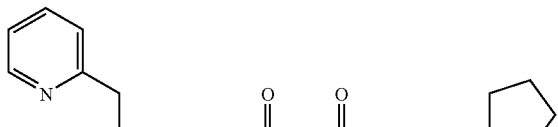
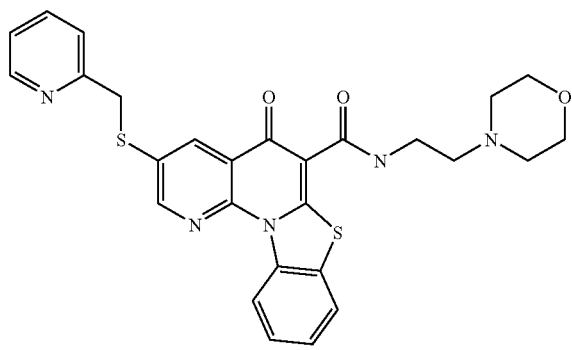
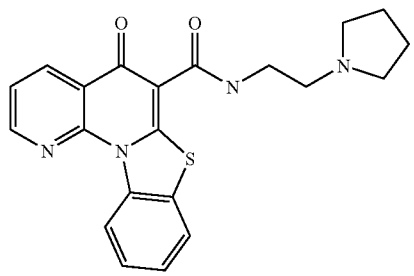
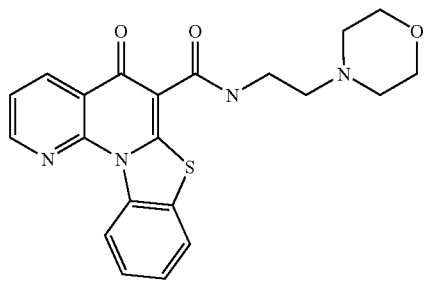
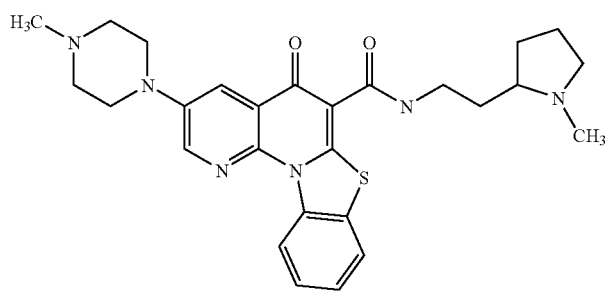

TABLE 1B-continued
MOL STRUCTURE
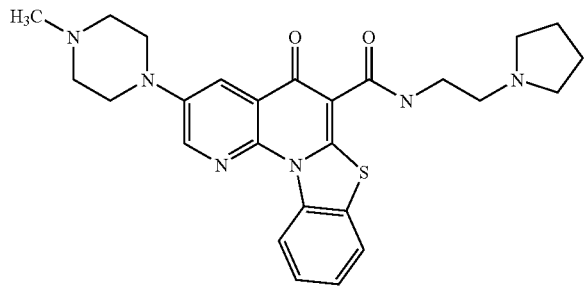
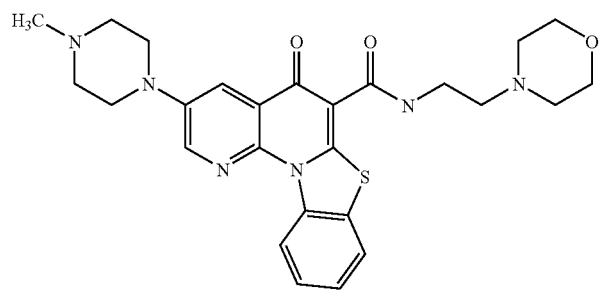
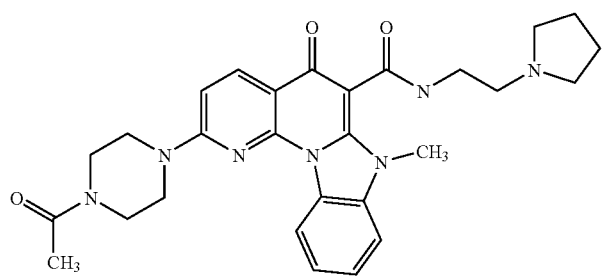
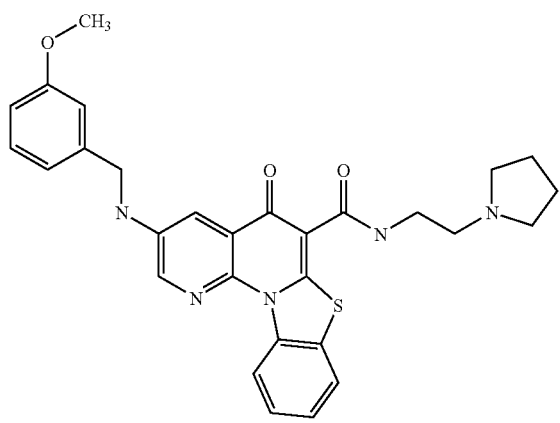

TABLE 1B-continued
MOL STRUCTURE
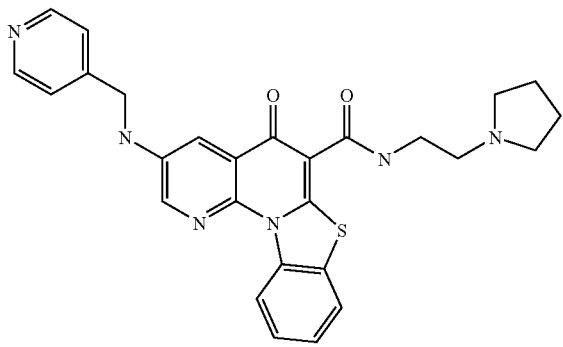
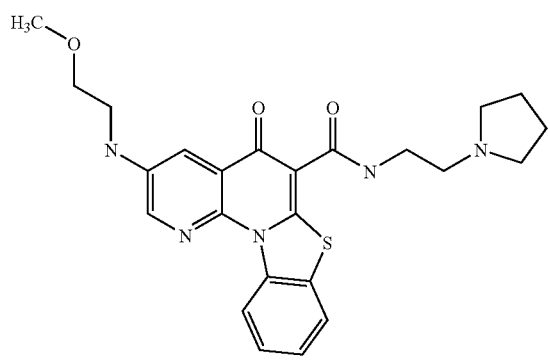
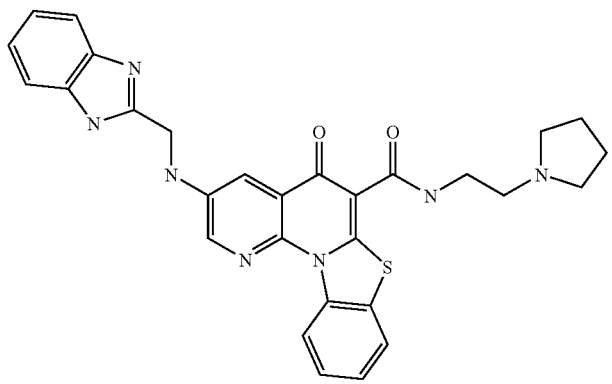
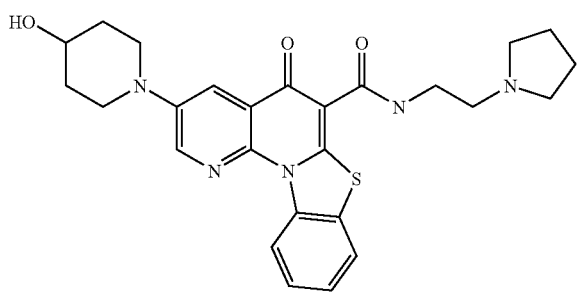

TABLE 1B-continued
| MOL STRUCTURE |
| --- |
| 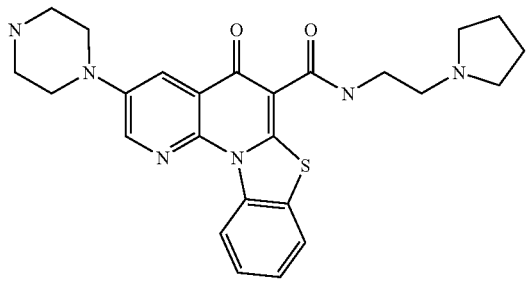 |
| 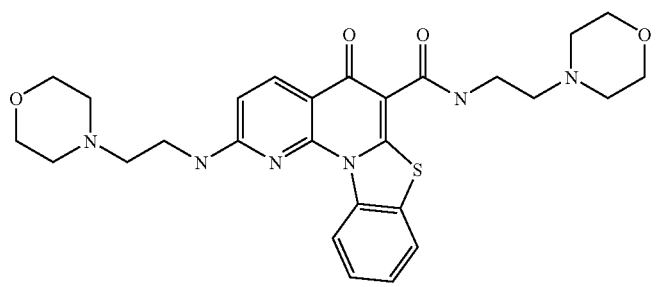 |
| 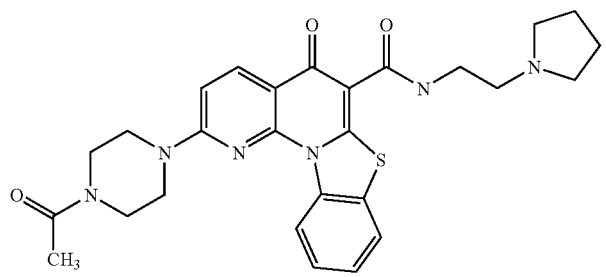 |
| 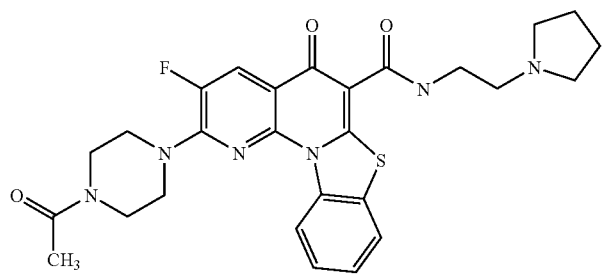 |
| 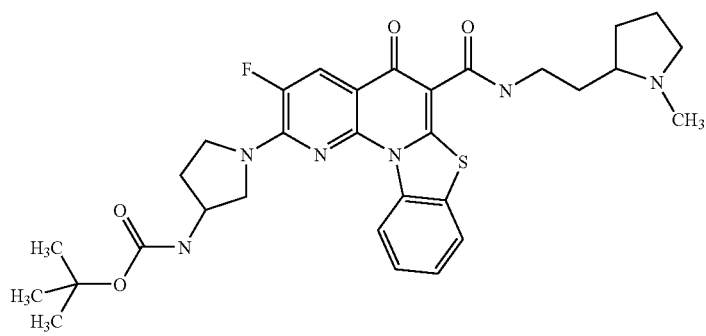 |

TABLE 1C

| MOL STRUCTURE | | M CELL | M DATA |
|---|---|---|---|
| (structure) | (structure) | | |
| (structure) | (structure) | | |
| (structure) | | HCT-116 | 0.03 |
| (structure) | | Miapaca | 0.02 |
| (structure) | | HCT-116 | 0.02 |

TABLE 1C-continued

| MOL STRUCTURE | M CELL | M DATA |
|---|---|---|
| | Miapaca | <0.01 |
| | HCT-116 | 0.16 |
| | Miapaca | 0.17 |
| | HCT-116 | <0.01 |
| | Miapaca | <0.01 |

TABLE 1C-continued
| MOL STRUCTURE | M CELL | M DATA |
|---|---|---|
| 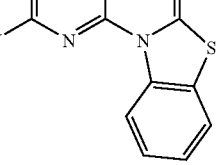 | HCT-116 | <0.01 |
| 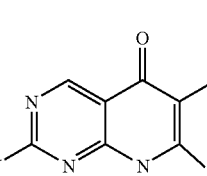 | Miapaca | <0.01 |
| 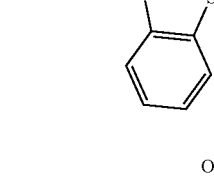 | HCT-116 | 0.03 |
| 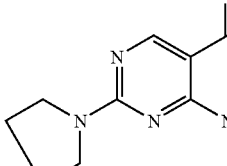 | Miapaca | 0.02 |
|  | HCT-116 | 0.25 |

TABLE 1C-continued

| MOL STRUCTURE | M CELL | M DATA |
|---|---|---|
| | MiaPaca | 0.1 |
| | HCT-116 | 0.06 |
| | Miapaca | 0.03 |
| | HCT-116 | 0.03 |
| | Miapaca | 0.02 |

TABLE 1C-continued
| MOL STRUCTURE | M CELL | M DATA |
|---|---|---|
| 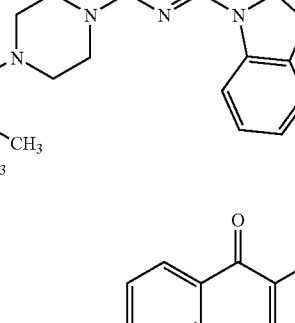 | HCT-116 | 0.32 |
| | Miapaca | 0.24 |
| 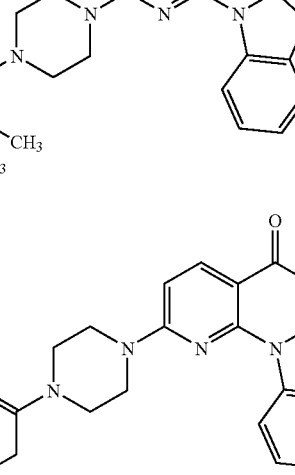 | HCT-116 | 0.18 |
| 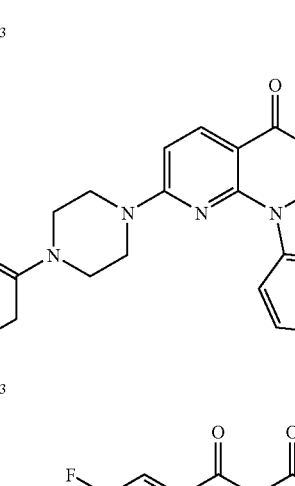 | HCT-116 | 0.06 |
| 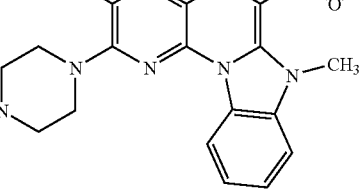 | HCT-116 | 0.28 |

TABLE 1C-continued
| MOL STRUCTURE | M CELL | M DATA |
|---|---|---|
| 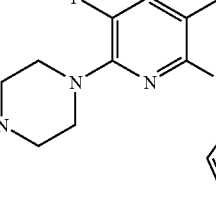 | Miapaca | 0.27 |
| 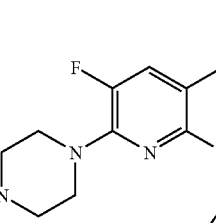 | Miapaca | 0.38 |
| 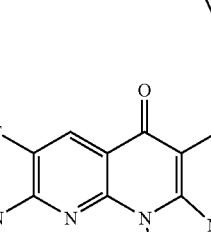 | HCT-116 | >10 |
| 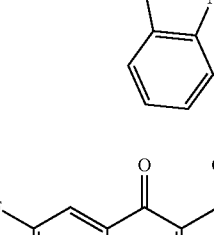 | Miapaca | >10 |
| 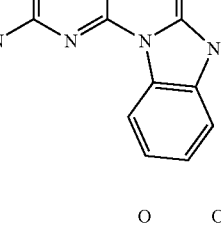 | HCT-116 | 3.00 |

TABLE 1C-continued
| MOL STRUCTURE | M CELL | M DATA |
|---|---|---|
| 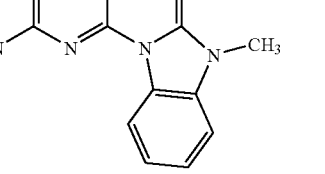 | Miapaca | 2.45 |
| 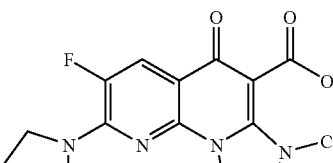 | HCT-116 | >10 |
| 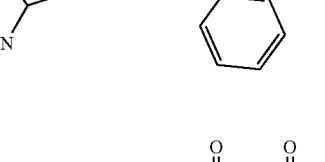 | Miapaca | >10 |
| 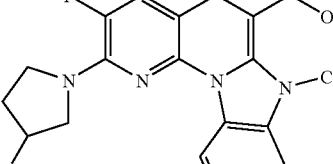 | HCT-116 | 0.11 |
| 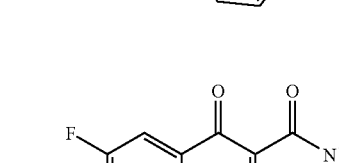 | HCT-116 | 0.1 |

TABLE 1C-continued

| MOL STRUCTURE | M CELL | M DATA |
| --- | --- | --- |
| | MiaPaca | 0.03 |
| | HCT-116 | 0.1 |
| | HCT-116 | 4.20 |
| | Miapaca | 3.00 |
| | HCT-116 | 0.17 |

TABLE 1C-continued

| MOL STRUCTURE | M CELL | M DATA |
|---|---|---|
| | Miapaca | 0.13 |
| | HCT-116 | 0.28 |
| | Miapaca | 0.3 |
| | HCT-116 | 0.28 |
| | Miapaca | 0.18 |

TABLE 1C-continued

| MOL STRUCTURE | M CELL | M DATA |
| --- | --- | --- |
| | HCT-116 | 1.8 |
| | Miapaca | 1.55 |
| | HCT-116 | 0.31 |
| | Miapaca | 0.16 |
| | HCT-116 | 0.27 |

TABLE 1C-continued
| MOL STRUCTURE | M CELL | M DATA |
|---|---|---|
| 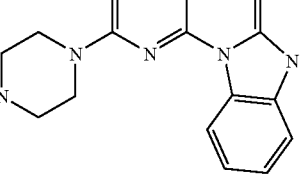 | Miapaca | 0.15 |
| 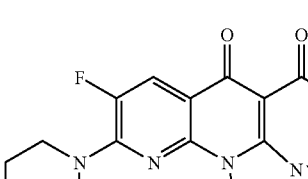 | HCT-116 | 0.04 |
| 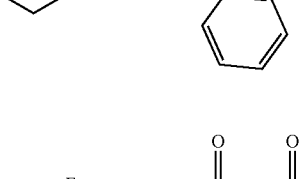 | Miapaca | 0.12 |
| 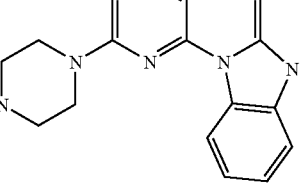 | HCT-116 | 0.09 |
| 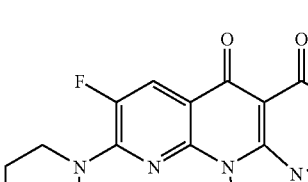 | Miapaca | 0.2 |

TABLE 1C-continued
| MOL STRUCTURE | M CELL | M DATA |
| --- | --- | --- |
| 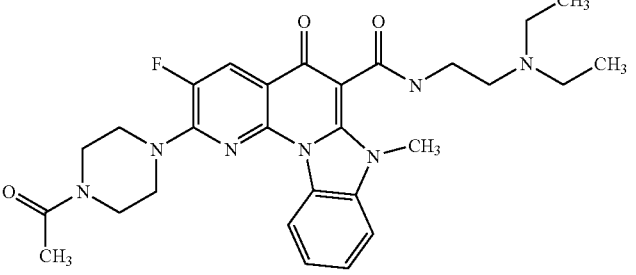 | HCT-116 | 0.1 |
| 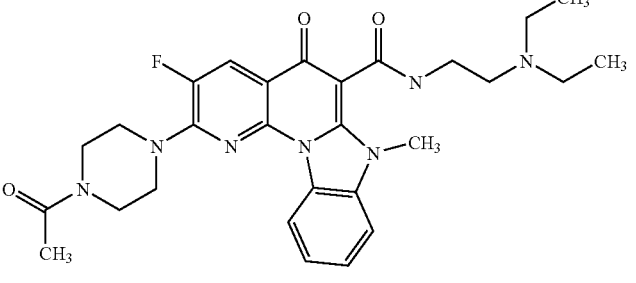 | Miapaca | 0.34 |
| 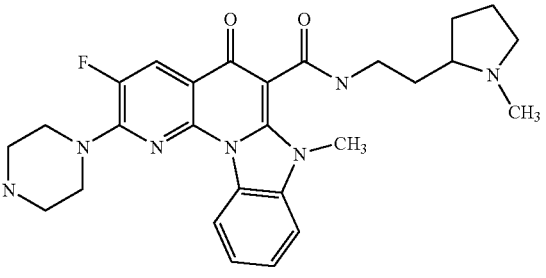 | HCT-116 | 0.03 |
| 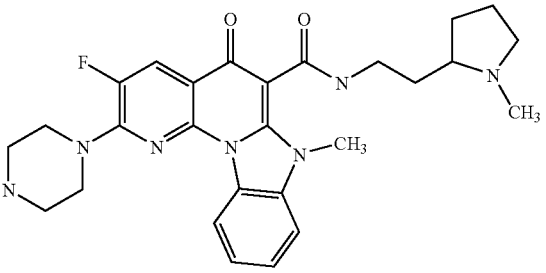 | Miapaca | 0.08 |
| 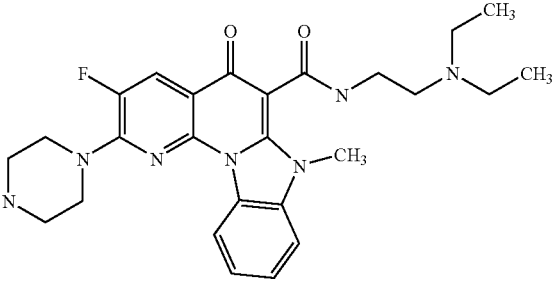 | HCT-116 | 0.03 |

TABLE 1C-continued

| MOL STRUCTURE | M CELL | M DATA |
|---|---|---|
| | Miapaca | 0.03 |
| | HCT-116 | 1.75 |
| | Miapaca | 1 |
| | HCT-116 | 0.03 |
| | Miapaca | 0.02 |

TABLE 1C-continued
| MOL STRUCTURE | M CELL | M DATA |
|---|---|---|
| 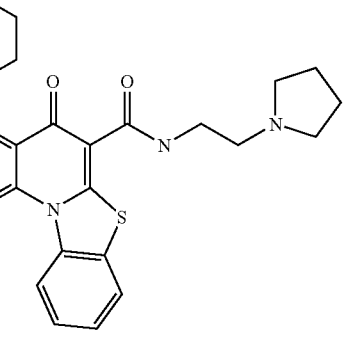 | HCT-116 | 0.26 |
| 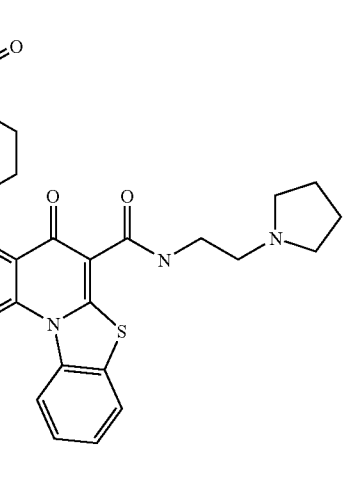 | Miapaca | 0.23 |
| 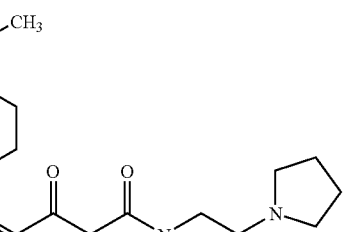 | HCT-116 | 3.3 |

TABLE 1C-continued
| MOL STRUCTURE | M CELL | M DATA |
|---|---|---|
| 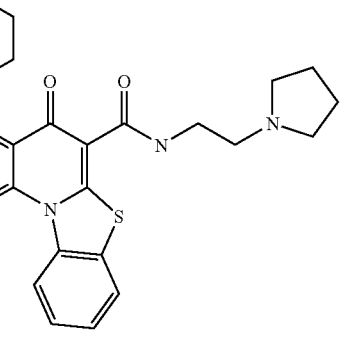 | MiaPaca | 0.3 |
| 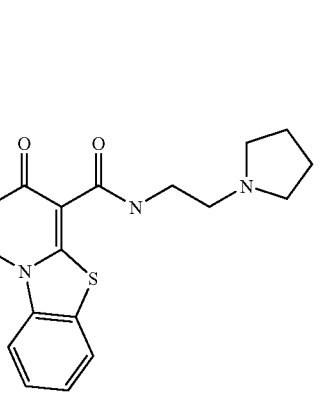 | HCT-116 | 3.7 |
| 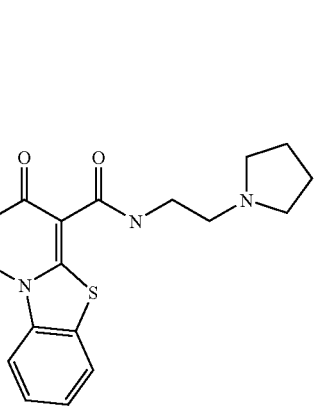 | MiaPaca | 0.2 |

TABLE 1C-continued
| MOL STRUCTURE | M CELL | M DATA |
|---|---|---|
| 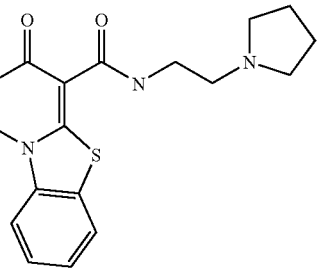 | HCT-116 | 4.1 |
| 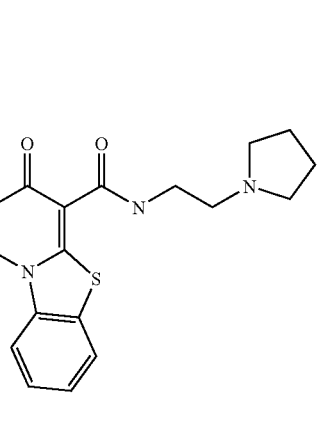 | MiaPaca | 0.3 |
| 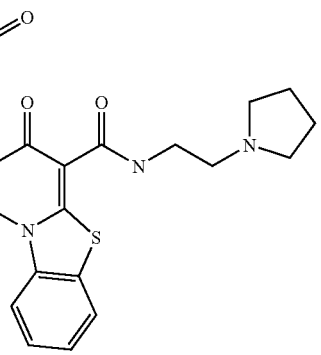 | HCT-116 | 3.4 |
| 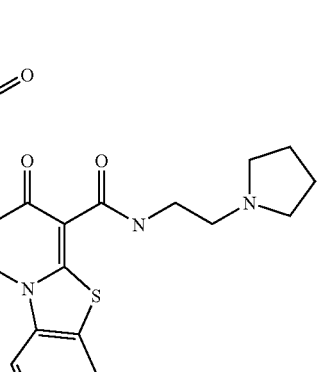 | MiaPaca | 0.4 |

TABLE 1C-continued

| MOL STRUCTURE | M CELL | M DATA |
|---|---|---|
| | HCT-116 | 3.5 |
| | MiaPaca | 2.3 |
| | HCT-116 | 3.4 |
| | MiaPaca | 0.7 |

TABLE 1C-continued
| MOL STRUCTURE | M CELL | M DATA |
|---|---|---|
| 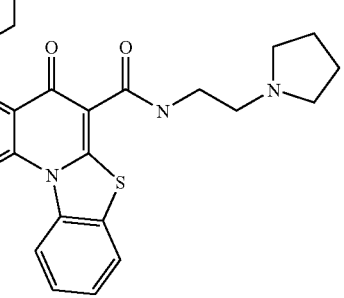 | HCT-116 | 3.7 |
| 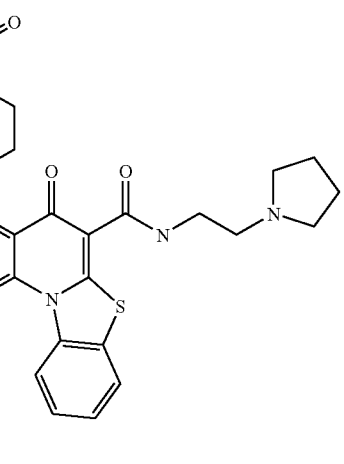 | MiaPaca | 0.2 |
| 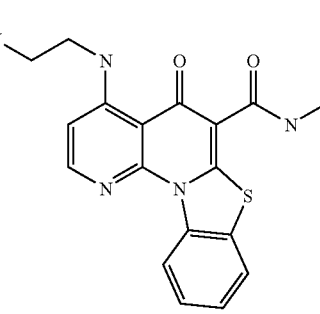 | HCT-116 | 0.3 |
| 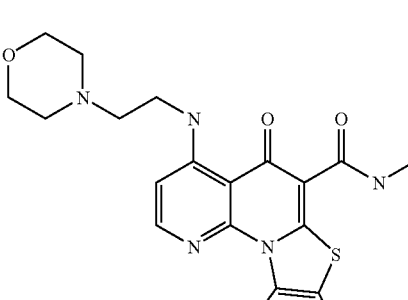 | MiaPaca | 0.2 |

TABLE 1C-continued

| MOL STRUCTURE | M CELL | M DATA |
| --- | --- | --- |
| | HCT-116 | 0.3 |
| | MiaPaca | 0.1 |
| | HCT-116 | 0.2 |
| | MiaPaca | 0.0 |
| | HCT-116 | 3.5 |

TABLE 1C-continued

| MOL STRUCTURE | M CELL | M DATA |
|---|---|---|
| | MiaPaca | 3.2 |
| | HCT-116 | 0.3 |
| | MiaPaca | 0.2 |
| | HCT-116 | 0.04 |
| | MiaPaca | 0.02 |

TABLE 1C-continued
| MOL STRUCTURE | M CELL | M DATA |
|---|---|---|
| 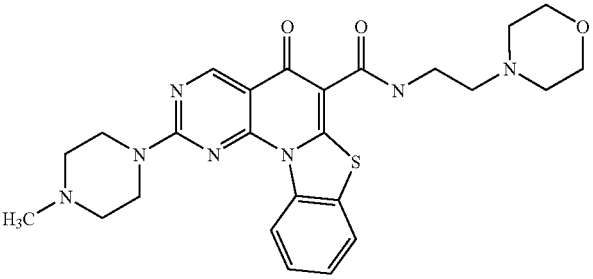 | HCT-116 | 0.04 |
| 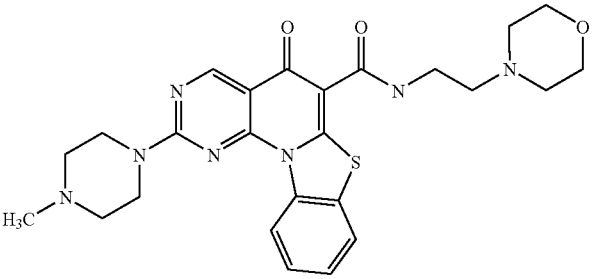 | MiaPaca | 0.02 |
| 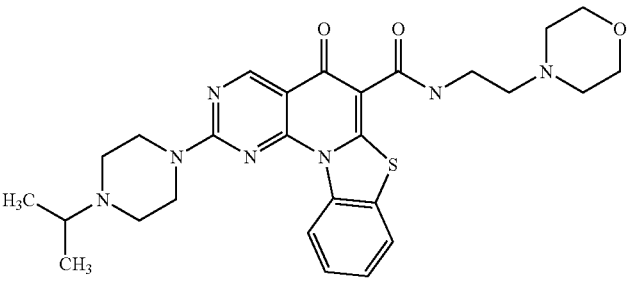 | HCT-116 | 0.04 |
| 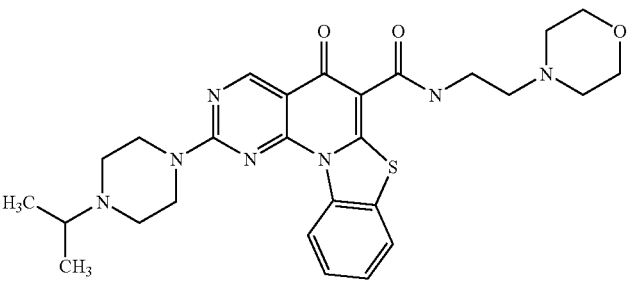 | MiaPaca | 0.03 |
| 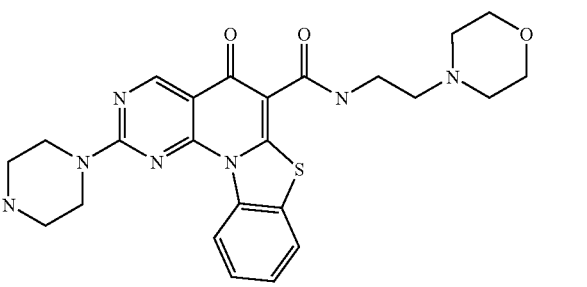 | MiaPaca | <0.01 |

TABLE 1C-continued

| MOL STRUCTURE | M CELL | M DATA |
|---|---|---|
| | HCT-116 | <0.01 |
| | HCT-116 | 3.4 |
| | MiaPaca | 2.3 |
| | HCT-116 | 0.7 |
| | MiaPaca | 0.5 |

TABLE 1C-continued
| MOL STRUCTURE | M CELL | M DATA |
|---|---|---|
| 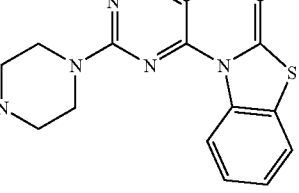 | HCT-116 | 0.2 |
| 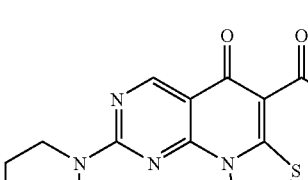 | MiaPaca | 0.2 |
| 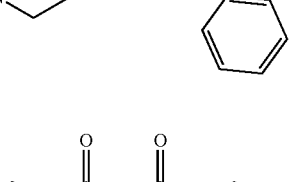 | HCT-116 | 0.2 |
| 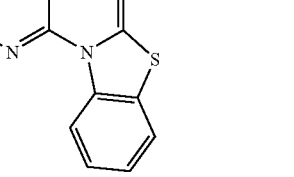 | MiaPaca | 0.03 |
| 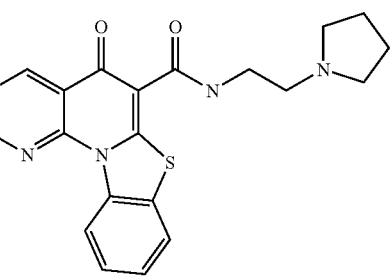 | HCT-116 | 0.3 |

TABLE 1C-continued

| MOL STRUCTURE | M CELL | M DATA |
|---|---|---|
| | MiaPaca | 0.02 |
| | HCT-116 | 0.2 |
| | MiaPaca | 0.2 |
| | HCT-116 | 2.8 |
| | MiaPaca | 2.1 |

TABLE 1C-continued

| MOL STRUCTURE | M CELL | M DATA |
|---|---|---|
| | HCT-116 | 0.04 |
| | MiaPaca | 0.02 |
| | HCT-116 | 0.2 |
| | MiaPaca | 0.05 |
| | HCT-116 | 0.04 |

TABLE 1C-continued

| MOL STRUCTURE | M CELL | M DATA |
| --- | --- | --- |
| | MiaPaca | 0.01 |
| | HCT-116 | 0.04 |
| | MiaPaca | 0.02 |
| | HCT-116 | >10 |
| | MiaPaca | 3.9 |

TABLE 1C-continued

| MOL STRUCTURE | M CELL | M DATA |
|---|---|---|
| | HCT-116 | 1.2 |
| | MiaPaca | 2.3 |
| | HCT-116 | >10 |
| | MiaPaca | 2.5 |
| | HCT-116 | 2.8 |

TABLE 1C-continued

| MOL STRUCTURE | M CELL | M DATA |
|---|---|---|
| | MiaPaca | 1.8 |
| | HCT-116 | 4.2 |
| | MiaPaca | 1.4 |
| | HCT-116 | 3.5 |
| | HCT-116 | 3.4 |

TABLE 1C-continued

| MOL STRUCTURE | M CELL | M DATA |
|---|---|---|
| | MiaPaca | 4 |
| | HCT-116 | >10 |
| | MiaPaca | 10 |
| | MiaPaca | <0.01 |

TABLE 1C-continued

| MOL STRUCTURE | M CELL | M DATA |
|---|---|---|
| | HCT-116 | 0.024 |
| | HCT-116 | 0.03 |
| | MiaPaca | 0.03 |
| | MiaPaca | 0.03 |
| | HCT-116 | 0.02 |

TABLE 1C-continued

| MOL STRUCTURE | M CELL | M DATA |
|---|---|---|
| | Miapaca | 0.05 |
| | HCT-116 | 0.21 |
| | MiaPaca | 0.3 |
| | HCT-116 | 2.40 |

TABLE 1C-continued
| MOL STRUCTURE | M CELL | M DATA |
|---|---|---|
| 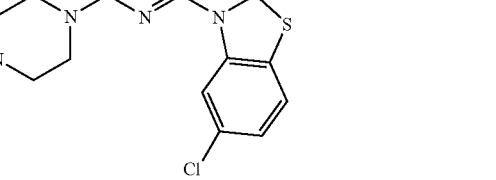 | MiaPaca | 0.02 |
|  | HCT-116 | 0.02 |
| 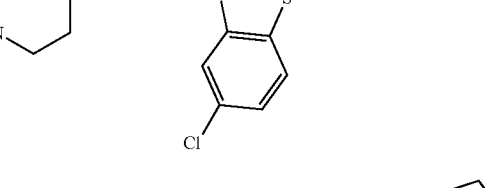 | MiaPaca | 0.03 |
| 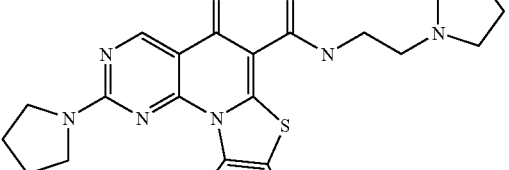 | HCT-116 | 0.11 |
| 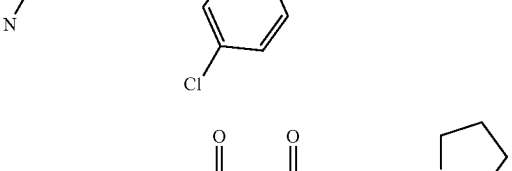 | MiaPaca | 0.12 |

TABLE 1C-continued

| MOL STRUCTURE | M CELL | M DATA |
|---|---|---|
| | HCT-116 | 0.16 |
| | MiaPaca | 0.3 |
| | HCT-116 | 0.28 |
| | HCT-116 | 0.22 |
| | MiaPaca | 0.39 |

TABLE 1C-continued

| MOL STRUCTURE | M CELL | M DATA |
|---|---|---|
| | MiaPaca | >10 |
| | HCT-116 | 10 |
| | HCT-116 | 10 |

TABLE 1C-continued
| MOL STRUCTURE | M CELL | M DATA |
|---|---|---|
| 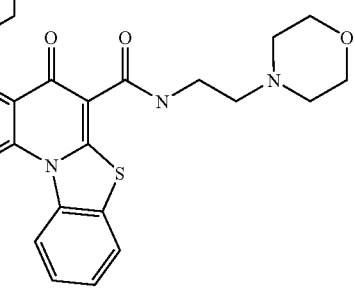 | MiaPaca | 4 |
| 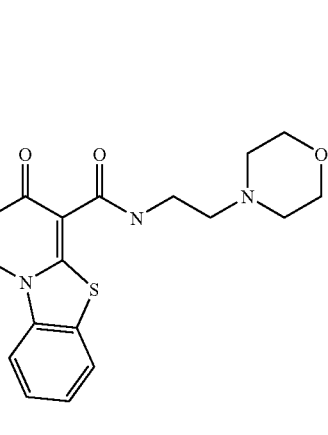 | HCT-116 | 10 |
| 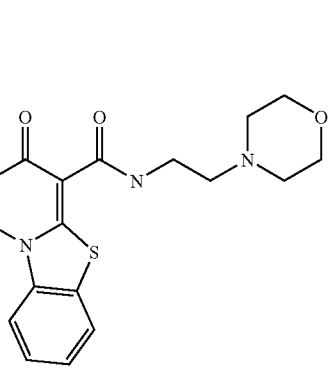 | MiaPaca | 4.2 |
| 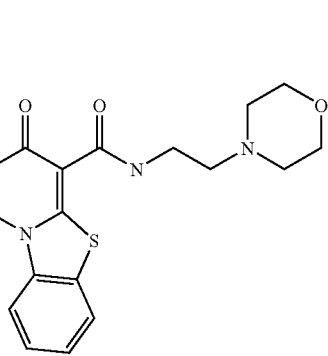 | HCT-116 | 3.0 |

TABLE 1C-continued
| MOL STRUCTURE | M CELL | M DATA |
|---|---|---|
| 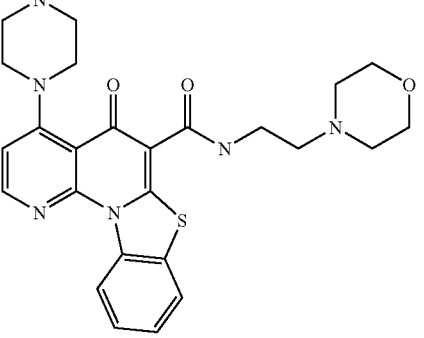 | MiaPaca | 3.9 |
| 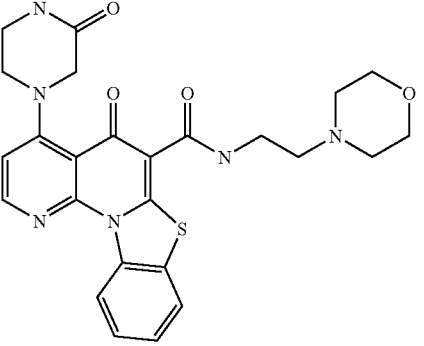 | HCT-116 | 4.5 |
| 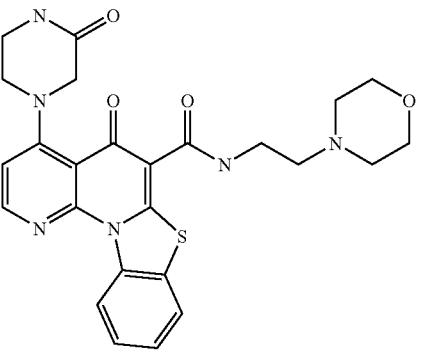 | MiaPaca | 6.6 |
| 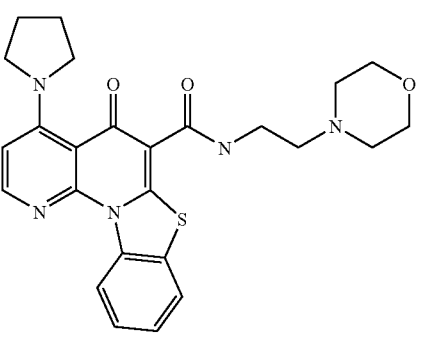 | HCT-116 | 3.5 |

TABLE 1C-continued

| MOL STRUCTURE | M CELL | M DATA |
|---|---|---|
| | MiaPaca | >10 |
| | HCT-116 | 10 |
| | MiaPaca | 4.3 |
| | HCT-116 | >10 |

TABLE 1C-continued

| MOL STRUCTURE | M CELL | M DATA |
| --- | --- | --- |
| | MiaPaca | >10 |
| | HCT-116 | 0.25 |
| | HCT-116 | 10 |
| | HCT-116 | >10 |

TABLE 1C-continued

| MOL STRUCTURE | M CELL | M DATA |
|---|---|---|
| | HCT-116 | 0.28 |
| | | |
| | HCT-116 | 0.03 |
| | HCT-116 | 2.10 |
| | HCT-116 | 0.02 |

TABLE 1C-continued
| MOL STRUCTURE | M CELL | M DATA |
|---|---|---|
| 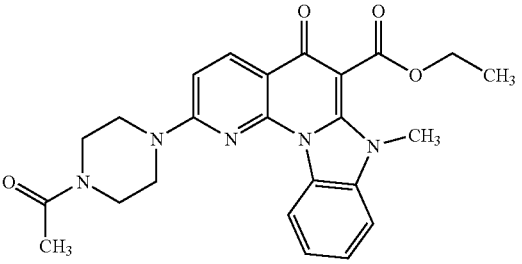 | HCT-116 | 2.30 |
| 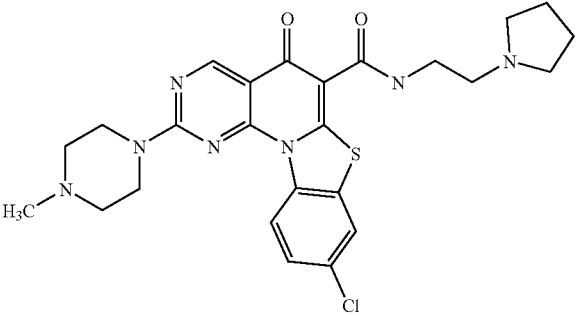 | HCT-116 | <0.01 |
| 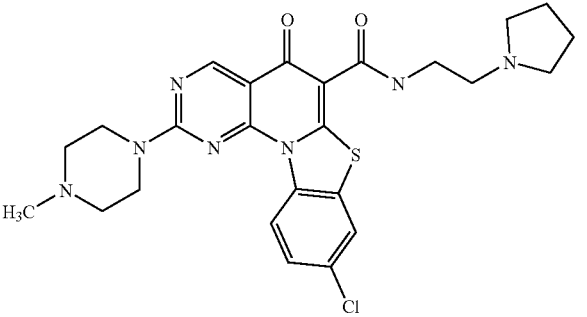 | MiaPaca | <0.01 |
| 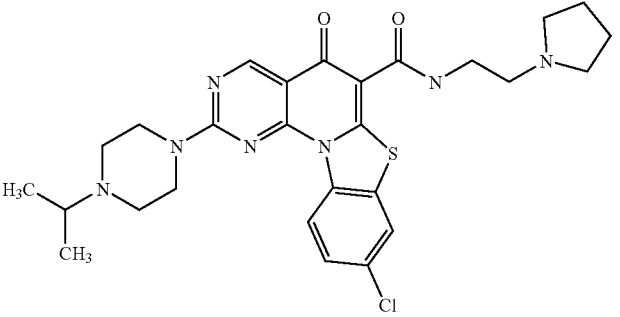 | HCT-116 | <0.01 |
| 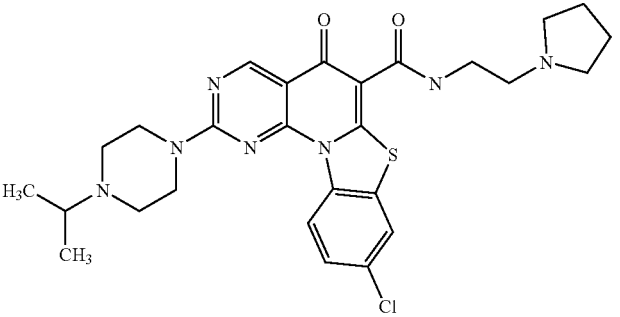 | MiaPaca | <0.01 |

TABLE 1C-continued

| MOL STRUCTURE | M CELL | M DATA |
| --- | --- | --- |
| | HCT-116 | 0.02 |
| | MiaPaca | 0.01 |
| | HCT-116 | 0.115 |
| | MiaPaca | 0.03 |

TABLE 1C-continued

| MOL STRUCTURE | M CELL | M DATA |
|---|---|---|
| | Miapaca | 0.65 |
| | HCT-116 | 1.3 |
| | HCT-116 | <0.01 |
| | MiaPaca | <0.01 |

TABLE 1C-continued

| MOL STRUCTURE | M CELL | M DATA |
|---|---|---|
| | HCT-116 | <0.01 |
| | MiaPaca | <0.01 |
| | HCT-116 | 0.03 |
| | MiaPaca | 0.04 |

TABLE 1C-continued

| MOL STRUCTURE | M CELL | M DATA |
|---|---|---|
| | Miapaca | 0.01 |
| | HCT-116 | 0.16 |
| | MiaPaca | 0.08 |
| | HCT-116 | 0.04 |
| | MiaPaca | 0.02 |

TABLE 1C-continued

| MOL STRUCTURE | M CELL | M DATA |
|---|---|---|
| | HCT-116 | 0.34 |
| | MiaPaca | 0.73 |
| | HCT-116 | 0.01 |
| | MiaPaca | <0.01 |
| | MiaPaca | <0.01 |

TABLE 1C-continued
| MOL STRUCTURE | M CELL | M DATA |
|---|---|---|
| 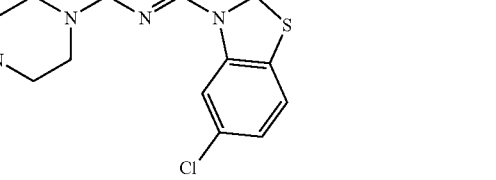 | HCT-116 | 0.03 |
| 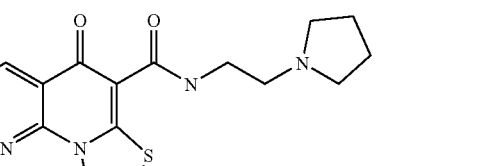 | HCT-116 | 0.34 |
|  | MiaPaca | 0.48 |
| 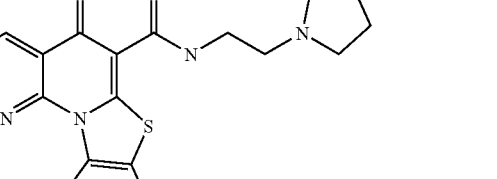 | MiaPaca | 0.04 |
| 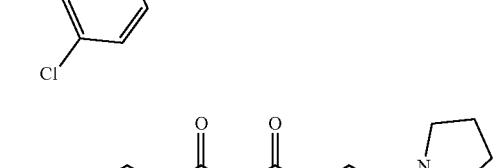 | HCT-116 | 0.10 |

TABLE 1C-continued

| MOL STRUCTURE | M CELL | M DATA |
| --- | --- | --- |
|  | HCT-116 | 0.24 |
|  | Miapaca | 0.17 |
|  | HCT-116 | 0.2 |
|  | MiaPaca | 0.45 |
|  | HCT-116 | 0.33 |

TABLE 1C-continued

| MOL STRUCTURE | M CELL | M DATA |
|---|---|---|
| | MiaPaca | 2.50 |
| | HCT-126 | 0.34 |
| | MiaPaca | 0.02 |
| | HCT-116 | 0.01 |
| | HCT-116 | 0.35 |

TABLE 1C-continued
| MOL STRUCTURE | M CELL | M DATA |
|---|---|---|
| 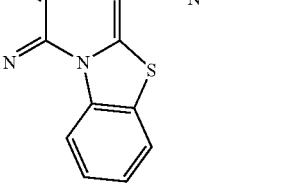 | Miapaca | 0.43 |
| 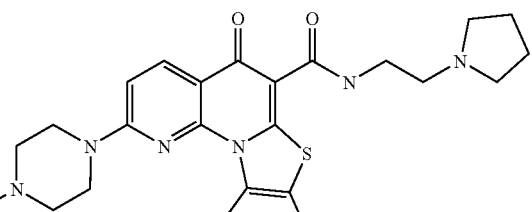 | MiaPaca | <0.01 |
| 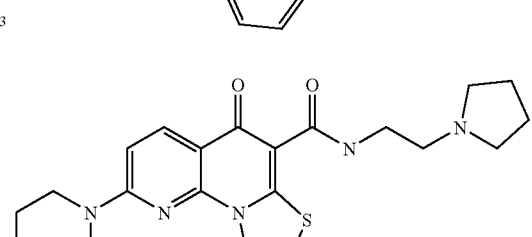 | HCT-116 | <0.01 |
| 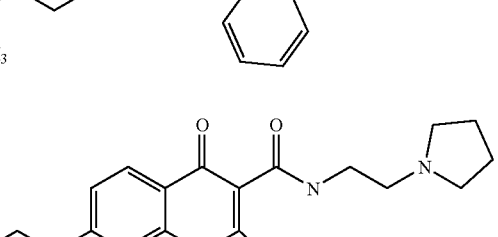 | MiaPaca | <0.01 |
| 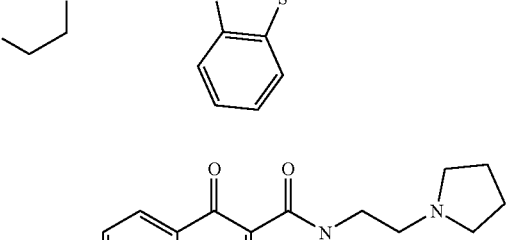 | HCT-116 | <0.01 |

TABLE 1C-continued

| MOL STRUCTURE | M CELL | M DATA |
| --- | --- | --- |
| | MiaPaca | 0.01 |
| | HCT-116 | <0.01 |
| | MiaPaca | 0.17 |
| | HCT-116 | 0.22 |
| | MiaPaca | 0.2 |

TABLE 1C-continued

| MOL STRUCTURE | M CELL | M DATA |
| --- | --- | --- |
|  | HCT-116 | 0.11 |
|  | MiaPaca | 0.03 |
|  | HCT-116 | 0.01 |
|  | MiaPaca | 0.05 |
|  | HCT-116 | 0.02 |

TABLE 1C-continued

| MOL STRUCTURE | M CELL | M DATA |
|---|---|---|
| | MiaPaca | 0.03 |
| | HCT-116 | 0.02 |
| | MiaPaca | 0.04 |
| | HCT-116 | 0.02 |
| | MiaPaca | 0.05 |

TABLE 1C-continued
| MOL STRUCTURE | M CELL | M DATA |
| --- | --- | --- |
| 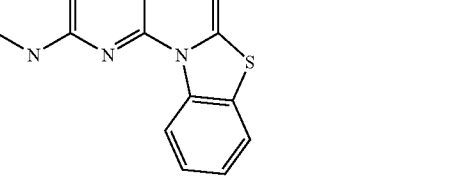 | HCT-116 | 0.03 |
| 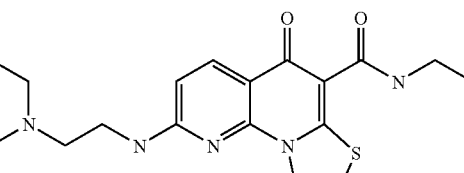 | MiaPaca | <0.01 |
| 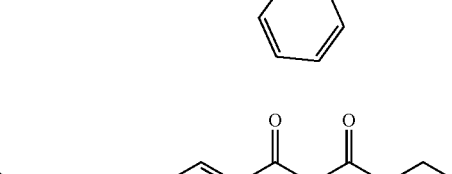 | HCT-116 | 0.02 |
| 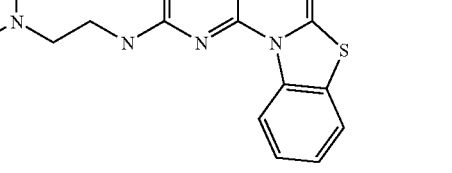 | MiaPaca | 0.07 |
| 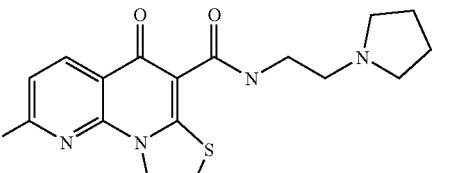 | HCT-116 | 0.03 |

TABLE 1C-continued

| MOL STRUCTURE | M CELL | M DATA |
|---|---|---|
| | MiaPaca | 0.24 |
| | HCT-116 | 0.16 |
| | MiaPaca | 0.03 |
| | HCT-116 | 0.01 |
| | MiaPaca | <0.01 |

TABLE 1C-continued

| MOL STRUCTURE | M CELL | M DATA |
|---|---|---|
| | HCT-116 | <0.01 |
| | MiaPaca | 0.03 |
| | HCT-116 | 0.01 |
| | MiaPaca | 0.04 |
| | HCT-116 | 0.02 |

TABLE 1C-continued
| MOL STRUCTURE | M CELL | M DATA |
|---|---|---|
| 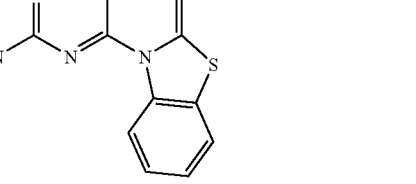 | MiaPaca | 0.05 |
| 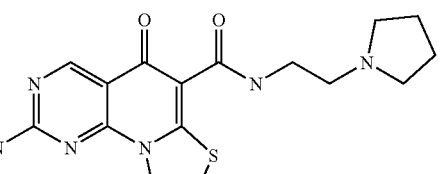 | HCT-116 | 0.03 |
| 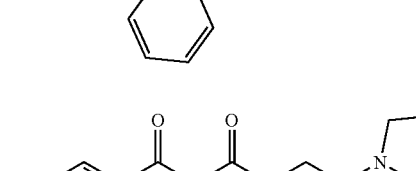 | MiaPaca | 0.04 |
| 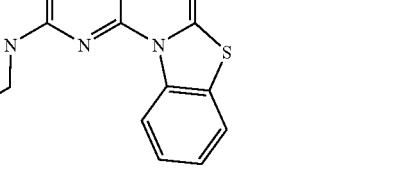 | HCT-116 | 0.04 |
| 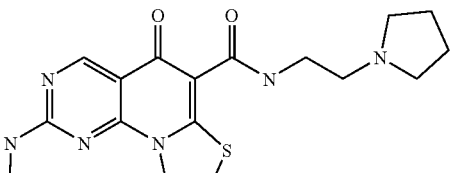 | MiaPaca | 0.11 |

TABLE 1C-continued

| MOL STRUCTURE | M CELL | M DATA |
|---|---|---|
| | HCT-116 | 0.03 |
| | MiaPaca | <0.01 |
| | HCT-116 | <0.01 |
| | MiaPaca | >10 |
| | HCT-116 | 6.00 |

TABLE 1C-continued
| MOL STRUCTURE | M CELL | M DATA |
|---|---|---|
| 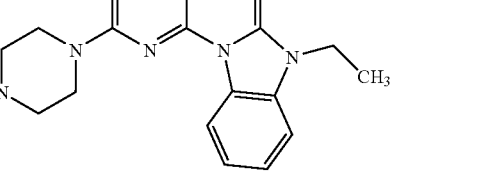 | MiaPaca | 0.27 |
| 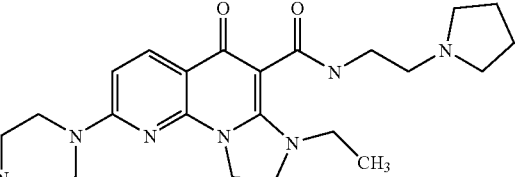 | HCT-116 | 0.26 |
| 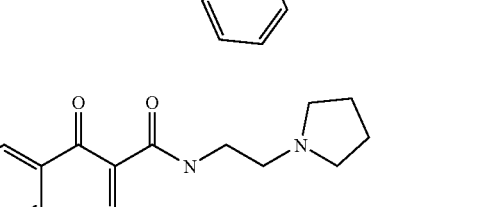 | MiaPaca | 0.3 |
|  | HCT-116 | 0.32 |

TABLE 1C-continued

| MOL STRUCTURE | M CELL | M DATA |
|---|---|---|
| | MiaPaca | 0.27 |
| | HCT-116 | 0.26 |
| | HCT-116 | 0.07 |

TABLE 1C-continued
| MOL STRUCTURE | M CELL | M DATA |
|---|---|---|
| 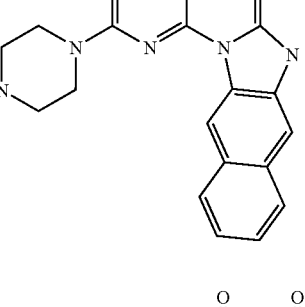 | Miapaca | 0.04 |
| 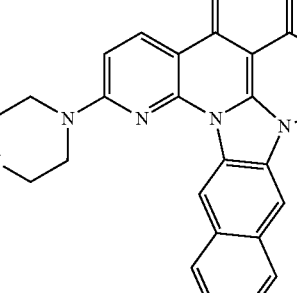 | MiaPaca | 0.08 |
| 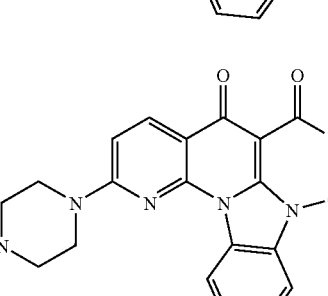 | HCT-116 | 0.04 |
| 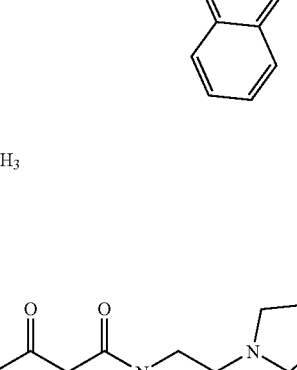 | Miapaca | 0.37 |

TABLE 1C-continued
| MOL STRUCTURE | M CELL | M DATA |
|---|---|---|
| 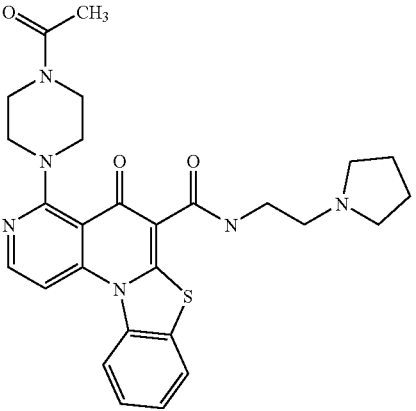 | HCT-116 | 0.27 |
| 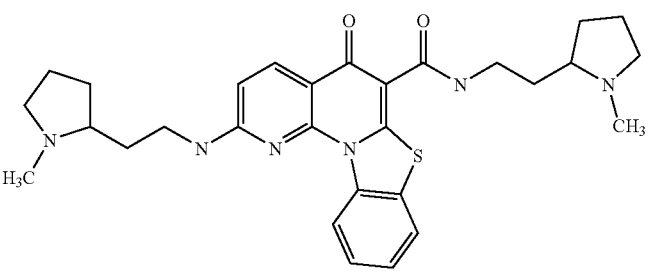 | Miapaca | 0.02 |
| 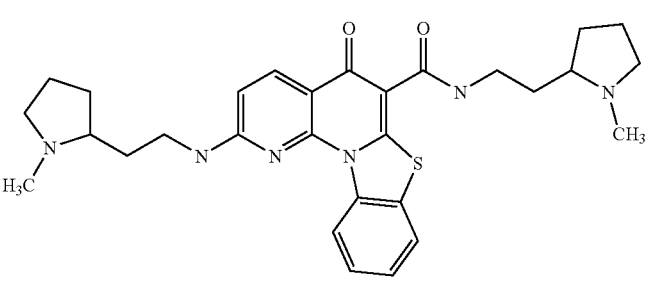 | HCT-116 | 0.03 |
| 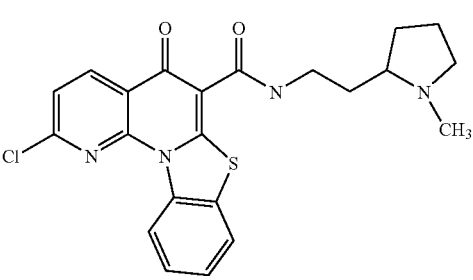 | Miapaca | 0.52 |
| 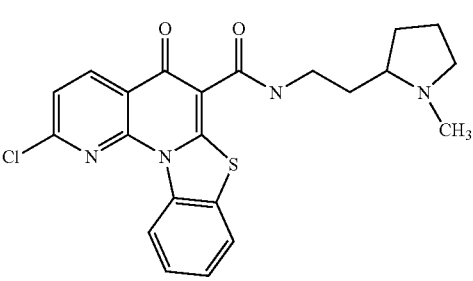 | HCT-116 | 0.18 |

TABLE 1C-continued
| MOL STRUCTURE | M CELL | M DATA |
|---|---|---|
| 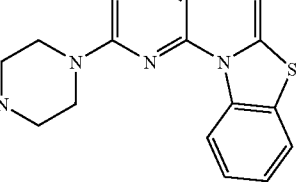 | Miapaca | 0.04 |
| 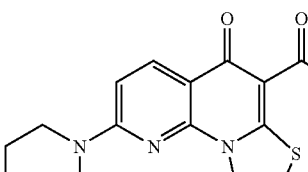 | HCT-116 | 0.04 |
| 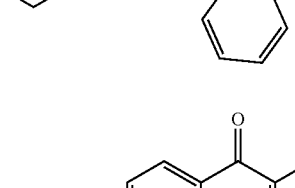 | Miapaca | 0.01 |
| 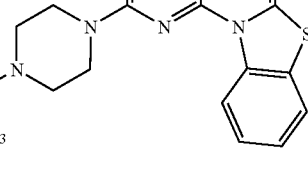 | HCT-116 | <0.01 |
| 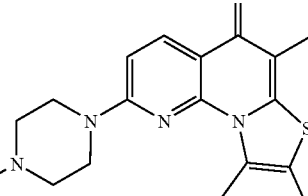 | Miapaca | 0.03 |

TABLE 1C-continued
| MOL STRUCTURE | M CELL | M DATA |
|---|---|---|
| 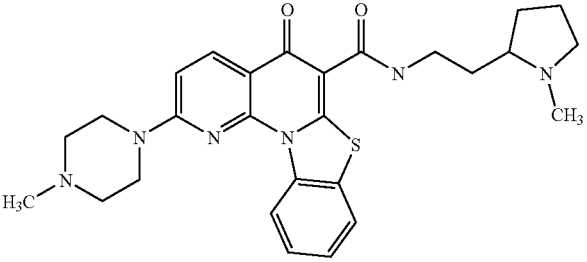 | HCT-116 | 0.03 |
| 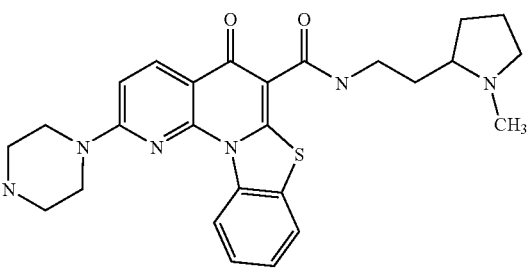 | Miapaca | 0.01 |
| 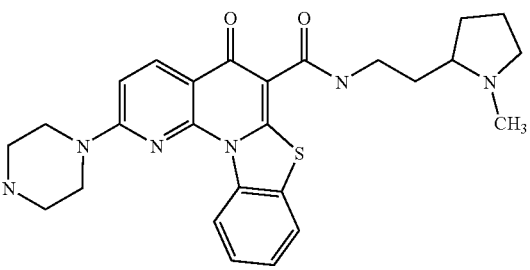 | HCT-116 | <0.01 |
| 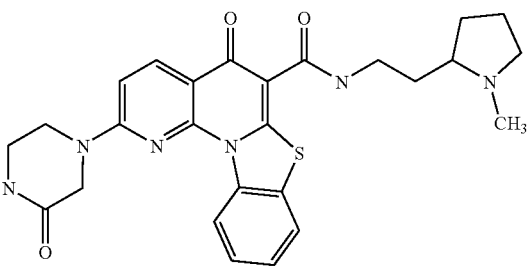 | Miapaca | 0.20 |
| 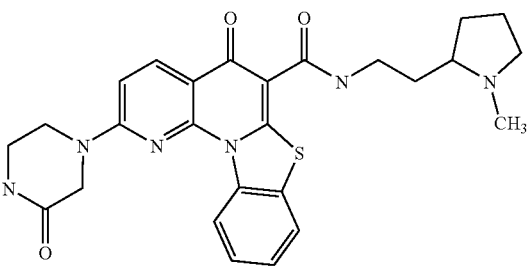 | HCT-116 | 0.14 |

TABLE 1C-continued

| MOL STRUCTURE | M CELL | M DATA |
|---|---|---|
| | Miapaca | 0.70 |
| | HCT-116 | 0.10 |
| | Miapaca | 0.03 |
| | HCT-116 | 0.03 |
| | Miapaca | 0.04 |

TABLE 1C-continued
| MOL STRUCTURE | M CELL | M DATA |
|---|---|---|
| 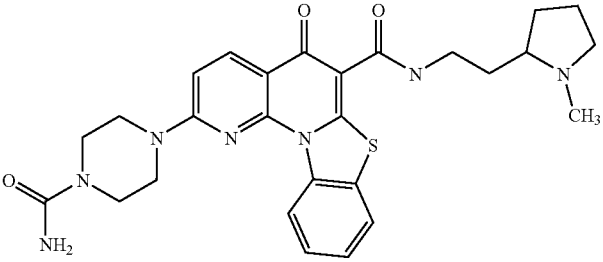 | HCT-116 | 0.04 |
| 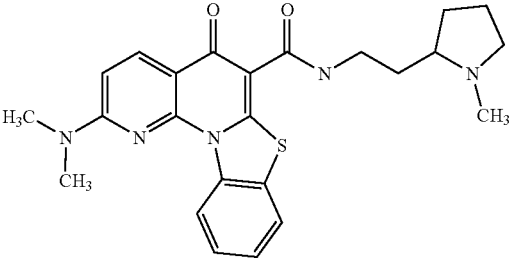 | Miapaca | 0.37 |
| 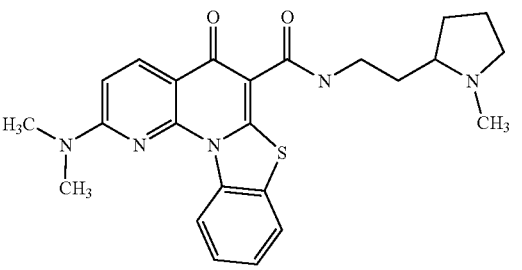 | HCT-116 | 0.98 |
| 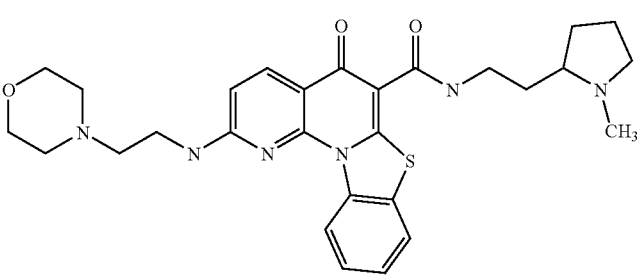 | Miapaca | 0.04 |
| 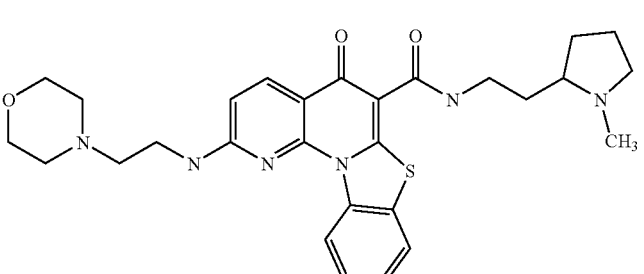 | HCT-116 | 0.05 |

TABLE 1C-continued
| MOL STRUCTURE | M CELL | M DATA |
|---|---|---|
| 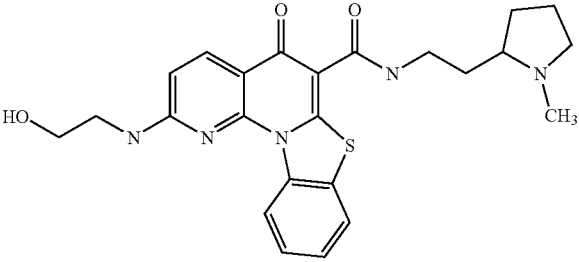 | Miapaca | 0.04 |
| 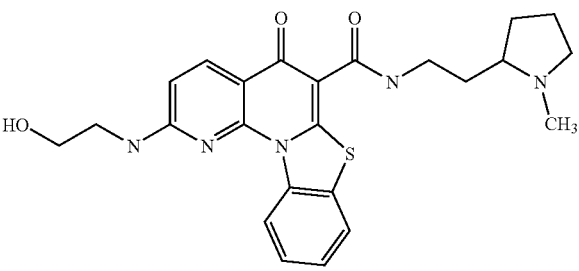 | HCT-116 | 0.08 |
| 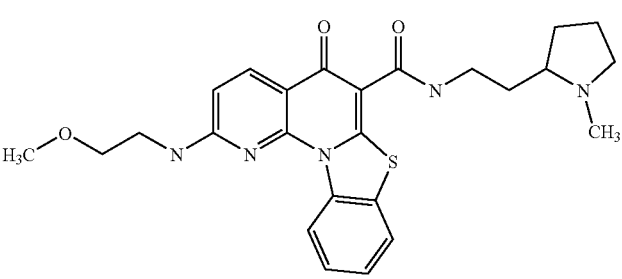 | Miapaca | 0.15 |
| 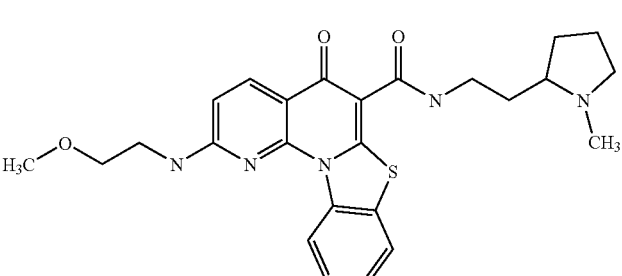 | HCT-116 | 0.11 |
| 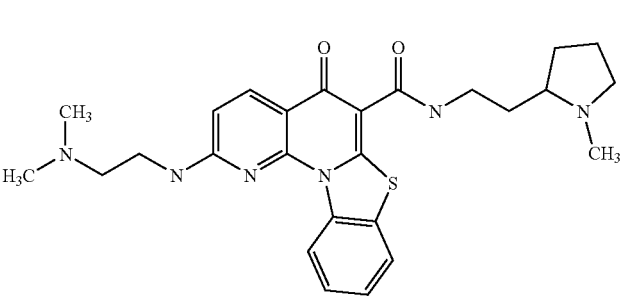 | Miapaca | 0.01 |

TABLE 1C-continued
| MOL STRUCTURE | M CELL | M DATA |
|---|---|---|
| 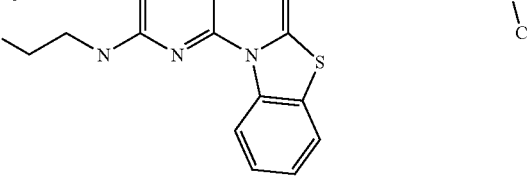 | HCT-116 | 0.01 |
| 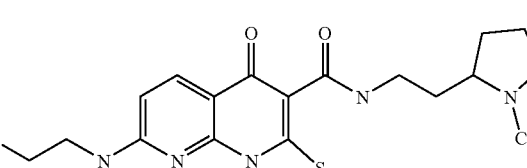 | Miapaca | <0.01 |
| 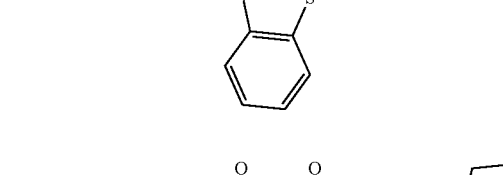 | HCT-116 | <0.01 |
| 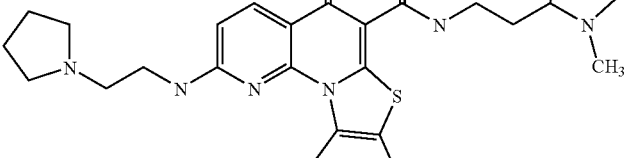 | Miapaca | 0.34 |
| 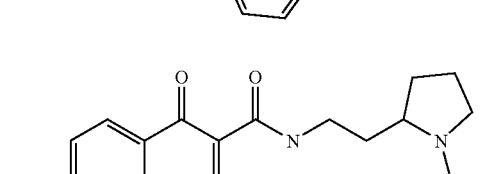 | HCT-116 | 0.19 |

TABLE 1C-continued

| MOL STRUCTURE | M CELL | M DATA |
|---|---|---|
| | Miapaca | 0.05 |
| | HCT-116 | 0.07 |
| | Miapaca | 0.02 |
| | HCT-116 | 0.02 |
| | Miapaca | 0.02 |

TABLE 1C-continued

| MOL STRUCTURE | M CELL | M DATA |
|---|---|---|
| | HCT-116 | 0.02 |
| | Miapaca | <0.01 |
| | HCT-116 | 0.02 |
| | Miapaca | 0.03 |
| | HCT-116 | 0.02 |

TABLE 1C-continued

| MOL STRUCTURE | M CELL | M DATA |
|---|---|---|
| | Miapaca | <0.01 |
| | HCT-116 | <0.01 |
| | Miapaca | 0.73 |
| | HCT-116 | 2.45 |

TABLE 1C-continued

| MOL STRUCTURE | M CELL | M DATA |
|---|---|---|
| | Miapaca | 0.02 |
| | HCT-116 | 0.04 |
| | Miapaca | 0.04 |
| | HCT-116 | 0.02 |

TABLE 1C-continued

| MOL STRUCTURE | M CELL | M DATA |
|---|---|---|
| | Miapaca | 0.16 |
| | HCT-116 | 1.7 |
| | Miapaca | 1.50 |
| | HCT-116 | 0.3 |

TABLE 1C-continued

| MOL STRUCTURE | M CELL | M DATA |
| --- | --- | --- |
| | Miapaca | 2.00 |
| | HCT-116 | 0.38 |
| | Miapaca | 0.43 |
| | HCT-116 | 0.27 |

TABLE 1C-continued

| MOL STRUCTURE | M CELL | M DATA |
| --- | --- | --- |
| | Miapaca | 0.04 |
| | HCT-116 | 0.15 |
| | Miapaca | 0.07 |
| | HCT-116 | 0.16 |

TABLE 1C-continued

| MOL STRUCTURE | M CELL | M DATA |
|---|---|---|
|  | Miapaca | 0.01 |
|  | HCT-116 | 0.01 |
|  | HCT-116 | >10 |
|  | Miapaca | 4.00 |

TABLE 1C-continued

| MOL STRUCTURE | M CELL | M DATA |
|---|---|---|
| | HCT-116 | 0.82 |
| | Miapaca | 0.16 |
| | HCT-116 | >10 |
| | Miapaca | 6.50 |

TABLE 1C-continued
| MOL STRUCTURE | M CELL | M DATA |
|---|---|---|
| 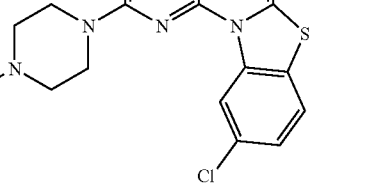 | HCT-116 | 0.07 |
| 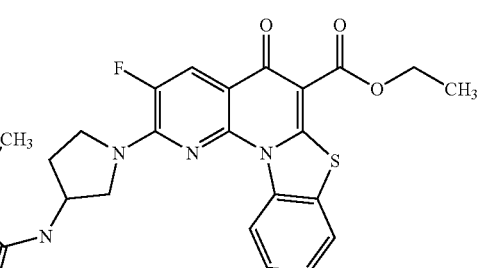 | HCT-116 | >10 |
| 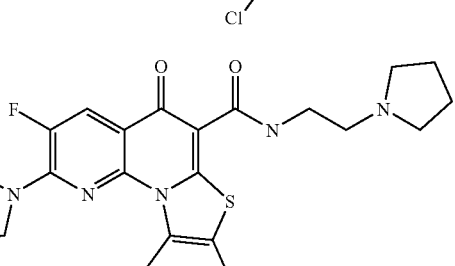 | HCT-116 | 0.02 |
| 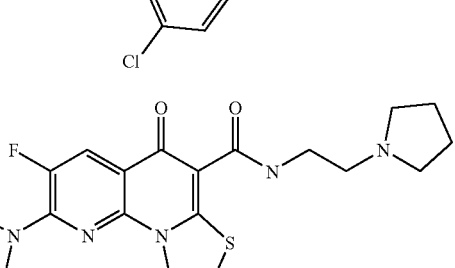 | Miapaca | 0.01 |
| 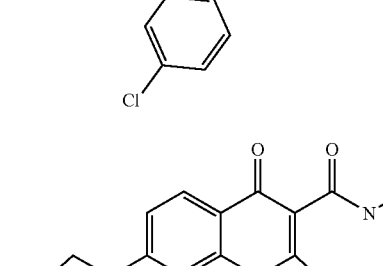 | HCT-116 | 1.2 |

TABLE 1C-continued

| MOL STRUCTURE | M CELL | M DATA |
|---|---|---|
| | HCT-116 | 0.19 |
| | HCT-116 | 0.57 |
| | HCT-116 | 0.15 |
| | HCT-116 | 0.03 |
| | HCT-116 | 0.07 |

TABLE 1C-continued
| MOL STRUCTURE | M CELL | M DATA |
|---|---|---|
| 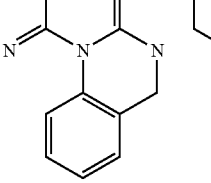 | HCT-116 | >10 |
| 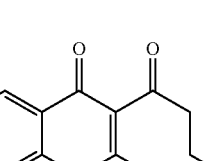 | HCT-119 | >10 |
| 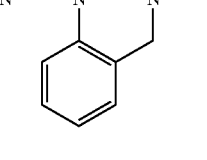 | HCT-116 | >10 |
| 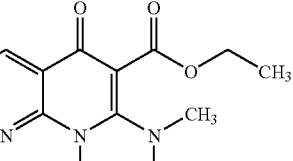 | HCT-116 | >10 |
| 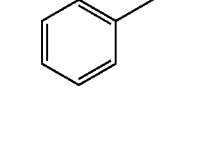 | HCT-116 | >10 |

TABLE 1C-continued
| MOL STRUCTURE | M CELL | M DATA |
|---|---|---|
| 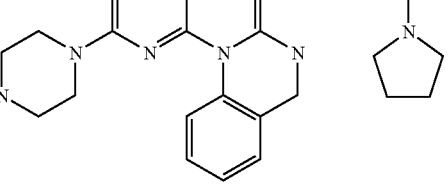 | HCT-116 | >10 |
| 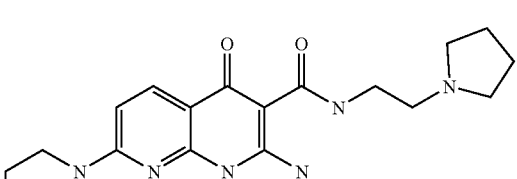 | HCT-116 | >10 |
| 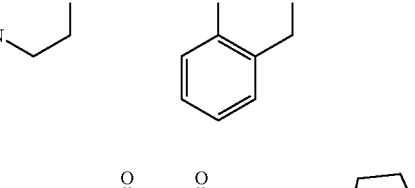 | HCT-116 | 0.04 |
| 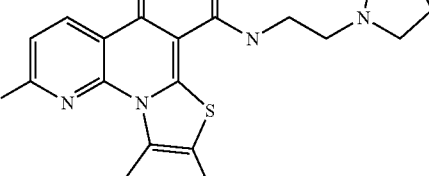 | HCT-116 | 0.31 |
| 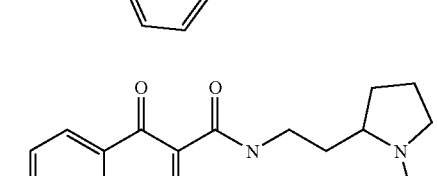 | HCT-116 | 3.6 |

TABLE 1C-continued

| MOL STRUCTURE | M CELL | M DATA |
| --- | --- | --- |
| | HCT-116 | 2.9 |
| | HCT-116 | 0.45 |
| | HCT-116 | 0.42 |
| | HCT-116 | 0.16 |
| | HCT-116 | 0.23 |

TABLE 1C-continued

| MOL STRUCTURE | M CELL | M DATA |
|---|---|---|
| | HCT-117 | 0.2 |
| | HCT-118 | 0.75 |
| | HCT-119 | 0.17 |
| | HCT-121 | >10 |
| | HCT-122 | 0.07 |

TABLE 1C-continued

| MOL STRUCTURE | M CELL | M DATA |
|---|---|---|
| | HCT-123 | 0.03 |
| | HCT-124 | 0.03 |
| | HCT-117 | >10 |
| | HCT-118 | 3.5 |
| | | |

TABLE 1C-continued

| MOL STRUCTURE | M CELL | M DATA |
|---|---|---|

TABLE 1C-continued

| MOL STRUCTURE | M CELL | M DATA |
| --- | --- | --- |

The compounds described herein may interact with regions of nucleic acids that can form quadruplexes. Because regions of DNA that can form quadruplexes are regulators of biological processes such as oncogene transcription, modulators of quadruplex biological activity can be utilized as cancer therapeutics. Molecules that interact with regions of DNA that can form quadruplexes can exert a therapeutic effect on certain cell proliferative disorders and related conditions. Particularly, abnormally increased oncogene expression can cause cell proliferative disorders, and quadruplex structures typically down-regulate oncogene expression. Examples of oncogenes include but are not limited to MYC, HIF, VEGF, ABL, TGF, PDGFA, MYB, SPARC, HUMTEL, HER, VAV, RET, H-RAS, EGF, SRC, BCL1, BCL2, DHFR, HMGA, and other oncogenes known to one of skill in the art. Furthermore, the compounds described herein may induce cell death (e.g., apoptosis) and not interact with regions of DNA that can form quadruplexes.

Molecules that bind to regions of DNA that can form quadruplexes can exert a biological effect according to different mechanisms, which include for example, stabilizing a native quadruplex structure, inhibiting conversion of a native quadruplex to duplex DNA by blocking strand cleavage, and stabilizing a native quadruplex structure having a quadruplex-destabilizing nucleotide substitution and other sequence specific interactions. Thus, compounds that bind to regions of DNA that can form quadruplexes described herein may be administered to cells, tissues, or organisms for the purpose of down-regulating oncogene transcription and thereby treating cell proliferative disorders.

Determining whether the biological activity of native DNA that can form quadruplexes is modulated in a cell, tissue, or organism can be accomplished by monitoring quadruplex biological activity. Quadruplex forming regions of DNA biological activity may be monitored in cells, tissues, or organisms, for example, by detecting a decrease or increase of gene transcription in response to contacting the quadruplex forming DNA with a molecule. Transcription can be detected by directly observing RNA transcripts or observing polypeptides translated by transcripts, which are methods well known in the art.

Molecules that interact with quadruplex forming DNA and quadruplex forming nucleic acids can be utilized to treat many cell proliferative disorders. Cell proliferative disorders include, for example, colorectal cancers and hematopoietic neoplastic disorders (i.e., diseases involving hyperplastic/neoplastic cells of hematopoietic origin such as those arising from myeloid, lymphoid or erythroid lineages, or precursor cells thereof). The diseases can arise from poorly differentiated acute leukemias, e.g., erythroblastic leukemia and acute megakaryoblastic leukemia. Additional myeloid disorders include, but are not limited to, acute promyeloid leukemia (APML), acute myelogenous leukemia (AML) and chronic myelogenous leukemia (CML) (Vaickus, Crit. Rev. in Oncol./Hemotol. 11:267-297 (1991)). Lymphoid malignancies include, but are not limited to acute lymphoblastic leukemia (ALL), which includes B-lineage ALL and T-lineage ALL, chronic lymphocytic leukemia (CLL), prolymphocytic leukemia (PLL), hairy cell leukemia (HLL) and Waldenstrom's macroglobulinemia (WM). Additional forms of malignant lymphomas include, but are not limited to non-Hodgkin lymphoma and variants thereof, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease. Cell proliferative disorders also include cancers of the colorectum, breast, lung, liver, pancreas, lymph node, colon, prostate, brain, head and neck, skin, liver, kidney, and heart. Compounds that interact with regions of DNA that may form quadruplexes also can be utilized to target cancer related processes and conditions, such as increased angiogenesis, by inhibiting angiogenesis in a subject.

The present invention provides a method for reducing cell proliferation or for treating or alleviating cell proliferative disorders, comprising contacting a system having a native DNA capable of forming a quadruplex region with a compound having any one of the above formula. The system may be a group of cells or one or more tissues. In one embodiment, the system is a subject in need of a treatment of a cell proliferative disorder (e.g., a mammal such as a mouse, rat, monkey, or human). The present invention also provides a method for treating colorectal cancer by administering a compound that interacts with a c-MYC quadruplex forming region to a subject in need thereof, thereby reducing the colorectal cancer cell proliferation. Furthermore, the present invention provides a method for inhibiting angiogenesis and optionally treating a cancer associated with angiogenesis, comprising administering a compound that interacts with a vascular endothelial growth factor (VEGF) quadruplex forming region to a subject in need thereof, thereby reducing angiogenesis and optionally treating a cancer associated with angiogenesis.

Compounds that interact with quadruplex forming regions of DNA can also be used to reduce a microbial infection, such as a viral infection. Retroviruses offer a wealth of potential targets for G-quadruplex targeted therapeutics. G-quadruplex structures have been implicated as functional elements in at least two secondary structures formed by either viral RNA or DNA in HIV, the dimer linker structure (DLS) and the central DNA flap (CDF). Additionally, DNA aptamers which are able to adopt either inter- or intramolecular quadruplex structures are able to inhibit viral replication. In one example, DNA aptamers are able to inhibit viral replication by targeting the envelope glycoprotein (putatively). In another example, DNA aptamers inhibit viral replication by targeting the HIV-integrase respectively, suggesting the involvement of native quadruplex structures in interaction with the integrase enzyme.

Dimer linker structures, which are common to all retroviruses, serve to bind two copies of the viral genome together by a non-covalent interaction between the two 5' ends of the two viral RNA sequences. The genomic dimer is stably associated with the gag protein in the mature virus particle. In the case of HIV, the origin of this non-covalent binding may be traced to a 98 base-pair sequence containing several runs of at least two consecutive guanines (e.g., the 3' for the formation of RNA dimers in vitro). An observed cation (potassium) dependence for the formation and stability of the dimer in vitro, in addition to the failure of an antisense sequence to effectively dimerize, has revealed the most likely binding structure to be an intermolecular G-quadruplex.

Prior to integration into the host genome, reverse transcribed viral DNA forms a pre-integration complex (PIC) with at least two major viral proteins, integrase and reverse transcriptase, which is subsequently transported into the nucleus. The Central DNA Flap (CDF) refers to 99-base length single-stranded tail of the + strand, occurring near the center of the viral duplex DNA, which is known to a play a role in the nuclear import of the PIC. Oligonucleotide mimics of the CDF have been shown to form intermolecular G-quadruplex structures in cell-free systems.

Thus, compounds that recognize quadruplex forming regions can be used to stabilize the dimer linker structure and thus prevent de-coupling of the two RNA strands. Also, by binding to the quadruplex structure formed by the CDF, protein recognition and/or binding events for nuclear transport of the PIC may be disrupted. In either case, a substantial advantage can exist over other anti-viral therapeutics. Current Highly Active Anti-Retroviral Therapeutic (HAART) regimes rely on the use of combinations of drugs targeted towards the HIV protease and HIV integrase. The requirement for multi-drug regimes is to minimize the emergence of resistance, which will usually develop rapidly when agents are used in isolation. The source of such rapid resistance is the infidelity of the reverse transcriptase enzyme which makes a mutation approximately once in every 10,000 base pairs. An advantage of targeting viral quadruplex structures over protein targets, is that the development of resistance is slow or is impossible. A point mutation of the target quadruplex can compromise the integrity of the quadruplex structure and lead to a non-functional copy of the virus. A single therapeutic agent based on this concept may replace the multiple drug regimes currently employed, with the concomitant benefits of reduced costs and the elimination of harmful drug/drug interactions.

The present invention provides a method for reducing a microbial titer in a system, comprising contacting a system having a native DNA quadruplex forming region with a compound having any one of the above formula. The system may be one or more cells or tissues. Examples of microbial titers include but are not limited to viral, bacterial or fungal titers. In a particular embodiment, the system is a subject in need of a treatment for a viral infection (e.g., a mammal such as a mouse, rat, monkey, or human). Examples of viral infections include infections by a hepatitis virus (e.g., hepatitis B or C), human immunodeficiency virus (HIV), rhinovirus, herpeszoster virus (VZV), herpes simplex virus (e.g., HSV-1 or HSV-2), cytomegalovirus (CMV), vaccinia virus, influenza virus, encephalitis virus, hantavirus, arbovirus, West Nile virus, human papilloma virus (HPV), Epstein-Barr virus, and respiratory syncytial virus. The present invention also provides a method for treating HIV infection by administering a compound having any one fo the above formula to a subject in need thereof, thereby reducing the HIV infection.

Identifying Compounds That Can Bind to Quadruplex Forming Regions of DNA

Compounds described herein may bind to quadruplex forming regions of DNA where a biological activity of this region, often expressed as a "signal," produced in a system containing the compound is different than the signal produced in a system not containing the compound. While background signals may be assessed each time a new molecule is probed by the assay, detecting the background signal is not required each time a new molecule is assayed.

Examples of quadruplex forming nucleotide sequences are set forth in the following Table 2:

| SEQUENCE | SEQ ID NO | ORIGIN |
| --- | --- | --- |
| $TG_4AG_3TG_4AG_3TG_4AAGG$ | 1 | CMYC |
| GGGGGGGGGGGGGCGGGGGCGGGGGCGGGGGAGGGGC | 2 | PDGFA |
| $G_8ACGCG_3AGCTG_5AG_3CTTG_4CCAG_3CG_4CGCTTAG_5$ | 3 | PDGFB/c-sis |
| AGGAAGGGGAGGGCCGGGGGGAGGTGGC | 4 | CABL |
| AGGGGCGGGGCGGGGCGGGGGC | 5 | RET |
| $AG_4CG_3CGCGGGAGGAAGGGGCGGGAGCGGGGCTG$ | 6 | BCL-2 |
| GGGGGGCGGGGGCGGGCGCAGGGGGAGGGGGC | 7 | Cyclin D1/BCL-1 |
| CGGGGCGGGGCGGGGGCGGGGGC | 8 | H-RAS |

-continued

| SEQUENCE | SEQ ID NO | ORIGIN |
|---|---|---|
| AGAGGAGGAGGAGGTCACGGAGGAGGAGGAGAAGGAGGAGGAGGAA or | 9 | CMYB |
| AGAGGAGGAGGAGGACACGGAGGAGGAGGAGAAGGAGGAGGAGGAA | | |
| (GGA)$_4$ | 10 | VAV |
| AGAGAAGAGGGGAGGAGGAGGAGGAGAGGAGGAGGCGC | 11 | HMGA2 |
| GGAGGGGGAGGGG | 12 | CPIM |
| AGGAGAAGGAGGAGGTGGAGGAGGAGG | 13 | HER2/neu |
| AGGAGGAGGAGAATGCGAGGAGGAGGGAGGAGA | 14 | EGFR |
| GGGGCGGGCCGGGGGCGGGGTCCCGGCGGGGCGGAG | 15 | VEGF |
| CGGGAGGAGGACGAAGCAGGAAGCGCG | 16 | CSRC |

In addition to determining whether a test molecule or test nucleic acid gives rise to a different signal, the affinity of the interaction between the nucleic acid and the compound may be quantified. $IC_{50}$, $K_d$, or $K_i$ threshold values may be compared to the measured $IC_{50}$ or $K_d$ values for each interaction, and thereby identify a test molecule as a quadruplex interacting molecule or a test nucleic acid as a quadruplex forming nucleic acid. For example, $IC_{50}$ or $K_d$ threshold values of 10 μM or less, 1 μM or less, and 100 nM or less are often utilized. In another example, threshold values of 10 nM or less, 1 nM or less, 100 pM or less, and 10 pM or less may be utilized to identify quadruplex interacting molecules and quadruplex forming nucleic acids.

Many assays are available for identifying compounds that have affinity for quadruplex forming regions of DNA. In some of these assays, the biological activity is the quadruplex nucleic acid binding to a compound and binding is measured as a signal. In other assays, the biological activity is a polymerase arresting function of a quadruplex and the degree of arrest is measured as a decrease in a signal. In certain assays, the biological activity is transcription and transcription levels can be quantified as a signal. In another assay, the biological activity is cell death and the number of cells undergoing cell death is quantified. Another assay monitors proliferation rates of cancer cells. Examples of assays are fluorescence binding assays, gel mobility shift assays (see, e.g., Jin & Pike, *Mol. Endocrinol.* (1996) 10:196-205), polymerase arrest assays, transcription reporter assays, cancer cell proliferation assays, and apoptosis assays (see, e.g., Amersham Biosciences (Piscataway, N.J.)), and embodiments of such assays are described hereafter. Also, topoisomerase assays can be utilized to determine whether the quadruplex interacting molecules have a topoisomerase pathway activity (see, e.g., TopoGEN, Inc. (Columbus, Ohio)).

Gel Electrophoretic Mobility Shift Assay (EMSA)

An EMSA is useful for determining whether a nucleic acid forms a quadruplex and whether a nucleotide sequence is quadruplex-destabilizing. EMSA is conducted as described previously (Jin & Pike, *Mol. Endocrinol.* 10: 196-205 (1996)) with minor modifications. Generally, synthetic single-stranded oligonucleotides are labeled in the 5'-terminus with T4-kinase in the presence of [γ-$^{32}$P] ATP (1,000 mCi/mmol, Amersham Life Science) and purified through a sephadex column. $^{32}$P-labeled oligonucleotides (~30,000 cpm) are then incubated with or without various concentrations of a testing compound in 20 μl of a buffer containing 10 mM Tris pH 7.5, 100 mM KCl, 5 mM dithiothreitol, 0.1 mM EDTA, 5 mM $MgCl_2$, 10% glycerol, 0.05% Nonedit P-40, and 0.1 mg/ml of poly(dI-dC) (Pharmacia). After incubation for 20 minutes at room temperature, binding reactions are loaded on a 5% polyacrylamide gel in 0.25× Tris borate-EDTA buffer (0.25× TBE, 1× TBE is 89 mM Tris-borate, pH 8.0, 1 mM EDTA). The gel is dried and each band is quantified using a phosphoimager.

DMS Methylation Protection Assay

Chemical footprinting assays are useful for assessing quadruplex structure. Quadruplex structure is assessed by determining which nucleotides in a nucleic acid are protected or unprotected from chemical modification as a result of being inaccessible or accessible, respectively, to the modifying reagent. A DMS methylation assay is an example of a chemical footprinting assay. In such an assay, bands from EMSA are isolated and subjected to DMS-induced strand cleavage. Each band of interest is excised from an electrophoretic mobility shift gel and soaked in 100 mM KCl solution (300 μl) for 6 hours at 4° C. The solutions are filtered (microcentrifuge) and 30,000 cpm (per reaction) of DNA solution is diluted further with 100 mM KCl in 0.1× TE to a total volume of 70 μl (per reaction). Following the addition of 1 μl salmon sperm DNA (0.1 μg/μl), the reaction mixture is incubated with 1 μl DMS solution (DMS:ethanol; 4:1; v:v) for a period of time. Each reaction is quenched with 18 μl of stop buffer (b-mercaptoethanol:water:NaOAc (3 M); 1:6:7; v:v:v). Following ethanol precipitation (twice) and piperidine cleavage, the reactions are separated on a preparative gel (16%) and visualized on a phosphoimager.

Polymerase Arrest Assay

An arrest assay includes a template nucleic acid, which may comprise a quadruplex forming sequence, and a primer nucleic acid which hybridizes to the template nucleic acid 5' of the quadruplex-forming sequence. The primer is extended by a polymerase (e.g., Taq polymerase), which advances from the primer along the template nucleic acid. In this assay, a quadruplex structure can block or arrest the advance of the enzyme, leading to shorter transcription fragments. Also, the arrest assay may be conducted at a variety of temperatures, including 45° C. and 60° C., and at a variety of ion concentrations.

An example of the Taq polymerase stop assay is described in Han, et al., *Nucl. Acids Res.* (1999) 27:537-542, which is a modification of that used by Weitzmann, et al., *J. Biol. Chem.* (1996) 271:20958-20964. Briefly, a reaction mixture of template DNA (50 nM), Tris-HCl (50 mM), $MgCl_2$ (10 mM), DTT (0.5 mM), EDTA (0.1 mM), BSA (60 ng), and 5'-end-labeled quadruplex nucleic acid (~18 nM) is heated to 90° C. for 5 minutes and allowed to cool to ambient temperature over 30 minutes. Taq Polymerase (1 µl) is added to the reaction mixture, and the reaction is maintained at a constant temperature for 30 minutes. Following the addition of 10 µl stop buffer (formamide (20 ml), 1 M NaOH (200 µl), 0.5 M EDTA (400 µl), and 10 mg bromophenol blue), the reactions are separated on a preparative gel (12%) and visualized on a phosphoimager. Adenine sequencing (indicated by "A" at the top of the gel) is performed using double-stranded DNA Cycle Sequencing System from Life Technologies. The general sequence for the template strands is TCCAACTATG-TATA (SEQ ID NO.19) -INSERT-TTAGCGACACGCAAT-TGCTATAGTGAGTCGTATTA (SEQ ID NO.20), Where "INSERT" refers to a nucleic acid sequence comprising a quadruplex forming sequence (See e.g., Table 2). Bands on the gel that exhibit slower mobility are indicative of quadruplex formation.

High Throughput Polymerase Arrest Assay

A high throughput polymerase arrest assay has been developed. The assay comprises contacting a template nucleic acid, often DNA, with a primer, which also is often DNA; contacting the primer/template complex with a compound described herein (also referred to as a "test compound"); contacting the primer/template complex with a polymerase; and separating reaction products. The assay often includes the step of denaturing the primer/template complex mixture and then renaturing the complex, which often is carried out before a test molecule is added to the system. Multiple assays often are carried out using varying concentrations of a test compound, such that an $IC_{50}$ value can be obtained, for example. The reaction products often include extended primers of different lengths. Where a test compound does not significantly interact with a quadruplex structure in the template, the primer often is extended to the end of the template.

Where a test compound significantly interacts with a quadruplex structure in the template, the primer often is extended only to the quadruplex structure in the template and no further. Thus, the reaction mixture often includes at least two reaction products when a test compound interacts with a quadruplex structure in the template, one having a completely extended primer and one having an incompletely extended primer, and these two reaction products are separated. The products may be separated using any convenient separation method, such as mass spectrometry and in one embodiment, capillary electrophoresis.

The reaction products often are identified by detecting a detectable label linked to the primer. The detectable label may be non-covalently linked to the 5' end of the primer (e.g., a biotin molecule covalently linked to the 5' end of the primer which is non-covalently linked to an avidin molecule joined to a detectable label). The detectable label may be joined to the primer at any stage of the assay, sometimes before the primer is added to the system, after the primer is extended, or after the products are separated. The detectable label often is covalently linked to the primer using a procedure selected based upon the nature of the chemical groups in the detectable label.

Many methods for covalently linking detectable labels to nucleic acids are available, such as chemically coupling an allylamine-derivatized nucleotide to a succinimidyl-ester derivative of a detectable label, and then generating a primer using the labeled nucleotide. (See, e.g., *Nature Biotech* (2000) 18:345-348 and http address info.med.yale.edu/genetics/ward/tavi/n_coupling.html). A spacer (often between 5-16 carbon atoms long) sometimes is incorporated between the detectable label and the nucleotide. Any convenient detectable label may be utilized, including but not limited to a radioactive isotope (e.g., $^{125}I$, $^{131}I$, $^{35}S$, $^{32}P$, $^{14}C$ or $^{3}H$); a light scattering label (e.g., a spherical gold or silver label; Genicon Sciences Corporation, San Diego, Calif. and U.S. Pat. No. 6,214,560); an enzymic or protein label (e.g., GFP or peroxidase); or another chromogenic label or dye sometimes is utilized. Often, a fluorescent label is utilized (e.g., amino-methyl coumarin (AMCA); diethyl aminomethyl coumarin (DEAC); cascade blue (CB); fluorescein isothiocyanate (FITC); Oregon green (OG); Alexa 488 (A488); rhodamine green (RGr); lanthanide chelate (e.g., europium), carboxy-rhodamine 6G (R6G); tetramethyl rhodamine (TAMRA); Texas Red (TxR); Cy3; Cy3.5; Cy5, Cy5.5 and carboxynaph-tofluorescein (CNF), digoxigenin (DIG); and 2,4-dinitrophenyl (DNP)). Other fluorophores and attendant excitation and emission wavelengths are described in Anantha, et al., *Biochemistry* (1998) 37:2709-2714 and Qu & Chaires, *Methods Enzymol* (2000) 321:353-369).

In an embodiment, a primer oligonucleotide covalently linked to a fluorescent label is contacted with template DNA. The resulting complex is contacted with a test molecule and then contacted with a polymerase capable of extending the primer. The reaction products then are separated and detected by capillary electrophoresis. A longer primer sequence was used for practicing this embodiment as compared to embodiments where the primer includes no covalently-linked fluorophore or where capillary electrophoresis is not utilized for separation. Deoxynucleotides are added at any stage of the assay before the separation, often when the primer is contacted with the template DNA. The template DNA/primer complex often is denatured (e.g., by increasing the temperature of the system) and then renatured (e.g., by cooling the system) before a test compound is added).

Quadruplex Binding Assay

Generally, a 5'-fluorescent-labeled (FAM) primer (P45, 15 nM) was mixed with template DNA (15 nM) in a Tris-HCL buffer (15 mM Tris, pH 7.5) containing 10 mM $MgCl_2$, 0.1 mM EDTA and 0.1 mM mixed deoxynucleotide triphosphates (dNTP's). In one example, the FAM-P45 primer (5'-6FAM-AGTCTGACTGACTGTACGTAGCTAATAC-GACTCACTATAG CAATT-3') (SEQ ID NO. 17) and the c-Myc template DNA (5'-TCCAACTATGTATACTGGGG AGGGTGGGGAGGGTGGGGAAGGTTAGC-GACACGCAATTGCTATAGTGAGTCGTATT AGCTACG-TACAGTCAGTCAGACT-3') (SEQ ID NO. 18) were synthesized and HPLC purified by Applied Biosystems. The mixture was denatured at 95° C. for 5 minutes and, after cooling down to room temperature, was incubated at 37° C. for 15 minutes.

After cooling down to room temperature, 1 mM $KCl_2$ and the test compound (various concentrations) were added and the mixture incubated for 15 minutes at room temperature. The primer extension was performed by adding 10 mM KCl and Taq DNA Polymerase (2.5 U/reaction, Promega) and incubating at 70° C. for 30 minutes. The reaction was stopped by adding 1 µl of the reaction mixture to 10 µl Hi-Di Formamide mixed and 0.25 µl LIZ120 size standard. Hi-Di Formamide and LIZ120 size standard were purchased from Applied Biosystems. The partially extended quadruplex arrest product was between 61 or 62 bases long and the full-length extended product was 99 bases long. The products were separated and analyzed using capillary electrophoresis. Capillary electrophoresis was performed using an ABI PRISM 3100-Avant Genetic Analyzer. The assay was performed using compounds described above and results are shown in Table 1. µM concentrations reported in Table 1 are concentrations at which 50% of the DNA was arrested in the assay (ie., the ratio of shorter partially extended DNA (arrested DNA) to full-length extended DNA is 1:1).

Transcription Reporter Assay

In a transcription reporter assay, test quadruplex DNA is coupled to a reporter system, such that a formation or stabilization of a quadruplex structure can modulate a reporter signal. An example of such a system is a reporter expression system in which a polypeptide, such as luciferase or green fluorescent protein (GFP), is expressed by a gene operably linked to the potential quadruplex forming nucleic acid and expression of the polypeptide can be detected. As used herein, the term "operably linked" refers to a nucleotide sequence which is regulated by a sequence comprising the potential quadruplex forming nucleic acid. A sequence may be operably linked when it is on the same nucleic acid as the quadruplex DNA, or on a different nucleic acid. An exemplary luciferase reporter system is described herein.

A luciferase promoter assay described in He, et al., *Science* (1998) 281:1509-1512 often is utilized for the study of quadruplex formation. Specifically, a vector utilized for the assay is set forth in reference 11 of the He, et al., document. In this assay, HeLa cells are transfected using the lipofectamin 2000-based system (Invitrogen) according to the manufacturer's protocol, using 0.1 µg of pRL-TK (Renilla luciferase reporter plasmid) and 0.9 µg of the quadruplex-forming plasmid. Firefly and Renilla luciferase activities are assayed using the Dual Luciferase Reporter Assay System (Promega) in a 96-well plate format according to the manufacturer's protocol.

Circular Dichroism Assay

Circular dichroism (CD) is utilized to determine whether another molecule interacts with a quadruplex nucleic acid. CD is particularly useful for determining whether a PNA or PNA-peptide conjugate hybridizes with a quadruplex nucleic acid in vitro. PNA probes are added to quadruplex DNA (5 µM each) in a buffer containing 10 mM potassium phosphate (pH 7.2) and 10 or 250 mM KCl at 37° C. and then allowed to stand for 5 minutes at the same temperature before recording spectra. CD spectra are recorded on a Jasco J-715 spectropolarimeter equipped with a thermoelectrically controlled single cell holder. CD intensity normally is detected between 220 nm and 320 nm and comparative spectra for quadruplex DNA alone, PNA alone, and quadruplex DNA with PNA are generated to determine the presence or absence of an interaction (see, e.g., Datta, et al., *JACS* (2001) 123:9612-9619). Spectra are arranged to represent the average of eight scans recorded at 100 nm/min.

Fluorescence Binding Assay

An example of a fluorescence binding assay is a system that includes a quadruplex nucleic acid, a signal molecule, and a test molecule. The signal molecule generates a fluorescent signal when bound to the quadruplex nucleic acid (e.g., N-methylmesoporphyrin IX (NMM)), and the signal is altered when a test compound competes with the signal molecule for binding to the quadruplex nucleic acid. An alteration in the signal when test molecule is present as compared to when test compound is not present identifies the test compound as a quadruplex interacting compound.

50 µl of quadruplex nucleic acid or a nucleic acid not capable of forming a quadruplex is added in 96-well plate. A test compound also is added in varying concentrations. A typical assay is carried out in 100 µl of 20 mM HEPES buffer, pH 7.0, 140 mM NaCl, and 100 mM KCl. 50 µl of the signal molecule NMM then is added for a final concentration of 3 µM. NMM is obtained from Frontier Scientific Inc, Logan, Utah. Fluorescence is measured at an excitation wavelength of 420 nm and an emission wavelength of 660 nm using a FluroStar 2000 fluorometer (BMG Labtechnologies, Durham, N.C.). Fluorescence often is plotted as a function of concentration of the test compound or quadruplex-targeted nucleic acid and maximum fluorescent signals for NMM are assessed in the absence of these molecules.

Cell Proliferation Assay

In a cancer cell proliferation assay, cell proliferation rates are assessed as a function of different concentrations of test compounds added to the cell culture medium. Any cancer cell type can be utilized in the assay. In one embodiment, colon cancer cells are cultured in vitro and test compounds are added to the culture medium at varying concentrations. A useful colon cancer cell line is colo320, which is a colon adenocarcinoma cell line deposited with the National Institutes of Health as accession number JCRB0225. Parameters for using such cells are available at the http address cellbank.nihs.gojp/cell/data/jcrb0225.htm.

Formulation of Compounds

As used herein, the term "pharmaceutically acceptable salts, esters and amides" includes but are not limited to carboxylate salts, amino acid addition salts, esters and amides of the compounds, as well as the zwitterionic forms thereof, which are known to those skilled in the art as suitable for use with humans and animals. (See, e.g., Gerge, S. M., et al., "Pharmaceutical Salts," *J. Pharm. Sci*. (1977) 66:1-19, which is incorporated herein by reference.)

Any suitable formulation of the compounds described herein can be prepared. In cases where compounds are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, α-ketoglutarate, and α-glycerophosphate. Suitable inorganic salts may also be formed, including hydrochloride, sulfate, nitrate, bicarbonate, and carbonate salts. Pharmaceutically acceptable salts are obtained using standard procedures well known in the art. For example, pharmaceutically acceptable salts may be obtained by reacting a sufficiently basic compound such as an amine with a suitable acid affording a physiologically acceptable anion. Alkali metal (e.g., sodium, potassium or lithium) or alkaline earth metal (e.g., calcium) salts of carboxylic acids also are made.

A compound may be formulated as a pharmaceutical composition and administered to a mammalian host in need of such treatment. In one embodiment, the mammalian host is human. Any suitable route of administration may be used, including but not limited to oral, parenteral, intravenous, intramuscular, topical and subcutaneous routes.

In one embodiment, a compound is administered systemically (e.g., orally) in combination with a pharmaceutically acceptable vehicle such as an inert diluent or an assimilable edible carrier. They may be enclosed in hard or soft shell gelatin capsules, compressed into tablets, or incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations should contain at least 0.1% of active compound. The percentage of the compositions and preparations may be varied and may conveniently be between about 2 to about 60% of the weight of a given unit dosage form. The amount of active compound in such therapeutically useful compositions is such that an effective dosage level will be obtained.

Tablets, troches, pills, capsules, and the like also may contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Any material used in preparing any unit dosage form is pharmaceutically acceptable and substantially non-toxic in the amounts employed. In addition, the active compound may be incorporated into sustained-release preparations and devices.

The active compound also may be administered intravenously or intraperitoneally by infusion or injection. Solutions of the active compound or its salts may be prepared in a buffered solution, often phosphate buffered saline, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms. The compound is sometimes prepared as a polymatrix-containing formulation for such administration (e.g., a liposome or microsome). Liposomes are described for example in U.S. Pat. No. 5,703,055 (Felgner, et al.) and Gregoriadis, Liposome Technology vols. I to III (2nd ed. 1993).

The pharmaceutical dosage forms suitable for injection or infusion can include sterile aqueous solutions or dispersions or sterile powders comprising the active ingredient that are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the active compound in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present compounds may be applied in liquid form. Compounds often are administered as compositions or formulations, in combination with a dermatologically acceptable carrier, which may be a solid or a liquid. Examples of useful dermatological compositions used to deliver compounds to the skin are known (see, e.g., Jacquet, et al. (U.S. Pat. No. 4,608,392), Geria (U.S. Pat. No. 4,992,478), Smith, et al. (U.S. Pat. No. 4,559,157) and Wortzman (U.S. Pat. No. 4,820,508).

Compounds may be formulated with a solid carrier, which include finely divided solids such as talc, clay, microcrystalline cellulose, silica, alumina and the like. Useful liquid carriers include water, alcohols or glycols or water-alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers. Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Generally, the concentration of the compound in a liquid composition often is from about 0.1 wt % to about 25 wt %, sometimes from about 0.5 wt % to about 10 wt %. The concentration in a semi-solid or solid composition such as a gel or a powder often is about 0.1 wt % to about 5 wt %, sometimes about 0.5 wt % to about 2.5 wt %. A compound composition may be prepared as a unit dosage form, which is prepared according to conventional techniques known in the pharmaceutical industry. In general terms, such techniques include bringing a compound into association with pharmaceutical carrier(s) and/or excipient(s) in liquid form or finely divided solid form, or both, and then shaping the product if required.

Table 3 shows examples of formulations for use with compounds described herein. For example, a compound may be formulated having dosages from 10 mg/mL to 20 mg/mL solution, using the formulations herein. In Table 3, the designation "D5W" refers to deionized water with 5% dextrose. Each component in each formulation may be varied without affecting the activity of the compound. In one example, the compound is formulated in a solution comprising polyethylene glycol and propylene glycol in a buffer solution such as a phosphate buffer.

of circulating concentrations for which the $ED_{50}$ is associated with little or no toxicity. The dosage may vary within this range depending upon the dosage form employed and the route of administration utilized. For any compounds used in the methods described herein, the therapeutically effective dose can be estimated initially from cell culture assays. A dose sometimes is formulated to achieve a circulating plasma concentration range covering the $IC_{50}$ (i.e., the concentration of the test compound which achieves a half-maximal inhibition of symptoms) as determined in in vitro assays, as such information often is used to more accurately determine useful doses in humans. Levels in plasma may be measured, for example, by high performance liquid chromatography.

TABLE 3

| Formulations | % (w/w) | Compound (mL) + Placebo solution (mL) | pH of the Placebo solution | pH of the formulated solution (10 mg/mL) |
|---|---|---|---|---|
| 1. Mannitol | 4 | 35 ml + 35 mL | 6.1 | 6.1 |
| Sucrose | 0.5 | | | |
| 5% D5W solution | 95.5 | | | |
| 2. Mannitol | 4 | 35 ml + 35 mL | 6 | 5.8 |
| 50 mM $PO_4$ buffer, pH = 6.0 | 96 | | | |
| 3. Mannitol | 4 | 35 ml + 35 mL | 5 | 5 |
| 50 mM Citrate buffer, pH = 5.0 | 96 | | | |
| 4. Mannitol | 4 | 35 ml + 35 mL | 6 | 6 |
| 5% D5W | 96 | | | |
| 5. Test compound (20 mg/mL) | 1 | 35 ml + 35 mL | 6.4 | 6.1 |
| 5% D5W | 99 | | | |
| 6. PEG 300 | 7 | 5 ml + 5 mL | N/A | 5.80 |
| Propylene glycol | 9 | | | |
| 5% D5W | 84 | | | |
| 7. PEG 300 | 7 | 5 ml + 5 mL | N/A | 5.8 |
| Propylene glycol | 9 | | | |
| 50 mM $PO_4$ buffer, pH = 6.0 | 84 | | | |
| 8. Mannitol | 4 | 5 ml + 5 mL | N/A | 5.7 |
| PEG 300 | 20 | | | |
| 50 mM $PO_4$ buffer, pH = 6.0 | 76 | | | |
| 9. Mannitol | 4 | 5 ml + 5 mL | N/A | 5.8 |
| Propylene glycol | 10 | | | |
| 50 mM $PO_4$ buffer, pH = 6.0 | 86 | | | |

The compound composition may be formulated into any dosage form, such as tablets, capsules, gel capsules, liquid syrups, soft gels, suppositories, and enemas. The compositions also may be formulated as suspensions in aqueous, non-aqueous, or mixed media. Aqueous suspensions may further contain substances which increase viscosity, including for example, sodium carboxymethylcellulose, sorbitol, and/or dextran. The suspension may also contain one or more stabilizers. The amount of the compound, or an active salt or derivative thereof, required for use in treatment will vary not only with the particular salt selected but also with the route of administration, the nature of the condition being treated and the age and condition of the patient and will be ultimately at the discretion of the attendant physician or clinician.

Dosages

A useful compound dosage often is determined by assessing its in vitro activity in a cell or tissue system and/or in vivo activity in an animal system. For example, methods for extrapolating an effective dosage in mice and other animals to humans are known to the art (see, e.g., U.S. Pat. No. 4,938, 949). Such systems can be used for determining the $LD_{50}$ (the dose lethal to 50% of the population) and the $ED_{50}$ (the dose therapeutically effective in 50% of the population) of a compound. The dose ratio between a toxic and therapeutic effect is the therapeutic index and it can be expressed as the ratio $ED_{50}/LD_{50}$. The compound dosage often lies within a range Another example of effective dose determination for a subject is the ability to directly assay levels of "free" and "bound" compound in the serum of the test subject. Such assays may utilize antibody mimics and/or "biosensors" generated by molecular imprinting techniques. The compound is used as a template, or "imprinting molecule", to spatially organize polymerizable monomers prior to their polymerization with catalytic reagents. Subsequent removal of the imprinted molecule leaves a polymer matrix which contains a repeated "negative image" of the compound and is able to selectively rebind the molecule under biological assay conditions (see, e.g., Ansell, et al., *Current Opinion in Biotechnology* (1996) 7:89-94 and in Shea, *Trends in Polymer Science* (1994) 2:166-173).

Such "imprinted" affinity matrixes are amenable to ligand-binding assays, whereby the immobilized monoclonal antibody component is replaced by an appropriately imprinted matrix (see, e.g., Vlatakis, et al., *Nature* (1993) 361:645-647). Through the use of isotope-labeling, "free" concentration of compound can be readily monitored and used in calculations of $IC_{50}$. Such "imprinted" affinity matrixes can also be designed to include fluorescent groups whose photon-emitting properties measurably change upon local and selective binding of compound. These changes can be readily assayed in real time using appropriate fiberoptic devices, in turn allowing the dose in a test subject to be quickly optimized based on its individual IC$_{50}$. An example of such a "biosensor" is discussed in Kriz, et al., *Analytical Chemistry* (1995) 67:2142-2144.

Exemplary doses include milligram or microgram amounts of the compound per kilogram of subject or sample weight, for example, about 1 microgram per kilogram to about 500 milligrams per kilogram, about 100 micrograms per kilogram to about 5 milligrams per kilogram, or about 1 microgram per kilogram to about 50 micrograms per kilogram. It is understood that appropriate doses of a small molecule depend upon the potency of the small molecule with respect to the expression or activity to be modulated. When one or more of these small molecules is to be administered to an animal (e.g., a human) in order to modulate expression or activity of a polypeptide or nucleic acid described herein, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The following examples are offered to illustrate but not to limit the invention.

EXAMPLE 1

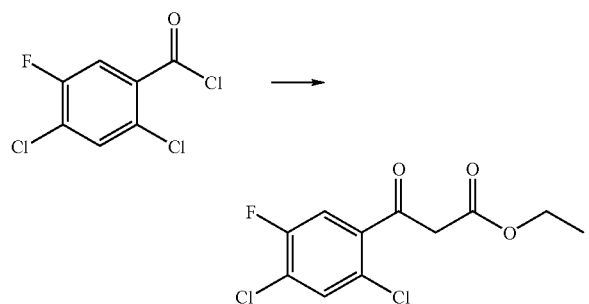

To a solution of magnesium chloride (6.74 g, 70.8 mmol) and potassium ethyl malonate (6.78 g, 39.8 mmol) in dry acetonitrile (100 mL) at 0° C. was added 2,4-dichloro-5-fluorobenzoyl chloride (5.0 g, 22.1 mmol) dropwise, keeping the internal temperature below 5° C. The mixture was stirred an additional 30 minutes and triethyl amine (6.1 mL, 44.25 mmol) was added dropwise, again keeping the temperature below 5° C. and the reaction mixture was allowed to stir overnight. The mixture was concentrated in vacuo, diluted with toluene (250 mL) and 1N HCl was added (100 mL) and the mixture was allowed to stir for 30 minutes. The layers were separated and the organic layer was washed once more with 1N HCl (100 mL), and brine (200 mL) and dried over sodium sulfate. The organic layer was then filtered, concentrated in vacuo and purified over silica gel (1:10 ethyl acetate/hexanes) to afford the ketoester as an oil that solidified on standing (5.02 g, 81%).

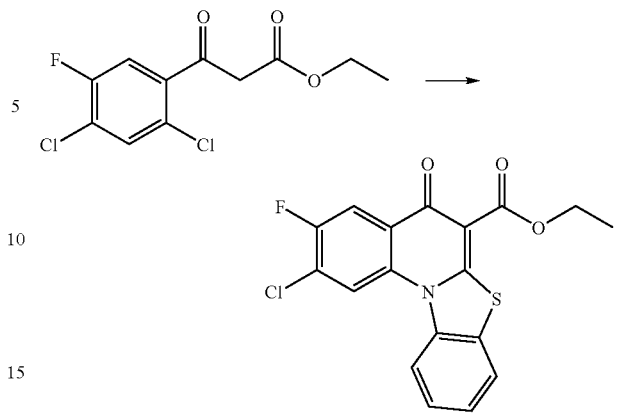

To a solution of the ketoester (5.0 g, 18 mmol) in diglyme (50 mL) was added 2-chlorobenzothiazole (3.66 g, 21.6 mmol) followed by sodium hydride (1.52 g, 39.6 mmol, 60% in oil) portion-wise over 10 minutes. The reaction was heated to 160° C. for 24 hours and allowed to cool to room temperature. The mixture was quenched by careful addition of water (250 mL) and the resulting brown precipitate was removed by filtration and washed with water. The product was then dissolved in methylene chloride (300 mL), washed with brine and filtered through celite. The resulting organic layer was dried over sodium sulfate, filtered and concentrated in vacuo. The product was purified over silica gel (7% ethyl acetate in hexanes) to afford the cyclized material (1.76 g, 26%) as a solid.

EXAMPLE 2

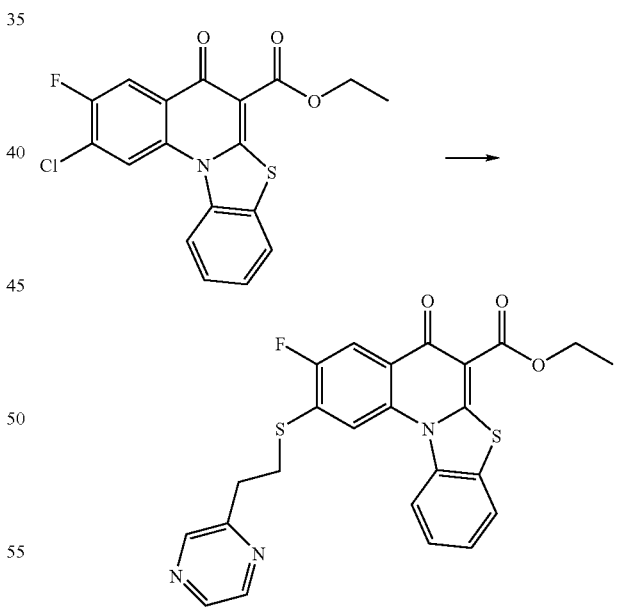

To a solution of the chloroester (250 mg, 0.66 mmol) in N-methylpyrrolidinone (NMP, 2 mL) was added 2-pyrazineethanethiol (81 µL, 0.66 mmol), and potassium carbonate (182 mg, 1.32 mmol) and the mixture was heated to 100° C. for 2 hours. The mixture was allowed to cool to room temperature and water (50 mL) was added and stirring continued overnight. The crude product was collected by filtration and purified by preparative TLC (2% methanol in methylene chloride) to afford the pure product as a tan fluffy solid (122 mg, 38%).

EXAMPLE 3

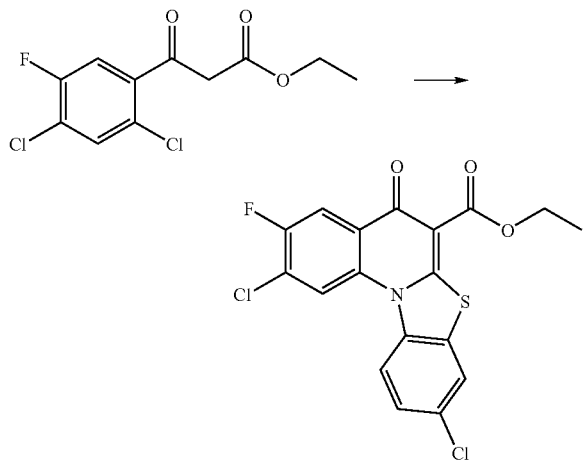

To a solution of the ketoester (2.0 g, 7.2 mmol) in diglyme (20 mL) was added the 2,6-dichlorobenzothiazole (1.76 g, 8.63 mmol) followed by sodium hydride (0.63 g, 15.8 mmol, 60% in oil) portion-wise over 10 minutes. The reaction was heated to 160° C. for 24 hours and allowed to cool to room temperature. The mixture was quenched by careful addition of water (200 mL) and the resulting brown precipitate was removed by filtration and washed with water. The product was then dissolved in methylene chloride (30 mL), washed with brine and filtered through celite. The resulting organic layer was dried over sodium sulfate, filtered and concentrated in vacuo. The product was purified over silica gel (5% ethyl acetate in hexanes) to afford the cyclized material (0.55 g, 18.8%) as a solid.

EXAMPLE 4

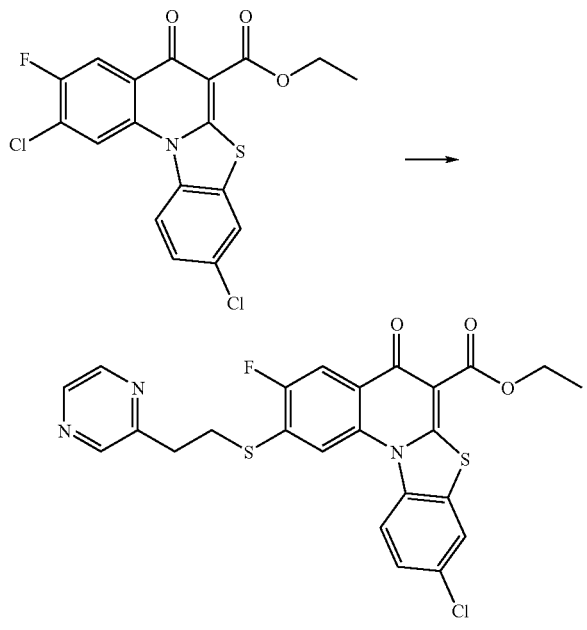

To a solution of the chloroester (250 mg, 0.61 mmol) in N-methylpyrrolidinone (NMP, 2 mL) was added 2-pyrazineethanethiol (75 µL, 0.61 mmol), and potassium carbonate (170 mg, 1.2 mmol) and the mixture was heated to 100° C. for 2 hours. The mixture was allowed to cool to room temperature and water (50 mL) was added and stirring continued overnight. The crude product was collected by filtration and purified by preparative TLC (2% methanol in methylene chloride) to afford the pure product as a tan fluffy solid (125 mg, 40%).

EXAMPLE 5

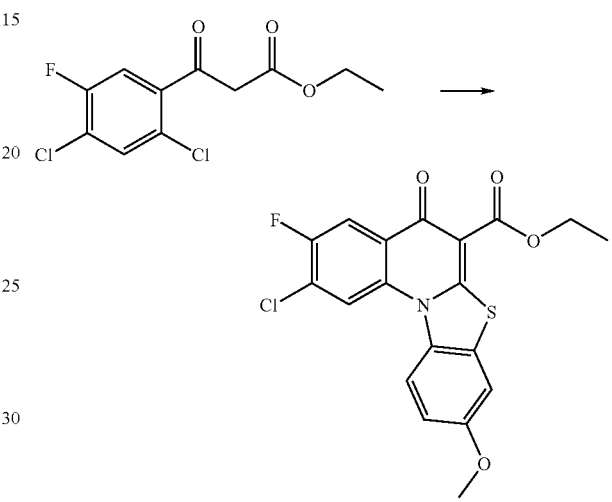

To a solution of the ketoester (2.0 g, 7.2 mmol) in diglyme (20 mL) was added the 2-chloro-6-methoxybenzothiazole (1.73 g, 8.63 mmol) followed by sodium hydride (0.63 g, 15.8 mmol, 60% in oil) portion-wise over 10 minutes. The reaction was heated to 160° C. for 24 hours and allowed to cool to room temperature. The mixture was quenched by careful addition of water (200 mL) and the resulting brown precipitate was removed by filtration and washed with water. The product was then dissolved in methylene chloride (30 mL), washed with brine and filtered through celite. The resulting organic layer was dried over sodium sulfate, filtered and concentrated in vacuo. The product was purified over silica gel (5% ethyl acetate in hexanes) to afford the cyclized material (0.23 g, 7.6%) as a solid.

EXAMPLE 6

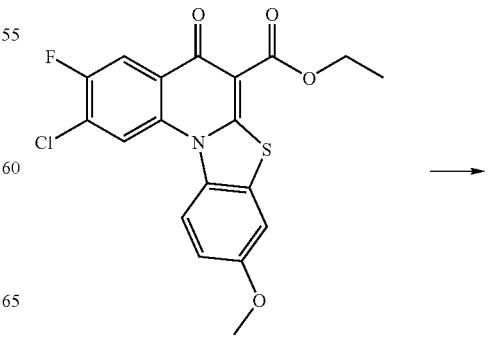

-continued

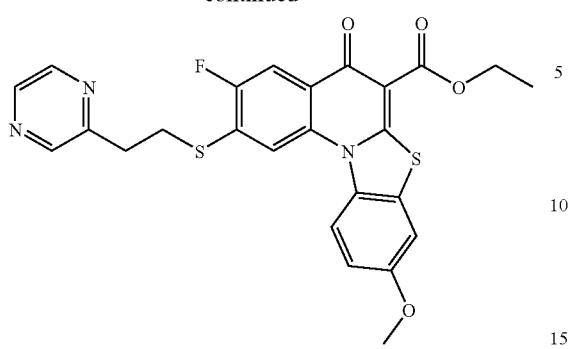

To a solution of the chloroester (220 mg, 0.54 mmol) in N-methylpyrrolidinone (NMP, 2 mL) was added 2-pyrazineethanethiol (66 µL, 0.54 mmol), and potassium carbonate (150 mg, 1.1 mmol) and the mixture was heated to 100° C. for 2 hours. The mixture was allowed to cool to room temperature and water (50 mL) was added and stirring continued overnight. The crude product was collected by filtration and purified by preparative TLC (2% methanol in methylene chloride) to afford the pure product as a tan fluff-y solid (75 mg, 28%).

EXAMPLE 7

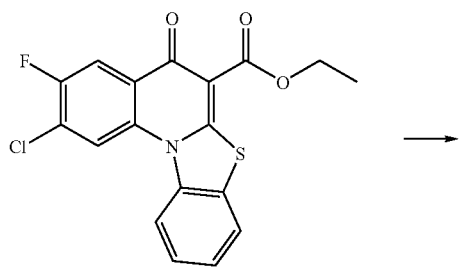

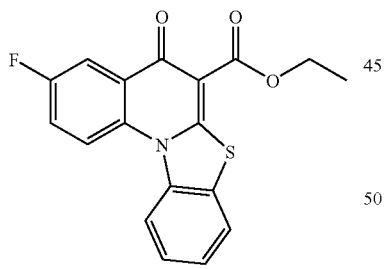

To a suspension of the chloroester (0.25 g, 0.67 mmol) in glacial acetic acid (5 mL) was added ammonium formate (0.6 g, 4.0 mmol) and the mixture was degassed with argon for 2 minutes. Next, palladium on charcoal (10% degussa type, 0.6 g) was added and the mixture was heated to 60° C. for 1 hour. More ammonium formate (0.1 g) and catalyst (0.1 g) were added and heating continued overnight. Finally, more ammonium formate and catalyst (150 mg each) were added and heating continued for 1.5 hr. The mixture was allowed to cool to room temperature and filtered through celite and the solvent was removed in vacuo and replaced with methylene chloride (100 mL). The organics were washed with water (100 mL) and brine (100 mL) and dried over sodium sulfate. The solvent was removed in vacuo to afford the benzothiazole as a tan solid (153 mg, 67%).

EXAMPLE 8

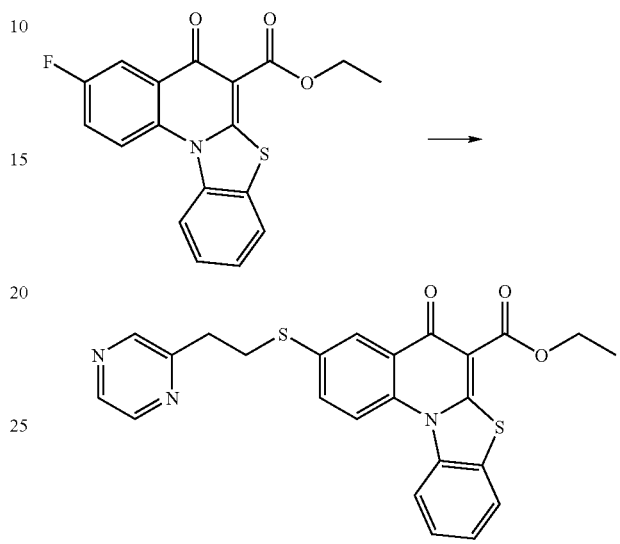

To a solution of the fluoroester (50 mg, 0.15 mmol) in N-methylpyrrolidinone (NMP, 0.5 mL) was added 2-pyrazineethanethiol 126 µL, 1.0 mmol), and potassium carbonate (40 mg, 0.3 mmol) and the mixture was heated to 100° C. for 2 hours. The mixture was allowed to cool to room temperature and water (50 mL) was added and stirring continued overnight. The crude product was collected by filtration and purified by preparative TLC (2% methanol in methylene chloride) to afford the pure product as a tan fluffy solid (17 mg, 25%).

EXAMPLE 9

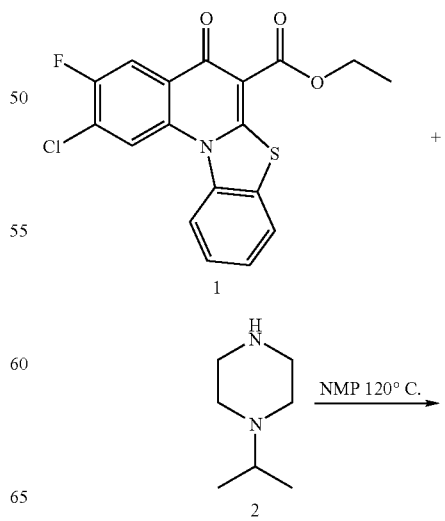

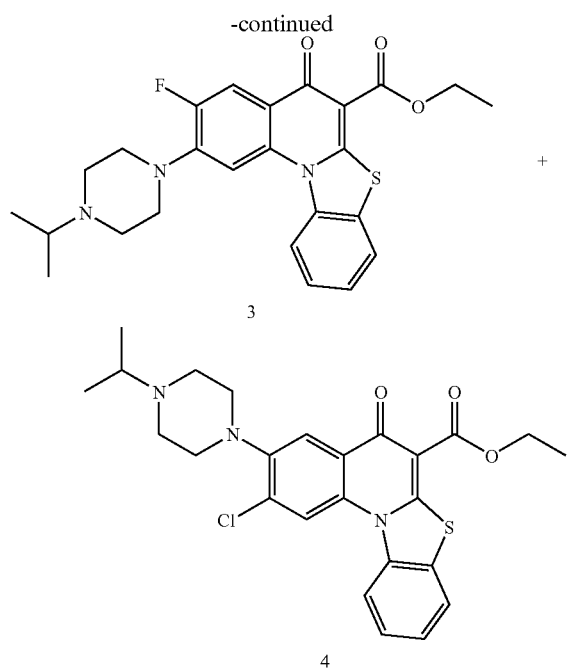

3

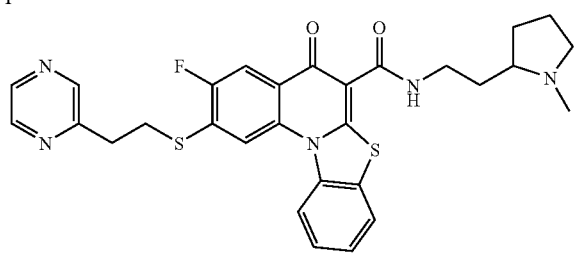

4

Compound 1 (1.0 eq, 399 mg, 1.06 mmol) and 1-isopropyl piperazine 2 (5.0 eq., 0.76 ml, 5.31 mmol) were dissolved in N-methylpyrrolidinone (NMP, 5 ml). The resulting mixture was stirred at 120° C. for 3 days. LC monitoring revealed formation of two main products 3 and 4 in equal amounts. The solution was poured into water and the resulting precipitate isolated by filtration. The two compounds were separated by flash chromatography on $SiO_2$ (gradient MeOH 0.5 to 7% in $CH_2Cl_2$) to afford 3 (135 mg, 27% yield) and 4 (135 mg, 26%).

3: Rf=0.40 ($SiO_2$, 5% MeOH in $CH_2Cl_2$), LCMS (ES): 95% pure, m/z 468 $[M+H]^+$.

4: Rf=0.26 ($SiO_2$, 5% MeOH in $CH_2Cl_2$), LCMS (ES): 95% pure, m/z 484 $[M]^+$, 486 $[M+2]^+$.

EXAMPLE 10

This example provides activity data for two particular compounds:

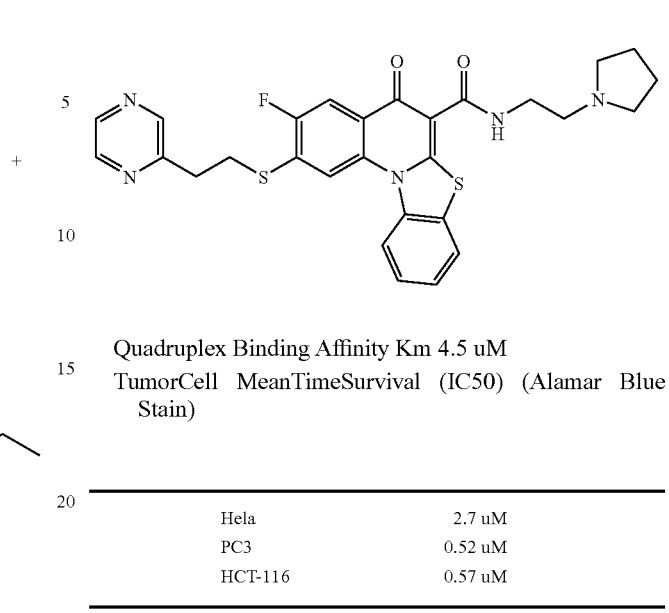

Quadruplex Binding Affinity Km 5.5 uM
TumorCell MeanTimeSurvival (IC50) (Alamar Blue Stain)

| Hela | 2.8 uM |
| PC3 | 2.7 uM |
| HCT-116 | 1.1 uM |

Quadruplex Binding Affinity Km 4.5 uM
TumorCell MeanTimeSurvival (IC50) (Alamar Blue Stain)

| Hela | 2.7 uM |
| PC3 | 0.52 uM |
| HCT-116 | 0.57 uM |

EXAMPLE 11

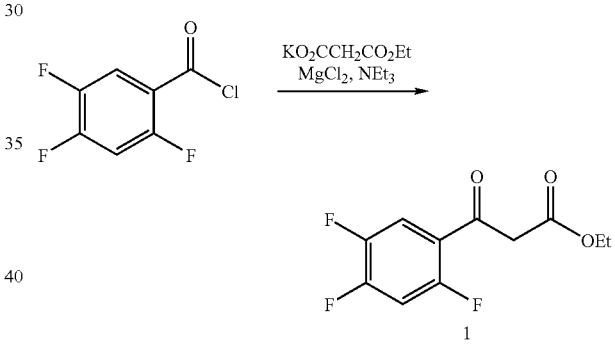

In a three necked flask equipped with a nitrogen inlet, potassium ethylmalonate (1.5 eq, 32.8 g, 0.192 mol) and $MgCl_2$ (1.5 eq., 18.4 g, 0.193 mol) were suspended in acetonitrile (120 ml) under mechanical stirring. The suspension was cooled down with an ice bath. A solution of 2,4,5-trifluorobenzoyl chloride (1.0 eq, 25 g, 0.128 mol) in acetonitrile (60 ml) was added dropwise. A solution of triethylamine (2.0 eq, 36 ml, 0.258 mol) in acetonitrile (50 ml) was added over 30 min while keeping the internal temperature below 10° C. by external cooling with an ice-salt mixture. The very thick slurry that resulted was allowed to warm to room temperature. An extra amount of acetonitrile (150 ml) was added to allow a proper stirring of the slurry. The reaction was stirred for 2 days and the volatiles were removed in vacuo. A 10% aqueous solution of HCl and EtOAc were added and the mixture stirred for 3 hours. The material was extracted with EtOAc (3×). The combined extracts were washed with brine and dried over $Na_2SO_4$. After evaporation of the solvent in vacuo, the material was recrystallized in a 10% water/EtOH mixture to provide compound 1 as a white crystalline material (17.8 g, 56% yield). LCMS (ES): 95% pure, m/z 269 $[M+23]^+$. Mixture of two tautomeric isomers.

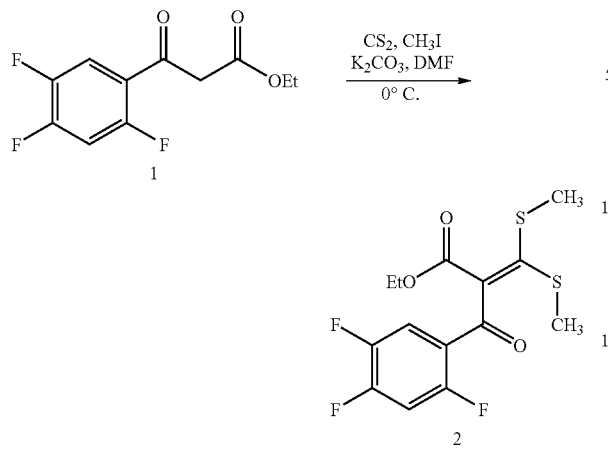

Compound 1 (1.0 eq, 3.27 g, 13.29 mmol) was dissolved in anhydrous DMF (30 ml). The solution was cooled down with ice, K$_2$CO$_3$ (3.0 eq, 5.51 g, 39.87 mmol) was added and the solution stirred for 15 min. To the resulting white slurry was quickly added carbon disulfide (1.5 eq, 1.20 ml, 19.86 mmol) and the mixture stirred at 0° C. for 5 min. Methyl Iodide (3.0 eq, 2.5 ml, 40.2 mmol) was added dropwise through syringe and the reaction stirred at 0° C. for 2 hours. After adding iced water, the compound was extracted with EtOAc (3×). The combined extracts were washed with water (1×) and brine (2×), dried over Na$_2$SO$_4$ and the volatiles removed in vacuo. Upon adding hexanes and bit of EtOAc the compound started to crystallize. The crude material was isolated by filtration and recrystallized in hexanes to afford a white crystalline solid (3.27 g, 70% yield). LCMS (ES): 95% pure, m/z 373 [M+23]$^+$, 351 [M+1]$^+$.

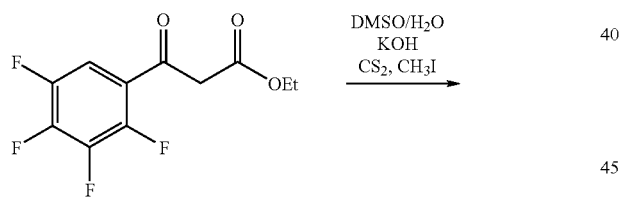

Ethyl 3-oxo-3-(2,3,4,5-tetrafluorophenyl)propanoate (1.0 eq, 5.77 g, 21.84 mmol) was dissolved in a mixture of DMSO (55 ml) and water (12 ml). A solution of KOH (2.3 eq, 2.82 g, 50.26 mmol) in water (25 ml) was added dropwise while keeping the internal temperatue below 15° C. using an ice bath. After stirring for 15 min, a mixture of carbon disulfide (3.2 eq, 4.2 ml, 69.50 mmol) and iodomethane (3.8 eq, 5.2 ml, 83.35 mmol) was added quickly and the resulting mixture stirred at room temperature overnight. After adding water, the material was extracted with EtOAc (2×). The combined extracts were washed with water, dried over Na$_2$SO$_4$ and the solvent removed in vacuo. The compound was purified by flash chromatography on silica gel (5 to 15% gradient of EtOAc in hexanes) to afford a yellow oil (1.69 g, 21% yield). LCMS (ES): 95% pure, m/z 323 [M+1−EtO]$^+$; $^1$H NMR (CDCl$_3$, 500 MHz) δ 1.15 (t, J=7.0, 3H), 2.40 (br s, 6H), 4.18 (q, J=7.2, 2H), 7.54-7.60 (m, 1H) ppm.

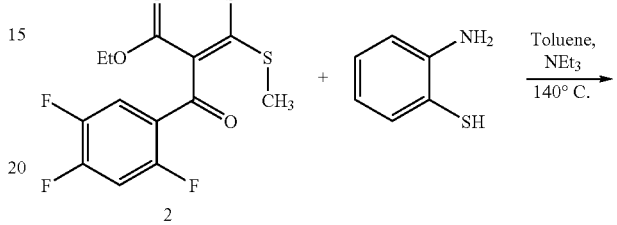

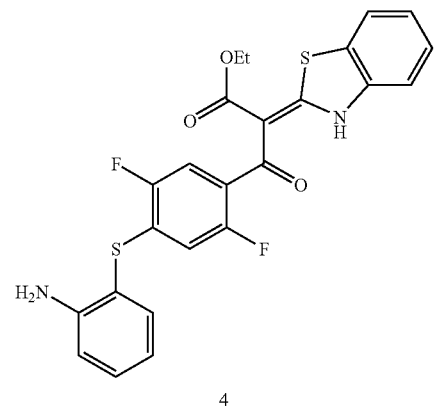

Compound 2 (1.0 eq, 993 mg, 2.84 mmol), 2-aminothiophenol (5.0 eq, 1.52 ml, 14.2 mmol) and NEt$_3$ (4.0 eq, 1.59 ml, 11.0 mmol) were mixed in anhydrous toluene (10 ml). The mixture was stirred at reflux for a few hours. After removal of the solvent in vacuo, the material was purified by sonication in EtOAc/hexanes to give a solid (724 mg, 53% yield). LCMS (ES): 95% pure, m/z 485 [M+1]$^+$.

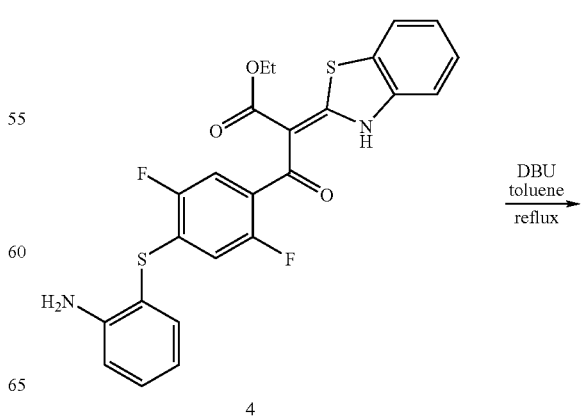

-continued

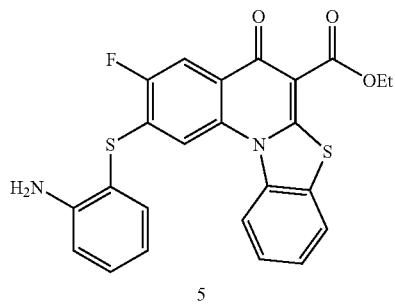

5

Compound 4 (1.0 eq, 70 mg, 0.144 mmol) was mixed with DBU (4.0 eq, 65 μl, 0.43 mmol) in toluene (1.5 ml). The solution was stirred under reflux for 45 min. The compound was purified by flash chromatography on silica gel (1% MeOH in CH$_2$Cl$_2$). LCMS (ES): 95% pure, m/z 465 [M+1]$^+$.

EXAMPLE 12

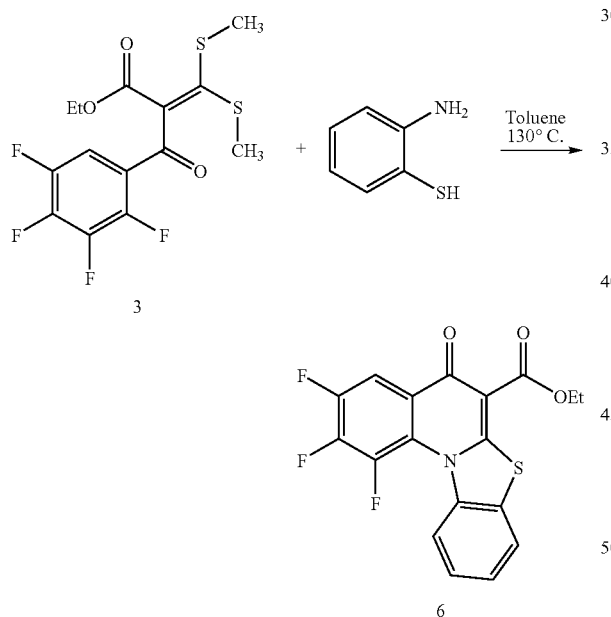

Compound 3 (1.0 eq, 347 mg, 0.942 mmol) and 2-aminothiophenol (1.0 eq, 0.10 ml, 0.934 mmol) were mixed in toluene (1 ml) and stirred at 130° C. for 14 hours. After cooling down some solid impurities were removed by filtration. The toluene solution was poured onto a silica gel column. Toluene was removed first by eluting with hexanes. The column was eluted then with a 10 to 30% gradient of EtOAc in hexanes to provide the expected compound. After evaporation of the volatiles, the solid was further purified by recrystallization using EtOAc/hexanes. Compound 6 was isolated as a gray solid (62 mg, 18% yield). LCMS (ES): 90% pure, m/z 378 [M+1]$^+$.

EXAMPLE 13

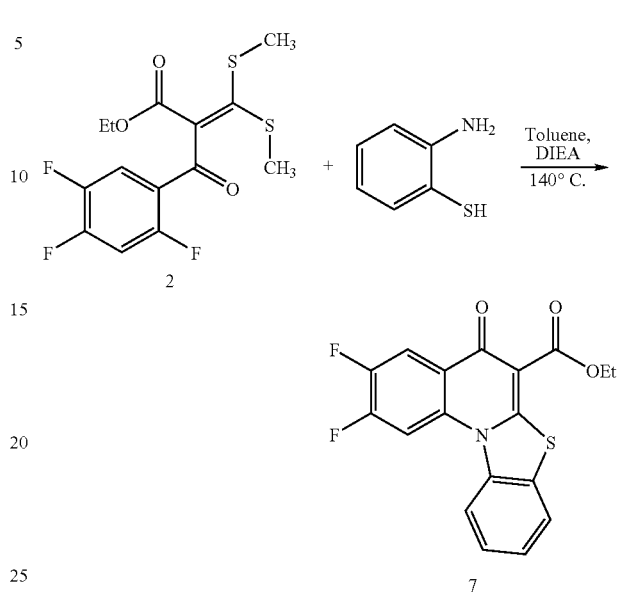

Compound 2 (1.0 eq, 3.15 g, 8.99 mmol) and 2-aminothiophenol (1.1 eq, 1.06 ml, 9.91 mmol) were mixed in toluene (150 ml). Nitrogen gas was bubbled into the solution for 10 min. The reaction was stirred at reflux (oil bath T=140° C.) for 30 hours. The volatiles were removed in vacuo and CH$_2$Cl$_2$ was added. Solid impurities were removed by filtration. The material was purified by flash chromatography on silica gel (10 to 50% gradient of EtOAc in hexanes) to afford compound 7 as an off-white powder (576 mg, 18% yield). LCMS (ES): 90% pure, m/z 360 [M+1]$^+$.

EXAMPLE 14

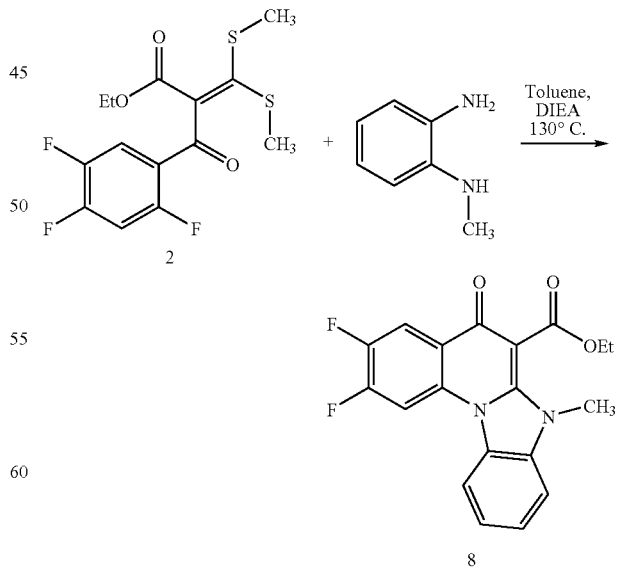

Compound 2 (1.0 eq, 2.52 g, 7.20 mmol) was mixed with N-methylbenzene-1,2-diamine (1.2 eq, 0.98 ml) and DIEA (1.2 eq, 1.5 ml) in toluene (10 ml) and the reaction stirred at 120° C. for one day. Compound 8 was isolated by filtration after cooling the reaction mixture (679 mg, 26% yield). LCMS (ES): 95% pure, m/z 358 [M+1]⁺.

EXAMPLE 15

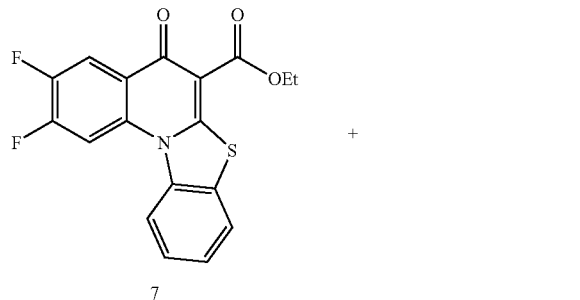

7

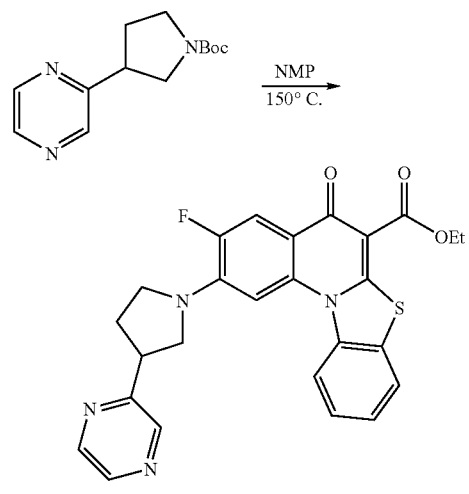

rac-9

Compound 7 (1.0 eq, 392 mg, 1.09 mmol) and racemic tert-butyl 3-(pyrazin-2-yl)pyrrolidine-1-carboxylate (1.6 eq, 436 mg, 1.74 mmol) were suspended in 1 ml of NMP. The mixture was heated by microwaves at 150° C. for 20 min. Water was added and the resulting solid isolated by filtration. Purification by flash chromatography afforded compound 9 (265 mg, 50% yield) as a solid. LCMS (ES): 95% pure, m/z 489 [M+1]⁺.

EXAMPLE 16

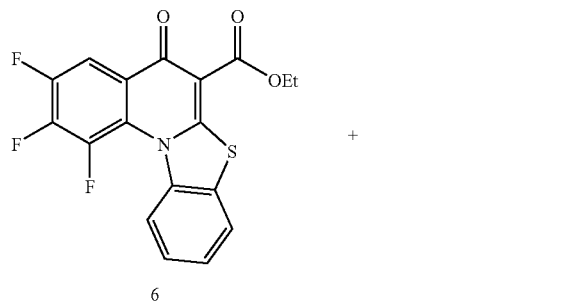

6

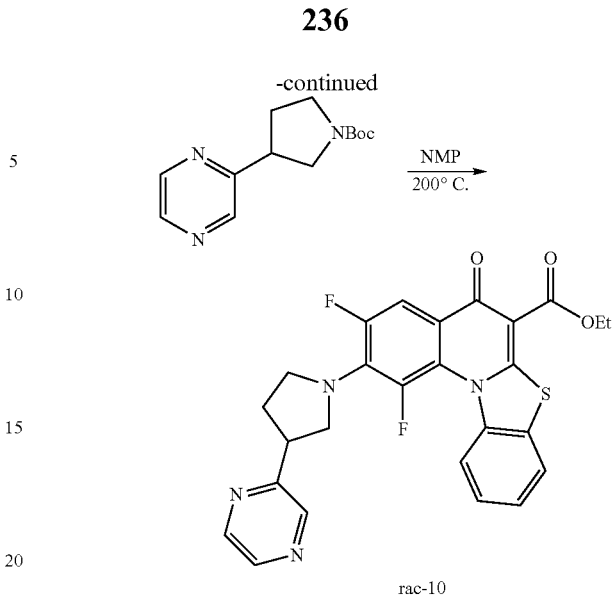

rac-10

Compound 6 (1.0 eq, 66 mg, 0.175 mmol) and racemic tert-butyl 3-(pyrazin-2-yl)pyrrolidine-1-carboxylate (3.8 eq, 165 mg, 0.661 mmol) were mixed in NMP (0.5 ml). The mixture was stirred at 200° C. for 23 hours. After adding water, the solid that formed was removed by filtration. Purification by flash chromatography on silica gel (1 to 4% gradient of MeOH in CH₂Cl₂) afforded compound 10 as a brown solid (70 mg, 79% yield). LCMS (ES): 90% pure, m/z 507 [M+1]⁺.

EXAMPLE 17

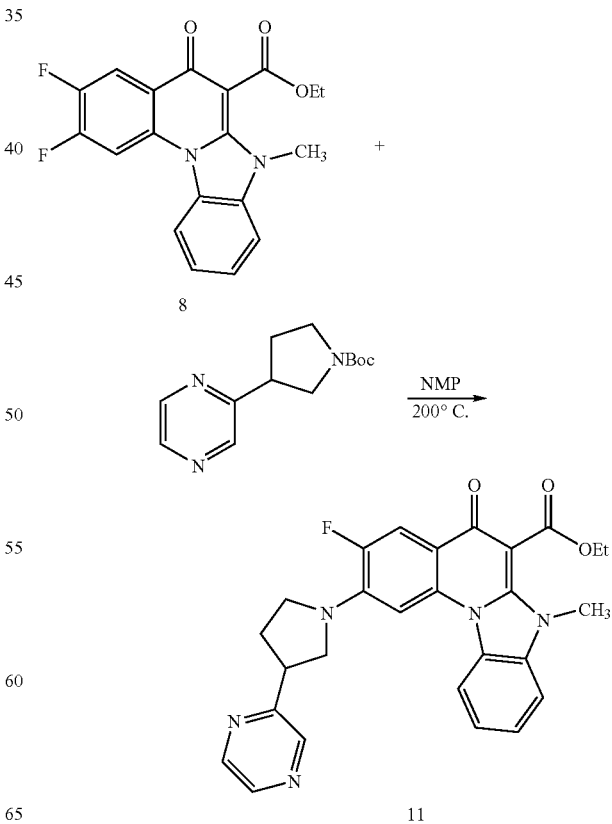

Compound 11 was prepared according to the procedure used for compound 10. The compound was purified by flash chromatography on silica gel (1 to 10% gradient of MeOH in CH$_2$Cl$_2$) to afford a solid (220 mg, 47%). LCMS (ES): 95% pure, m/z 486 [M+1]$^+$.

EXAMPLE 18

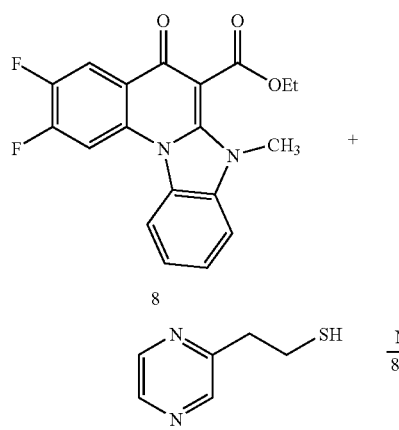

Compound 8 (1.0 eq, 202 mg, 0.56 mmol) was mixed with 2-(pyrazin-2-yl)ethanethiol (1.05 eq, 76 µl) and K$_2$CO$_3$ (1.2 eq, 94 mg) in NMP. The mixture was stirred for 3 hours at 80° C. After adding water, the solid was filtered and dried to afford compound 12 (202 mg, 85% yield). LCMS (ES): 95% pure, m/z 477 [M+1]$^+$.

EXAMPLE 19

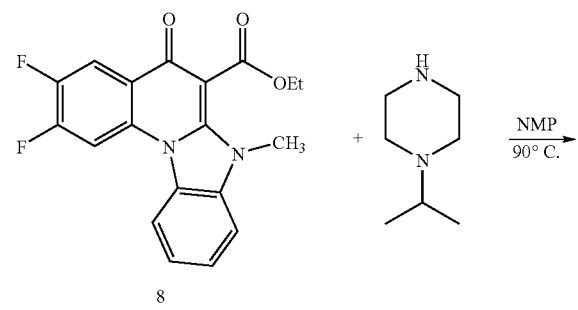

-continued

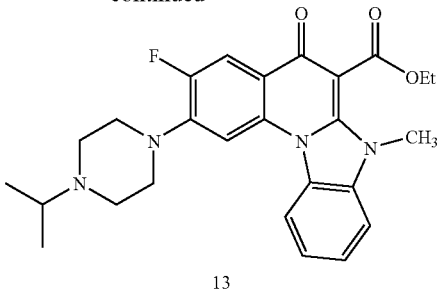

Compound 8 (313 mg) was mixed with N-isopropyl piperazine (1.5 eq, 188 µl) in NMP and the mixture was stirred at 90° C. for several hours. The compound was isolated by filtration after adding water. Purification by flash chromatography on silica gel (MeOH/CH$_2$Cl$_2$) afforded pure compound 13 (222 mg, 54% yield). LCMS (ES): 95% pure, m/z 465 [M+1]$^+$.

EXAMPLE 20

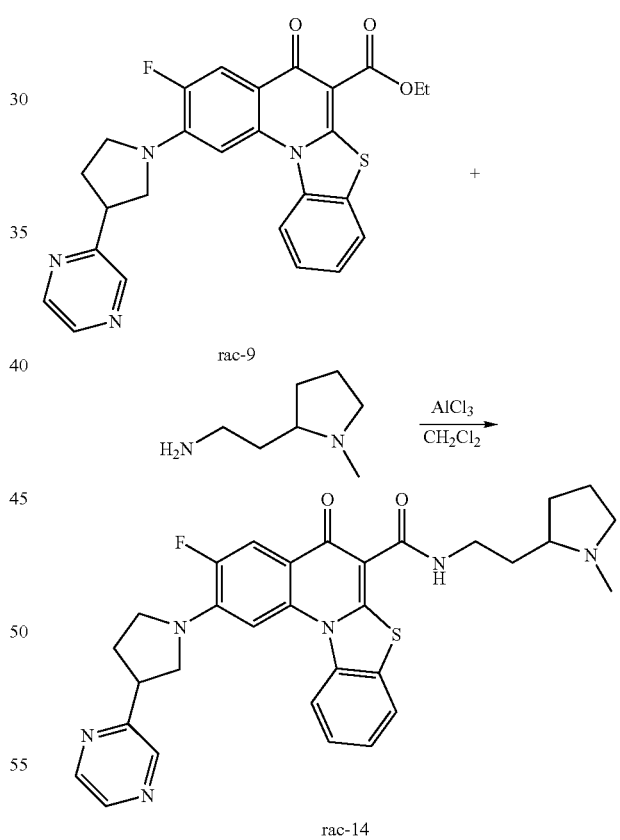

Compound 9 (1.0 eq, 181 mg, 0.370 mmol) and racemic 2(1-methylpyrrolidin-2-yl)ethanamine (4.0 eq, 0.21 ml, 1.449 mmol) were mixed in CH$_2$Cl$_2$ (1.5 ml). AlCl$_3$ (2.9eq, mg, 1.06 mmol) was added and the solution stirred for 22 hours. After removal of CH$_2$Cl$_2$ in vacuo, the resulting slurry was treated with a saturated aqueous tartaric acid solution (ca. 1 ml) and stirred until all solid disappeared (about 1 hr for completion of the hydrolysis). Water was added and the pH was adjusted to 14 by adding NaOH. The material was extracted with CH$_2$Cl$_2$ (3×) and the combined extracts washed with water (2×). After drying over Na$_2$SO$_4$, the volatiles were removed in vacuo. The material was purified by flash chromatography on alumina (0.1 to 1% gradient of MeOH in CH$_2$Cl$_2$). The CH$_2$Cl$_2$/MeOH solution was concentrated in vacuo. Addition of EtOAc induced precipitation of 14 as a yellow solid (93 mg, 44% yield). LCMS (ES): 95 pure, m/z 571 [M+1]$^+$.

The following compounds were prepared by the same method, using the appropriate amines and quinolone ethyl esters.

| Structure | M.W. | LCMS (ES) m/z |
|---|---|---|
| 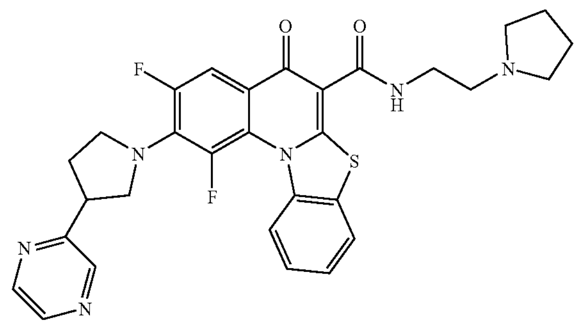 | 574.20 | 575 [M + 1]$^+$ |
| 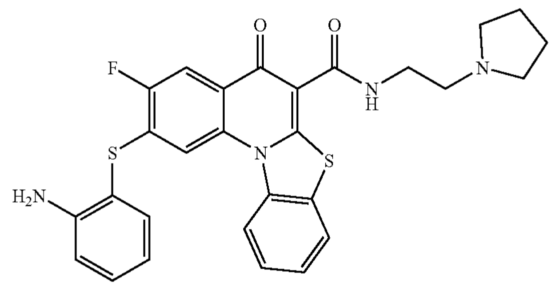 | 532.65 | 533 [M + 1]$^+$ |
| 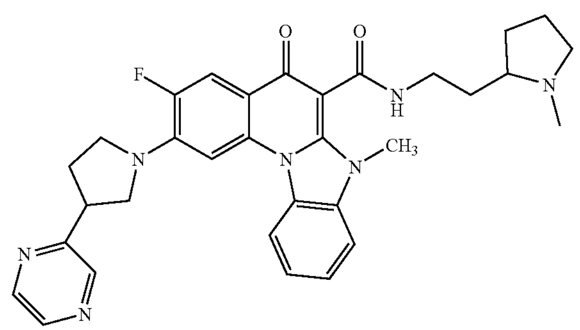 | 567.66 | 568 [M + 1]$^+$ |
| 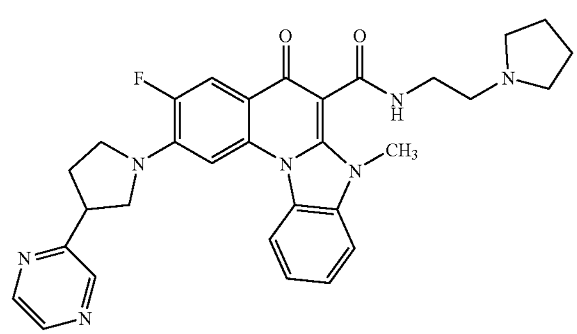 | 553.63 | 554 [M + 1]$^+$ |

-continued

| Structure | M.W. | LCMS (ES) m/z |
|---|---|---|
| 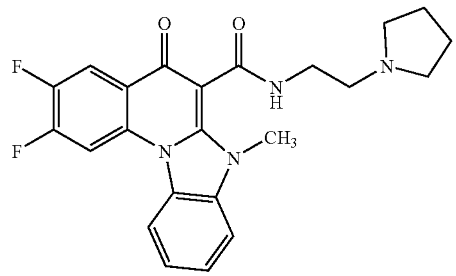 | 424.44 | 425 [M + 1]+ |
| 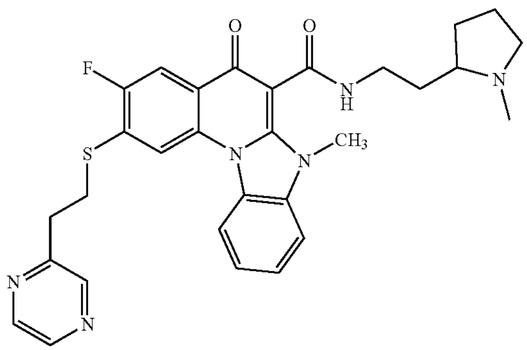 | 558.67 | 559 [M + 1]+ |
| 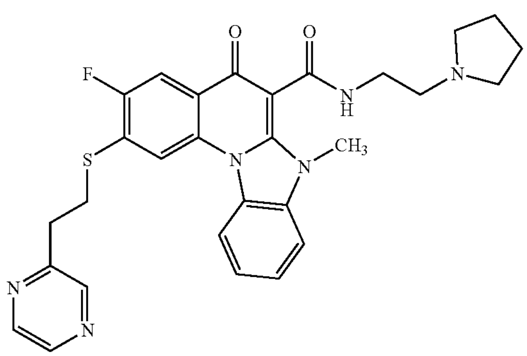 | 544.64 | 545 [M + 1]+ |
| 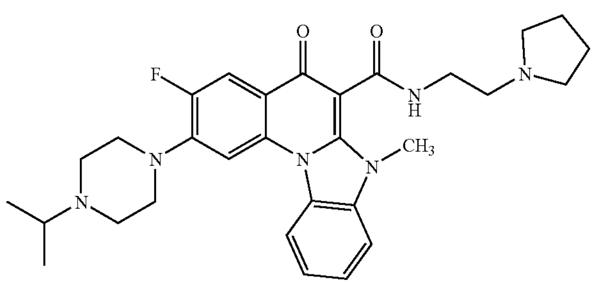 | 532.65 | 533 [M + 1]+ |
| 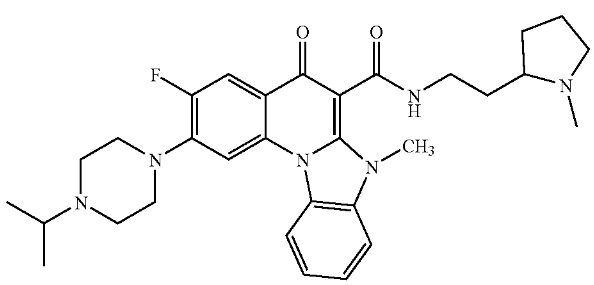 | 546.68 | 547 [M + 1]+ |

EXAMPLE 21

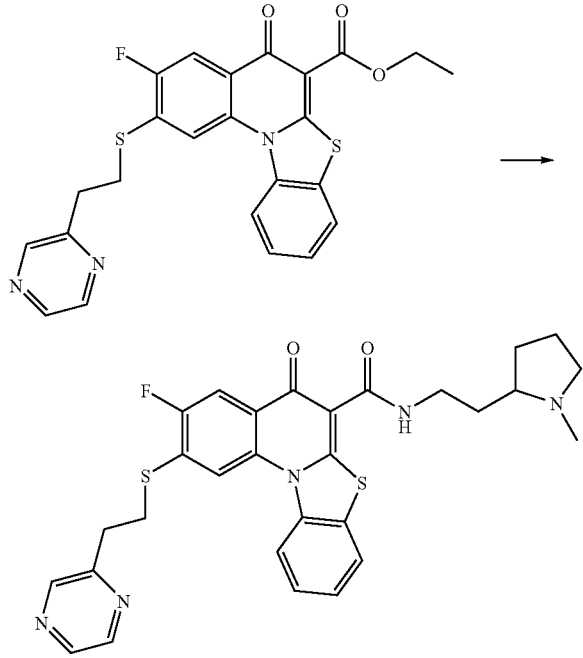

To a solution of the quinolone ester (60 mg, 0.13 mmol) and 2-(2-aminoethyl)-1-methyl pyrrolidine (30 µL, 0.19 mmol) in methylene chloride (1.0 mL) was added aluminum chloride (25 mg, 0.19 mmol) and the reaction mixture was allowed to stir for 30 minutes. The solvent was removed in vacuo and saturated L-tartaric acid (1.0 mL) was added, stirring for 45 minutes, until all of the solid dissolved. The aqueous solution was washed with methylene chloride (1.0 mL), basified with 1N NaOH and extracted with methylene chloride. The resulting extract was washed with brine, dried over sodium sulfate, filtered and the solvent was removed in vacuo. The resulting yellow material was purified on preparative TLC (Alumina, 2% Methanol in CH$_2$Cl$_2$) to afford the product as a yellowish solid (30 mg, 43%).

EXAMPLE 22

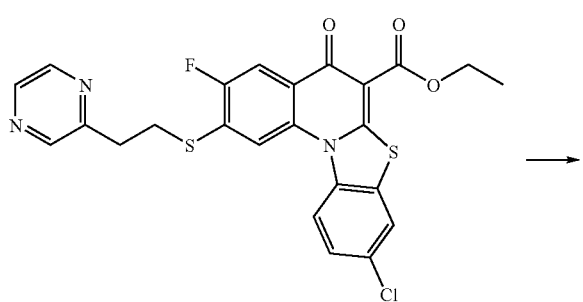

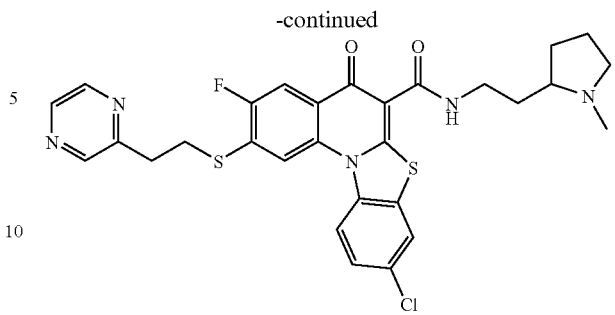

To a solution of the quinolone ester (60 mg, 0.11 mmol) and 2-(2-aminoethyl)-1-methyl pyrrolidine (25 µL, 0.17 mmol) in methylene chloride (1.0 mL) was added aluminum chloride (23 mg, 0.17 mmol) and the reaction mixture was allowed to stir for 30 minutes. The solvent was removed in vacuo and saturated L-tartaric acid (1.0 mL) was added, stirring for 45 minutes, until all of the solid dissolved. The aqueous solution was washed with methylene chloride (1.0 mL), basified with 1N NaOH and extracted with methylene chloride. The resulting extract was washed with brine, dried over sodium sulfate, filtered and the solvent was removed in vacuo. The resulting yellow material was purified on preparative TLC (Alumina, 2% Methanol in CH$_2$Cl$_2$) to afford the product as a yellowish solid (30 mg, 46%).

EXAMPLE 23

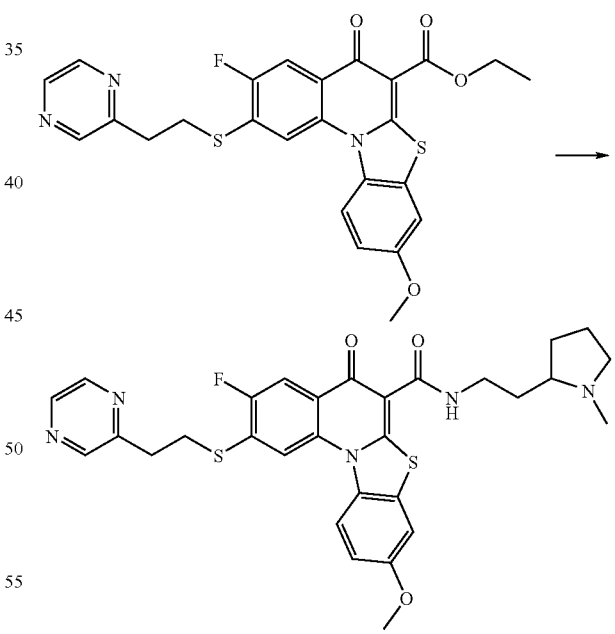

To a solution of the quinolone ester (75 mg, 0.15 mmol) and 2-(2-aminoethyl)-1-methyl pyrrolidine (32 µL, 0.22 mmol) in methylene chloride (1.0 mL) was added aluminum chloride (29 mg, 0.22 mmol) and the reaction mixture was allowed to stir for 30 minutes. The solvent was removed in vacuo and saturated L-tartaric acid (1.0 mL) was added, stirring for 45 minutes, until all of the solid dissolved. The aqueous solution was washed with methylene chloride (1.0 mL), basified with 1N NaOH and extracted with methylene chloride. The resulting extract was washed with brine, dried over sodium sulfate, filtered and the solvent was removed in vacuo. The resulting yellow material was purified on preparative TLC (Alumina, 2% Methanol in $CH_2Cl_2$) to afford the product as a yellowish solid (30 mg, 34%).

EXAMPLE 24

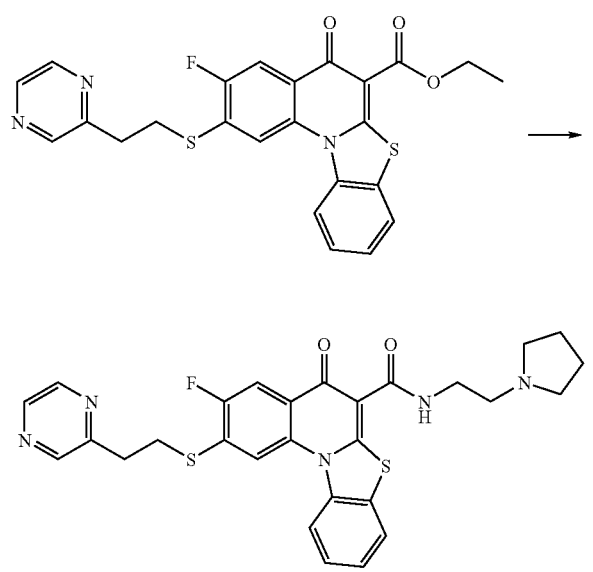

To a solution of the quinolone ester (34 mg, 0.7 mmol) and 1-(2-aminoethyl) pyrrolidine (15 μL, 0.11 mmol) in methylene chloride (1.0 mL) was added aluminum chloride (15 mg, 0.11 mmol) and the reaction mixture was allowed to stir for 30 minutes. The solvent was removed in vacuo and saturated L-tartaric acid (1.0 mL) was added, stirring for 45 minutes, until all of the solid dissolved. The aqueous solution was washed with methylene chloride (1.0 mL), basified with 1N NaOH and extracted with methylene chloride. The resulting extract was washed with brine, dried over sodium sulfate, filtered and the solvent was removed in vacuo. The resulting yellow material was purified on preparative TLC (Alumina, 2% Methanol in $CH_2Cl_2$) to afford the product as a yellowish solid (28 mg, 73%).

EXAMPLE 25

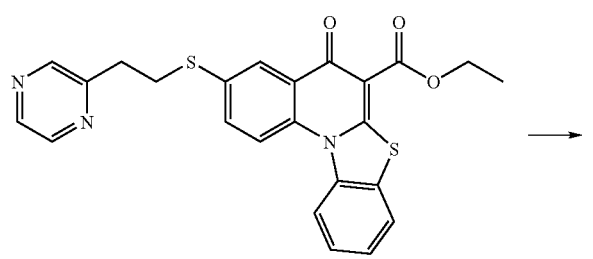

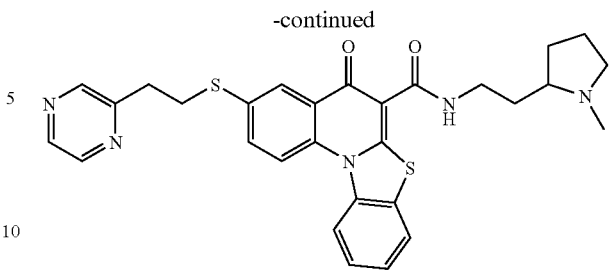

To a solution of the quinolone ester (146 mg, 0.65 mmol) and 2-(2-aminoethyl)-1-methyl pyrrolidine (1 mmol) in methylene chloride (1.0 mL) was added aluminum chloride (1 mmol) and the reaction mixture was allowed to stir for 30 minutes. The solvent was removed in vacuo and saturated L-tartaric acid (1.0 mL) was added, stirring for 45 minutes, until the entire solid dissolved. The aqueous solution was washed with methylene chloride (1.0 mL), basified with 1N NaOH and extracted with methylene chloride. The resulting extract was washed with brine, dried over sodium sulfate, filtered and the solvent was removed in vacuo. The resulting yellow material was purified on preparative TLC (Alumina, 2% Methanol in $CH_2Cl_2$) to afford the product as a yellowish solid (1.7 mg, 5%).

EXAMPLE 26

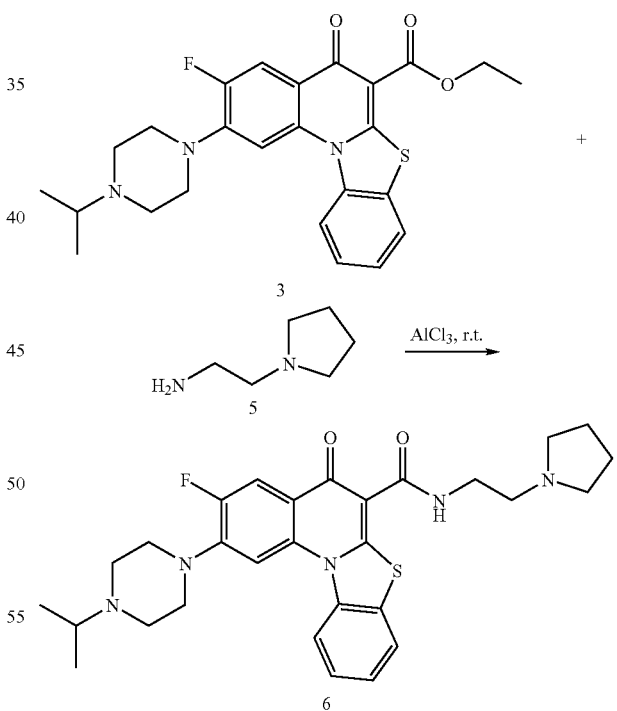

Compound 3 (1.0 eq, 126 mg, 0.27 mmol) and amine 5 (2.0 eq, 68 μL, 0.54 mmol) were dissolved in anhydrous $CH_2Cl_2$ (1 ml). $AlCl_3$ (2.0 eq, 72 mg, 0.54 mmol) was added and the mixture was stirred at room temperature for 3 hours. The volatiles were removed in vacuo. The resulting slurry was treated with a saturated aqueous tartaric acid solution (10 ml) and stirred until all solid disappeared (about 1 hr for completion of the hydrolysis). The solution was neutralized by 1N NaOH (to reach pH =14) and the compound extracted with $CH_2Cl_2$ (4×). The organic phase was washed with a concentrated aqueous Sodium Potassium tartrate solution, water (2×) and dried over $Na_2SO_4$. The $CH_2Cl_2$ solution was concentrated. Addition of AcOEt induced crystallization of the expected compound. After filtration, compound 6 was isolated as a pale yellow fluffy solid (76 mg, 53% yield). LCMS (ES): 95% pure, m/z 536 [M+H]$^+$; $^1$H NMR (CDCl$_3$, 500 MHz) δ 1.12 (d, J=6.6, 6H), 1.80 (br s, 4H), 2.62 (br s, 4H), 2.79 (m, 7H), 3.36 (m, 4H), 3.67 (q, J=6.0, 2H), 7.45 (t, J=7.2, 1H), 7.53 (td, J=7.3, J=1.3, 1H), 7.84 (dd, J=7.8, J=1.2, 1H), 7.89 (d, J=6.9, 1H), 8.16 (d, J=13.1, 1H), 8.23 (d, J=8.5, 1H), 10.46 (br t, 1H) ppm.

EXAMPLE 27

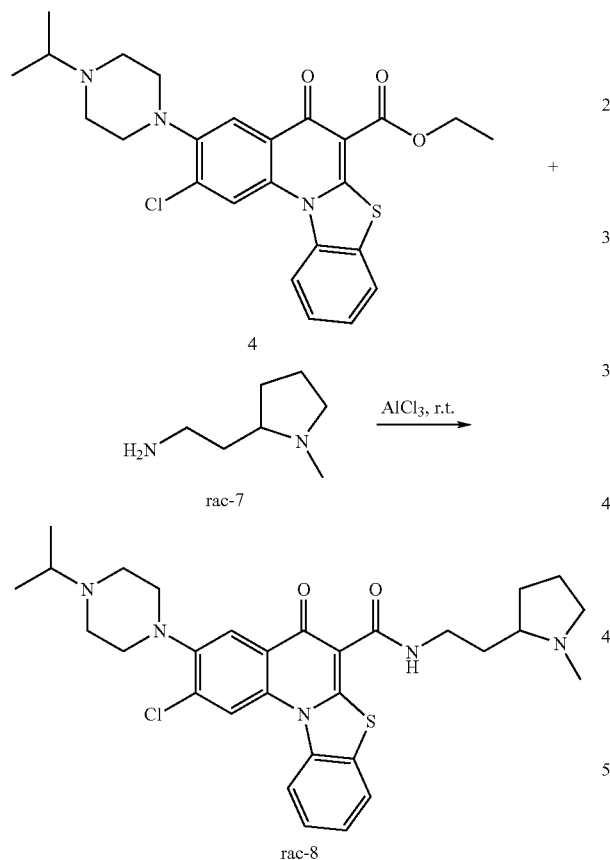

The compound was prepared according to the procedure used in Example 26, starting from 4 (101 mg, 0.21 mmol) and 7, providing compound 8 as a white fluffy solid (37 mg, 31% yield). LCMS (ES): 95% pure, m/z 566 [M]$^+$, 568 [M+2]$^+$; $^1$H NMR (CDCl$_3$, 500 MHz) δ 1.13 (d, J=6.5, 6H), 1.57 (m overlapped with water signal, 2H), 1.71 (m, 1H), 1.81 (m, 1H), 2.04-2.18 (m, 4H), 2.34 (s, 3H), 2.78 (m, 5H), 3.06 (br t, J=8.6, 1H), 3.27 (br s, 4H), 3.52-3.59 (m, 2H), 7.47 (t, J=7.3, 1H), 7.57 (td, J=8.4, J=1.1, 1H), 7.84 (d, J=7.8, 1H), 8.19 (s, 1H), 8.27 (d, J=8.4, 1H), 8.57 (s, 1H), 10.38 (br t, J=5.6, 1H) ppm.

EXAMPLE 28

Example 28 describes a method for preparing a substituted benzoxazine analog from reaction of the corresponding ester with an amine, and aluminum chloride.

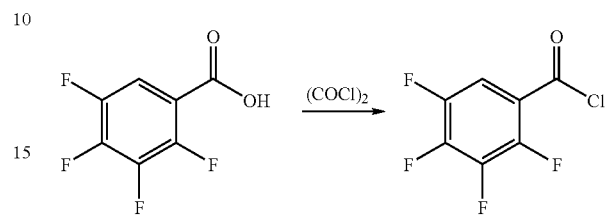

To a solution of 2,3,4,5-tetrafluorobenzoic acid (100 g, 510 mmol), in methylene chloride (0.5 L) was added oxalyl chloride (68 g, 540 mmol) and DMF (ca 3 drops) and the reaction mixture was allowed to stir at room temperature overnight allowing for the produced gasses to escape. The solvent was removed in vacuo and the vessel was placed on high vacuum (ca 0.5 mm Hg) for 2 hours to afford the acid chloride as a viscous oil (105 g) and was used in the subsequent reaction without further purification.

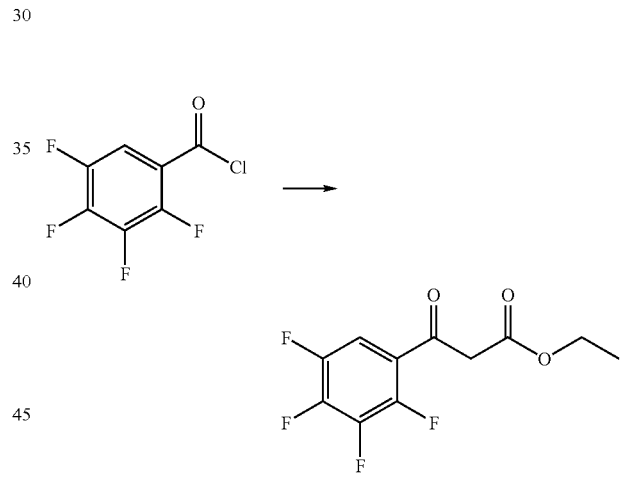

To a suspension of potassium ethyl malonate (97 g, 570 mmol) and magnesium chloride (55 g, 570 mmol) in acetonitrile and the suspension was chilled to 0° C. To this suspension was added the crude 2,3,4,5-benzoyl chloride (105 g, 520 mmol) over 5 minutes. Triethylamine was slowly added at a rate sufficient to keep the reaction temperature below 10° C. and the mixture was allowed to warm to room temperature and was stirred overnight. The solvent was removed in vacuo and replaced with toluene (300 mL) and 1N HCl (500 mL) was added and the mixture was allowed to stir for 1 hour. The organic layer was separated and washed with 1N HCl (100 mL) and brine (100 mL) and dried over sodium sulfate, filtering over a pad of silica gel (50×100 mm), eluting with ethyl acetate. The solvent was removed in vacuo and the resulting oil was dissolved in ethanol/water (9:1) and was allowed to crystallize overnight. The resulting crystals were Isolated by filtration, washing with ethanol/water (8:2) to afford the ketoester (43.75 g, 166 mmol) as a white crystalline solid.

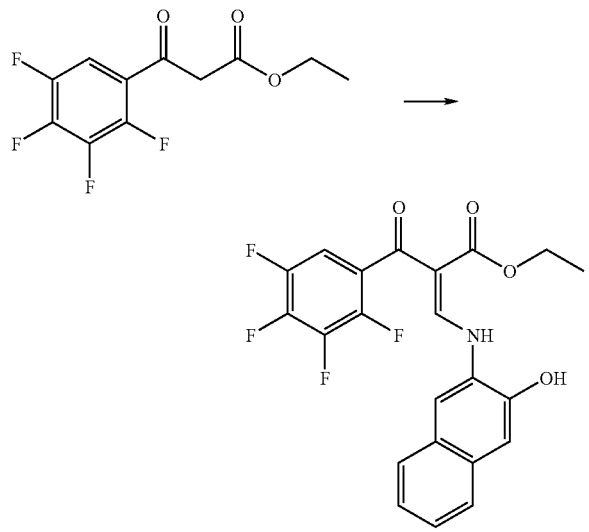

To a 250 mL round bottom flask was added the tetrafluoroketoester (10.0 g, 37.9 mmol), triethylorthoformate (8.6 mL, 56.8 mmol) and acetic anhydride (7.15 mL, 75.8 mmol) and the reaction mixture was heated to 145° C. for 2 hours. The reaction was allowed to cool to room temperature and placed on high vacuum (ca 0.5 mm Hg) for 1 hour. The resulting oil was dissolved in ethanol (100 mL) and 2-amino-1-naphthol (6.02 g, 37.9 mmol) was added at room temperature and the solution became briefly clear and then product began to precipitate. The reaction was allowed to stir for 2 hours and was then filtered and washed with ethanol (100 mL) to afford the enamine as a yellow solid (12.5 g, 28.9 mmol).

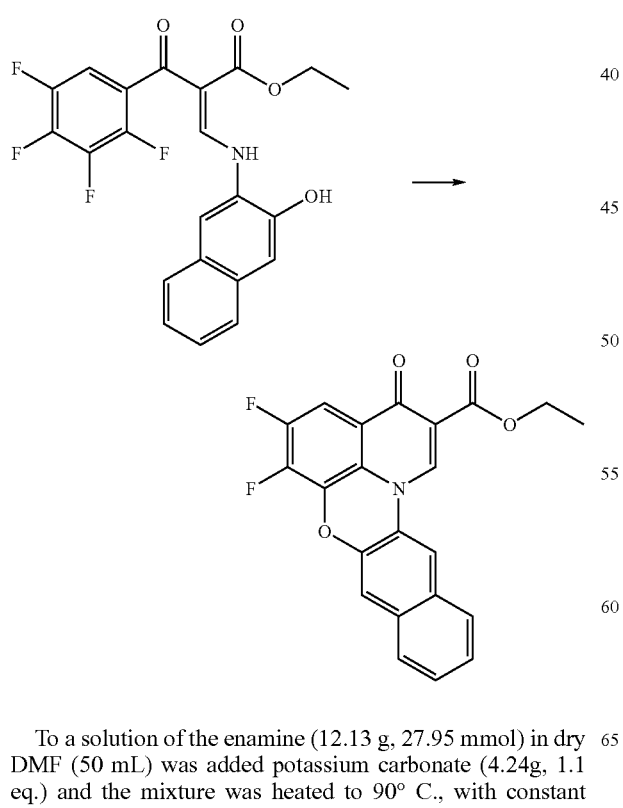

To a solution of the enamine (12.13 g, 27.95 mmol) in dry DMF (50 mL) was added potassium carbonate (4.24g, 1.1 eq.) and the mixture was heated to 90° C., with constant stirring, for 2 hours. The mixture was allowed to cool to room temperature without stirring and was allowed to remain at room temperature for an additional hour. The crystalline solid was collected by filtration, washing with water. Recrystallization from THF afforded the difluoroester as a white crystalline solid (9.3 g, 23.6 mmol).

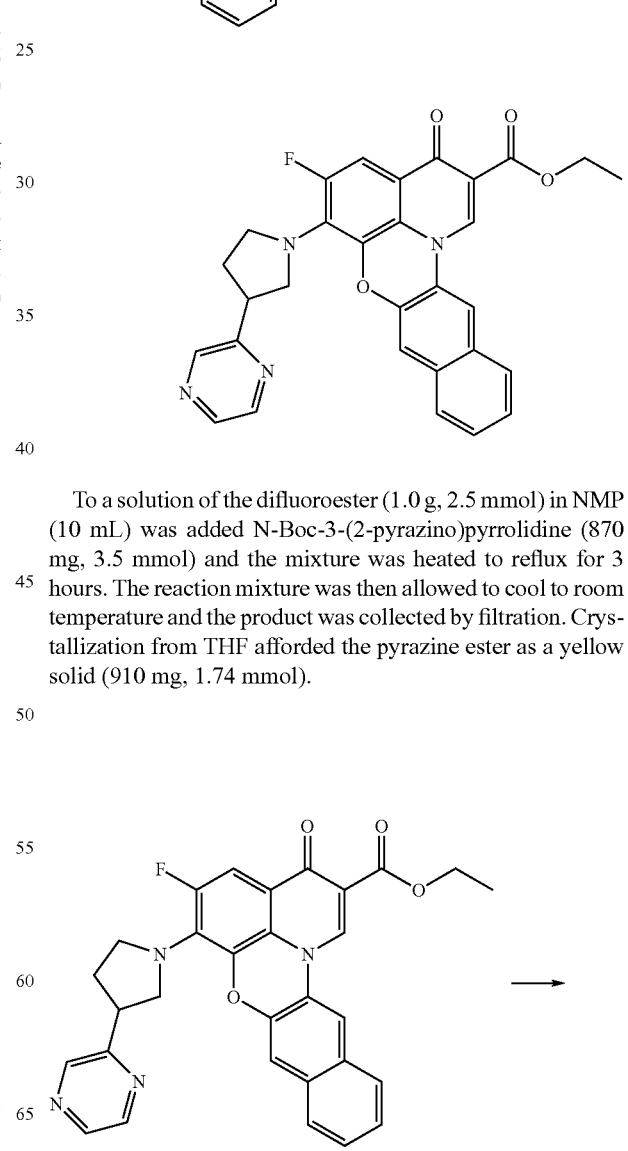

To a solution of the difluoroester (1.0 g, 2.5 mmol) in NMP (10 mL) was added N-Boc-3-(2-pyrazino)pyrrolidine (870 mg, 3.5 mmol) and the mixture was heated to reflux for 3 hours. The reaction mixture was then allowed to cool to room temperature and the product was collected by filtration. Crystallization from THF afforded the pyrazine ester as a yellow solid (910 mg, 1.74 mmol).

-continued

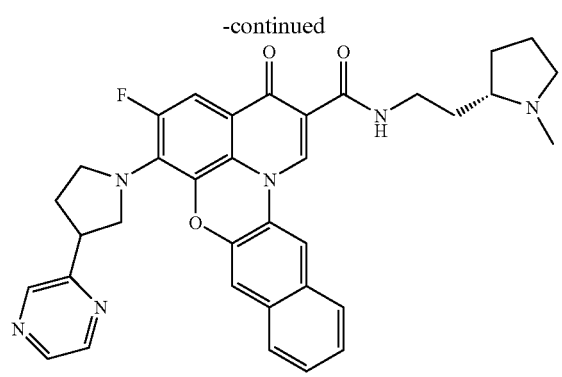

To a solution of the pyrazine ester (250 mg, 0.48 mmol) and 2-(2-aminoethyl)-1-methylpyrrolidine (80 mg, 0.63 mmol) in methylene chloride at room temperature was added aluminum chloride (83 mg, 0.63 mmol) and the reaction mixture was allowed to stir for 2 hours. The solvent was removed in vacuo and saturated L-tartaric acid was added (5 mL) and the mixture was allowed to stir for 1 hour. Methylene chloride (10 mL) was then added and the mixture was basified with 1N NaOH. The organic layer was separated and washed with a saturated solution of Rochelle's salt, brine and dried over sodium sulfate. The solvent was removed in vacuo and the resulting solid was dissolved in THF and filtered and the solvent was removed again. The crude solid was recrystallized in ethyl acetate to afford the amide as a yellow solid (225 mg, 0.37 mmol, 98.5% pure).

EXAMPLE 29

As shown in Example 29, amide coupling from the corresponding ester resulted in slight or no reaction, where zinc chloride was used as the Lewis acid.

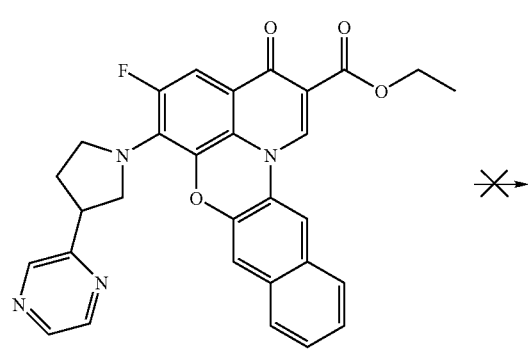

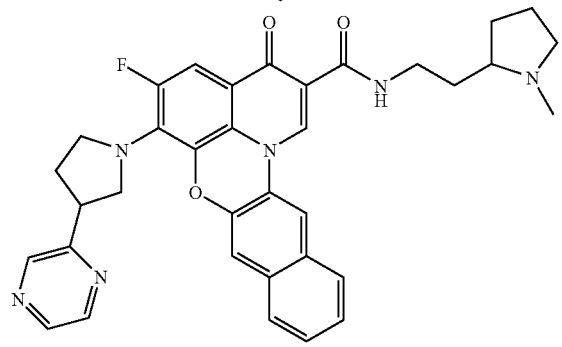

To a solution of the ester (100 mg, 0.19 mmol) and 2-(2-aminoethyl)-1-methylpyrrolidine (80 mg, 0.63 mmol) in methylene chloride at room temperature was added zinc chloride (86 mg, 0.63 mmol) and the reaction mixture was allowed to stir overnight. LCMS indicated that there was no reaction progress, and the reaction was discontinued.

EXAMPLE 30

Example 30 describes a method for preparing a substituted benzoxazine analog from reaction of the corresponding carboxylic acid with an amine.

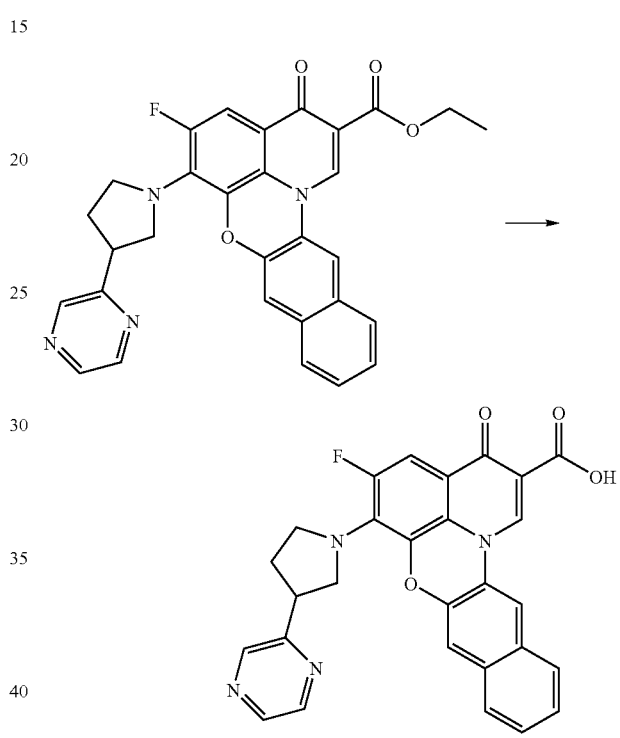

The pyrazinoester (2.0 g, 3.8 mmol) was dissolved in ethanol (100 mL) and conc HCl was added (20 mL) and the mixture was refluxed overnight. The mixture was allowed to cool to room temperature and the solid was collected by vacuum filtration, washing with ethanol to afford the pyrazinoacid as a light tan powder (1.6 g, 3.2 mmol).

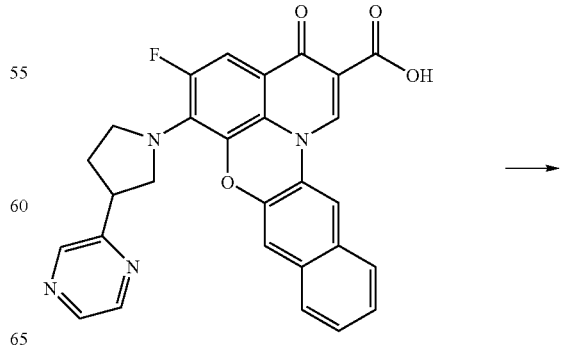

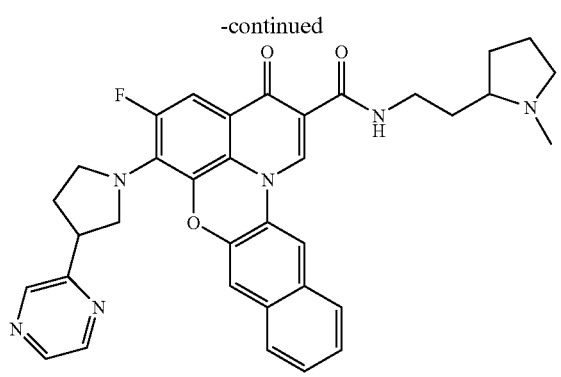

To a mixture of the fluoroaminoacid (1.6 g, 3.2 mmol) and HBTU (2.0g, 5.3 mmol) in NMP (20 mL) was added N,N-diisopropyl-N-ethylamine (1.0 mL, 6 mmol) and the mixture was allowed to stir at room temperature, under argon, for 1 hour (the solution became clear). (S)-2-(2-aminoethyl)-1-methylpyrrolidine (Mizuno, A.; Hamada, Y.; Shioiri, T., Synthesis, 1980, 12 1007)(1.0 mL, 6.9 mmol) was added and the mixture was allowed to stir for 30 minutes. Water (200 mL) was added and the resulting solid was collected by vacuum filtration, washing with water, and dried to afford the pyrazine as a yellow solid. The yellow solid was purified on silica gel (10% MeOH/CH$_2$Cl$_2$ first eluting off impurities followed by eluting with 5% NH$_4$OH/15% MeOH/CH$_2$Cl$_2$. The combined fractions were evaporated to afford the compound as a yellow solid. (1.2 g, 2.0 mmol, 85% pure).

EXAMPLE 31

Example 31 describes the preparation of a Boc-protected pyrrolidine reagent, used as an intermediate in the preparation of benzoxazine and benzothiazole compounds.

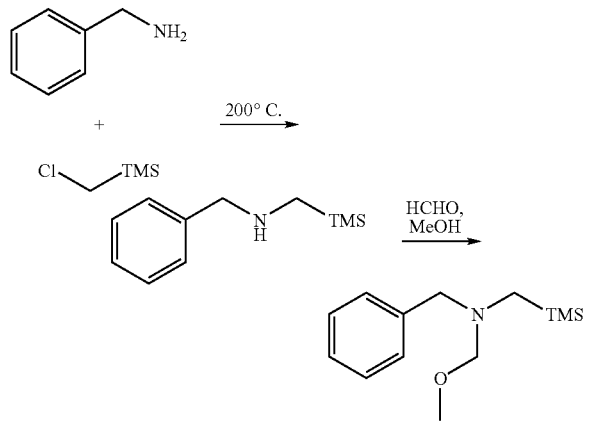

A mixture of benzyl amine (90 g, 841 mmol) and chloromethyltrimethylsilane (30 g, 246 mmol) was heated at 200° C. for 2.5 hours. In general, the trimethylsilyl group may be replaced with a —SiR$^1$R$^2$R$^3$ moiety, wherein R$^1$, R$^2$ and R$^3$ are independently alkyl or substituted alkyl. The benzyl groups may also be replaced with other suitable protecting groups.

The mixture was allowed to cool to room temperature and treated with 1N sodium hydroxide (250 mL) and ether (200 mL) with stirring. The aqueous layer was extracted with ether (3×100 mL) and the combined organic extracts were washed with brine, dried over magnesium sulfate and filtered over a pad of silica gel (70×50 mm), eluting with ether. The solvent was removed in vacuo and the resulting oil was vacuum distilled (bp=70° C. ca 1 mm Hg) to afford the amine as a colorless oil (60.8 g) that contained a significant amount of benzyl amine. The resulting oil was then chromatographed on a single biotage column (90 g, silica gel, ANALOGIX) eluting with ethyl acetate. The solvent was removed in vacuo to afford the pure amine as a colorless oil (43.55 g, 225 mmol). The resulting amine was then added to 37% formalin (25 mL) and the mixture was stirred at room temperature for 10 minutes, followed by the addition of methanol (25 mL) and potassium carbonate (20 g). The resulting mixture was allowed to stir overnight and then extracted with methylene chloride (3×100 mL) and the combined organic extracts were dried with sodium sulfate. The solvent was removed in vacuo and the resulting oil was vacuum distilled (bp=80° C. ca 1 mm Hg) to afford the amine as a colorless liquid (39.9 g, 168 mmol).

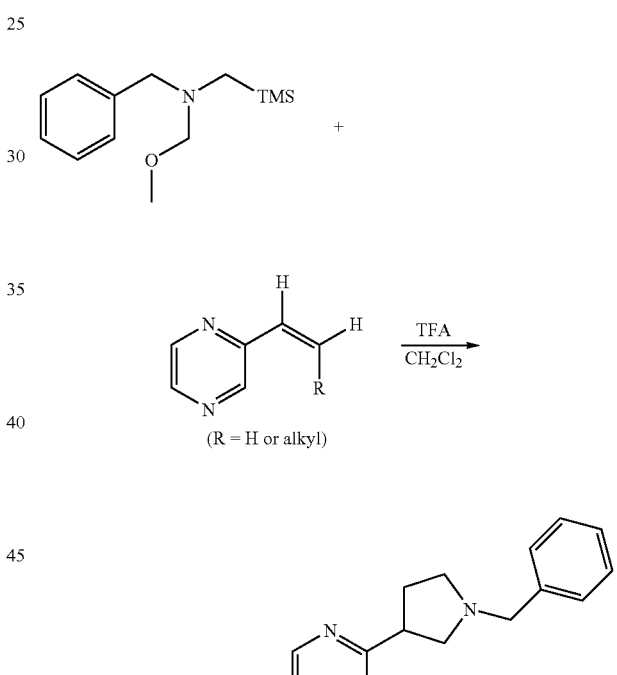

To a solution of vinylpyrazine (10 g, 94.3 mmol) in methylene chloride (200 mL) and trifluoroacetic acid (2 mL) was added dropwise a solution of the silylated amine ether (24.33 g, 102.7 mmol) dissolved in methylene chloride (100 mL) over 4 hours. The volume was then reduced to 100 mL and extracted with 1N HCl (3×75 mL). The aqueous layer was then basified with NaOH and extracted with methylene chloride (3×100 mL), dried over magnesium sulfate and filtered over a pad of silica gel (30×150 mm) eluting with ethyl acetate. The solvent was evaporated to afford the benzylated pyrazinopyrrolidine (26.19 g) as a brownish clear liquid. In general, the pyrazine heterocycle may be replaced with other suitable heterocyclic groups.

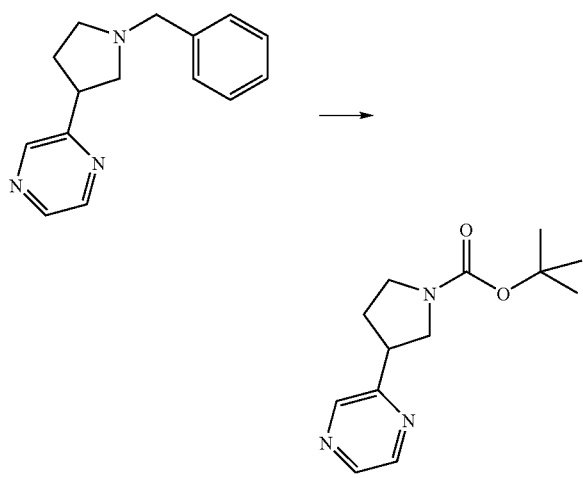

To a solution of the benzyl pyrrolidine (7.0 g, 29.3 mmol) and di-tert-butyldicarbonate (44.7 g, 205 mmol) in methanol (35 mL) was added 10% Pd/C (degussa type, wet) and the vessel was pressurized with Hydrogen (50 PSI) with shaking. The vessel was vented 3 times to control pressure. After 5 hours the reaction was complete and the mixture was filtered and the solvent was removed in vacuo. The resulting material was chromatographed on silica gel (1:1 hexanes/ethyl acetate) to afford the Boc protected pyrrolidine as a light yellow oil (2.3 g, 9.2 mmol).

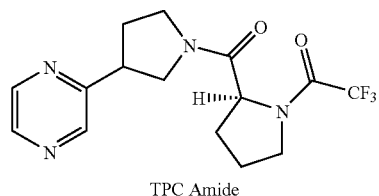

TPC Amide

Enantiomeric ratios can be determined by making a TPC (N-trifluoromethylacetyl-L-prolyl chloride, Regis #440001) and using GCMS (HP 6890N/5973 MSD) on a Phenomenex Zebron capillary column (ZB-50, 50% Phenyl, 50% Diemthylpolysiloxane, 30M×0.25 mm, 0.25 uM film thickness). Chromatography conditions: 1 µL injection split 50:1. Constant Flow He=1.0 mL/min. Oven; 100° C. for 5 min, 5° C./min to 300° C. and hold for 8 minutes. The compound comes at 39.08 and 39.31 min but the resolution is very good.

EXAMPLE 32

Example 32 describes the preparation of a chiral amine reagent used in amide coupling.

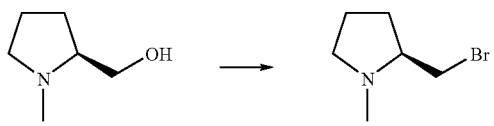

To a solution of the hydroxymethyl pyrrolidine (50 g, 434 mmol) in methylene chloride (1 L) was added triphenylphosphine (148 g, 564 mmol) followed by careful addition of carbon tetrabromide (187 g, 564 mmol) at room temperature. The reaction mixture was allowed to stir for 1 hour at room temperature. Water was added and the organic layer was washed with brine, dried over sodium sulfate and the solvent was removed in vacuo. The resulting oil was purified by silica gel chromatography (1:1 hexanes/ethyl acetate) to afford the bromide as a clear oil (35 g, 197 mmol).

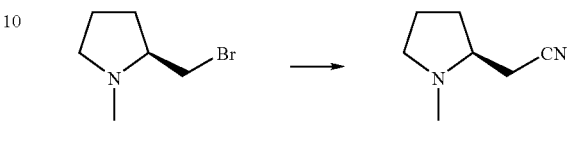

To a solution of the bromide (23.0 g, 129 mmol) in a solution of acetonitrile and water (75:15, 200 mL) was added potassium cyanide (12.6 g, 194 mmol) and 18-crown-6 (340 mg, 1.3 mmol) and the reaction was allowed to stir overnight at room temperature. The volume was then reduced to 50 mL, under vacuum, and was extracted twice with methylene chloride (2×200 mL). The resulting extracts were combined and washed with brine, dried over sodium sulfate and the solvent was carefully removed in vacuo to afford the cyanide as a clear oil (17 g).

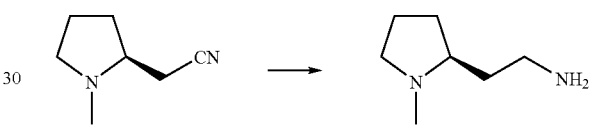

To a solution of the cyanide (17 g, 137 mmol) in methanol (90 mL) was added Raney Nickel (2.0 g, water solution) and the mixture was pressurized with hydrogen (60 PSI) with shaking for 24 hours. The solution was filtered and the solvent was removed in vacuo. The pure amine was isolated by distillation (BP=50° C., ca 10 mm Hg) as a clear oil (7.54 g, 58.9 mmol).

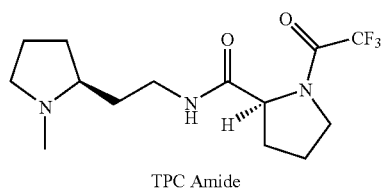

TPC Amide

Enantiomeric ratios can be determined by making a TPC (N-trifluoromethylacetyl-L-prolyl chloride, Regis #440001) and using GCMS (HP 6890N/5973 MSD) on a Phenomenex Zebron capillary column (ZB-50, 50% Phenyl, 50% Diemthylpolysiloxane, 30M×0.25 mm, 0.25 uM film thickness). Chromatography conditions: 1 µL injection split 50:1. Constant Flow He=1.0 mL/min. Oven; 100° C. for 5 min, 5° C./min to 300° C. and hold for 8 minutes. The compound comes at 28.51 and 28.68 min but the resolution is very good.

It is understood that the foregoing detailed description and accompanying examples are merely illustrative, and are not to be taken as limitations upon the scope of the invention. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof. U.S. patents and publications referenced herein are incorporated by reference.

EXAMPLE 33

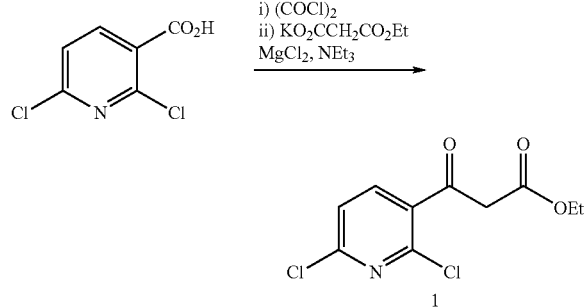

To a solution of the 2,6-dichloronicotinic acid (1.0 eq, 31.24 g, 162.7 mmol) in methylene chloride (500 mL) was added oxalyl chloride (1.2 eq, 23.7 g, 187.5 mmol) followed by 3 drops of DMF and the mixture was allowed to stir overnight at room temperature. The solvent was then removed in vacuo to afford the crude acid chloride as oil. In a separate flask was dissolved potassium ethyl malonate (1.5 eq., 41.5 g, 244 mmol) in acetonitrile (500 mL) and the mixture was cooled to 5° C. Magnesium chloride (1.5 eq, 23.4 g, 245.8 mmol) was then added over 5 minutes, keeping the temperature below 25° C. The crude acid chloride was then dissolved in acetonitrile (50 mL) and was added via dropping funnel keeping the temperature below 5° C. over 30 minutes. Triethylamine (2.0 eq, 42.8 ml, 325 mmol) was then added as quickly as possible while still keeping the temperature below 10° C. Upon complete addition the reaction was allowed to warm to room temperature overnight with constant stirring. The solvent was removed in vacuo and replaced with ethyl acetate. 1N HCl was added (500 mL) and the mixture was stirred for an additional 30 minutes. The organic layer was separated, washed with brine and dried over sodium sulfate and the solvent was removed in vacuo to afford the ketoester as orange oil (35.04 g). The product was purified by recrystalization from 10% water/methanol to afford the pure ketoester 1 as a white crystalline solid (31.21 g, 74%). LCMS (ES): 95% pure, elutes as 2 peaks, m/z 216, 262.

EXAMPLE 34

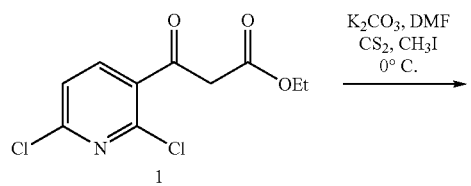

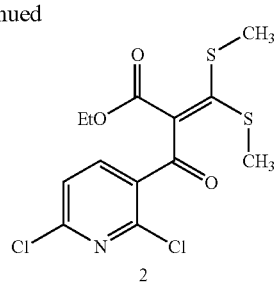

Ketoester 1 (1.0 eq, 11.45 g, 43.87 mmol) was dissolved in DMF (60 ml) and the mixture was chilled to 0° C. with an ice bath. Methyl iodide (3.0 eq, 8.2 ml, 132.mmol) was then added and the mixture was cooled to −5° C. Carbon disulfide was then added (1.5 eq, 4.0 mL, 65.8 mmol) followed by potassium carbonate (2.0 eq, 12.1 g, 88 mmol) keeping the temperature below 5° C. The mixture was allowed to warm to room temperature with stirring over 2 hours then was extracted with ethyl acetate (5×100 mL) and dried over sodium sulfate. The solvent was removed in vacuo and the resulting oil was purified by silica gel chromatography (10% ethyl acetate/hexanes) to afford the bisthioether 2 as a yellow oil (70% yield). LCMS (ES): 90% pure, m/z 388 [M+22]$^+$, 320 [M+1−OEt]$^+$.

EXAMPLE 35

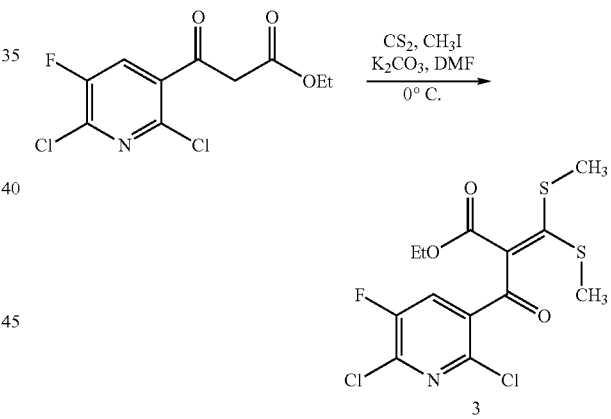

Ethyl 2,6-dichloro-5-fluoro-3-pyridine-β-keto propionate (1.0 eq., 31.79 g, 0.113 mol) was dissolved in DMF (180 ml). The solution was cooled down using an ice-salt mixture. Iodomethane (3.0 eq, 21 ml, 0.887 mol) and carbon disulfide (1.5 eq, 10.3 ml, 0.170 mol) were added and the mixture stirred until internal temperature reached T=−2° C. K$_2$CO$_3$ (2.0 eq, 31.4 g, 0.227 mmol) was added fairly quickly (over 2-3 min) which induced the internal temperature to reach T=12° C. The mixture was stirred in an ice bath for 5 hours. After adding water and brine, the compound was extracted with EtOAc (3×). The combined extracts were washed with brine (2×), dried over Na$_2$SO$_4$ and the volatiles removed in vacuo. Purification by flash chromatography on silica gel (5 to 30% gradient of EtOAc in hexanes) afforded compound 3 as a thick yellow oil (22.86 g, 52% yield). Rf=0.14 (10% EtOAc in hexanes) ; LCMS (ES): 95% pure, m/z 384 [M]$^+$, 338 [M−EtOH]$^+$, 340 [M+2−EtOH]$^+$, 342 [M+4−EtOH]$^+$; $^1$H NMR (CDCl₃, 500 MHz) δ 1.16 (t, J=7.4, 3H), 2.43 (s, 6H), 4.18 (q, J=7.4, 2H), 7.86 (dd, J=0.6, J=7.4, 1 H) ppm.

EXAMPLE 36

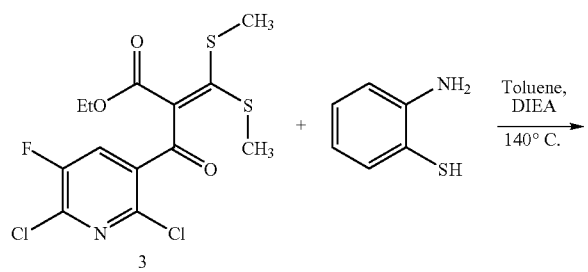

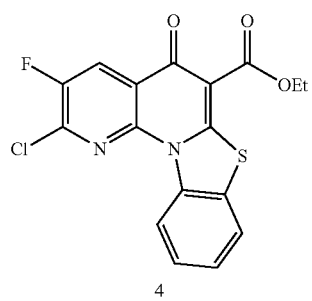

Compound 3 (1.0 eq, 18.93 g, 49.18 mmol) was dissolved in toluene (400 ml). The solution was carefully degassed by bubbling nitrogen for 10 min. After adding of 2-aminothiophenol (0.9 eq, 4.7 ml, 43.92 mmol) the mixture was stirred at 130-140° C. (oil bath temperature) for 6 hours with continuous bubbling of nitrogen inside the reaction. DIEA (1.0 eq, 8.6 ml, 49.37 mmol) was added and the mixture was stirred at 140° C. overnight. Upon cooling, compound 4 started to precipitate. The solid was filtered and washed with a bit of toluene. The material was suspended in MeOH and sonicated for a few minutes. After filtration and drying, compound 4 was isolated as a tan solid (9.19 g, 56% yield). LCMS (ES): 95% pure, m/z 377 [M+1]⁺, 379 [M+3]⁺, 331 [M+1−EtOH]⁺, 333 [M+3−EtOH]⁺; ¹H NMR (CDCl₃, 500 MHz) δ 1.50 (t, J=7.0, 3H), 4.53 (d, J=7.0, 2H), 7.52 (td, J=0.9, J=7.1, 1H), 7.63 (td, J=1.4, J=6.0, 1H), 7.84 (dd, J=1.2, J=7.9, 1H), 8.62 (d, J=7.4, 1H), 9.49 (d, J=8.6, 1H) ppm.

EXAMPLE 37

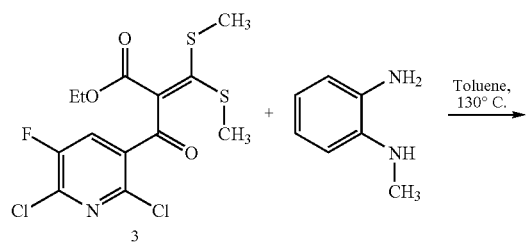

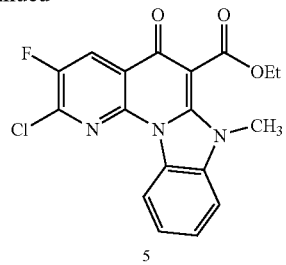

In a vial, compound 3 (1.0 eq., 202 mg, 0.526 mmol) and N-methyl-benzene-1,2-diamine (1.0 eq., 60 μl, 0.528 mmol) were stirred at 130° C. in anhydrous toluene (5 ml) for 16 hours. After removal of the volatiles in vacuo the crude mixture was purified by flash chromatography on silica gel (gradient 0.5 to 3% MeOH in CH₂Cl₂). Upon addition of MeOH to the resulting oil, pure 5 precipitated out. The material was filtered and dried to afford 5 as a yellow solid (29 mg, 15% yield).). Rf=0.26 (5% MeOH in CH₂Cl₂) ; LCMS (ES): 95% pure, m/z 374 [M+1]⁺, 376 [M+3]⁺, 328 [M+1−EtOH]⁺, 330 [M+3−EtOH]⁺; ¹H NMR (CDCl₃, 500 MHz) δ 1.47 (t, J=7.0, 3H), 3.70 (s, 3H), 4.50 (q, J=7.0, 2H), 7.37 (dd, J=8.1, J=1.0, 1H), 7.44-7.51 (m, 2H), 8.55 (d, J=7.6, 1H), 8.94 (dd, J=1.1, J=8.1, 1H) ppm.

EXAMPLE 38

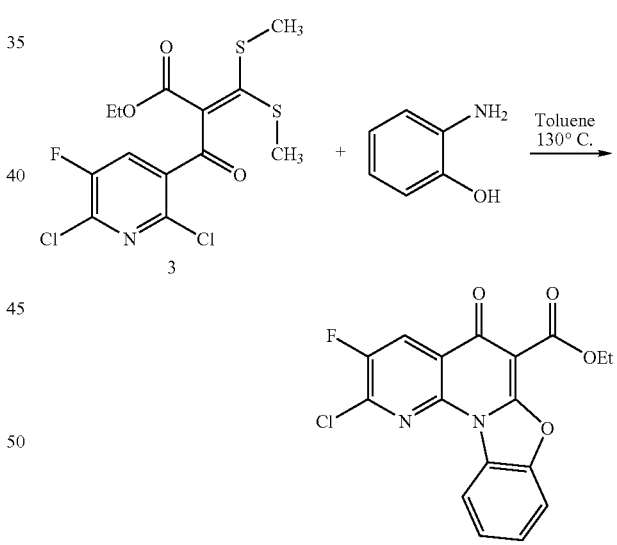

In a vial, compound 3 (1.0 eq., 221 mg, 0.575 mmol) and 2-aminophenol (1.1 eq., 70 mg, 0.641 mmol) were stirred at 130° C. in anhydrous toluene (5 ml) for 6 hrs. After cooling down the mixture, a brown precipitate that formed was filtered. This material was dissolved in CH₂Cl₂ and the solution filtered through a pad of celite. Recrystallization in toluene afforded 6 (48 mg, 24% yield) as a beige solid. LCMS (ES): 95% pure, m/z 361 [M+1]⁺, 363 [M+3]⁺, 315 [M+1−EtOH]⁺, 317 [M+3−EtOH]⁺; ¹H NMR (CDCl₃, 500 MHz) shows purity around 80%, δ 1.46 (t, J=7.0, 3H), 4.50 (q, J=7.3, 2H), 7.48-7.54 (m, 2H), 7.65 (dd, J=1.4, J=7.9, 1H), 8.57 (d, J=7.4, 1H), 8.68 (dd, J=1.4, J=7.9, 1H) ppm.

EXAMPLE 39

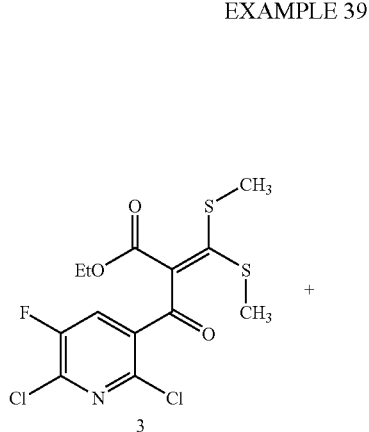

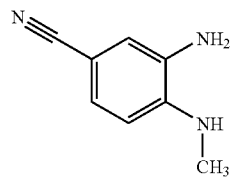

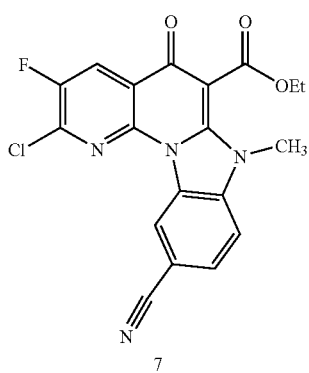

In a vial, compound 3 (1.0 eq., 266 mg, 0.692 mmol) and 3-amino-4-(methylamino)benzonitrile (1.0 eq., 100 mg, 0.689 mmol) were stirred at 130° C. in anhydrous toluene (5 ml) for 2 days. After evaporation of the solvents, the crude mixture was passed through a silica gel column (0.5 to 3% gradient of MeOH in CH$_2$Cl$_2$). Purification by preparative TLC on silica gel (1 mm, two plates, 4% MeOH in CH$_2$Cl$_2$) afforded compound 7 as a yellow solid (32 mg, 12% yield). LCMS (ES): 95% pure, m/z 399 [M+1]$^+$, 401 [M+3]$^+$, 353 [M+1−EtOH]$^+$, 355 [M+3−EtOH]$^+$; $^1$H NMR (CDCl$_3$, 500 MHz) δ1.47 (t, J=7.1, 3H), 3.72 (s, 3H), 4.51 (q, J=7.3, 2H), 7.42 (d, J=8.4, 1H), 7.79 (dd, J=1.5, J=8.4, 1H), 8.55 (d, J=7.3, 1H), 9.22 (d, J=1.4, 1H) ppm.

EXAMPLE 40

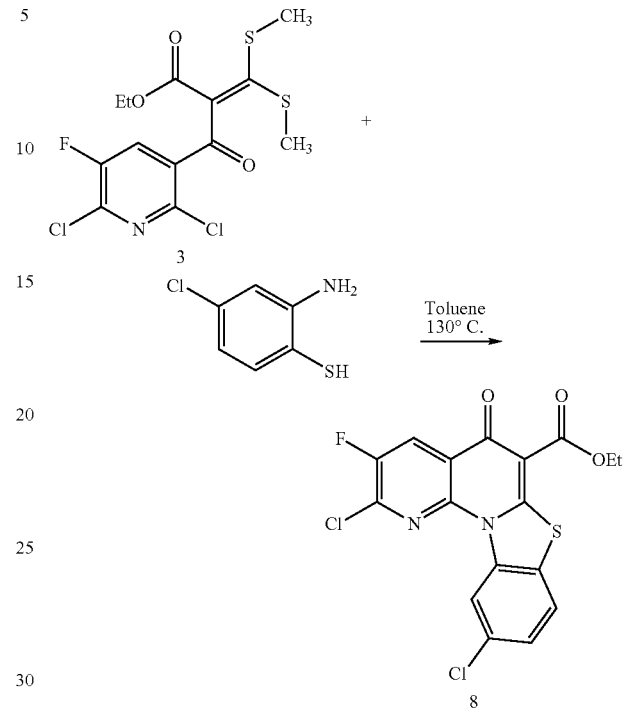

In a vial, compound 3 (1.0 eq., 288 mg, 0.749 mmol) and 2-amino-4-chloro benzenethiol (1.0 eq., 120 mg, 0.752 mmol) were stirred at 130° C. in anhydrous toluene (5 ml) for 2 days. The solid formed during the reaction was filtered and dissolved in a mixture of MeOH and CH$_2$Cl$_2$ (200 ml). The resulting cloudy solution was filtered through a pad of celite. After evaporation of the volatiles, the material was purified by flash chromatography on silica gel (CH$_2$Cl$_2$ then 0.5% MeOH in CH$_2$Cl$_2$). Compound 8 was isolated as a yellow solid (20 mg, 6% yield). LCMS (ES): >85% pure, m/z 411 [M]$^+$, 413 [M+2]$^+$, 415 [M+4]$^+$, 365 [M−EtOH]$^+$, 367 [M+2−EtOH]$^+$, 369 [M+4−EtOH]$^+$.

EXAMPLE 41

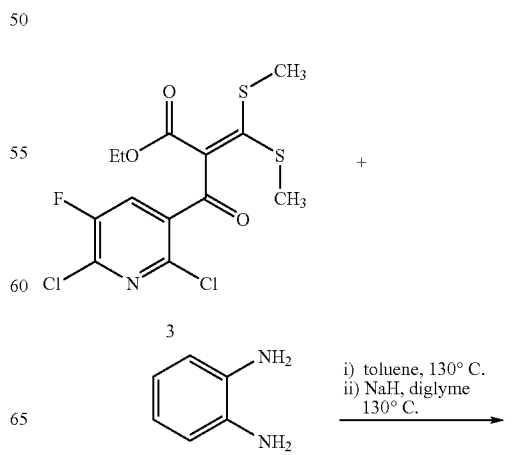

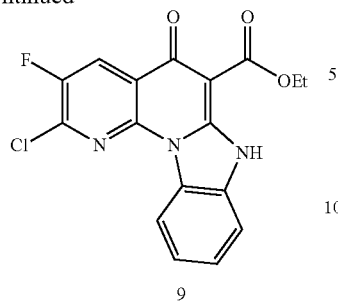

9

In a vial, compound 3 (1.0 eq, 255 mg, 0.664 mmol) and benzene-1,2-diamine (1.0 eq, 72 mg, 0.666 mmol) were stirred at 130° C. in anhydrous toluene (5 ml) for 5 hours. The volatiles were removed in vacuo and the material dissolved in diglyme (2 ml). A 60% suspension of NaH in oil (1.0 eq, 26 mg, 0.63 mmol) was added and the mixture stirred at 130° C. for 3 hours. The resulting precipitate was filtered and washed with water. After trituration in MeOH and filtration, compound 9 was isolated as a brown solid (91 mg, 38% yield). LCMS (ES): 95% pure, m/z 360 [M+1]$^+$, 362 [M+3]$^+$; $^1$H NMR (CDCl$_3$, 500 MHz) δ 1.44 (t, J=7.1, 3H), 4.44 (q, J=7.1, 2H), 7.40-7.46 (m, 2H), 7.49 (m, 1H), 8.50 (d, J=7.7, 1H), 8.81 (d, J=6.8, 1H) ppm.

EXAMPLE 42

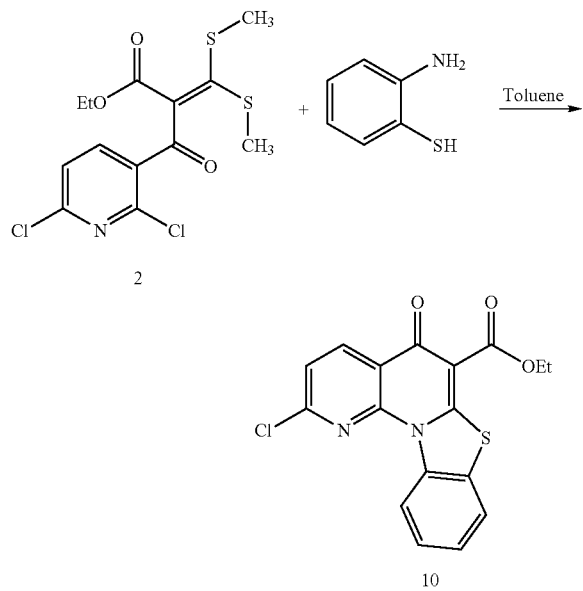

10

To a solution of the bisthioether 2 (1.0 eq, 10.14 g, 27.7 mmol) in toluene (300 mL) was added 2-aminothiophenol (1.1 eq, 3.81 g, 30.5 mmol) and the mixture was refluxed overnight with constant nitrogen degassing. The mixture was then allowed to cool to room temperature and diisopropyl ethylamine (1.5 eq, 7.0 mL, 41.55 mmol) was added and the mixture was heated to reflux for 3 hours. The mixture was allowed to cool to room temperature and the product was collected by filtration to afford the cyclized ester 10 as a tan solid (6.6 g, 66% yield)). LCMS (ES): 95% pure, m/z 359 [M+1]$^+$.

EXAMPLE 43

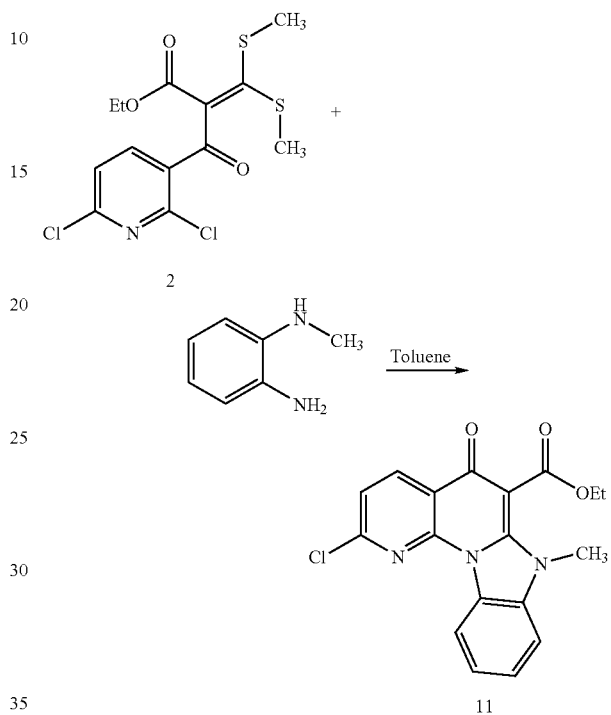

11

To a solution of the bisthioether 2 (1.0 eq, 5.0 g, 13.66 mmol) in toluene (150 ml) was added N-methyl-1,2-phenylenediamine (1.2 eq, 2.0 g, 16.4 mmol) and the mixture was refluxed overnight with constant nitrogen degassing. The mixture was then allowed to cool to room temperature and diisopropyl ethylamine (1.5 eq, 3.5 mL, 20.75 mmol) was added and the mixture was heated to reflux for 3 hours. The mixture was allowed to cool to room temperature and methanol was added. The volume was reduced to about 100 ml by rotary evaporation and allowed to sit for 2 days. The product was collected by filtration and recrystallized from ethanol to afford the cyclized ester 11 as a tan solid (2.6 g, 53% yield). LCMS (ES): 95% pure, m/z 356 [M+1]$^+$.

EXAMPLE 44

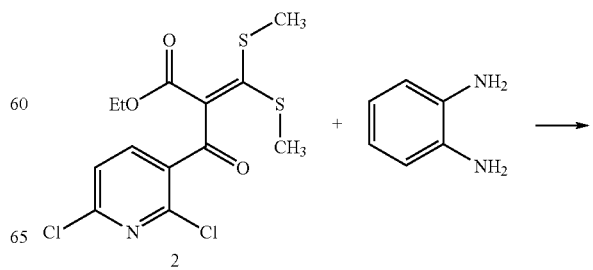

-continued

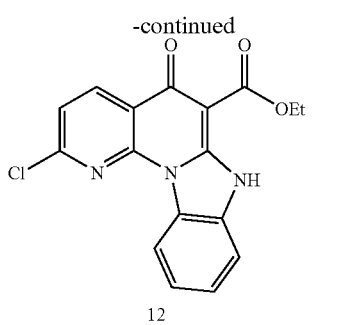

12

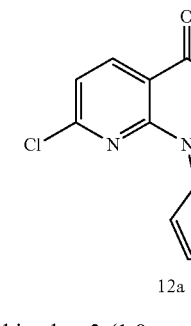

12a

To a solution of the bisthioether 2 (1.0 eq, 10.14 g, 27.7 mmol) in toluene (300 mL) was added 1,2-phenylenediamine (1.1 eq, 3.3 g, 30.5 mmol) and the mixture was refluxed overnight with constant nitrogen degassing. The mixture was then allowed to cool to room temperature and diisopropyl ethylamine (1.5 eq, 7.0 mL, 41.55 mmol) was added and the mixture was heated to reflux for 3 hours. The mixture was allowed to cool to room temperature and the product was collected by filtration to afford the cyclized acid 12a as a tan solid (3.5 g, 11.2 mmol, 40% yield). LCMS (ES): 95% pure, m/z 314 [M+1]$^+$. The resulting filtrate was concentrated in vacuo and triturated with ether (100 mL). The product was collected by filtration to afford the cyclized ester 12 as a tan solid (3.5 g, 10.3 mmol, 37% yield). LCMS (ES): 95% pure, m/z 342 [M+1]$^+$.

EXAMPLE 45

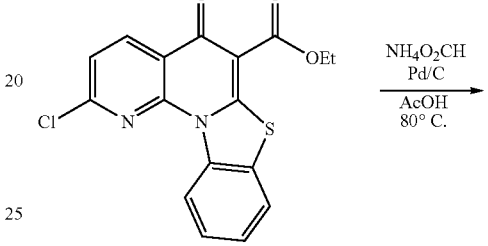

4

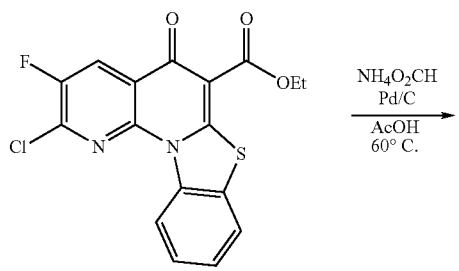

13

Compound 4 (1.0 eq, 1.57 g, 4.17 mmol) was suspended in acetic acid (15 ml). The suspension was degassed by bubbling nitrogen for 10 min. Ammonium Formate (10 eq, 2.63 g, 41.6 mmol) and Pd/C (10% wet degussa type, 2.5 g) were added and the mixture vigorously stirred at 60° C. for 3 hours. The mixture was filtered through a pad of celite. The carbon was treated several times with a hot mixture of CH$_2$Cl$_2$, MeOH and acetic acid to achieve a complete recovery of the expected material. The combined filtrates were evaporated and CH$_2$Cl$_2$ was added. The organic phase was washed with water (2×), dried over Na$_2$SO$_4$ and the solvents removed in vacuo. The resulting solid was sonicated in a mixture of EtOAc and hexanes, filtered and dried to afford pure 13 as an off-white solid (1.11 g, 78% yield). LCMS (ES): 95% pure, m/z 343 [M+1]$^+$.

EXAMPLE 46

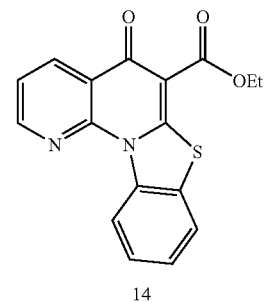

10

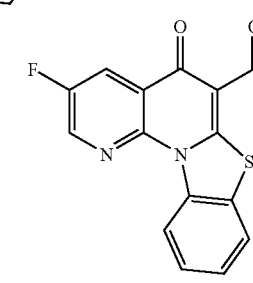

14

Compound 14 was prepared according to the procedure used for product 13 using a higher temperature (80° C.) and longer reaction times. A larger excess of reagents was added several times in order to complete the transformation. The compound was isolated as an off white solid (41 mg, 15% yield). LCMS (ES): 95% pure, m/z 325 [M+1]$^+$.

EXAMPLE 47

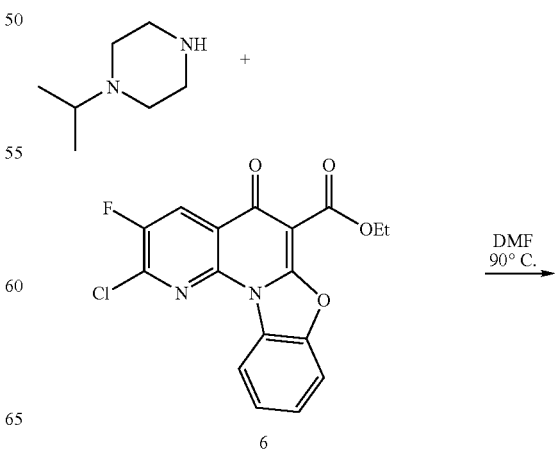

6

-continued

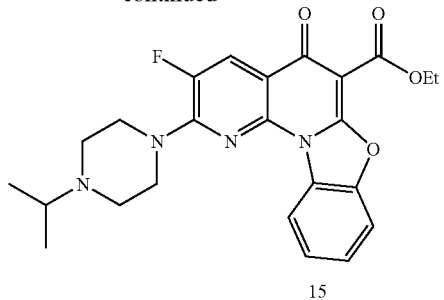

In a vial, compound 6 (1.0 eq., 13 mg, 0.0360 mmol) and N-isopropyl piperazine (4.0 eq., 21 μl, 0.147 mmol) were stirred in DMF (0.1 ml) at 90° C. for 4.5 hrs. After adding water, the precipitate was filtered and dried. The product 15 was purified by precipitation with AcOEt/hexanes to afford a beige solid (7 mg, 43% yield). LCMS (ES): >90% pure, m/z 453 [M+1]$^+$.

The following analogues were prepared by the same method, using the appropriate amines and chloro-azabenzofluorenones.

| Structure | M.W. | LCMS (ES) m/z |
|---|---|---|
| 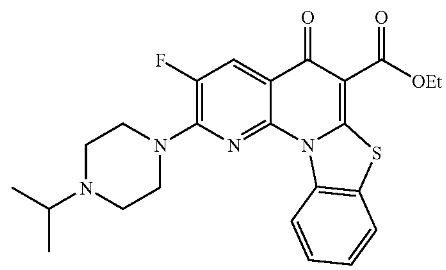 | 468.54 | 469 [M + 1]$^+$ |
| 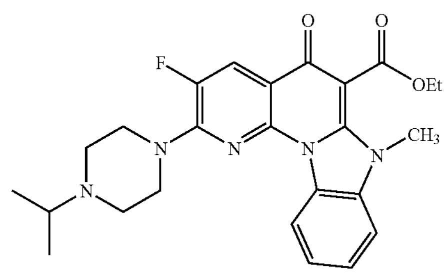 | 465.52 | 466 [M + 1]$^+$ |
| 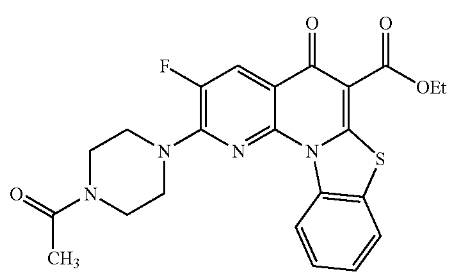 | 468.50 | 469 [M + 1]$^+$ |
| 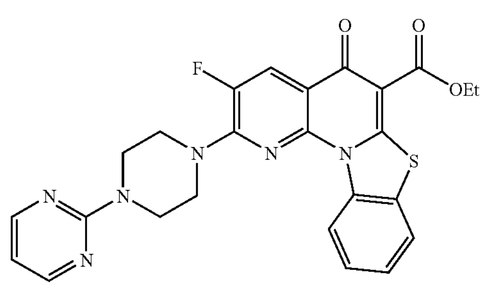 | 504.54 | 505 [M + 1]$^+$ |

-continued

| Structure | M.W. | LCMS (ES) m/z |
|---|---|---|
| 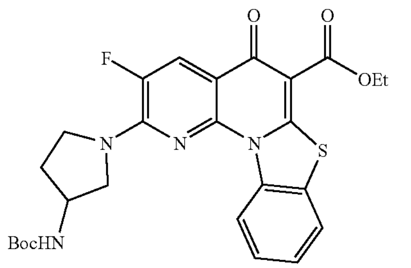 | 526.58 | 527 [M + 1]⁺ |
| 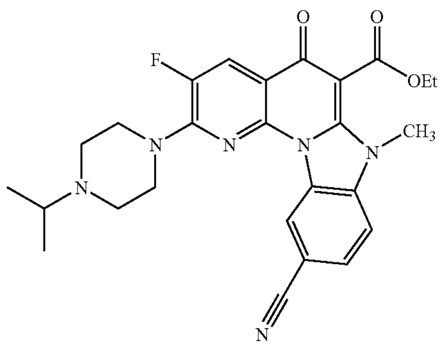 | 490.53 | 491 [M + 1]⁺ |
| 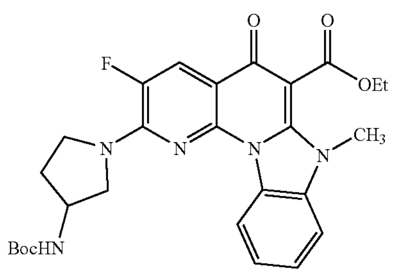 | 523.56 | 524 [M + 1]⁺ |
| 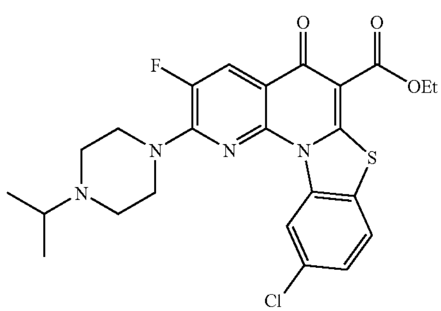 | 502.99 | 503 [M + 1]⁺ |
| 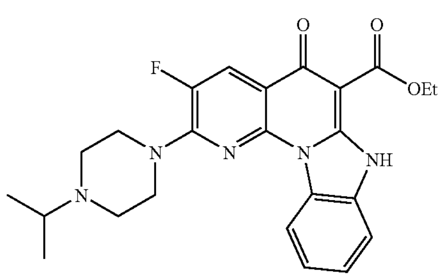 | 451.49 | 452 [M + 1]⁺ |

-continued
| Structure | M.W. | LCMS (ES) m/z |
|---|---|---|
| 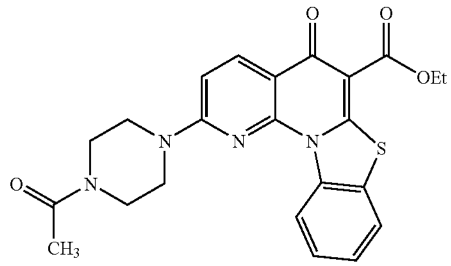 | 450.51 | 451 [M + 1]⁺ |
| 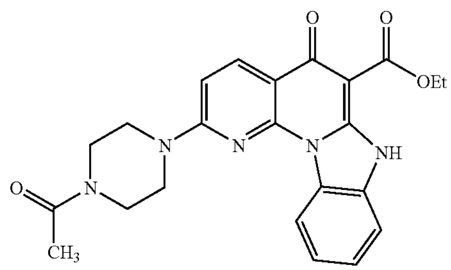 | 433.46 | 434 [M + 1]⁺ |
| 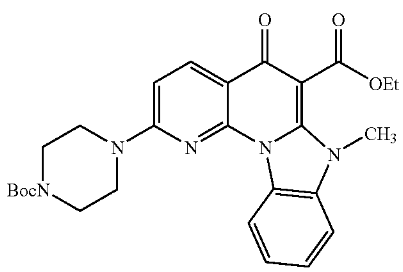 | 505.57 | 506 [M + 1]⁺ |
EXAMPLE 48
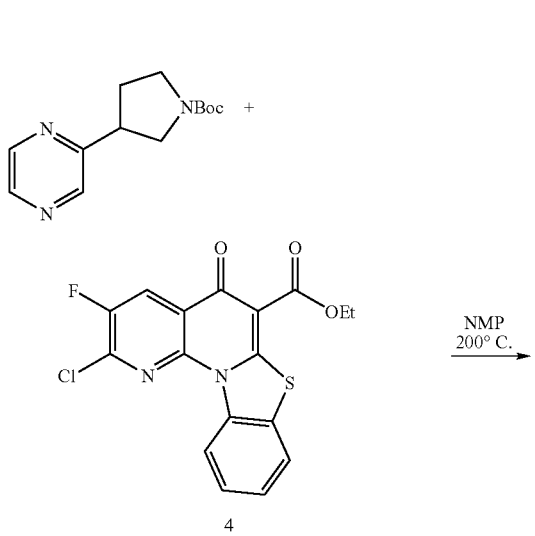
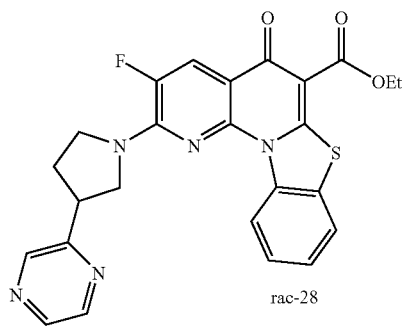
In a vial, compound 4 (1.0 eq., 14 mg, 0.0372 mmol) and racemic tert-butyl 3-(pyrazin-2-yl)pyrrolidine-1-carboxylate (4.0 eq., 50 mg, 0.160 mmol) were stirred in anhydrous NMP (0.2 ml) at 200° C. for 1 hr. After adding water, the precipitate was filtered and dried. This material was purified by preparative TLC on silica gel (1 mm plate, eluted twice with 4%

MeOH in CH₂Cl₂). Compound 28 was isolated as a brown solid (9 mg, 50% yield). LCMS (ES): 90% pure, m/z 490 [M+1]⁺.

EXAMPLE 49

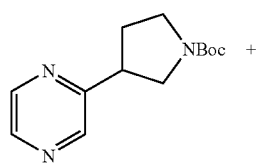

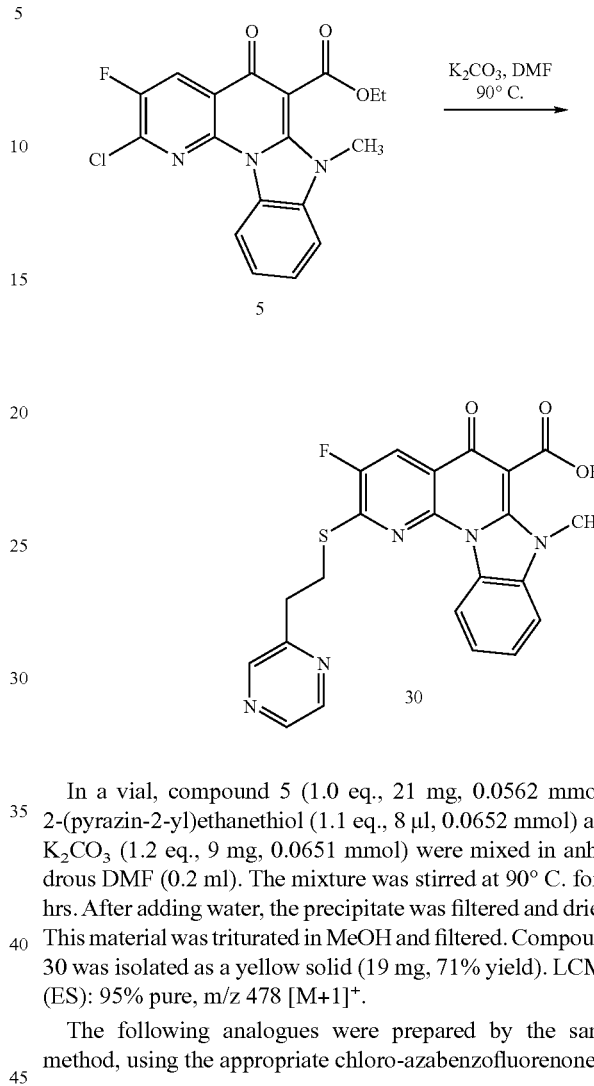

In a vial, compound 5 (1.0 eq., 21 mg, 0.0562 mmol) and racemic tert-butyl 3-(pyrazin-2-yl)pyrrolidine-1-carboxylate (4.0 eq., 56 mg, 0.225 mmol) were stirred in anhydrous NMP (0.2 ml) at 200° C. for 3 hrs. After adding water, the precipitate was filtered and dried. This material was purified by preparative TLC on silica gel (1 mm plate, eluted twice with 5% MeOH in CH₂Cl₂), and by precipitation using CH₂Cl₂/hexanes. Compound 29 was isolated as beige solid (15 mg, 55% yield). LCMS (ES): 95% pure, m/z 487 [M+1]⁺.

EXAMPLE 50

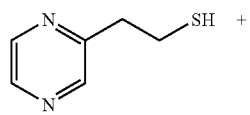

In a vial, compound 5 (1.0 eq., 21 mg, 0.0562 mmol), 2-(pyrazin-2-yl)ethanethiol (1.1 eq., 8 μl, 0.0652 mmol) and K₂CO₃ (1.2 eq., 9 mg, 0.0651 mmol) were mixed in anhydrous DMF (0.2 ml). The mixture was stirred at 90° C. for 3 hrs. After adding water, the precipitate was filtered and dried. This material was triturated in MeOH and filtered. Compound 30 was isolated as a yellow solid (19 mg, 71% yield). LCMS (ES): 95% pure, m/z 478 [M+1]⁺.

The following analogues were prepared by the same method, using the appropriate chloro-azabenzofluorenones:

| Structure | M.W. | LCMS (ES) m/z |
|---|---|---|
| 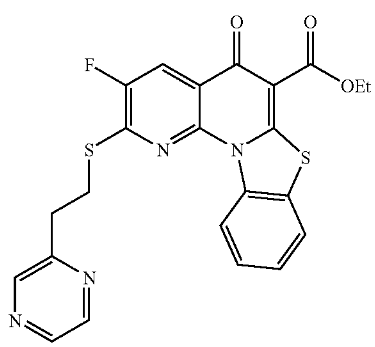 | 480.53 | 481 [M + 1]⁺ |

| Structure | M.W. | LCMS (ES) m/z |
|---|---|---|
| 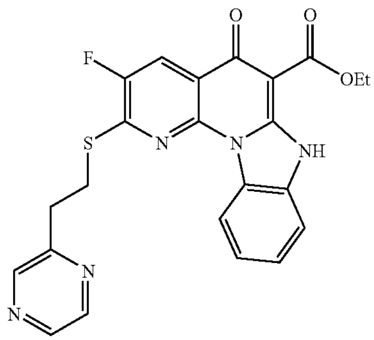 | 463.58 | 464 [M + 1]⁺ |
| 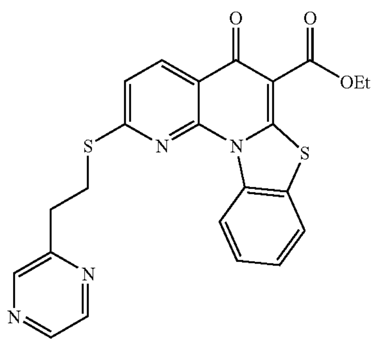 | 462.54 | 463 [M + 1]⁺ |

EXAMPLE 51

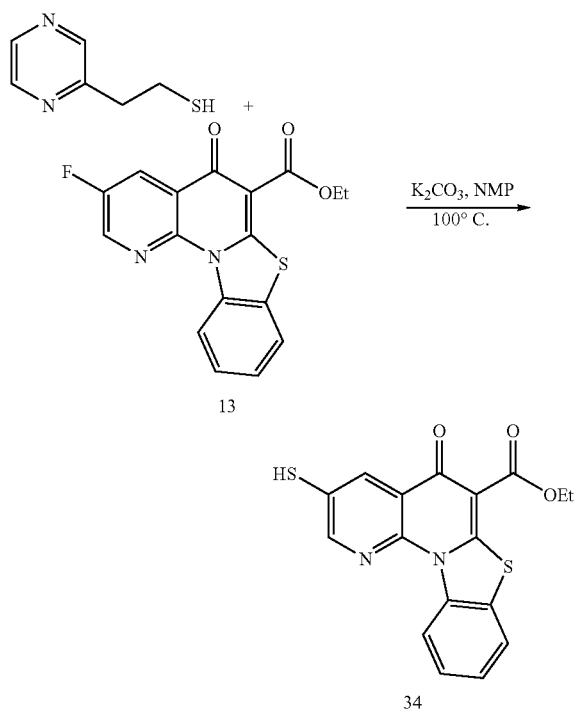

Compound 13 (1.0 eq, 266 mg, 0.777 mmol) was suspended in anhydrous NMP (3 ml). Nitrogen was bubbled into the mixture for a few minutes. 2-(pyrazin-2-yl)ethanethiol (5.0 eq, 0.48 ml, 3.91 mmol) and $K_2CO_3$ (10.0 eq, 1.0 g, 7.23 mmol) were added and the reaction mixture vigorously stirred at 100° C. for 1 hour. Water was added to dissolve all the materials. The pH was adjusted to 1-2 by adding a 3N aqueous HCl solution. The resulting orange precipitate was filtered, suspended in a small amount of MeOH and filtered a second time. Crude compound 34 was isolated as an orange-brown solid and was used for next step without any further purification (188 mg, 68% yield). LCMS (ES): 80-90% pure, m/z 357 [M+1]⁺.

EXAMPLE 52

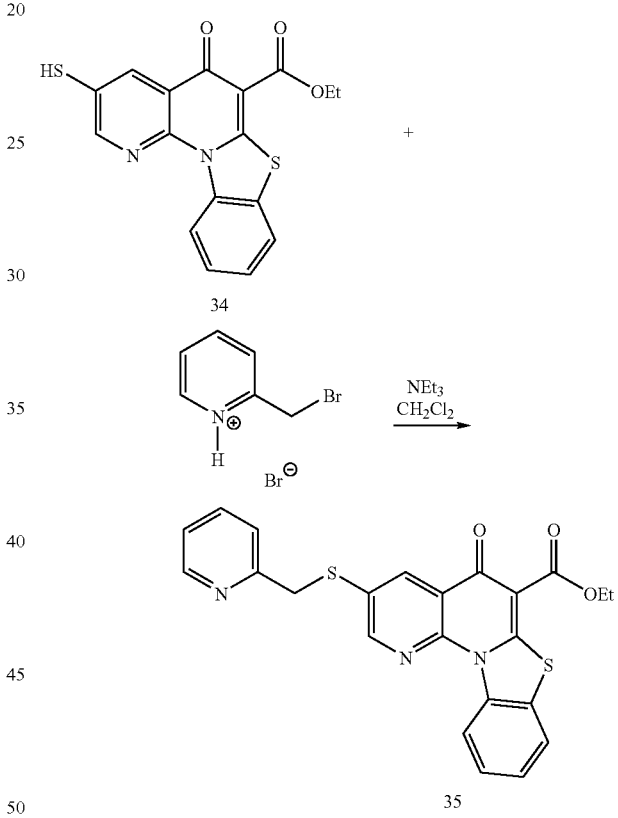

Compound 34 (1.0 eq, 188 mg, 0.527 mmol) was suspended in $CH_2Cl_2$ (4 ml). Triethylamine (2.2 eq, 0.16 ml, 1.148 mmol) and 2-(bromomethyl)pyridinium bromide (1.2 eq, 160 mg, 0.6325 mmol) were added and the mixture stirred at room temperature for 15 min. After addition of a saturated aqueous $NaHCO_3$, the material was extracted by $CH_2Cl_2$ (3×). The combined extracts were dried over $Na_2SO_4$ and the solvents removed in vacuo. The compound was purified by preparative HPLC. The resulting solution was concentrated and the pH adjusted to 10 by adding aqueous NaOH. Compound 35 was filtered and triturated in a $CH_2Cl_2$/hexanes mixture and filtered to give a pale brown solid (59 mg, 25%yield). LCMS (ES): 95% pure, m/z 448 [M+1]⁺.

EXAMPLE 53

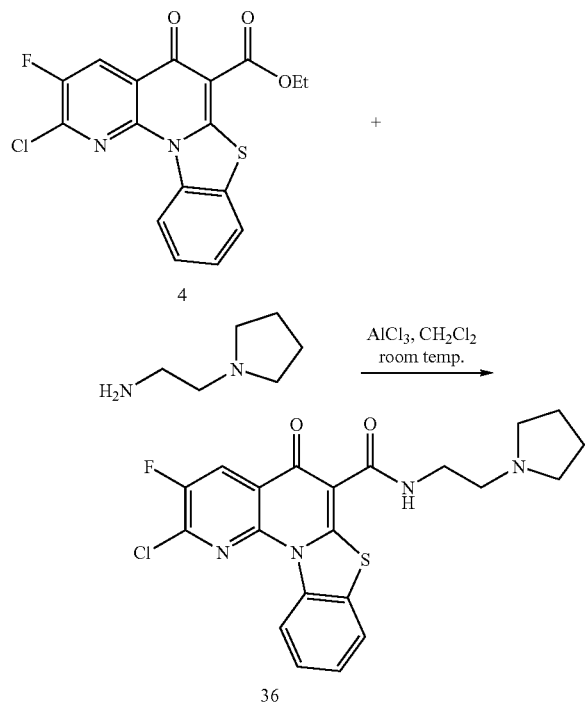

In a round bottom flask, compound 4 (1.0 eq, 1.28 g, 3.397 mmol) and 2-(pyrrolidin-1-yl)ethanamine (2.0 eq, 0.86 ml, 6.786 mmol) were mixed in $CH_2Cl_2$ (50 ml). $AlCl_3$ (1.5 eq, 680 mg, 5.10 mmol) was added and the mixture was vigorously stirred at room temperature for 1 hour. After removal of $CH_2Cl_2$ in vacuo, the resulting slurry was treated with a saturated aqueous tartaric acid solution (ca. 20 ml) and stirred until all solid disappeared (about 1 hr for completion of the hydrolysis). Water was added and the pH was adjusted to 14 by adding NaOH. The yellow precipitate was filtered and washed with water. The solid was dissolved in a large amount of a $CH_2Cl_2$/MeOH mixture and the cloudy solution filtered through a pad of celite. The volatiles were removed in vacuo and the solid material triturated in hot MeOH. Filtration and drying afforded compound 36 (1.09 g, 72% yield) as a yellow solid. LCMS (ES): 95% pure, m/z 445 $[M+1]^+$; $^1H$ NMR ($CDCl_3$, 400 MHz) δ 1.84 (m, 4H), 2.65 (m, 4H), 2.80 (t, J=7.2, 2H), 3.68 (t, J=7.2, 2H), 7.52 (td, J=1.2, J=7.2, 1H), 7.62 (td, J=1.2, J=8.4, 1H), 7.81 (dd, J=0.8, J=8.0, 1H), 8.62 (d, J=7.2, 1H), 9.49 (d, J=8.8, 1H) ppm.

The following compounds were prepared by the same method, using the appropriate amines and azabenzofluorenone ethyl esters. Some compounds were alternatively isolated by extraction with $CH_2Cl_2$ from the basic aqueous solution. Some compounds were purified by preparative TLC on alumina (eluted with 1 to 5% MeOH in $CH_2Cl_2$), preparative HPLC or trituration in EtOAc or $CH_2Cl_2$/hexanes mixtures.

| Structure | M.W. | LCMS (ES) m/z |
|---|---|---|
| 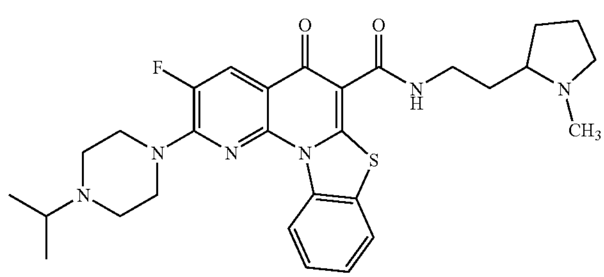 | 550.69 | 551 $[M + 1]^+$ |
| 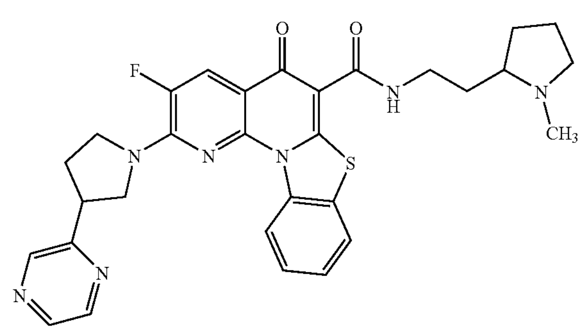 | 571.67 | 572 $[M + 1]^+$ |

-continued
| Structure | M.W. | LCMS (ES) m/z |
|---|---|---|
| 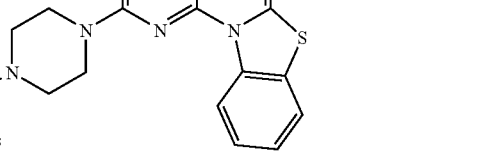 | 550.65 | 551 [M + 1]+ |
| 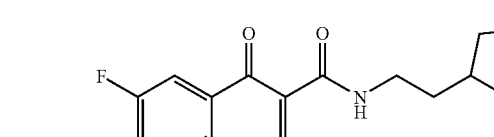 | 586.68 | 587 [M + 1]+ |
| 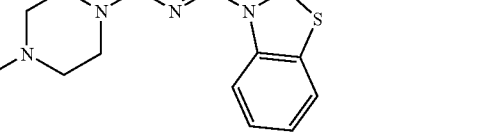 | 562.68 | 563 [M + 1]+ |
| 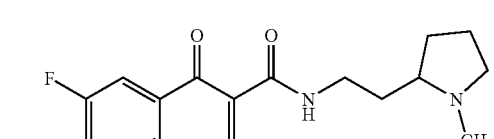 | 547.67 | 548 [M + 1]+ |
| 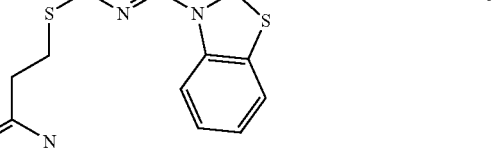 | 572.68 | 573 [M + 1]+ |

| Structure | M.W. | LCMS (ES) m/z |
|---|---|---|
| 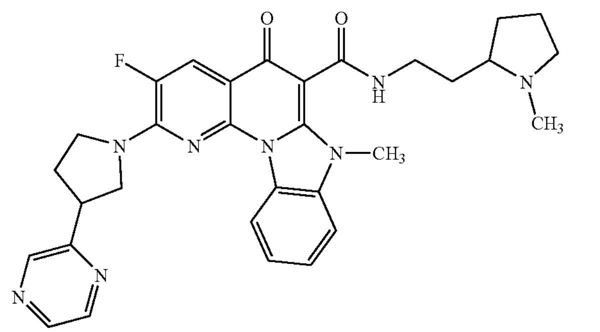 | 568.64 | 569 [M + 1]+ |
| 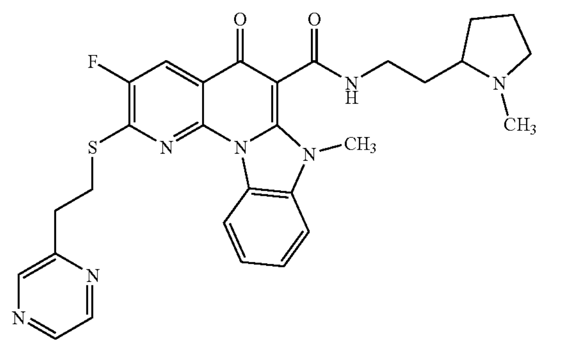 | 559.66 | 560 [M + 1]+ |
| 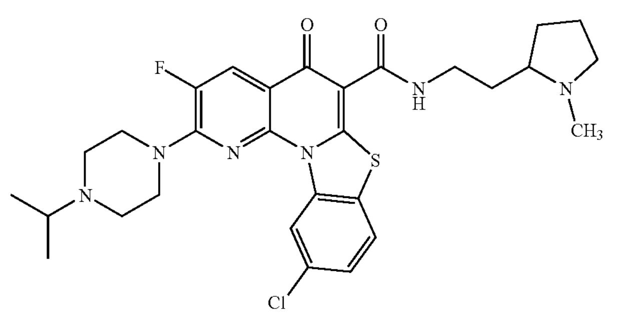 | 585.14 | 585 [M]+, 587 [M + 2]+ |
| 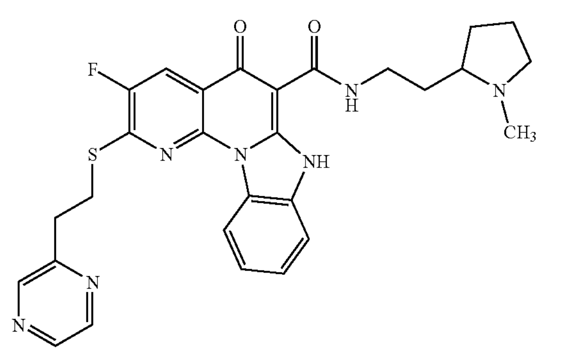 | 545.63 | 546 [M + 1]+ |

| Structure | M.W. | LCMS (ES) m/z |
|---|---|---|
| 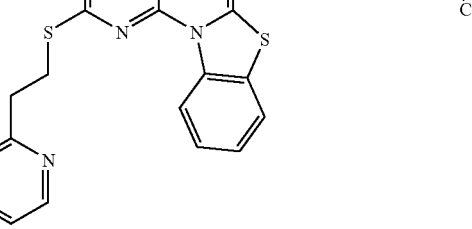 | 544.69 | 545 [M + 1]+ |
| 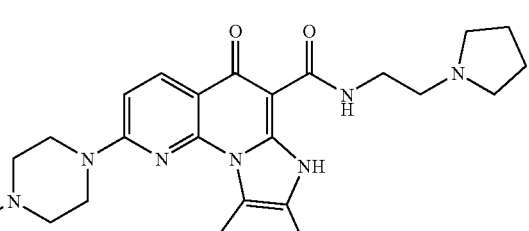 | 501.58 | 502 [M + 1]+ |
| 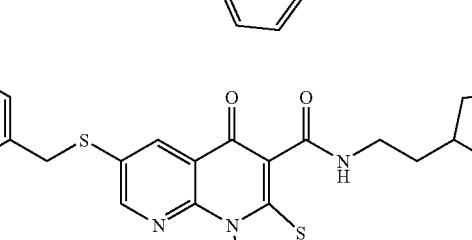 | 529.68 | 530 [M + 1]+ |
| 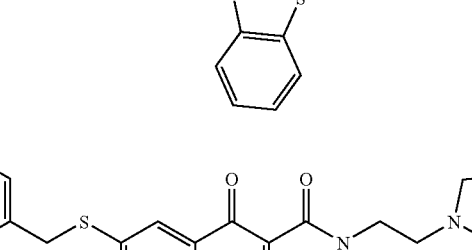 | 515.65 | 516 [M + 1]+ |
| 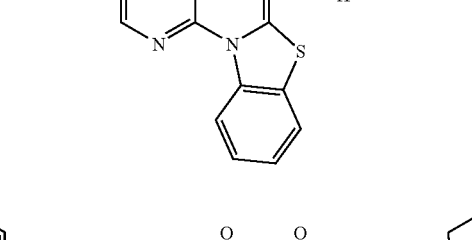 | 531.65 | 532 [M + 1]+ |

| Structure | M.W. | LCMS (ES) m/z |
|---|---|---|
| 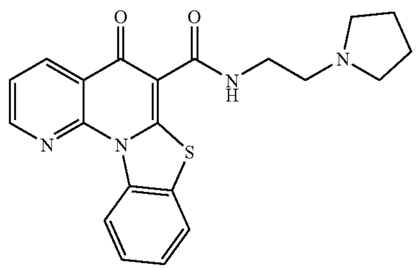 | 392.47 | 393 [M + 1]⁺ |
| 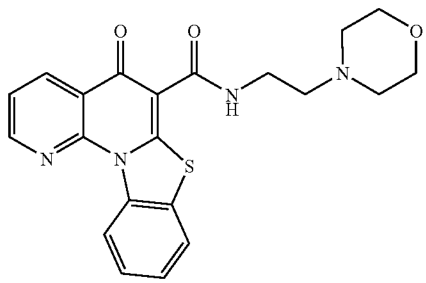 | 408.47 | 409 [M + 1]⁺ |
| 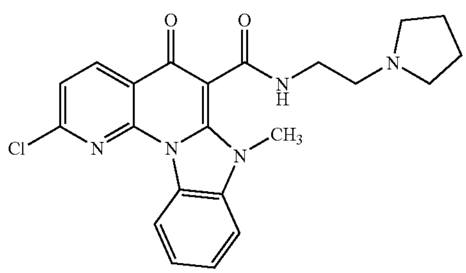 | 423.90 | 424 [M + 1]⁺ |
| 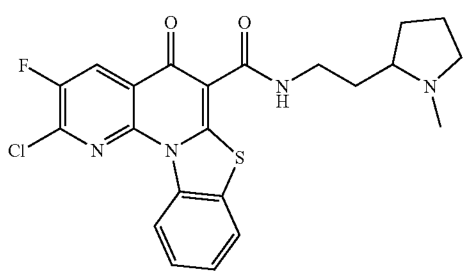 | 458.94 | 459 [M + 1]⁺ |
| 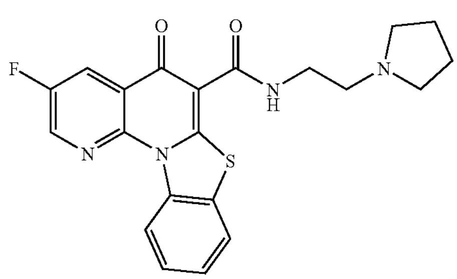 | 410.46 | 411 [M + 1]⁺ |

-continued
| Structure | M.W. | LCMS (ES) m/z |
|---|---|---|
| 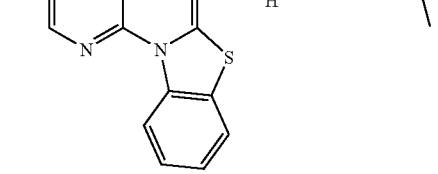 | 424.49 | 425 [M + 1]+ |
| 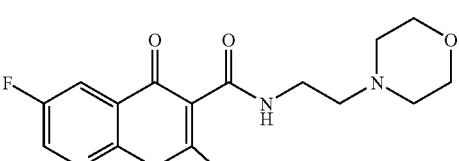 | 426.46 | 427 [M + 1]+ |
| 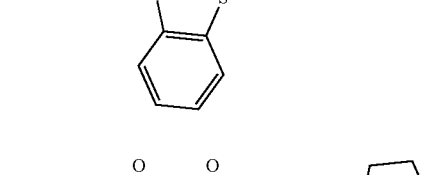 | 392.47 | 393 [M + 1]+ |
| 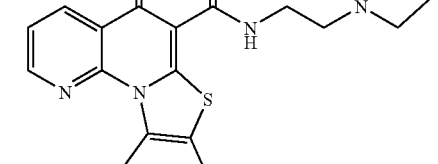 | 408.47 | 409 [M + 1]+ |
| 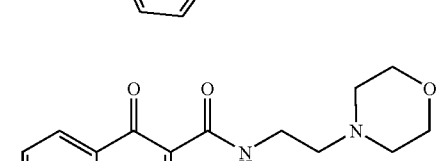 | 518.63 | 519 [M + 1]+ |

-continued

| Structure | M.W. | LCMS (ES) m/z |
|---|---|---|
| 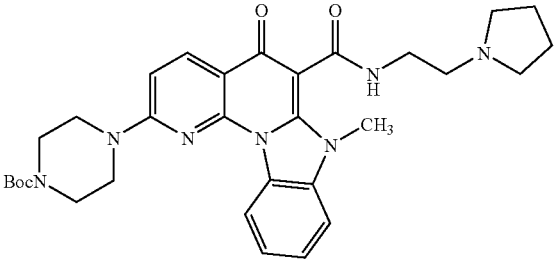 | 573.70 | 574 [M + 1]+ |

EXAMPLE 54

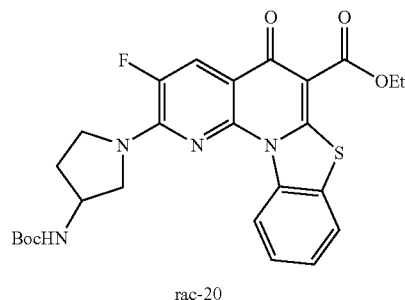

rac-20

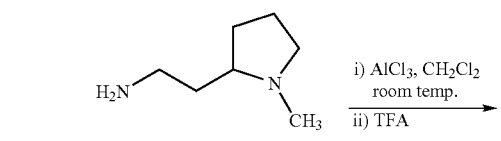

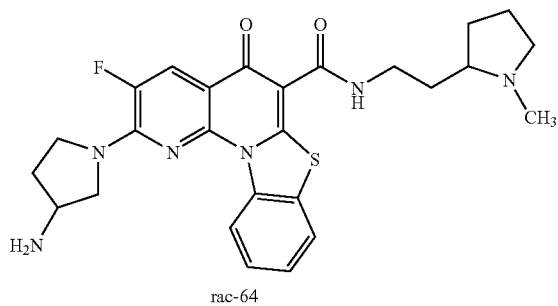

rac-64

Compound 64 protected by a Boc group was prepared according to the procedure used for product 36. The crude boc-amine was treated with neat trifluoroacetic acid (0.5 ml) for 45 min. After evaporation of the acid, water was added and the pH was adjusted to 14 by adding 1N NaOH. After extraction with $CH_2Cl_2$ (4×), the extracts were washed with water (1×) and dried over $Na_2SO_4$. Racemic compound 64 was purified by preparative TLC on alumina (1.5 mm plate, eluted 3 times with 4% MeOH in $CH_2Cl_2$) to afford a yellow solid (6 mg, 37% yield). LCMS (ES): 95% pure, m/z 509 [M+1]+.

EXAMPLE 55

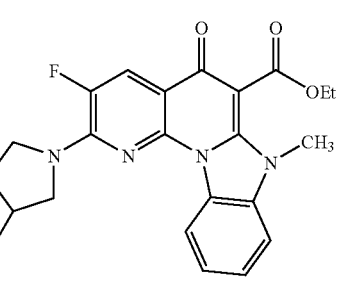

rac-22

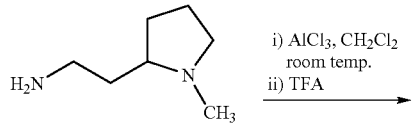

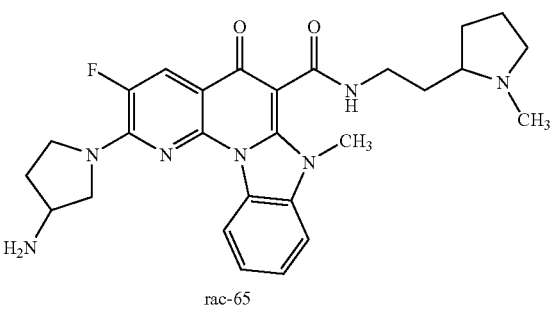

rac-65

Compound 65 was prepared according to the procedure used for product 64. Compound 65 was purified by preparative TLC on alumina (1.5 mm plate, eluted twice with 4% MeOH in $CH_2Cl_2$ and four times with 5% MeOH in $CH_2Cl_2$) and precipitation with $CH_2Cl_2$/hexanes to afford a yellow solid (2.7 mg, 12% yield). LCMS (ES): >85% pure, m/z 506 [M+1]+.

EXAMPLE 56

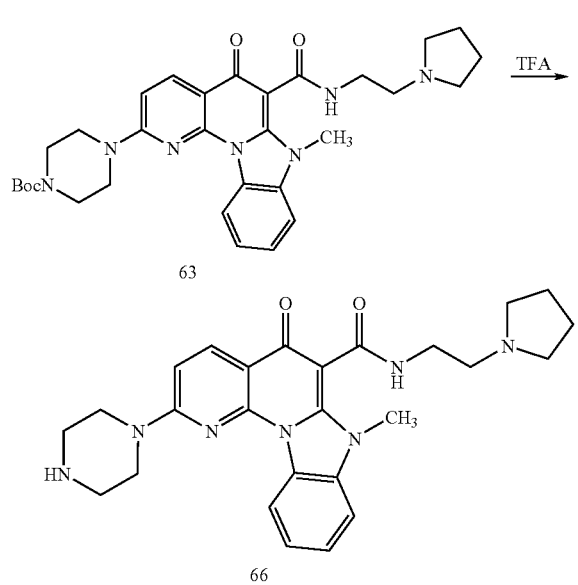

Compound 63 (300 mg, 0.523 mmol) was suspended in neat trifluoroacetic acid (2 ml). The mixture was stirred at ca. 50° C. for a few minutes and the volatiles removed in vacuo. MeCN (5 ml) was added and the material crashed out with Et$_2$O (200 ml). Compound 66 was purified by preparative HPLC and isolated after evaporation as a double TFA salt. (215 mg, 59% yield). LCMS (ES): >95% pure, m/z 474 [M+1]$^+$.

EXAMPLE 57

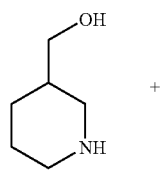

+

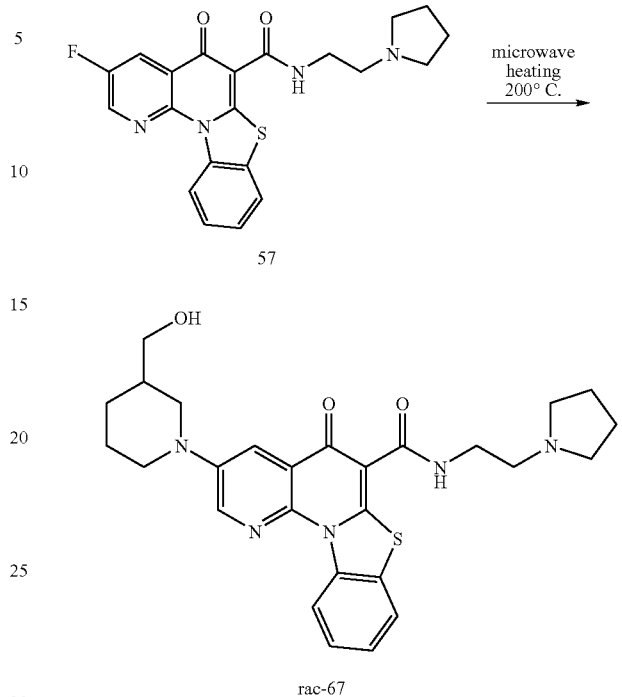

Compound 57 (20 mg) was suspended in NMP (0.2 ml) and racemic piperidin-3-ylmethanol (0.2 ml). The mixture was heated by microwaves at 200° C. for 15 min. After purification by preparative HPLC, the H$_2$O/MeCN solution of 67 was concentrated in vacuo, the pH adjusted to 9 by saturated NaHCO$_3$ and the compound extracted by CH$_2$Cl$_2$ (4×). The combined extracts were dried over Na$_2$SO$_4$ and the solvents removed in vacuo. The resulting solid was triturated in EtOAc/hexanes to afford racemic 67 as a tan solid (13 mg, 54% yield). LCMS (ES): >95% pure, m/z 506 [M+1]$^+$.

The following compounds were prepared by the same method, using the appropriate amines and fluoro azabenzofluorenones. When using less reactive amines the reaction was carried out at 220° C. for 20 min.

| Structure | M.W. | LCMS (ES) m/z |
|---|---|---|
| 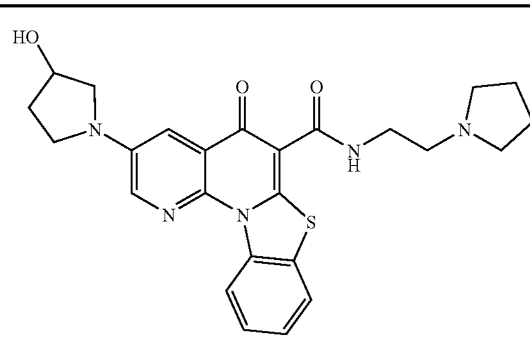 | 477.58 | 478 [M + 1]$^+$ |

-continued

| Structure | M.W. | LCMS (ES) m/z |
|---|---|---|
| 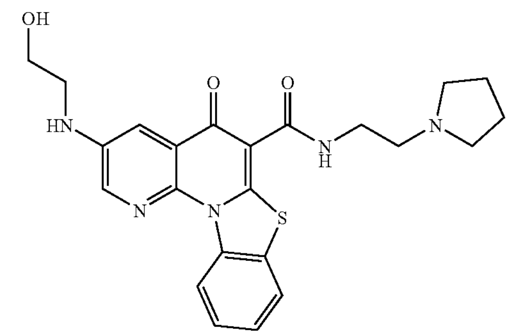 | 451.17 | 452 [M + 1]+ |
| 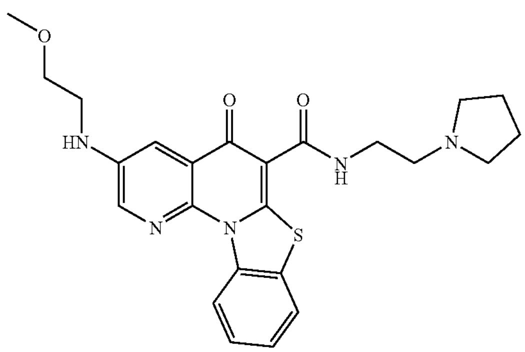 | 465.57 | 466 [M + 1]+ |
| 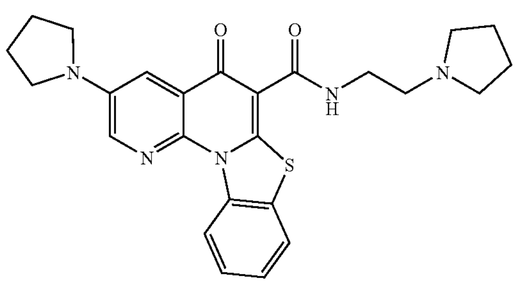 | 461.58 | 462 [M + 1]+ |
| 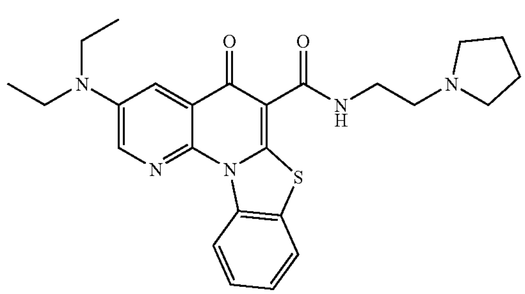 | 463.60 | 464 [M + 1]+ |
| 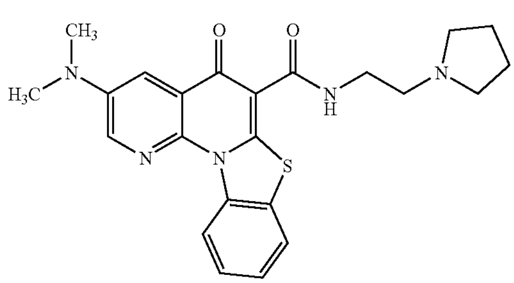 | 435.54 | 436 [M + 1]+ |

-continued

| Structure | M.W. | LCMS (ES) m/z |
|---|---|---|
| 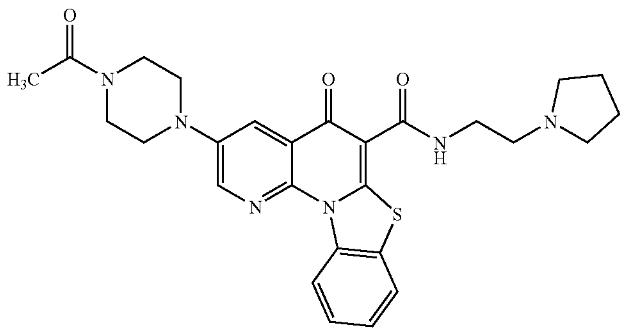 | 518.63 | 519 [M + 1]⁺ |
| 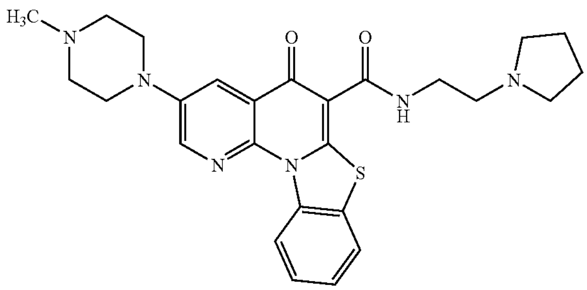 | 490.22 | 491 [M + 1]⁺ |
| 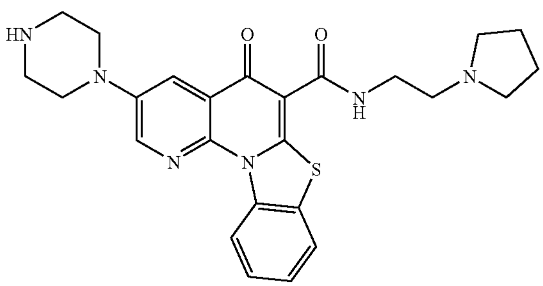 | 476.59 | 477 [M + 1]⁺ |
| 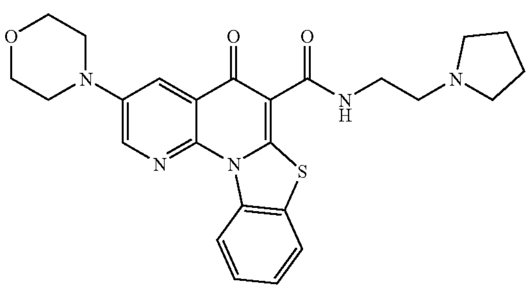 | 477.58 | 478 [M + 1]⁺ |
| 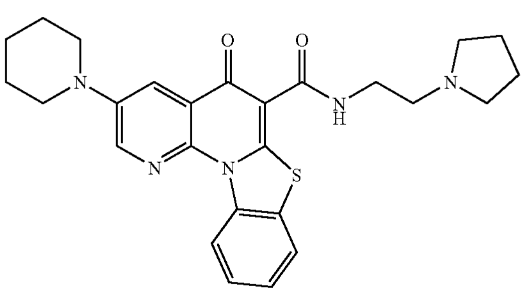 | 475.61 | 476 [M + 1]⁺ |

| Structure | M.W. | LCMS (ES) m/z |
|---|---|---|
| 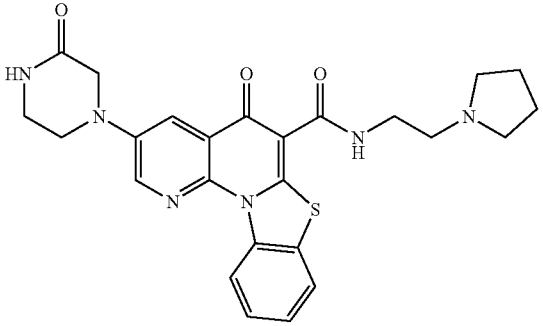 | 490.58 | 491 [M + 1]+ |
| 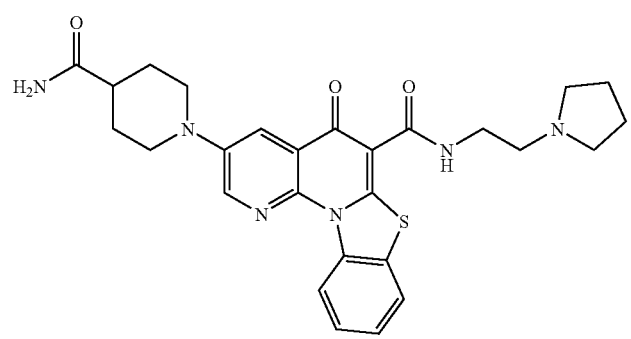 | 518.63 | 519 [M + 1]+ |
| 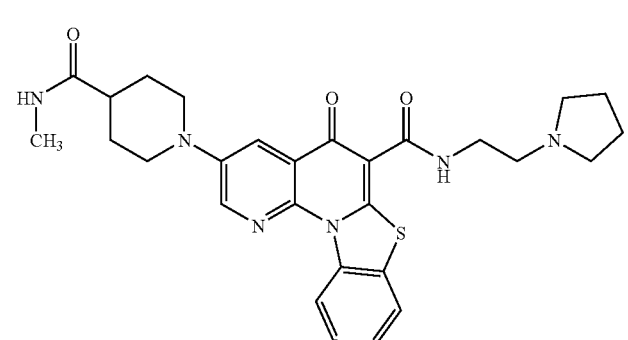 | 532.66 | 533 [M + 1]+ |
| 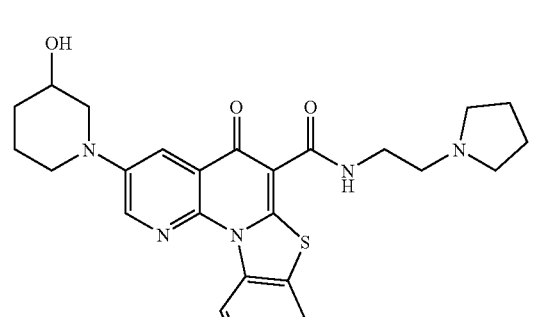 | 491.61 | 492 [M + 1]+ |

-continued

| Structure | M.W. | LCMS (ES) m/z |
|---|---|---|
| 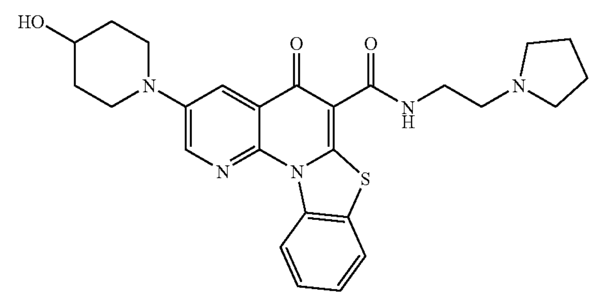 | 491.61 | 492 [M + 1]+ |
| | 498.60 | 499 [M + 1]+ |
| | 498.60 | 499 [M + 1]+ |
| 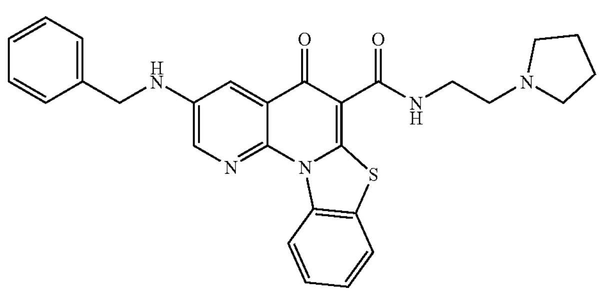 | 497.61 | 498 [M + 1]+ |
| 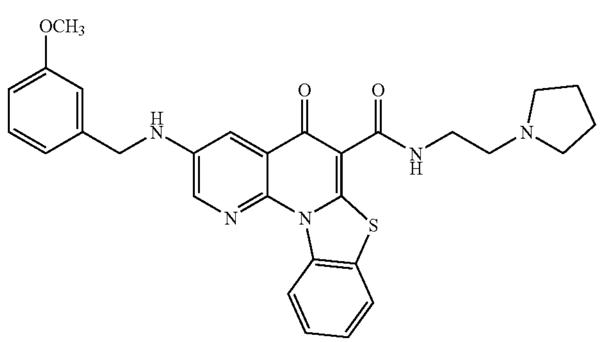 | 527.64 | 528 [M + 1]+ |

-continued

| Structure | M.W. | LCMS (ES) m/z |
|---|---|---|
| 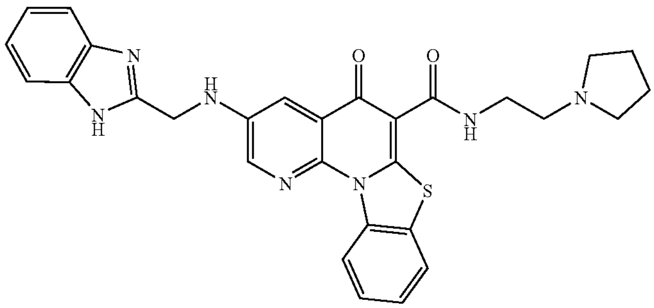 | 537.64 | 538 [M + 1]+ |
| 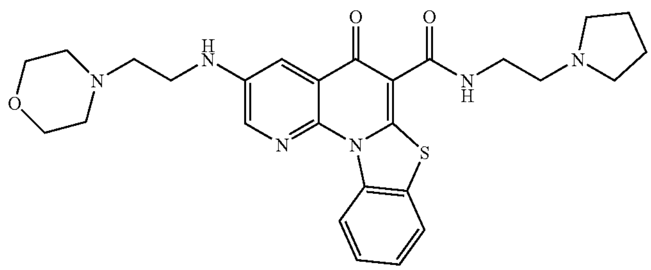 | 520.65 | 521 [M + 1]+ |
| 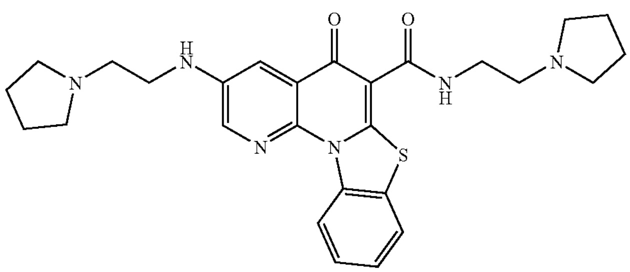 | 504.65 | 505 [M + 1]+ |
| 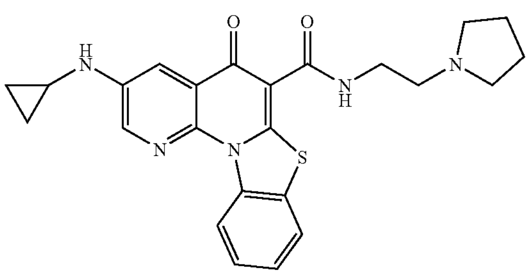 | 447.55 | 448 [M + 1]+ |
| 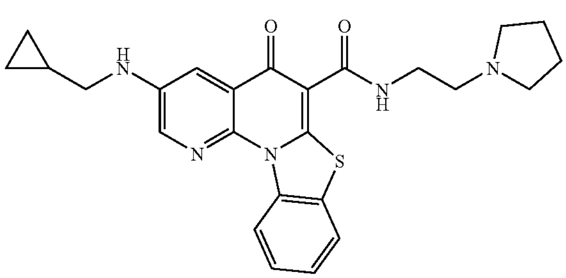 | 461.58 | 462 [M + 1]+ |

-continued
| Structure | M.W. | LCMS (ES) m/z |
|---|---|---|
| 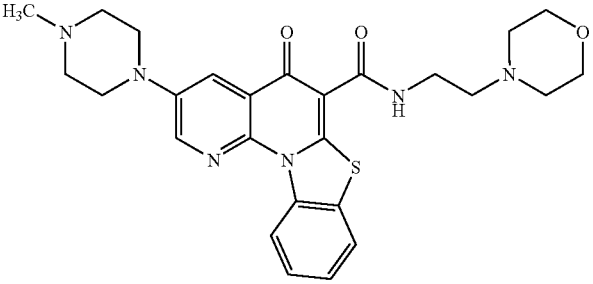 | 506.62 | 507 [M + 1]+ |
| 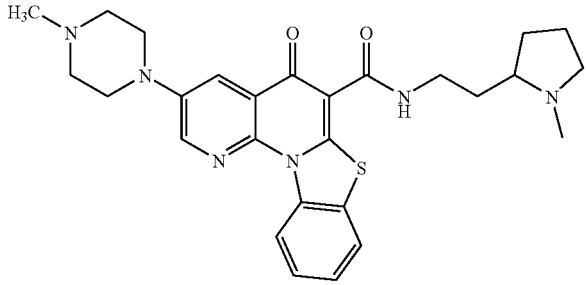 | 504.65 | 505 [M + 1]+ |
The following compounds were prepared by the same method, using the appropriate amines and chloro azabenzofluorenones. The reaction was carried out using microwave heating at 100° C. for 5 min or 150° C. for 3 min.
| Structure | M.W. | LCMS (ES) m/z |
|---|---|---|
| 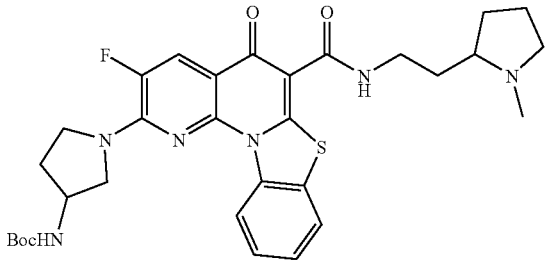 | 608.73 | 609 [M + 1]+ |
| 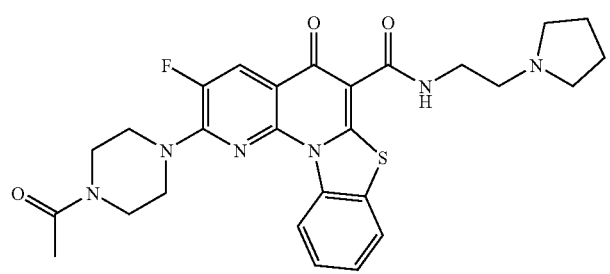 | 536.62 | 537 [M + 1]+ |

-continued

| Structure | M.W. | LCMS (ES) m/z |
|---|---|---|
| 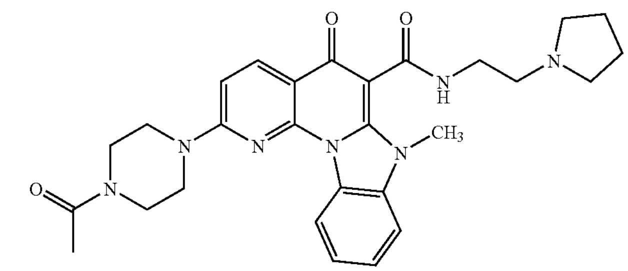 | 515.61 | 516 [M + 1]+ |
| 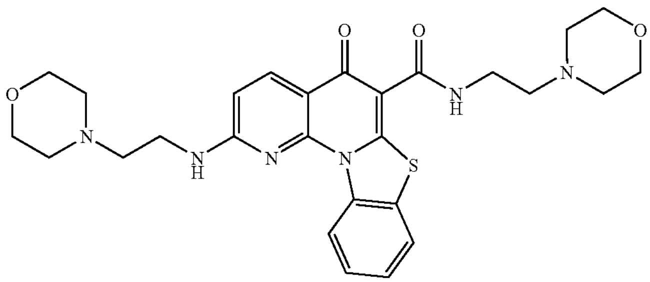 | 536.65 | 537 [M + 1]+ |

EXAMPLE 58

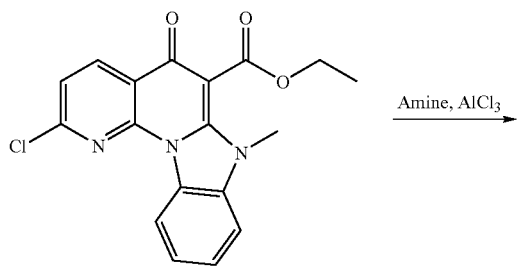

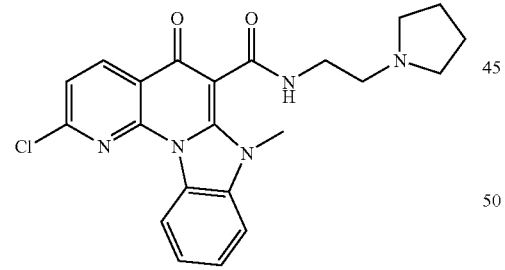

To a solution of the chloroester (1.0 g, 2.81 mmol) and 1-(2-aminoethyl)pyrrolidne (0.50 g, 4.4 mmol) in methylene chloride (20 mL) was added aluminum chloride (585 mg, 4.4 mmol) and the reaction was allowed to stir for 4 hours at room temperature. The reaction was then quench with a saturated solution of Rochelle's salt and kept basic with 1N NaOH and stirred for an additional hour. The mixture was extracted with methylene chloride, dried over magnesium sulfate and the solvent was removed in vaccuo. The resulting crude solid was triturated from ethyl acetate to afford the chloroamide as a tan solid (0.5 g, 1.1 mmol); LCMS (ES): 95% pure, m/z 437 [M+1]+.

EXAMPLE 59

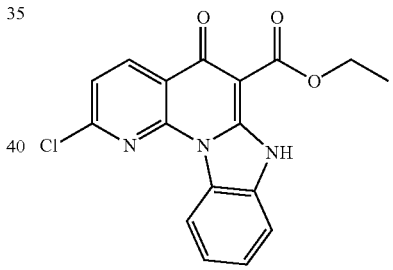

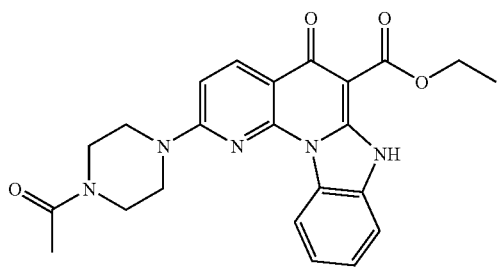

To a solution of the chloroester (1.0 g, 2.81 mmol) in N-methylpyrrolidinone (10 mL) was added N-acetylpiperazine (540 mg, 4.2 mmol) and the mixture was heated at 110° C. for 4 hours. Water was added and the crude product was collected by filtration. The resulting solid was dissolved in methylene chloride, dried over sodium sulfate and the solvent was removed in vaccuo. The resulting crude solid was triturated from ethyl acetate to afford the aminoester as a tan solid (0.70 g, 1.62 mmol); LCMS (ES): 95% pure, m/z 434 [M+1]+.

EXAMPLE 60

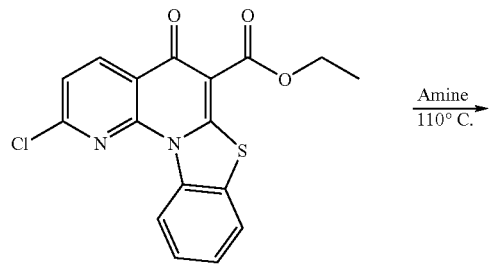

To a solution of the chloroester (1.0 g, 2.81 mmol) in N-methylpyrrolidinone (10 mL) was added N-acetylpiperazine (540 mg, 4.2 mmol) and the mixture was heated at 110° C. for 4 hours. Water was added and the crude product was collected by filtration. The resulting solid was dissolved in methylene chloride, dried over sodium sulfate and the solvent was removed in vaccuo. The resulting crude solid was triturated from ethyl acetate to afford the aminoester as a tan solid (0.75 g, 1.67 mmol); LCMS (ES): 95% pure, m/z 451 [M+1]$^+$.

EXAMPLE 61

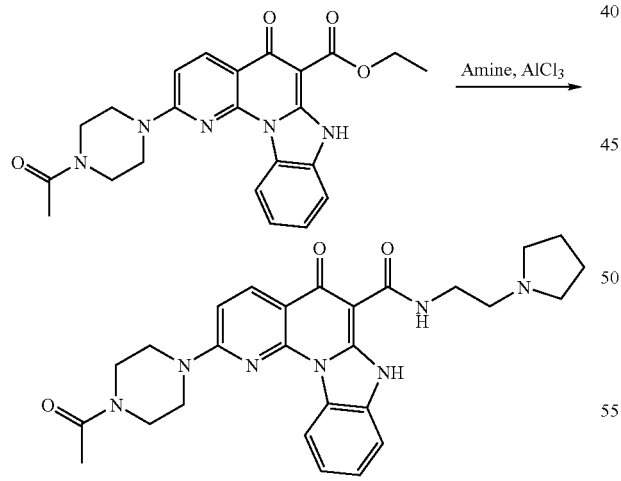

The following procedure was used to generate a library of analogs.

To a solution of the aminoester (200 mg, 0.46 mmol) and 1-(2-aminoethyl) pyrrolidne (80 mg g, 1.5 eq.) in methylene chloride (3 mL) was added aluminum chloride (100 mg, 1.5 eq.) and the reaction was allowed to stir for 4 hours at room temperature. The reaction was then quench with a saturated solution of Rochelle's salt and kept basic with 1N NaOH and stirred for an additional hour. The mixture was extracted with methylene chloride, dried over magnesium sulfate and the solvent was removed in vaccuo. The resulting crude solid was purified by mass selective LCMS to afford the amide as a white solid (71 mg, 0.14 mmol); LCMS (ES): 95% pure, m/z 502 [M+1]$^+$.

EXAMPLE 62

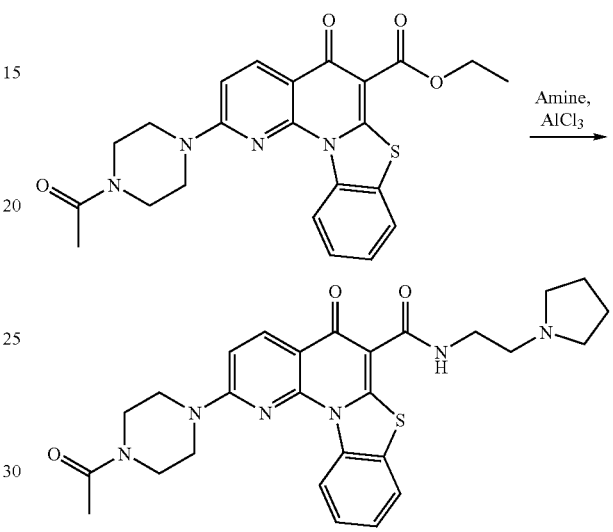

The following procedure was used to generate a library of analogs.

To a solution of the aminoester (200 mg, 0.46 mmol) and 1-(2-aminoethyl) pyrrolidine (80 mg g, 1.5 eq.) in methylene chloride (3 mL) was added aluminum chloride (100 mg, 1.5 eq.) and the reaction was allowed to stir for 4 hours at room temperature. The reaction was then quench with a saturated solution of Rochelle's salt and kept basic with 1N NaOH and stirred for an additional hour. The mixture was extracted with methylene chloride, dried over magnesium sulfate and the solvent was removed in vaccuo. The resulting crude solid was purified by mass selective LCMS to afford the amide as a white solid (200 mg, 0.38 mmol); LCMS (ES): 95% pure, m/z 519 [M+1]$^+$.

EXAMPLE 63

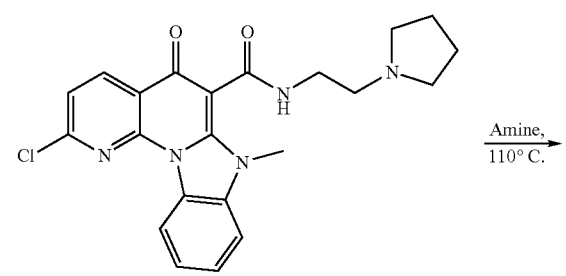

-continued

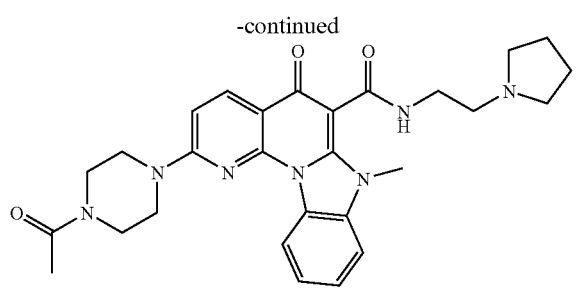

The following procedure was used to generate a library of analogs.

To a solution of the chloroamide (350 mg, 0.83 mmol) in N-methylpyrrolidinone (2 mL) was added N-acetylpiperazine (160 mg, 1.24 mmol) and the mixture was heated at 110° C. for 4 hours. Water was added and the crude product was collected by filtration. The resulting solid was dissolved in methylene chloride, dried over sodium sulfate and the solvent was removed in vaccuo. The resulting crude solid was triturated from ethyl acetate to afford the amide as a white solid (200 mg, 0.4 mmol); LCMS (ES): 98% pure, m/z 516 [M+1]$^+$.

EXAMPLE 64

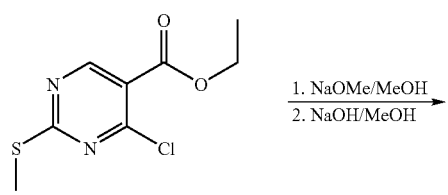

4-Methoxy-2-(methylthio)pyrimidine-5-carboxylic acid. To a solution of ethyl 4-chloro-2-(methylthio)pyrimidine-5-carboxylate (24.40 g, 104.9 mmol) in MeOH (125 mL) was added solid sodium methoxide (11.40 g, 211.0 mmol) at rt. The reaction mixture was stirred at rt for 5 h and then treated with NaOH (17.70 g, 315.5 mmol) in H$_2$O (100 mL). It was then stirred at the same temperature for an additional 1 h. The reaction mixture was concentrated to half of the volume and then acidified to pH=4 with HCl (6N). The reaction was extracted with EtOAc (5×200 mL) and the organic layer was washed with brine (200 mL), dried over Na$_2$SO$_4$, and concentrated to yield the desired product as a white solid (19.28 g, 92%). MS (m/z): 201 (MH$^+$). $^1$H NMR (DMSO-d$^6$) δ: 8.72 (s, 1H), 3.98 (s, 3H), 2.54 (s, 3H).

EXAMPLE 65

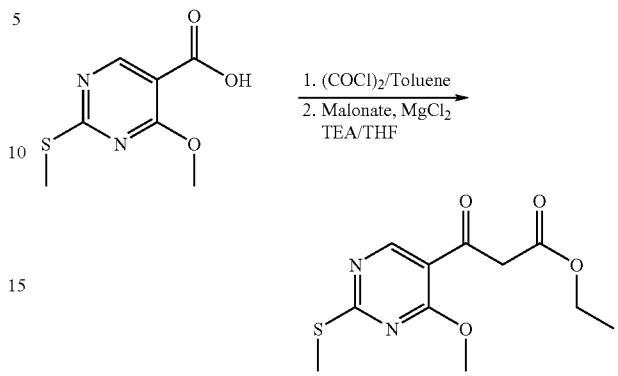

Ethyl 3-(4-methoxy-2-(methylthio)pyrimidin-5-yl)-3-oxopropanoate. A solution of 4-methoxy-2-(methylthio)pyrimidine-5-carboxylic acid (10.92 g, 54.6 mmol) and oxalyl chloride (19.0 mL, 217.8 mmol) in toluene (100 mL) was heated at 100° C. for 1 h. The solvent was removed under reduced pressure and the crude acid chloride was used without purification in the next step. To a solution of MgCl$_2$ (7.80 g, 81.9 mmol) and ethyl magnesium malonate (14.10 g, 82.6 mmol) in THF (100 mL) was added the above acid chloride in THF (100 mL) at 0° C. followed by TEA (15.0 mL, 107.6 mmol). The reaction mixture was stirred at 0° C. for 30 min and at rt for 2 h. EtOAc (200 mL) and H$_2$O (100 mL) were added and stirred for additional 30 min. The layers were separated and the organic layer was washed with brine (100 mL), dried over Na$_2$SO$_4$, and concentrated. The crude was purified by flash chromatography (15% EtOAc/hexanes) to yield the desired compound as a white solid (7.73 g, 52%). MS (m/z): 271 (MH$^+$). $^1$H NMR (CDCl$_3$) δ: 12.65 (s, 1H×⅔), 8.85 (s, 1H×⅓), 8.84 (s, 1H×⅔), 6.03 (s, 1H×⅔), 4.26 (q, 2H×⅔), 4.19 (q, 2H×⅓), 4.10 (s, 3H×⅔), 4.09 (s, 3H×⅓), 3.92 (s, 2H×⅓), 2.60 (s, 3H×⅓), 2.59 (s, 3H×⅔), 1.34 (t, 3H×⅔), 1.26 (3H×⅓).

EXAMPLE 66

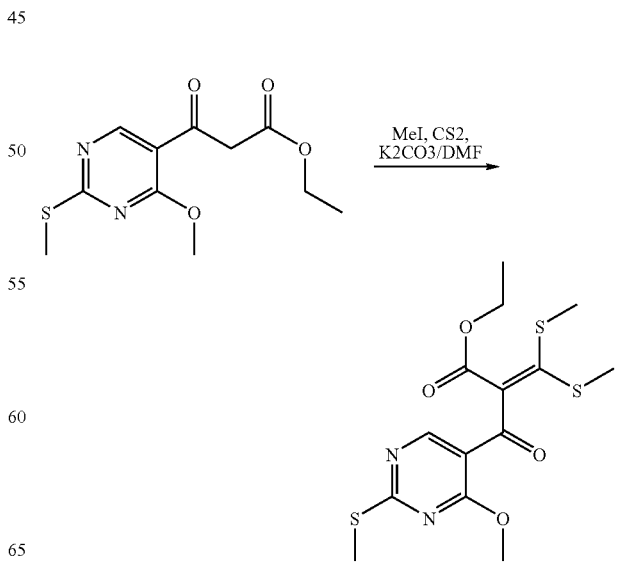

Ethyl 2-(4-methoxy-2-(methylthio)pyrimidine-5-carbonyl)-3,3-bis(methylthio)acrylate. To a solution of ethyl 3-(4-methoxy-2-(methylthio)pyrimidin-5-yl)-3-oxopropanoate in DMF (85 mL) was added methyl iodide (5.3 mL, 85.1 mmol), carbon disulfide (2.6 mL, 43.0 mmol) at −5° C. Solid K₂CO₃ was slowly added keeping the internal temperature below −3° C. The reaction mixture was stirred at −5° C. for 1 h and at rt for 1 h. It was diluted with EtOAc (300 mL), washed with H₂O (2×200 mL) and dried over Na₂SO₄. The solvent was removed under reduced pressure and the crude was purified by flash chromatography (20% EtOAc/hexanes) to yield the desired product as a yellow oil (7.60 g, 71%). MS (mn/z): 375 (MH⁺). ¹H NMR (CDCl3) δ: 8.82 (s, 1H), 4.16 (q, 2H), 4.03 (s, 3H), 2.61 (s, 3H), 2.51 (br s, 3H), 2.28 (br s, 3H), 1.15 (t, 3H).

EXAMPLE 67

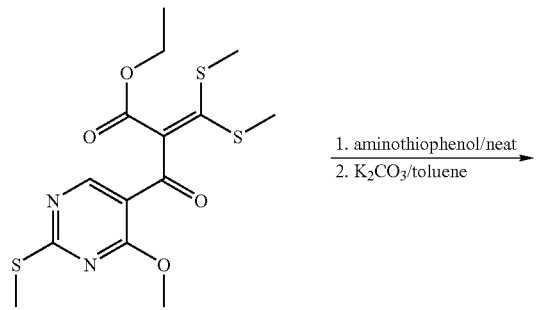

2-Methylsulfanyl-5-oxo-5H-7-thia-1,3,11b-triaza-benzo[c]fluorene-6-carboxylic acid ethyl ester. A solution of ethyl 2-(4-methoxy-2-(methylthio)pyrimidine-5-carbonyl)-3,3-bis(methylthio)acrylate (475 mg, 1.27 mmol) and 2-aminobenzenethiol (200 mg, 1.60 mmol) in toluene (5 mL) was heated to dryness and continued heating neat at 140° C. for 1 h. Toluene (30 mL) and K₂CO₃ (350 mg, 2.53 mmol) were added to the reaction and it was heated for an additional 1 h. The reaction mixture was cooled to rt and EtOAc (100 mL) and H₂O (50 mL) were added. The layers were separated and the organic layer was washed with brine (100 mL), dried over Na₂SO₄, and concentrated. The crude solid was triturated in Et₂O to afford the desired product as a yellow solid (260 mg, 55%). MS (m/z): 372 (MH⁺). ¹H NMR (DMSO-d⁶) δ: 9.37 (d, 1H), 9.30 (s, 1H), 8.06 (m, 1H), 7.65 (m, 1H), 7.54 (m, 1H), 4.35 (q, 2H), 2.78 (s, 3H), 1.34 (t, 3H).

EXAMPLE 68

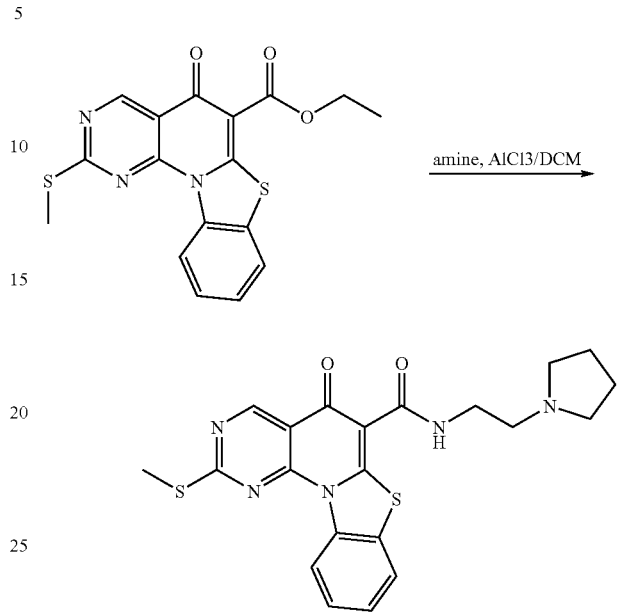

2-Methylsulfanyl-5-oxo-5H-7-thia-1,3,11b-triaza-benzo[c]fluorene-6-carboxylic acid (2-cyclopentyl-ethyl)-amide. To a solution of 2-methylsulfanyl-5-oxo-5H-7-thia-1,3,11b-triaza-benzo[c]fluorene-6-carboxylic acid ethyl ester (230 mg, 0.619 mmol) and 2-(pyrrolidin-1-yl)ethanamine (0.24 mL, 1.854 mmol) in DCM (15 mL) was added solid AlCl₃ (250 mg, 1.875 mmol) at rt. The reaction was stirred for 1 h at rt and diluted with DCM (100 mL), conc. sodium potassium tartrate (30 mL), and NaOH (6N, 10 mL). The mixture was stirred for 15 min and the layers were separated. The aqueous layer was extracted with DCM (50 mL) and the combined organic layer was washed with brine (50 mL). The crude reaction mixture was dried over Na₂SO₄, and concentrated to yield the desired product as a yellow solid (250 mg, 92%). MS (m/z): 440 (MH⁺). ¹H NMR (CDCl3) δ: 10.26 (br, 1H), 9.61 (s, 1H), 9.55 (m, 1H), 7.77 (m, 1H), 7.57 (m, 1H), 7.50 (m, 1H), 3.67 (q, 2H), 2.81 (s, 3H), 2.77 (t, 2H), 2.63 (m, 4H), 1.82 (m, 4H).

EXAMPLE 69

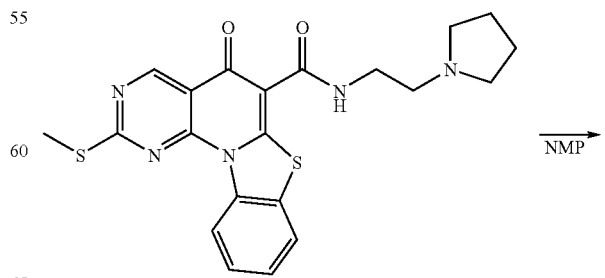

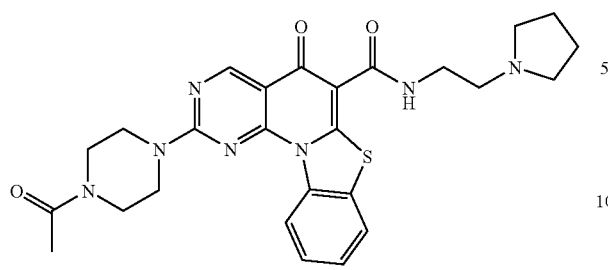

2-(4-Acetyl-piperazin-1-yl)-5-oxo-5H-7-thia-1,3,11b-triaza-benzo[c]fluorene-6-carboxylic acid (2-pyrrolidin-1-yl-ethyl)-amide. A solution of 2-methylsulfanyl-5-oxo-5H-7-thia-1,3,11b-triaza-benzo[c]fluorene-6-carboxylic acid (2-cyclopentyl-ethyl)-amide (25 mg, 0.057 mmol) and 1-(piperazin-1-yl)ethanone (75 mg, 0.585 mmol) in NMP (1.0 mL) was heated for 20 min at 200° C. in a microwave. The crude reaction mixture was purified by reverse phase HPLC. MS (m/z): 520 (MH+).

EXAMPLE 70

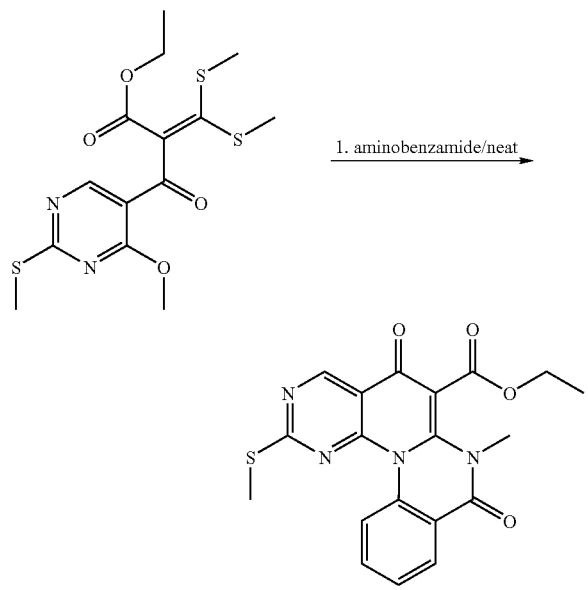

7-Methyl-2-methylsulfanyl-5,8-dioxo-7,8-dihydro-5H-1,3,7,12b-tetraaza-benzo[c]phenanthrene-6-carboxylic acid ethyl ester. A solution of ethyl 2-(4-methoxy-2-(methylthio)pyrimidine-5-carbonyl)-3,3-bis(methylthio)acrylate (775 mg, 2.069 mmol) and 2-amino-N-methylbenzamide (475 mg, 3.163 mmol) in toluene (5 mL) was heated over stream of nitrogen allowing toluene to evaporate and continued heating as neat at 140° C. for over night. Cooled to rt and precipitate formed from DCM (10 mL) was filtered off. The solvent of mother liquor was removed under reduced pressure and repeated the precipitation process with Et$_2$O (10 mL). Trituration in methanol (10 mL) afforded the desired product as a yellow solid (30 mg, 4 %). MS (m/z): 397 (MH+). $^1$H NMR (CDCl$_3$) δ: 9.37 (s, 1H), 8.37 (d, 1H), 8.26 (dd, 1H), 7.70 (m, 1H), 7.49 (m, 1H), 4.46 (q, 2H), 3.61 (s, 3H), 2.60 (s, 3H), 1.43 (t, 3H).

EXAMPLE 71

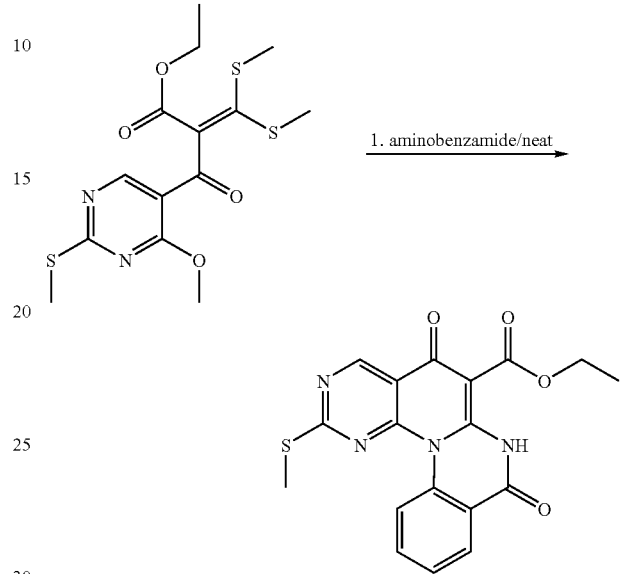

2-Methylsulfanyl-5,8-dioxo-7,8-dihydro-5H-1,3,7,12b-tetraaza-benzo[c]phenanthrene-6-carboxylic acid ethyl ester. A solution of ethyl 2-(4-methoxy-2-(methylthio)pyrimidine-5-carbonyl)-3,3-bis(methylthio)acrylate (250 mg, 0.668 mmol) and 2-aminobenzamide (118 mg, 0.867 mmol) in DCM (5 mL) was heated over stream of nitrogen allowing DCM to evaporate and continued heating as neat at 140° C. for over night. The residue was dissolved in DMF (7 mL) after cooling to rt and treated with NaH (60 mg, 1.500 mmol). The reaction was stirred at rt for 1 h and diluted with DCM (20 mL) and H$_2$O (20 mL). The layers were separated and DCM was removed under reduced pressure. Trituration of the crude in Et$_2$O (10 mL) afforded the desired product as a yellow solid (50 mg, 20%). MS (m/z): 383 (MH+). $^1$H NMR (CDCl$_3$) δ: 13.58 (br s, 1H), 9.43 (s, 1H), 8.60 (d, 1H), 8.33 (dd, 1H), 7.79 (m, 1H), 7.59 (m, 1H), 4.48 (q, 2H), 2.62 (s, 3H), 1.46 (t, 3H).

EXAMPLE 72

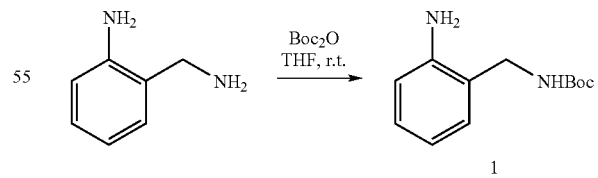

The material was prepared according to a published procedure, which was slightly modified (*J. Med. Chem.* 2003, 46, 1661-1669). Under nitrogen atmosphere, 2-aminobenzylamine (2.0 eq., 2.45 g, 20.05 mmol) was dissolved in THF (25 ml). A solution of di-tert-butyldicarbonate (1.0 eq, 2.19 g, 10.03 mmol) in TFH (25 ml) was added slowly via a syringe pump over 30 min. After a few minutes, extra THF (25 ml)

was added to enable efficient stirring of the thick suspension. After stirring at room temperature overnight, a white solid that formed was filtered off. The filtrate was concentrated in vacuo and poured on top of a silica gel column and purified by chromatography (10 to 20% gradient of EtOAc in hexanes). The resulting solid was recrystallized in EtOAc/hexanes to afford a white crystalline solid (1.95 g, 87% yield based on Boc$_2$O). LCMS (ES): 95% pure, m/z 224 [M+H]$^+$, 245 [M+Na]$^+$; $^1$H NMR (CDCl$_3$, 400 MHz) δ 1.44 (s, 9H), 4.23 (d, J=6.0, 2H), 4.2 (br s, 2H), 4.80 (br s, 1H), 6.68 (t, J=7.6, 2H), 7.02 (d, J=6.8, 1H), 7.10 (dt, J=8.0, J=1.6, 1H) ppm.

EXAMPLE 73

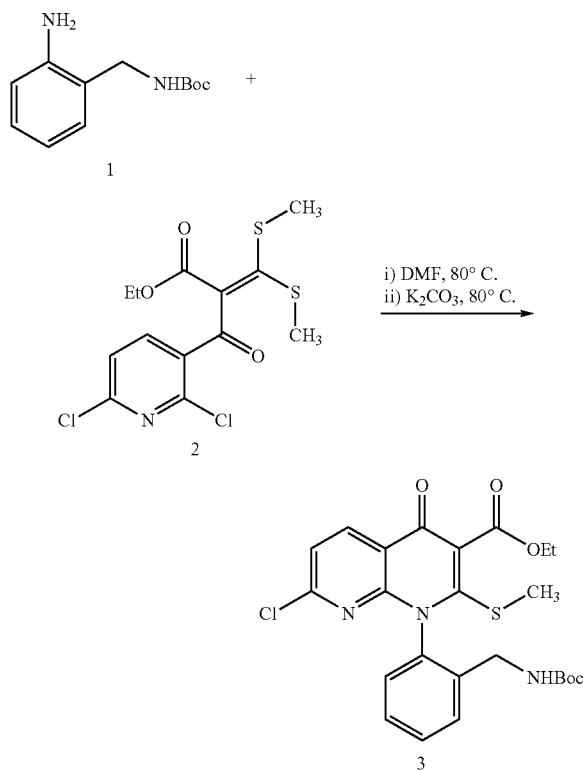

A mixture of compound 1 (1.22 g, 5.49 mmol) and 2 (2.01 g, 5.49 mmol) in DMF (10 ml) was stirred at 80° C. for 5 hours, while maintaining bubbling of nitrogen into the solution. K$_2$CO$_3$ (1.2 eq, 910 mg, 6.58 mmol) was added and the mixture stirred at 80° C. for 40 minutes. Water was added and the resulting gummy material extracted with CH$_2$Cl$_2$ (3×). The combined extracts were washed with water (1×), dried over Na$_2$SO$_4$ and the volatiles removed in vacuo to afford a thick oil (3.2 g of solvent-containing material, >100% yield). The obtained material was over 85% pure and used for the following step without any further purification. A small part was purified by preparative HPLC for characterization. LCMS (ES): 95% pure, m/z 504 [M]$^+$, 506 [M+2]$^+$; $^1$H NMR (CDCl$_3$, 400 MHz) δ1.38 (s, 9H), 1.40 (m, 3H), 2.32 (s, 3H), 3.93 (dd, J=15.2, J=5.5, 1H), 4.24 (dd, J=14.8, J=4.2, 1H), 4.43 (m, 2H), 4.84 (br t, 1H), 7.15 (m, 1H), 7.29 (m, 1H), 7.45 (m, 1H), 7.57 (m, 2H), 8.61 (d, J=8.8, 1H) ppm.

EXAMPLE 74

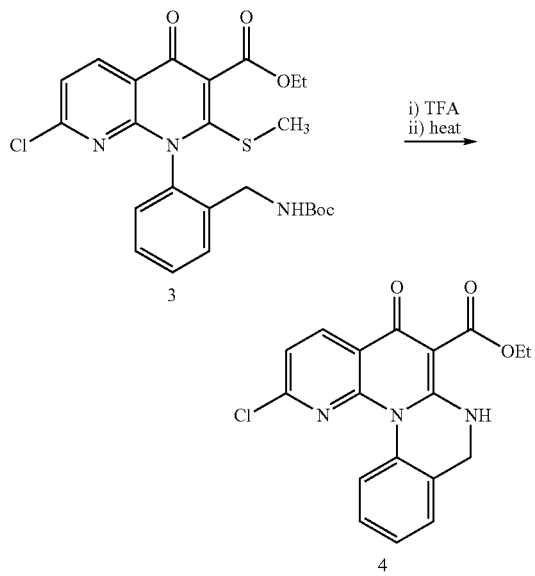

Compound 3 (1.5 g, 2.98 mmol) was dissolved in 5 ml of trifluoroacetic acid. The mixture was stirred at room temperature for 2 hours. The volatiles were removed in vacuo and the resulting thick oil was heated with a heat gun while being kept in vacuo. This operation was pursued until the formation of 4 by cyclization was complete (LCMS monitoring). The compound was purified by flash chromatography on silica gel (30 to 80% gradient of EtOAc in hexanes). The solid that precipitated upon concentration of the solvents was filtered and dried to afford compound 4 as a white microcrystalline solid (434 mg, 41% yield). LCMS (ES): 95% pure, m/z 356 [M+H]$^+$, 378 [M+Na]$^+$, 310 [M+1−EtOH]$^+$; $^1$H NMR (CDCl$_3$, 400 MHz) δ 1.43 (t, J=6.8, 3H), 4.40 (q, J=7.2, 2H), 4.46 (d, J=2.4, 2H), 7.24-7.40 (m, 4H), 7.69 (d, J=8.4, 1H), 8.62 (d, J=8.0, 1H), 10.74 (br s, 1H) ppm.

EXAMPLE 75

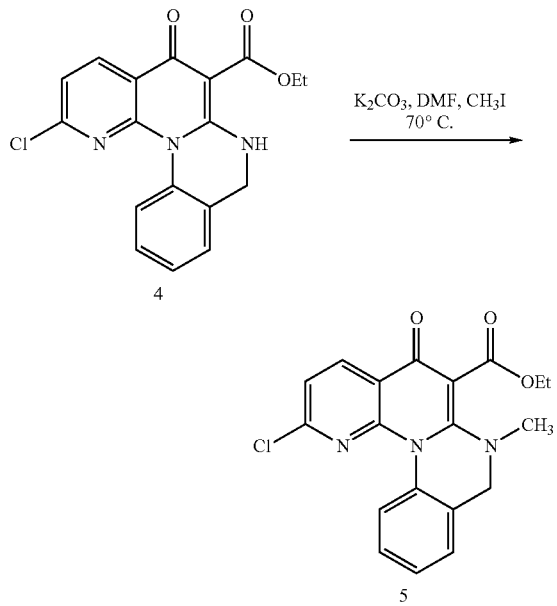

Compound 4 (1.0 eq, 198 mg, 0.556 mmol) and $K_2CO_3$ (2.0 eq, 154 mg, 1.11 mmol) were suspended in DMF (1.5 ml). Iodomethane (1.4 eq, 0.05 ml, 0.80 mmol) was added and the mixture was stirred at 70° C. for 45 min. Water was added and the material was extracted with $CH_2Cl_2$ (3×). Combined extracts were washed with water, dried over $Na_2SO_4$ and the volatiles removed in vacuo. After purification by flash chromatography on silica gel (40 to 80% gradient of EtOAc in hexanes), compound 5 was isolated as an off white solid (181 mg, 88% yield). LCMS (ES): 95% pure, m/z 370 [M+H]$^+$, 324 [M+1–EtOH]$^+$; $^1$H NMR (CDCl$_3$, 400 MHz) δ 1.41 (t, J=7.2, 3H), 3.17 (s, 3H), 4.29 (s, 2H), 4.41 (q, J=7.2, 2H), 7.27 (d, J=7.2, 1H), 7.33 (t, J=7.6, 1H), 7.36 (d, J=8.4, 1H), 7.39 (td, J=7.2, J=1.2, 1H), 7.57 (d, J=8.4, 1H), 8.61 (d, J=8.4, 1H) ppm.

EXAMPLE 76

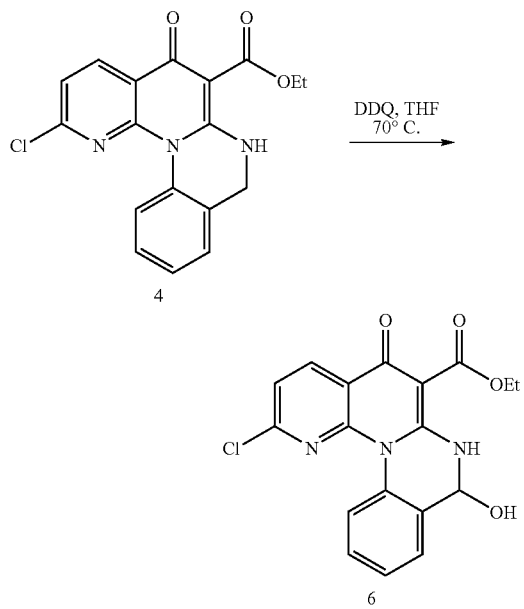

Compound 4 (1.0 eq, 104 mg, 0.29 mmol) was suspended in THF. A solution of DDQ (1.1 eq, 73 mg, 0.32 mmol) in THF (1 ml) was added dropwise and the resulting mixture stirred at 70° C. for 24 hours. An aqueous solution of 1N NaOH was added and the solution was extracted with $CH_2Cl_2$ (4×). The combined extracts were washed with a saturated $NaHCO_3$ aqueous solution, dried over $Na_2SO_4$ and the solvents removed in vacuo. The compound was purified by preparative HPLC (MeCN/water). MeCN was evaporated, $NaHCO_3$ was added and the substance extracted with $CH_2Cl_2$. Combined extracts were dried over $Na_2SO_4$ and the solvent removed in vacuo to afford 6 as an off-white solid (18 mg, 17% yield). LCMS (ES): 95% pure, m/z 372 [M+H]$^+$, 326 [M+1–EtOH]$^+$; $^1$H NMR (CDCl$_3$, 400 MHz) δ 1.44 (t, J=6.8, 3H), 4.42 (q, J=7.2, 2H), 6.01 (d, J=4.4, 1H), 7.4-7.55 (m, 4H), 7.98 (d, J=8.8, 1H), 8.64 (d, J=8.4, 1H), 11.53 (br s, 1H) ppm.

EXAMPLE 77

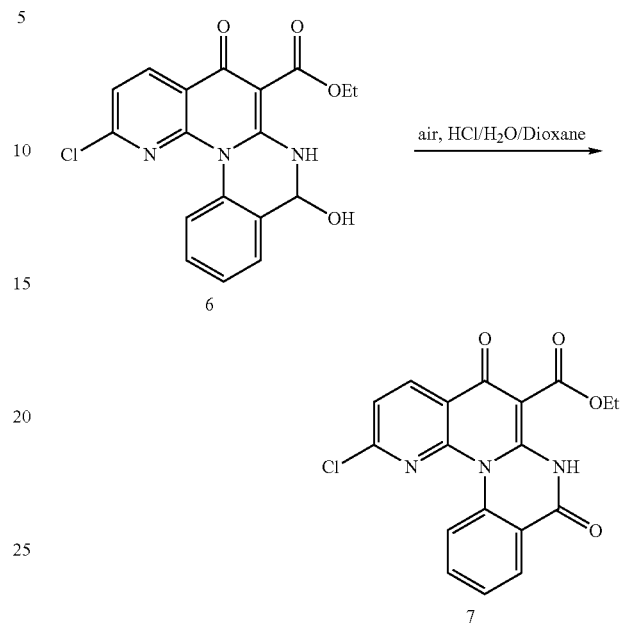

Compound 6 (8 mg, 0.021 mmol) was suspended in dioxane (0.5 ml). One drop of concentrated aqueous HCl was added and the resulting yellow solution stirred at room temperature. After 2 hours, one extra drop of concentrated HCl was added and some air was bubbled into the solution. The solution was stirred at room temperature for 24 hours. The solvent were removed in vacuo, NMP was added and the compound was purified by preparative HPLC (MeCN/water). Acetonitrile was evaporated, the product was extracted with $CH_2Cl_2$ (3×) and the combined extracts dried over $Na_2SO_4$. Solvents were removed to afford 7 as a solid (5 mg, 62% yield). LCMS (ES): 95% pure, m/z 370 [M+H]$^+$, 392 [M+23], 324 [M+1–EtOH]$^+$; $^1$H NMR (CDCl$_3$, 400 MHz) δ1.46 (t, J=7.2, 3H), 4.48 (q, J=7.2, 2H), 7.52 (d, J=8.0, 1H), 7.58 (t, J=6.8, 1H), 7.81 (dt, J=6.8, J=1.6, 1H), 8.33 (dd, J=7.6, J=1.2, 1H), 8.56 (d, J=8.8, 1H), 8.70 (d, J=8.0, 1H), 13.58 (br s, 1H) ppm.

EXAMPLE 78

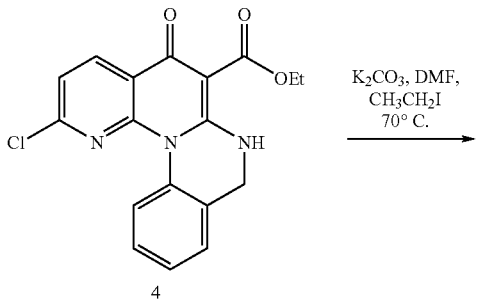

-continued

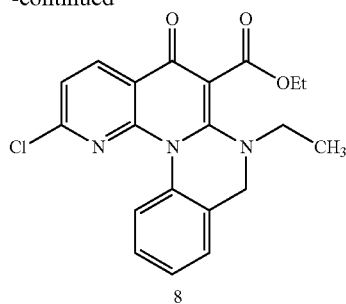

8

Compound 4 (1.0 eq, 218 mg, 0.613 mmol) and $K_2CO_3$ (2.0 eq, 169 mg, 1.22 mmol) were suspended in DMF (1.5 ml). Iodomethane (1.2 eq, 0.059 ml, 0.74 mmol) was added and the mixture was stirred at 70° C. for 35 min. Water was added and the material was extracted with $CH_2Cl_2$ (4×). Combined extracts were dried over $Na_2SO_4$ and the volatiles removed in vacuo. After purification by preparative HPLC, the pH of the resulting MeCN/water solution was adjusted by adding $NaHCO_3$ and MeCN was evaporated. The material was extracted with $CH_2Cl_2$ and the combined extracts were dried over $Na_2SO_4$. Precipitation using $CH_2Cl_2$/hexanes afforded 8 as an off-white solid (77 mg, 33% yield). LCMS (ES): 95% pure, m/z 384 [M+H]+, 406 [M+Na]+, 338 [M+1−EtOH]+.

EXAMPLE 79

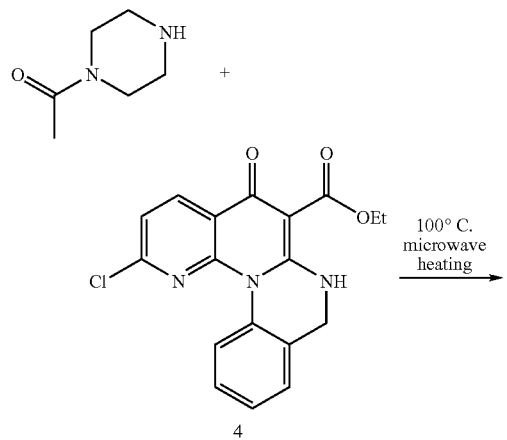

9

Compound 4 (1.0 eq, 110 mg, 0.309 mmol) and N-acetyl piperazine (4.0 eq, 158 mg, 1.233 mmol) were mixed in NMP (0.3 ml) and the resulting solution heated by microwave at 100° C. for 5 min. A mixture of EtOAc and hexanes was added and the resulting solid filtered and dried. Compound 9 was isolated as an off-white solid (145 mg, 100% yield). LCMS (ES): 95% pure, m/z 448 [M+H]+.

EXAMPLE 80

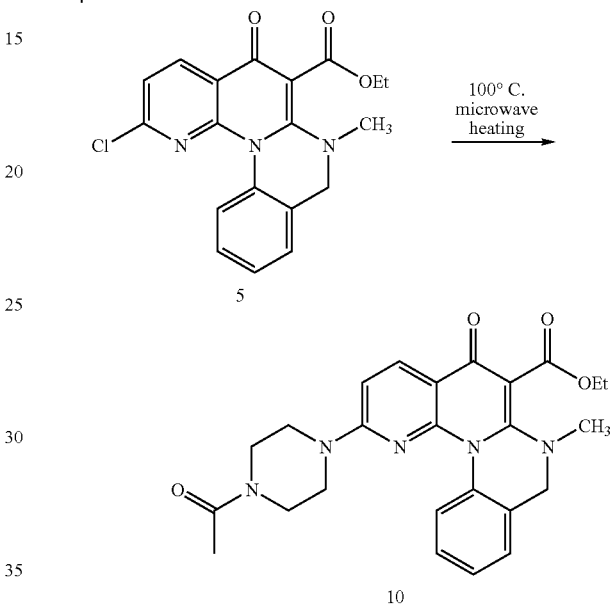

10

Compound 10 was prepared according to the procedure used for preparation of compound 9. Compound 10 was isolated as an off-white solid (147 mg, 70% yield). LCMS (ES): 95% pure, m/z 462 [M+H]+, 416 [M+H−EtOH]+.

EXAMPLE 81

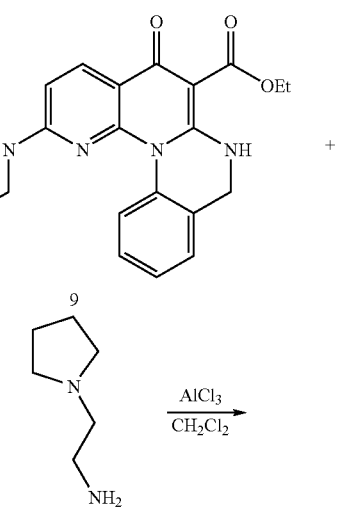

-continued

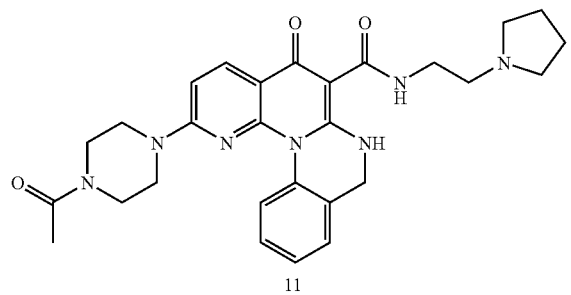

11

Compound 9 (1.0 eq, 131 mg, 0.293 mmol) and 1-(2-aminoethyl)pyrollidine (1.5 eq, 0.05 ml, 0.394 mmol) were mixed in $CH_2Cl_2$ (5 ml). $AlCl_3$ (2.0 eq, 80 mg, 0.60 mmol) was added and the resulting solution was vigorously stirred at room temperature. After 3 hours, another 0.1 ml of the 1-(2-aminoethyl)pyrollidine and 2 ml of $CH_2Cl_2$ were added and the reaction was stirred overnight. After removal of $CH_2Cl_2$ in vacuo, the resulting slurry was treated with a saturated aqueous tartaric acid solution and stirred until all solid disappeared (about 1 hr for completion of the hydrolysis). Water was added and the pH was adjusted to 14 by adding NaOH. The product was extracted by $CH_2Cl_2$ (4×). Combined extracts were washed with brine (1×) and dried over $Na_2SO_4$. After removal of the solvent, the crude material was dissolved in a mixture of NMP and trifluoroacetic acid and purified by preparative HPLC (MeCN, water). After adjusting pH with NaOH and evaporation of MeCN, the material was extracted with $CH_2Cl_2$. After drying over $Na_2SO_4$ and evaporation of the volatiles, compound 11 was precipitated by EtOAc/hexanes, filtered and dried to provide a white solid (60 mg, 40% yield). LCMS (ES): 95% pure, m/z 516 [M+H]$^+$.

EXAMPLE 82

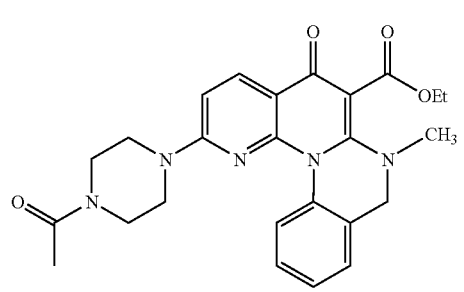

10

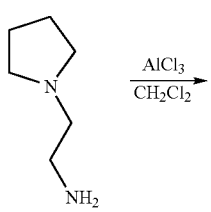

AlCl$_3$
CH$_2$Cl$_2$

-continued

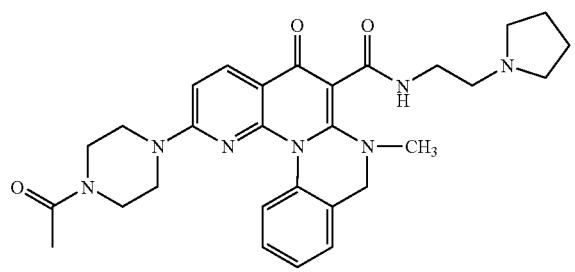

12

Compound 12 was prepared according to the procedure used for preparation of compound 11. Compound 12 was isolated as an off-white solid (28 mg, 17% yield). LCMS (ES): 95% pure, m/z 530 [M+H]$^+$.

EXAMPLE 83

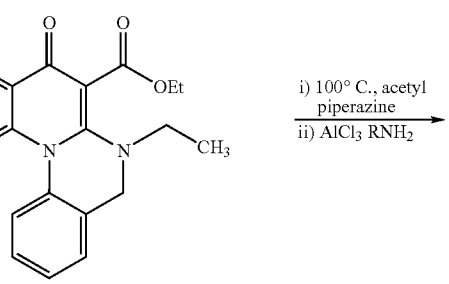

8 i) 100° C., acetyl piperazine
ii) AlCl$_3$ RNH$_2$

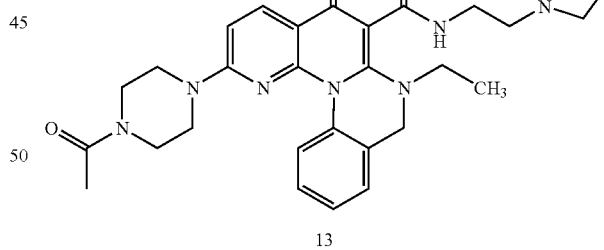

13

Compound 8 (1.0 eq, 77 mg, 0.201 mmol) and N-acetyl piperazine (4.0 eq., 103 mg, 0.803 mmol) were mixed in NMP (0.5 ml) and heated by microwave at 100° C. for 10 min. Water and brine were added and a gummy solid was isolated by filtration. This crude material was dissolved in $CH_2Cl_2$, the solution dried over $Na_2SO_4$ and the volatiles removed in vacuo. The final reaction step was then carried out on the crude ester according to the procedure used for the preparation of compound 11. Compound 13 was isolated as an off-white solid (7 mg, 6% yield). LCMS (ES): 95% pure, m/z 544 [M+H]$^+$.

EXAMPLE 84

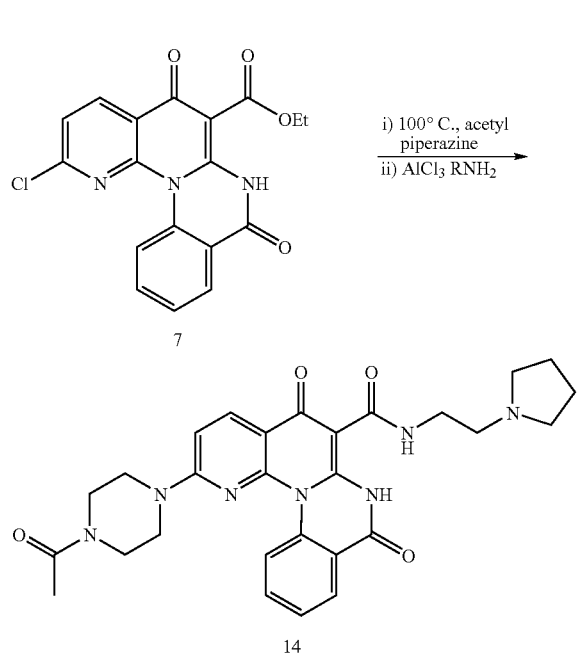

Compound 14 was prepared according to the procedure used for preparation of compound 13 as described in Example 83. Compound 14 was isolated as an off white solid. LCMS (ES): 91% pure, m/z 530 [M+H]$^+$.

EXAMPLE 85

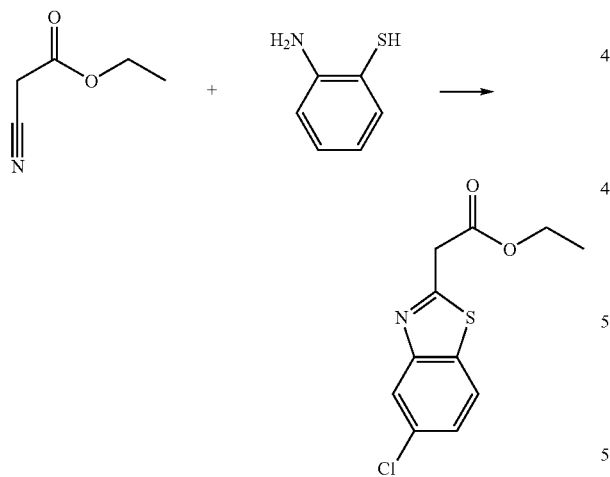

Ethyl 2-(4-chloro-benzothiazol-2-yl)acetate was prepared by the method of Abbotto, Bradamante et. al. (*J. Org. Chem.* 2002, 16, 5753. A neat mixture of 4-chloro-2-aminothiophenol (6.36 g, 40 mmol) and ethyl cyanoacetate (6.8 g, 60 mmol) was heated at 125° C. for 2 hours at which time TLC analysis indicated that the reaction was complete as judged by the disappearance of starting material. The mixture was triturated with diethyl ether and hexanes to give 7.91 g of yellow crystals in the first batch and 0.75 g of crystals in a second batch for a total of 8.66 g (85%). LCMS: 256.2 (M+H)$^+$.

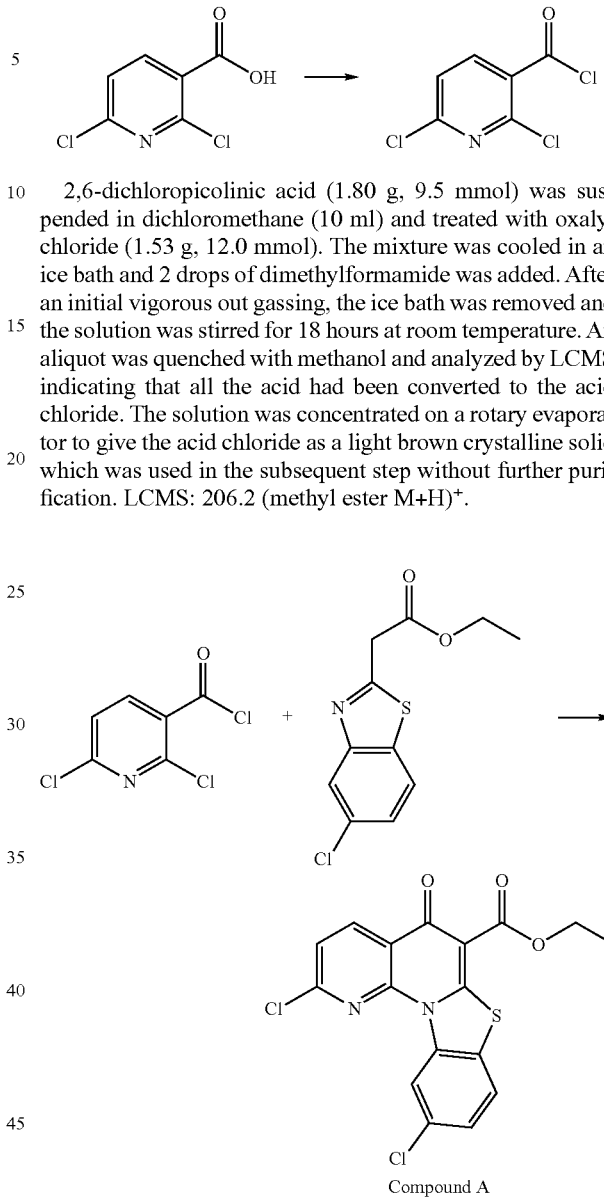

2,6-dichloropicolinic acid (1.80 g, 9.5 mmol) was suspended in dichloromethane (10 ml) and treated with oxalyl chloride (1.53 g, 12.0 mmol). The mixture was cooled in an ice bath and 2 drops of dimethylformamide was added. After an initial vigorous out gassing, the ice bath was removed and the solution was stirred for 18 hours at room temperature. An aliquot was quenched with methanol and analyzed by LCMS indicating that all the acid had been converted to the acid chloride. The solution was concentrated on a rotary evaporator to give the acid chloride as a light brown crystalline solid which was used in the subsequent step without further purification. LCMS: 206.2 (methyl ester M+H)$^+$.

Tetrahydrofuran (25 ml) was added to a mixture of ethyl 2-(4-chloro-benzothiazol-2-yl)acetate (2.2 g, 8.6 mmol), magnesium chloride (1.19 g, 12.9 mmol) and 2,6-dichloropicolinyl chloride from the previous step. The resulting suspension was cooled in an ice bath and triethylamine (2.4 g, 17.2 mmol) was added drop wise at such a rate that the internal temperature did not go over 10° C. as measured with an internal thermocouple probe. Once the addition was complete, the ice bath was removed and the mixture was allowed to stir while warming to room temperature over 2 hours. The reaction was diluted with dimethylformamide and potassium carbonate (1.19 g, 8.6 mmol) and warmed to 80° C. for 1 hour at which time LCMS indicated that the reaction was done. The reaction was diluted with water and filtered. The solid was dissolved in a mixture of dichloromethane and chloroform washed with water and the organic phase was dried over sodium sulfate. After concentration on a rotary evaporator, the product was purified by trituration with diethyl ether to give 2.5 g (74%) of the dichloro-ester as a beige solid. LCMS: 393.2 (M+H)⁺.

EXAMPLE 86

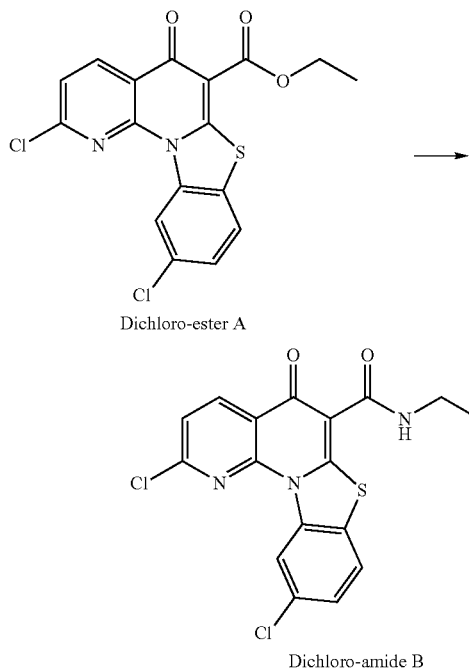

Dichloro-ester A

Dichloro-amide B

A solution of 2-(1-methylpyrrolidin-2-yl)ethylamine (295 mg, 2.3 mmol) in dichloromethane (5 ml) was treated with trimethylaluminum (0.99 ml, 25% in hexanes, 2.37 mmol). This solution was added to a solution containing dichloro-ester A (600 mg, 1.53 mmol) and dichloromethane (10 ml) at such a rate that the internal temperature did not exceed 10° C. The solution was allowed to stir for 18 hours at which time the reaction was judged to be complete by LCMS. The reaction was treated with Rochelle's salt and extracted three times with dichloromethane. The organic extracts were dried over sodium sulfate to give a residue which was purified by trituration with dichloromethane and diethyl ether to give 450 mg (62%) of dichloro-amide B as a beige solid. LCMS: 475.5 (M+H)⁺.

EXAMPLE 87

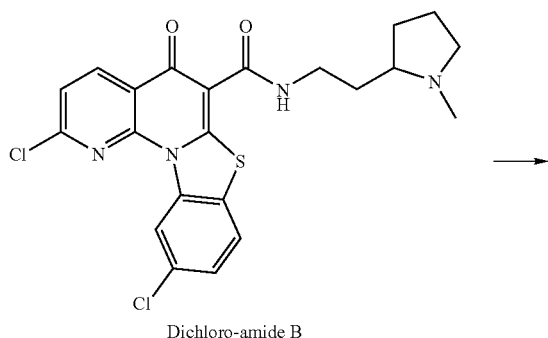

Dichloro-amide B

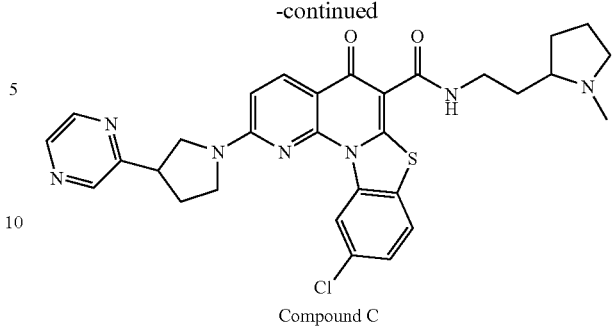

Compound C

A mixture of boc-amine (250 mg, 1.0 mmol) was deprotected by treatment with trifluoroacetic acid (1 ml) and dichloromethane (1 ml) at 50° C. for 2 hours. The resulting residue was concentrated on a rotary evaporator followed by high vacuum. To this residue was added dichloro-amide B (200 mg, 0.42 mmol) and N-methyl pyrrolidinone (0.8 ml) and diisopropylethylamine (0.5 ml). The mixture was allowed to stir at 80° C. for 72 hours at which time LCMS indicated that the reaction was done. The mixture was diluted with water (containing 10% trifluoroacetic acid) and purified by preparative HPLC to give 286 mg (97%) of compound C as the corresponding trifluoroacetate salt. LCMS: 588.3 (M+H)⁺.

EXAMPLE 88

This example evaluates the activity of the test compound below administered intravenously,

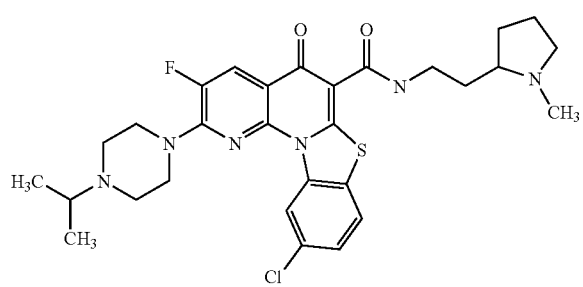

Methodology 6 wk old female nu/nu mice were purchased from Taconic Farms, Germantown N.Y. They were injected with 5×10⁶ HCT116 cells SQ in right flank. When tumors reached sufficient size for study, they were randomized into groups.

Vehicle: 242.9 mm³

Test compound: 251.0 mm³

Figure 3:
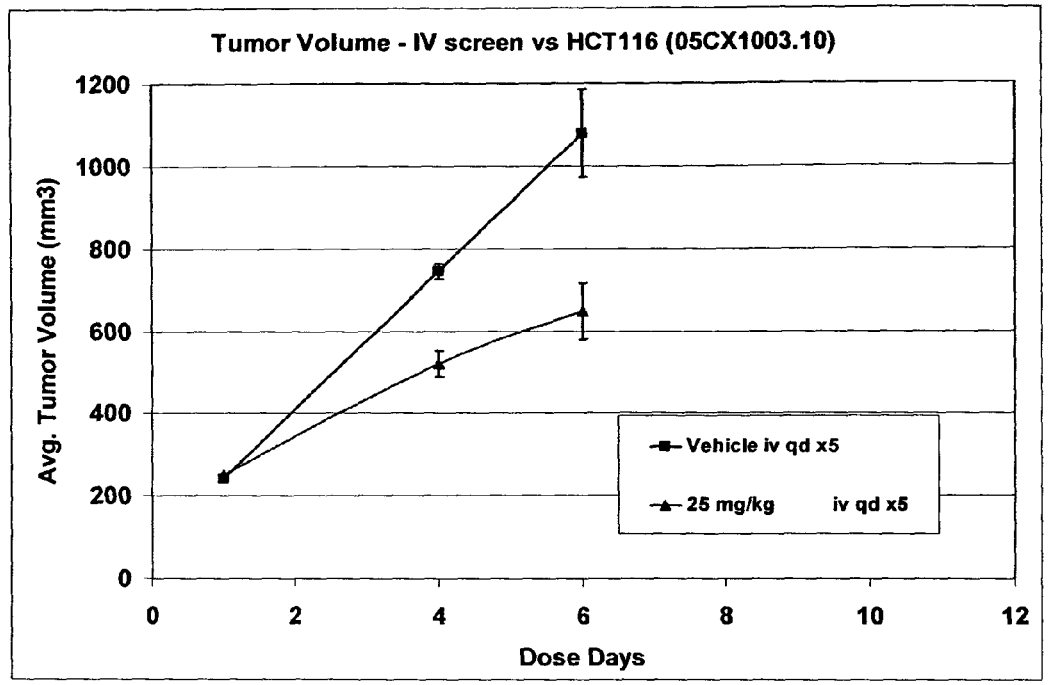

Animals dosed by bolus injection—IV through lateral tail vein for five consecutive days. Caliper measurements were taken on Day 1, 4, 6. FIG. 3 shows the activity of the test compound at a 25 mg/kg dose with no adverse effects observed.

EXAMPLE 89

This example evaluates the activity of the test compound below administered intravenously.

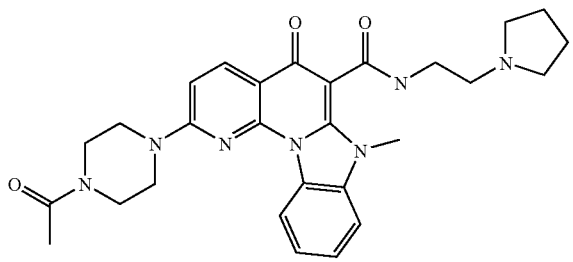

Methodology 6 wk old female nu/nu mice were purchased from Simonsen Labs, Gilroy, Calif. They were injected with 5×10⁶ HCT116 cells SQ in right flank. When tumors reached sufficient size for study, they were randomized into groups.

Vehicle: 101.9 mm³
Test compound: 152.8 mm³

Figure 4:
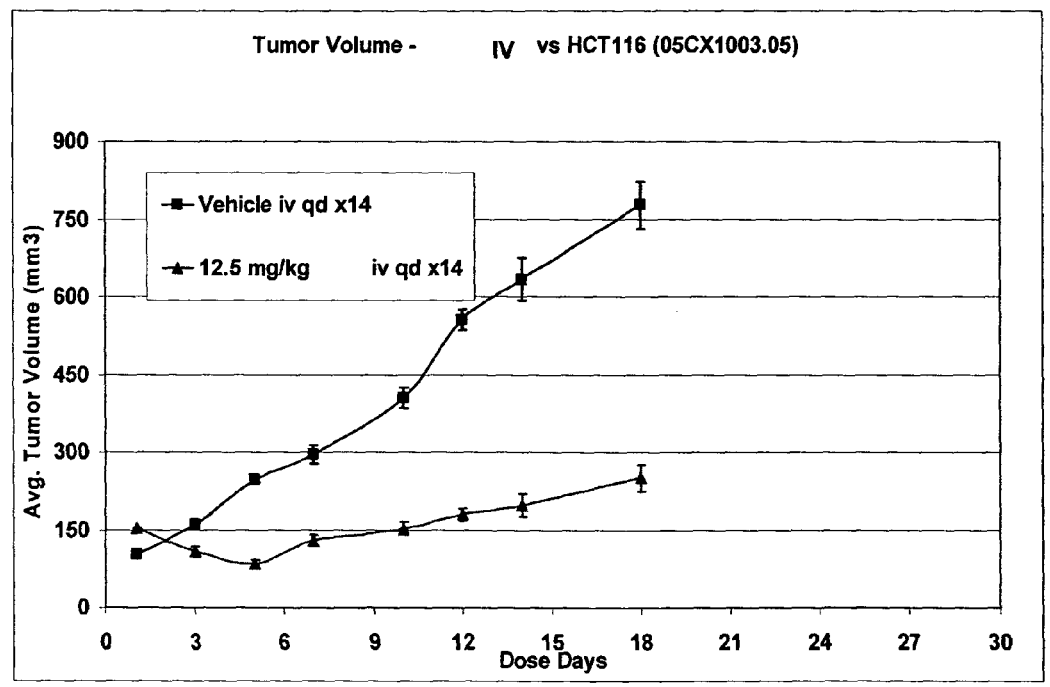

Animals dosed by bolus injection—IV through lateral tail vein for fourteen consecutive days. Caliper measurements were taken on Day 1, 3, 5, 7, 10, 12, 14, and 18. FIG. 4 shows the activity at a 12.5 mg/kg dose with no adverse effects observed.

EXAMPLE 90

This example evaluates the activity of the test compound in Example 89, administered intravenously at different dose levels.

Methodology 6 wk old female nu/nu mice were purchased from Simonsen Labs, Gilroy, Calif. They were injected with 5×10⁶ HCT116 cells SQ in right flank. When tumors reached sufficient size for study, they were randomized into groups.

Vehicle: 114.6 mm³
Test compound: 106.1 mm³
Test compound: 84.1 mm³

Figure 5:
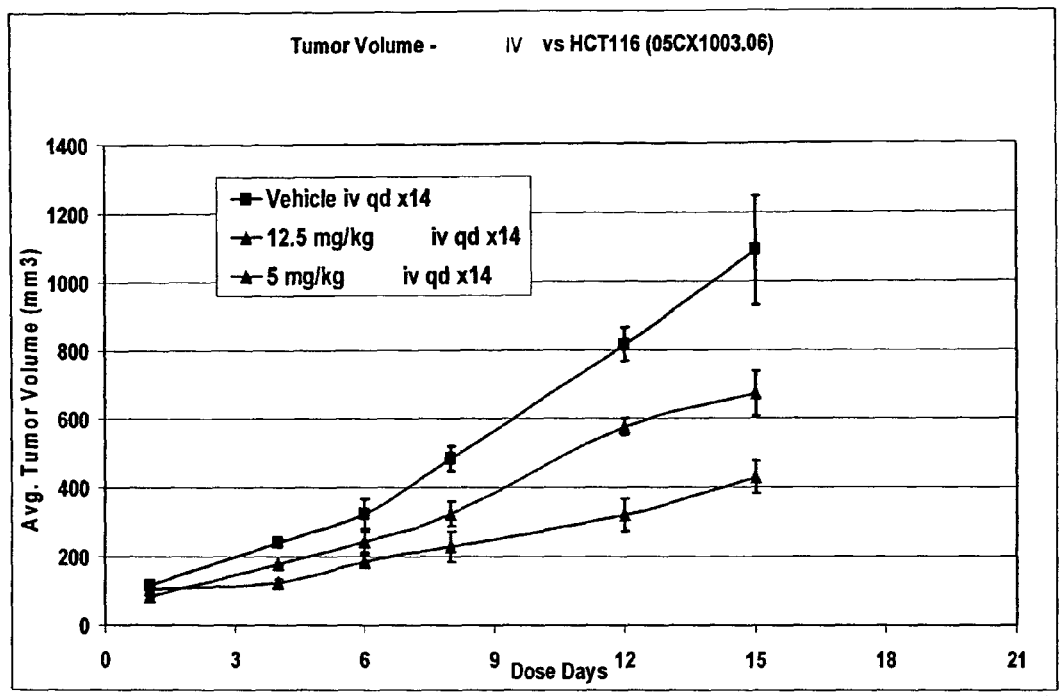

Animals dosed by bolus injection—IV through lateral tail vein for fourteen consecutive days. Caliper measurements were taken on Day 1, 4, 6, 8, 12, and 15. FIG. 5 shows dose dependent activity with no adverse effects observed.

EXAMPLE 91

This example evaluates the activity of the test compound below administered intravenously.

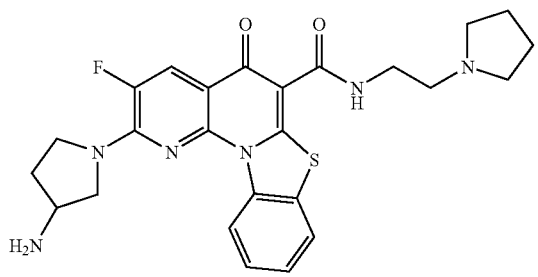

Methodology 6 wk old female nu/nu mice were purchased from Taconic Farms, Germantown N.Y. They were injected with 5×10⁶ HCT116 cells SQ in right flank. When tumors reached sufficient size for study, they were randomized into groups.

Vehicle: 242.9 mm³
Test compound: 252.1 mm³

Figure 6:
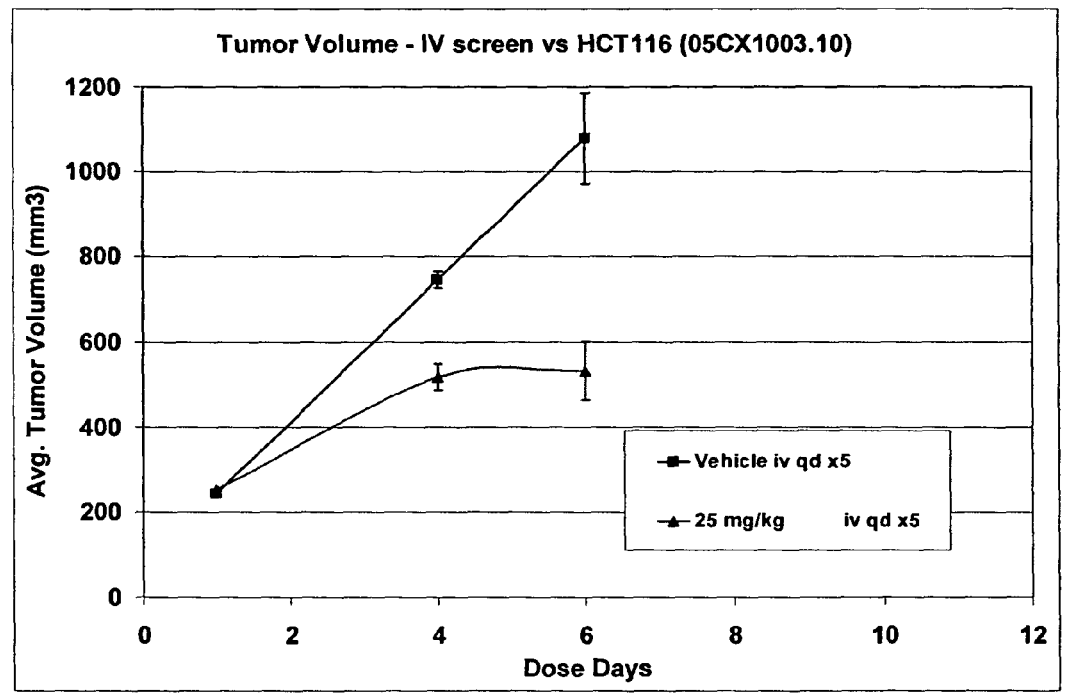

Animals dosed by bolus injection—IV through lateral tail vein for five consecutive days. Caliper measurements were taken on Day 1, 4, and 6. FIG. 6 shows the activity of the test compound at a 25 mg/kg dose with no adverse effects observed.

EXAMPLE 92

This example evaluates the activity of the test compound below administered intravenously.

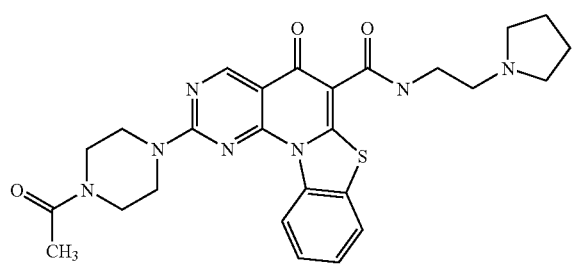

Methodology 6 wk old female nu/nu mice were purchased from Taconic Farms, Germantown N.Y. They were injected with 5×10⁶ HCT116 cells SQ in right flank. When tumors reached sufficient size for study, they were randomized into groups.

Vehicle: 242.9 mm³
Test compound: 236.1 mm³

Figure 7:
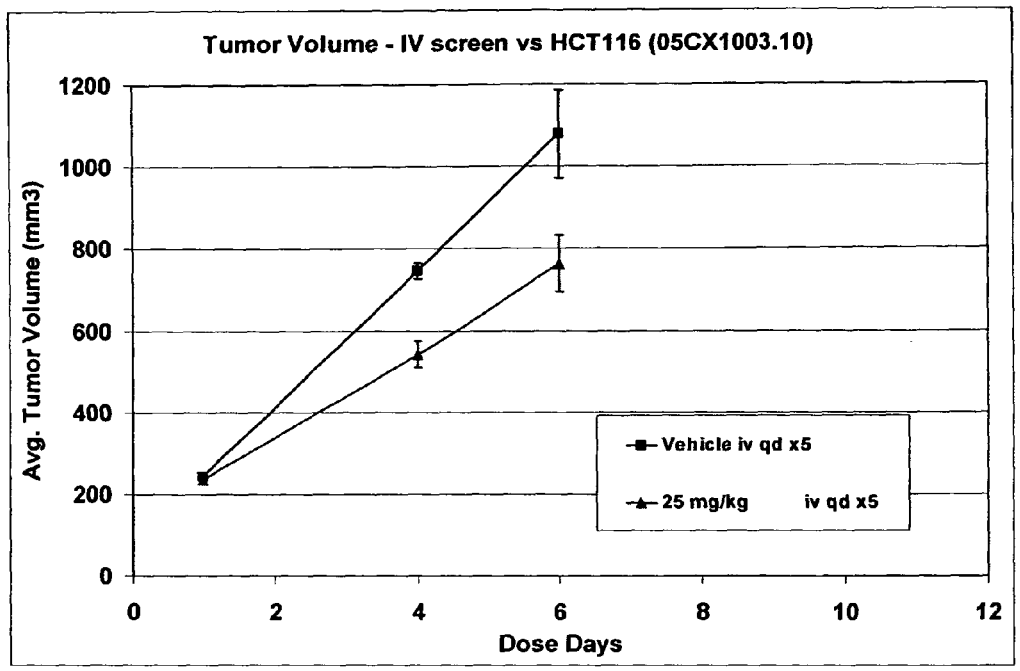

Animals dosed by bolus injection—IV through lateral tail vein for five consecutive days. Caliper measurements were taken on Day 1, 4, and 6. FIG. 7 shows the activity of the test compound at a 25 mg/kg dose with no adverse effects observed.

EXAMPLE 93

This example evaluates the activity of the test compound below administered intravenously.

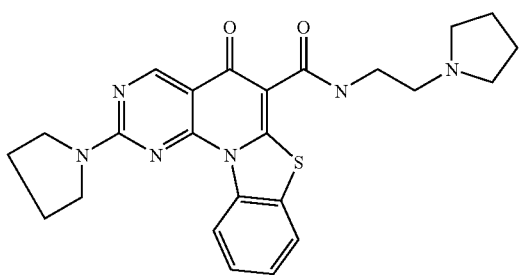

Methodology 6 wk old female nu/nu mice were purchased from Taconic Farms, Germantown N.Y. They were injected with 5×10⁶ HCT116 cells SQ in right flank. When tumors reached sufficient size for study, they were randomized into groups.

Vehicle: 242.9 mm³
Test compound: 254.7 mm³

Figure 8:
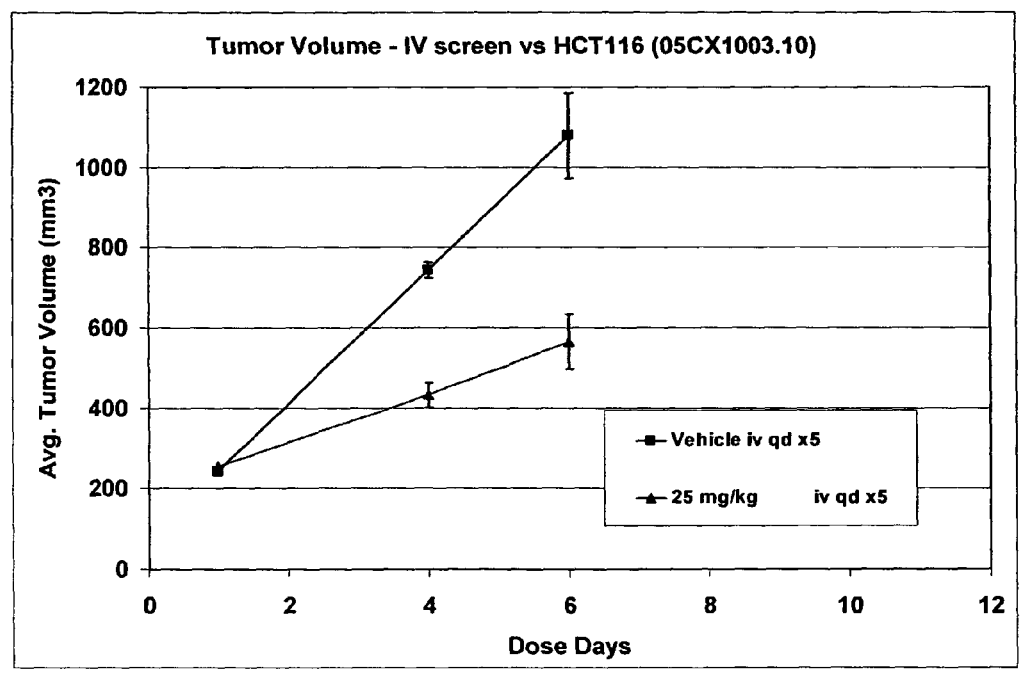

Animals dosed by bolus injection—IV through lateral tail vein for five consecutive days. Caliper measurements were taken on Day 1, 4, and 6. FIG. 8 shows the activity of the test compound at a 25 mg/kg dose with no adverse effects observed.

EXAMPLE 94

This example evaluates the activity of the test compound below administered intravenously.

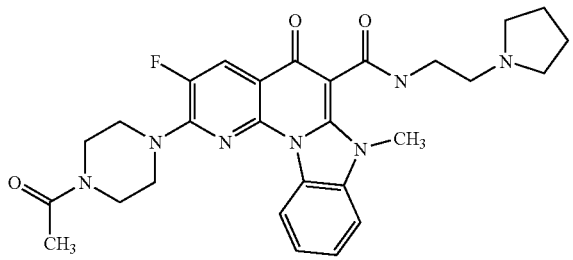

Methodology 6 wk old female nu/nu mice were purchased from Taconic Farms, Germantown N.Y. They were injected with $5 \times 10^6$ HCT116 cells SQ in right flank. When tumors reached sufficient size for study, they were randomized into groups.

| | | |
|---|---|---|
| Vehicle: | 112.7 mm³ | |
| Test compound: | 113.1 mm³ | 25 mg/kg |
| Test compound: | 110.1 mm³ | 12.5 mg/kg |
| CPT11: | 109.4 mm³ | |

Figure 9:
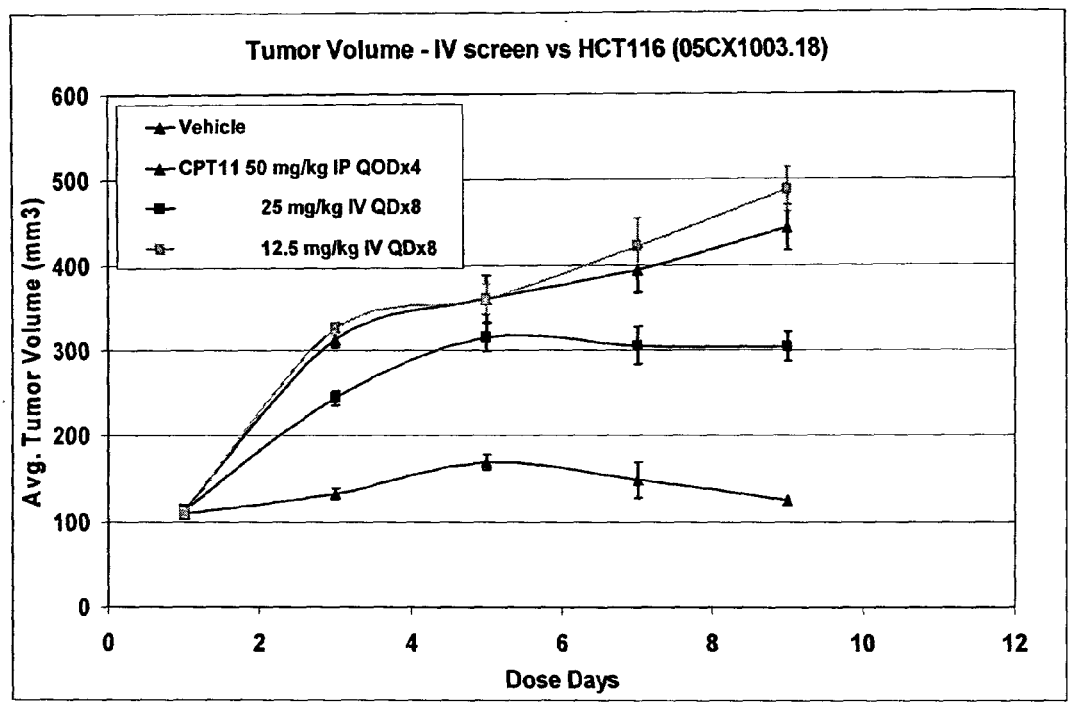

Animals dosed by bolus injection—IV through lateral tail vein for nine consecutive days. Caliper measurements were taken on Day 1, 3, 5, 7, and 9. FIG. 9 shows limited activity at the high dose and no activity at the mid dose with no adverse effects observed.

EXAMPLE 95

This example evaluates the activity of the test compound below administered intravenously.

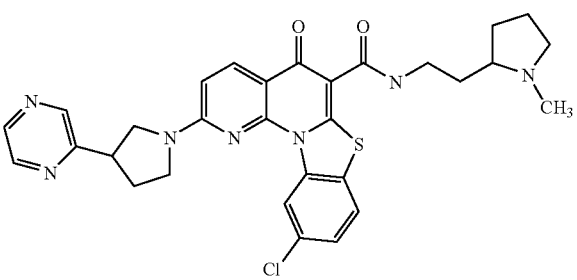

Methodology 6 wk old female nu/nu mice were purchased from Taconic Farms, Germantown N.Y. They were injected with $5 \times 10^6$ HCT116 cells SQ in right flank. When tumors reached sufficient size for study, they were randomized into groups.

| | | |
|---|---|---|
| Vehicle: | 112.7 mm³ | |
| Test compound: | 107.1 mm³ | 25 mg/kg |
| Test compound: | 108.9 mm³ | 12.5 mg/kg |
| CPT11: | 109.4 mm³ | |

Figure 10:
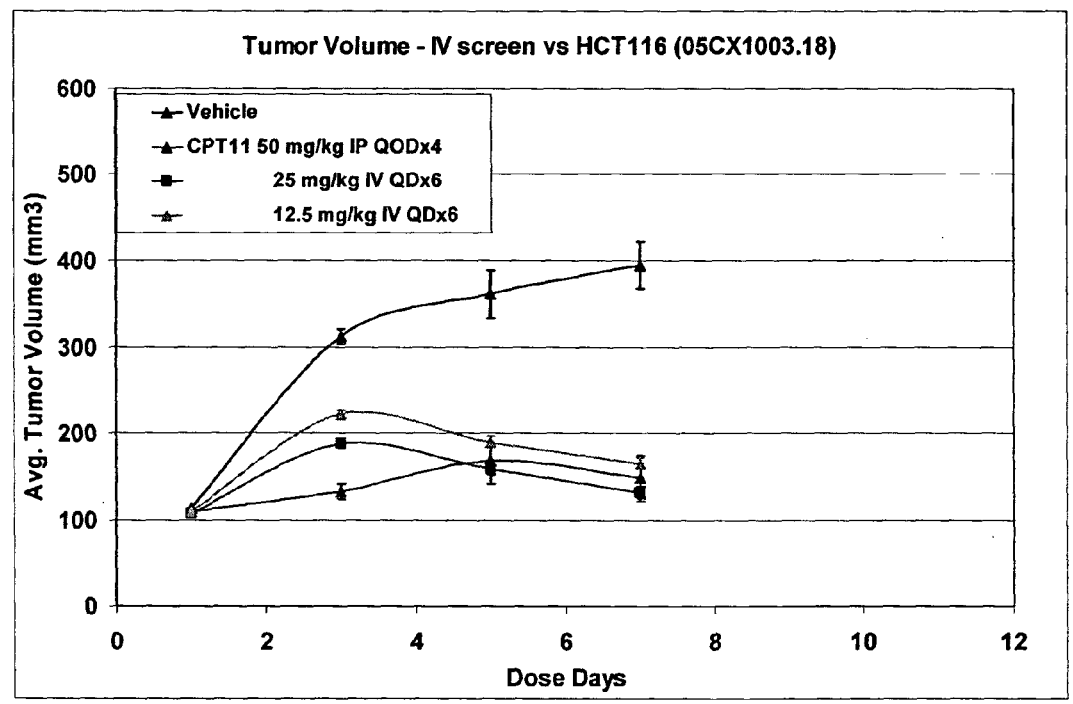

Animals dosed by bolus injection—IV through lateral tail vein for seven consecutive days. Caliper measurements were taken on Day 1, 3, 5, and 7. FIG. 10 shows excellent activity with minimal dose dependency. No adverse effects were observed.

EXAMPLE 96

Cell Proliferation and/or Cytotoxicity Assay

The antiproliferative effects of the present compounds may be tested using a cell proliferation and/or cytotoxicity assay, following protocols described below.

Cell culture. Human cervical epithelial cells (HeLa cells) are obtained from American Type Culture Collection (Manassas, Va.). Cells are grown in Eagle's minimum essential medium (MEM, Hyclone, Utah) supplemented with 2 mM Glutamine, 0.1 mM nonessential amino acid, 1 mM Na Pyruvate, 1.5 g/L NaHCO₃, 50 mg/L gentamicin, and 10% fetal bovine serum (Hyclone, USA) in a humidified atmosphere of 5% $CO_2$ at 37° C.

MTS assays. Antiproliferative effects of anticancer drugs are tested by the CellTiter 96 AQ$_{ueous}$ assay (Promega, WI), which is a colorimetric assay for determining the number of viable cells. (See, e.g., Wang, L., et al., *Methods Cell Sci* (1996) 18:249-255). Generally, cells (2,000 to 5,000 cells/well) are seeded on 96 well flat bottom plates (Corning, NY) in 100 µl of culture medium without any anticancer drug on day 0, and the culture medium is exchanged for that contained anticancer drugs at various concentrations on day 1. After incubation for 3 days under normal growth conditions (on day 4), the monolayers are washed once in PBS, and the medium is switched to 100 µl of PBS in each of the 96 well plate. After mixing MTS and PMS at the ratio of 20:1, 20 µl of MTS/PMS solution is added to each of the 96 well plate and incubated for 4 hours in a humidified atmosphere of 5% $CO_2$ at 37° C. The absorbance is read at 490 nm using FLUOstar Galaxy 96 well plate reader (BMG Labtechnologies, Germany).

EXAMPLE 97

Measurement of mRNA values in Cell Assays

Real-time quantitative PCR (QPCR) method may be used to detect the changes of the target c-myc and the endogenous reference GAPDH gene copies in the same tube. Generally, cells (15,000 cells/well) are seeded on 96 well flat bottom plates (Corning, NY) and incubated under normal growth conditions for overnight. The next day, the culture medium is exchanged for that containing anticancer drugs at various concentrations and incubated for 4 hrs in a humidified atmosphere of 5% $CO_2$ at 37° C. Total RNA (tRNA) is extracted using the RNeasy 96 Kit (QIAGEN, CA). The concentration of the tRNA is determined by the RiboGreen RNA Quantitation Reagent (Molecular Probes, OR).

A reverse-transcription (RT) reaction may be conducted using 50 ng of tRNA from each well in a 25 µl reaction containing 1× TaqMan RT buffer, 2.5 uM random hexamers, 5.5 mM MgCl₂, 0.5 mM each deoxynucleoside triphosphate (dNTP), 30 U MultiScribe Reverse Transcriptase, and 10 U RNase inhibitor. RT reactions are incubated for 10 min at 25° C., reverse-transcribed for 30 min at 48° C., inactivated for 5 min at 95° C., and placed at 4° C. All RT reagents may be purchased from Applied Biosystems, CA.

Real-Time QPCR reaction may be performed in a 50 µl reaction containing the 5 µl of cDNA, 1× Universal PCR Master Mix, 1× c-myc Pre-Developed Primers and Probe set, and 0.8× GAPDH Pre-Developed Primers and Probe set. Because of the relative abundance of GAPDH gene in Hela, GAPDH primers and probe concentration may be adjusted to get accurate threshold cycles ($C_T$) for both genes in the same tube. The threshold cycle ($C_T$) indicates the fractional cycle number at which the amount of amplified target reaches a fixed threshold. By doing so, the GAPDH amplification is stopped before it can limit the common reactants available for amplification of the c-myc. The ΔRn value represents the normalized reporter signal minus the baseline signal. ΔRn increases during PCR as amplicon copy number increases until the reaction approaches a plateau.

The c-myc probe is labeled with 6FAM™ dye-MGB and the GAPDH probe is labeled with VIC™ dye-MGB. Preincubation is performed for 2 min at 50° C. to activate AmpErase UNG enzyme and then for 10 min at 95° C. to activate AmpliTaq DNA Polymerase. DNA is amplified for 40 cycles of 15 sec at 95° C. and 1 min at 60° C. Human c-myc and GAPDH cDNA are amplified, detected, and quantitated in real time using the ABI Prism 7000 Sequence Detection system (Applied Biosystems, CA), which is set to detect both 6-FAM and VIC reporter dyes simultaneously.

The data may be analyzed using the ABI PRISM Sequence Detection System and Microsoft Excel. Relative quantitation is done using the standard curve and comparative $C_T$ method at the same time, and both methods gave equivalent results. The cycle at which the amplification plot crosses the $C_T$ is known to accurately reflect relative mRNA values. (See, Heid, et al., *Genome Res*. (1996) 6:986-994; Gibson, et al., *Genome Res*. (1996) 6:995-1001). QPCR reactions are set up in triplicate at each cDNA sample and the triplicate $C_T$ values are averaged. All reagents including Pre-Developed Primers and probe set may be purchased from Applied Biosystems, CA.

EXAMPLE 98

In Vitro Characterization

Various methods may be used for in vitro characterization of the compounds of the present invention, including but not limited to i) stop assays; ii) quadruplex/duplex competition assay; iii) quadrome footprints; and iv) direct assay in the absence of a competitor molecule.

Stop Assays. Stop assays are high throughput, first-pass screens for detecting drugs that bind to and stabilize the target G-quadruplex. Generally, DNA template oligonucleotide is created, which contains the nucleotide sequence of the "target" quadruplex against which drug screening is desired. A fluorescently labeled primer DNA is then annealed to the 3' end of the template DNA. A DNA polymerase such as Taq polymerase is then introduced to synthesize a complementary strand of DNA by extending from the fluorescently labeled primer. When the progress of the Taq polymerase is unhindered, it synthesizes a full-length copy of the template. Addition of a test drug that merely binds to duplex DNA but does not bind selectively the quadruplex region results in a decrease in synthesis of full length product and a concomitant increase in variable-length DNA copies. If, however, the test drug selectively binds to and stabilizes the quadruplex, the progress of polymerase arrests only at the quadruplex, and a characteristic "Stop Product" is synthesized.

Compounds are initially screened at a single concentration, and "hits" are re-assayed over a range of doses to determine an $IC_{50}$ value (i.e., the concentration of drug required to produce an arrest product/full-length product ratio of 1:1). These products are visualized by capillary electrophoresis.

Quadruplex/Duplex Competitor Assay. The selectivity of compounds for the target quadruplex sequence relative to duplex DNA may be measured using a competition assay (i.e., "selectivity screen"). This selectivity screen uses the stop assay as a reporter system to measure the relative ability of an externally added DNA sequence to compete with the target quadruplex structure formed in the DNA template for binding of the drug. For example, the competitors are the c-myc quadruplex sequence, which is identical to the quadruplex sequence present in the template DNA; or a plasmid DNA which mimics complex genomic duplex DNA. The degree to which each competitor successfully "soaks up" drug in solution is reflected by the quantitative decrease in synthesis of the stop product. In this manner, the relative binding affinities of drug to both the target quadruplex and duplex DNA are determined.

Quadrome Footprints. Compounds may also be evaluated for their ability to bind to other native quadruplex structures of biological relevance, including quadruplex control elements that regulate a range of different oncogenes. The resulting data are used to create a Quadrome footprint.

Direct Interaction Assay. Compounds may be evaluated for their ability to interact directly with nucleic acids capable of forming a quadruplex structure, wherein the nucleic acid is not a telomeric nucleic acid. The assay may be performed in the same or different vessels. For example, a compound may be contacted with each nucleic acid in the same vessel. Alternatively, a compound may be separately contacted with each of the nucleic acids tested in a different vessel. A telomeric nucleic acid as used herein represents a region of highly repetitive nucleic acid at the end of a chromosome. As used herein, a direct interaction is measured without the presence of a competitor nucleic acid.

An interaction between the compound and the nucleic acid may be determined for example, by measuring $IC_{50}$ values, which are indicative of the binding and/or quadruplex stabilization. The selectivity of interactions may be determined, for example, by comparing measured $IC_{50}$ values. For example, the lowest $IC_{50}$ values may be used to indicate a strong interaction between the compound and the nucleic acid, while highest $IC_{50}$ values show a poor interaction; thus, showing selectivity of interaction. The reaction products may be characterized by capillary electrophoresis.

EXAMPLE 99

Direct Interaction Assay

Generally, a 5'-fluorescent-labeled (FAM) primer (P45, 15 nM) is mixed with template DNA (15 nM) in a Tris-HCL buffer (15 mM Tris, pH 7.5) containing 10 mM $MgCl_2$, 0.1 mM EDTA and 0.1 mM mixed deoxynucleotide triphosphates (dNTP's). The mixture is denatured at 95° C. for 5 minutes and, after cooling down to room temperature, is incubated at 37° C. for 15 minutes. After cooling down to room temperature, 1 mM $KCl_2$ and the test compound (various concentrations) are added and the mixture incubated for 15 minutes at room temperature.

The primer extension is performed by adding 13 mM KCl and Taq DNA Polymerase (2.5 U/reaction, Promega) and incubating at 70° C. for 20 minutes. The reaction is stopped by adding 1 μl of the reaction mixture to 10 μl Hi-Di Formamide mixed and 0.25 μl LIZ120 size standard. The method is repeated with the addition of various concentrations of competitor nucleic acids at the first step, along with the primer and template sequences. The G-quadruplex binding ligand is added at the concentration previously established to produce a 1:1 ratio of stop-product to full-length product. A CC50 for each nucleic acid competitor is defined as the concentration of competitor required to change the ratio of arrest product to full-length product from 1:1 to 1:2. The nucleic acid sequences of quadruplexes that may be used for this assay are set forth in Table 4.

TABLE 4

(STOP TEMPLATES)

TGFB3-81
TATACGGGGTGGGGGAGGGAGGGATTAGCGACACGCAATTGCTATAGTGAGTCGTA
TTAGCTACGTACAGTCAGTCAGACT (SEQ ID NO. 21)

HRAS-85
TATACCGGGGCGGGGCGGGGGCGGGGGCTTAGCGACACGCAATTGCTATAGTGAGT
CGTATTAGCTACGTACAGTCAGTCAGACT (SEQ ID NO. 22)

BCL2-97(full)
TAGGGGCGGGCGCGGGAGGAAGGGGGCGGGAGCGGGGCTGTTAGCGACACGCAAT
TGCTATAGTGAGTCGTATTAGCTACGTACAGTCAGTCAGACT (SEQ ID NO. 23)

HMGA-97
TTAGAGAAGAGGGGAGGAGGAGGAGGAGAGGAGGAGGCGCTTAGCGACACGCAA
TTGCTATAGTGAGTCGTATTAGCTACGTACAGTCAGTCAGACT (SEQ ID NO. 24)

MYC99
TCCAACTATGTATACTGGGGAGGGTGGGGAGGGTGGGGAAGGTTAGCGACACGCA
ATTGCTATAGTGAGTCGTATTAGCTACGTACAGTCAGTCAGACT (SEQ ID NO. 25)

IMOTIF99
TCCAACTATGTATACCCTTCCCCACCCTCCCCACCCTCCCCATTAGCGACACGCAAT
TGCTATAGTGAGTCGTATTAGCTACGTACAGTCAGTCAGACT (SEQ ID NO. 26)

Humtel-95
TCATATATGACTACTTAGGGTTAGGGTTAGGGTTAGGGTTACTGCCACGCAATTGCT
ATAGTGAGTCGTATTAGCTACGTACAGTCAGTCAGACT (SEQ ID NO. 27)

SRC89
ATGATCACCGGGAGGAGGAGGAAGGAGGAAGCGCGCTGCCACGCAATTGCTATAG
TGAGTCGTATTAGCTACGTACAGTCAGTCAGACT (SEQ ID NO. 28)

Primer:
(45 MER)
AGTCTGACTGACTGTACGTAGCTAATACGACTCACTATAGCAATT (SEQ ID NO. 29)

EXAMPLE 100

Cytochrome P450 (CYP450) Inhibition Assay

The compounds of the present invention may be evaluated for potential inhibitory activity against cytochrome P450 isoenzymes. Generally, six reaction tubes with 100 µL of a solution containing 50 mM potassium phosphate, pH 7.4, 2.6 mM NADP+, 6.6 mM glucose 6-phosphate, 0.8 U of glucose 6-phosphate dehydrogenase/mL and 1:6 serial dilutions of the test compound will be prepared along with six tubes of 1:6 serial dilutions of a suitable positive control inhibitor. The reactions will be initiated by adding 100 µL of a pre-warmed enzyme/substrate solution to the reaction tubes. A zero time-point control reaction will be prepared by adding 50 µL of acetonitrile to 100 µL of cofactor solution to inactivate the enzymes, then adding 100 µL of enzyme/substrate solution. A control reaction with no inhibitor may also be prepared. After a suitable incubation at 37 C, the reactions will be terminated by the addition of 50 µL of acetonitrile. The reactions will be analyzed for the metabolite forms of the probe substrate using LC/MS/MS.

EXAMPLE 101

Evaluation of Compound Efficacy in Tumor Suppression

A representative experiment for evaluating the efficacy of compounds of the present invention in athymic nude mouse models of human carcinoma may be designed as follows. Male or female animals (mouse, Sim) (NCR, nu/nu) aged five to six weeks and weighing more than 20 grams will be used. The animals will be purposely bred and will be experimentally naive at the outset of the study. Tumors will be propagated either from injected cells or from the passage of tumor fragments. Cell lines to be used include, but are not limited to, alia Paca-2, HPAC, Hs700T, Panc10.05, Panc 02.13, PL45, SW 190, Hs 766T, CFPAC-1 and PANC-1.

Cell implantation. One to ten million cells suspended in 0.1 ml culture media with or without Matrigel (Collaborative Biomedical Products, Inc, Bedford, Mass.) will be inoculated subcutaneously in the right flank of sixty animals. There will only be one injection per animal. Within 7-14 days of injection tumors will develop to a study use size of approximately 1.0 cm$^3$. A small subset (<10/60) animals will be considered. Donors and tumors will be grown 10-28 days and to a size of 1.5 cm$^3$ in order to be used for serial transplantation.

Fragment transplantation. Donor animals will be euthanized and tumors surgically excised and cut into 2 mm$^3$ size fragments using aseptic technique. Animals to be implanted will be lightly anesthetized with isoflurane. The area to implanted will be cleansed with 70% alcohol and betadine. A single fragment will then be implanted subcutaneously using a trocar.

Efficacy studies. Groups of 50-60 tumor bearing animals will be randomly divided. For example, in a representative study, animals may be randomly divided into three to eight groups containing 7 animals each, as described in Table 5.

TABLE 5

| Group No. | Number of Males/ Females | Dose Level | Dose Vol. (μL) | Dose Solution Conc. (mg/mL) | Number Euthanized on: Day 28-42 |
|---|---|---|---|---|---|
| 1 | N = 7 | Negative Control* | 250 | | all |
| 2 | N = 7 | Positive Control** | 10-400 IP | 2 to 5 IP | all |
| | | | 10-250 IV | 2.5 to 5 IV | |
| | | | 125-500 PO | ≦10 PO | |
| Groups 3-8 | N = 7/grp <56 total | Test Compound 1 to 25 IP 1 to 50 IV 50 to 200 PO | 10-400 IP 10-250 IV 125-500 PO | 2.5 to 5 IP 2.5 to 5 IV 10 PO | all |

*Vehicle/Diluent
**Commercially available anticancer compounds including, but not limited to, Taxol, CPT11 and Gemcitabine will be used as positive controls.

Dosing Procedure. Compounds will be administered QD, QOD, Q3D or once weekly via IP, IV (lateral tail vein) or PO. Animals will be dosed in a systematic order that distributes the time of dosing similarly across all groups. For bolus IP and PO dosing, animals will be manually restrained. For IV bolus dosing or short term IV infusion (one minute), animals will be mechanically restrained but not sedated. Disposable sterile syringes will be used for each animal/dose. A test compound in combination with about 10-100 mg/kg (e.g., about 40 mg/kg) chemotherapeutic agent such as gemcitabine also will be tested, normally by IP administration once per week.

EXAMPLE 102

Evaluation of Maximum Tolerated Doses

A representative experiment for evaluating the maximum tolerate dose (MTD) of compounds of the present invention may be designed as follows. Selection for animal models is as described in Example 101.

Acute Toxicity Studies. In a representative study to determine the MTD after a single dose, sixty naive animals, for example, will be randomly divided into groups containing 10 animals (5 male and 5 female) and will receive either one compound via two routes of administration or two compounds via a single route of administration. A single 50 mg/kg IV dose has been shown to be tolerated, and is used as the preliminary low dose levels. The low dose for oral studies is based on projected tolerability and will be adjusted downward if necessary. A representative design of dose levels, dose volumes and dose solution concentration are described in Table 6.

TABLE 6

| Group No. | Number of Males and Females | Dose Level (mg/kg) | Dose Vol. (μL) | Dose Solution Conc. (mg/mL) | Number Euthanized on: Day 7 |
|---|---|---|---|---|---|
| 1 | N = 5 M | Test compound #1 | 250 IV | 5 IV | all |
| | N = 5 F | 50 IV | 500 PO | 5 PO | |
| | | 100 PO | | | |
| 2 | N = 5 M | Test compound #1 | 250 IV | 8.25 IV | all |
| | N = 5 F | 75 IV | 500 PO | 10 PO | |
| | | 200 PO | | | |
| 3 | N = 5 M | Test compound #1 | 250 IV | 10 IV | all |
| | N = 5 F | 100 IV | 500 PO | 15 PO | |
| | | 300 PO | | | |
| 4 | N = 5 M | Test compound #2 | 250 IV | 5 IV | all |
| | N = 5 F | 50 IV | 500 PO | 5 PO | |
| | | 100 PO | | | |
| 5 | N = 5 M | Test compound #2 | 250 IV | 8.25 IV | all |
| | N = 5 F | 75 IV | 500 PO | 10 PO | |
| | | 200 PO | | | |
| 6 | N = 5 M | Test compound #2 | 250 IV | 10 IV | all |
| | N = 5 F | 100 IV | 500 PO | 15 PO | |
| | | 300 PO | | | |

SubChronic Studies. In a representative study to characterize dose-response relationships following repeated dosing, twenty-five naive animals, for example, will be randomly divided into groups containing 5 animals each as described in Table 7. Each two week study will test only one compound via a single route of administration at an optimal dose derived from data collected in prior acute toxicity studies.

TABLE 7

| Group No. | Number of Males or Females | Dose Level (mg/kg) | Dose Vol. (µL) | Dose Solution Conc. (mg/mL) | Number Euthanized on: Day 14 |
| --- | --- | --- | --- | --- | --- |
| 1 | N = 5 | Negative Control | 250 IV 500 PO | Depends on Dose Level | all |
| 2 QD | N = 5 | Test Compound As Determined in MTD Studies | 250 IV 500 PO | Depends on Dose Level | all |
| 3 QOD | N = 5 | Test Compound As Determined in MTD Studies | 250 IV 500 PO | Depends on Dose Level | all |
| 4 Q3D | N = 5 | Test Compound As Determined in MTD Studies | 250 IV 500 PO | Depends on Dose Level | all |
| 5 Q7D | N = 5 | Test Compound As Determined in MTD Studies | 250 IV 500 PO | Depends on Dose Level | all |

Dosing Procedure. Compounds will be administered QD, QOD, Q3D or Q7D via IV (lateral tail vein) or PO. Animals will be dosed in a systematic order that distributes the time of dosing similarly across all groups. For PO dosing, animals will be manually restrained. For IV bolus dosing or short term IV infusion (one minute), animals will be mechanically restrained but not sedated. Disposable sterile syringes will be used for each animal/dose.

EXAMPLE 103

Evaluation of Pharmacokinetic Properties

A representative pharmacokinetic study for evaluating pharmacokinetic properties of the compounds herein may be designed as follows. Male animals (mouse, Balb/c or rat, SD) aged five to six weeks. For rat models, rats weighing more than 200 grams will be used. In a representative study, twenty animals, for example, will randomly divided into 4 groups, as shown in Table 8. One group with be untreated and samples taken to be used as a base line. The other three groups will be and administered a single dose of compounds by intravenous injection.

TABLE 8

| Group No. | No. of Animals | Time followed by injection (h) |
| --- | --- | --- |
| 1 | 2 | Naïve |
| 2 | 6 | .25, 2, 8 |
| 3 | 6 | .5, 4, 12 |
| 4 | 6 | 1, 6, 24 |

Dosing Procedure. Compounds will be administered via IV (lateral tail vein), IP or PO. Animals will be dosed in a systematic order that distributes the time of dosing similarly across all groups. For IP and PO dosing, animals will be manually restrained. For IV bolus dosing or short term IV infusion (one minute), animals will be mechanically restrained but not sedated. Disposable sterile syringes will be used for each animal/dose.

Approximately 0.5 ml of blood will be collected from the naive animals via cardiac puncture prior to the first dose Terminal blood samples (0.5 ml) will be collected via cardiac puncture from two animals per group per time point according to the above chart. All samples will be placed in tubes containing lithium heparin as anticoagulant and mixed immediately by inverting. They will be centrifuged and the plasma flash frozen in liquid nitrogen, stored at −70° C. or greater and analyzed for drug levels.

EXAMPLE 104

Determination of In Vitro Metabolic Stability in Hepatocytes

A representative protocol to determine the stability of a new chemical entity in the presence of hepatocytes (human, rat, dog, monkey) in in vitro incubations may be designed as follows. The test article will be incubated with hepatocytes and suitable media for various times at 37° C. The reaction mixtures will be extracted and analyzed by LC/MS/MS for the parent compound and anticipated metabolites. If applicable, a half-life will be calculated for the consumption of the test article. Metabolism controls will be run for comparison of the half-life values with that obtained for the test article. The metabolism controls may be tolbutamide, desipramine and naloxone, which have defined pharmacokinetics corresponding to low, moderate and high in vivo clearance values, respectively.

Metabolic Stability Study. Generally, solutions of the test compounds will be prepared along with a cocktail solution of metabolism controls that are intended to provide a reference for enzyme activity. The reactions will be initiated by combining these pre-warmed solutions with hepatocyte suspensions and with a media control solution. Control zero samples will be taken from these reactions immediately after initiation. Additional samples may be taken at appropriate time points. Each sample will be immediately placed in a terminating solution (acidified MeCN containing IS) to stop the reaction. Hepatocyte blank suspensions and test compound standard solutions will be prepared.

Samples and standards for the test compound as well as appropriate blanks may be subjected to a custom sample preparation procedure and analyzed for the parent and/or metabolite form of the test compound using HPLC coupled with tandem mass spectrometry. Samples and standards for the metabolism controls may be subjected to the analytical method described herein. Where Krebs Henseleit buffer will be added, the buffer is bubbled with 5% $CO_2$ in air at room temperature for 5-10 minutes before adding BSA to a final concentration of 0.2% w/v. The volume of terminating solution and the method of sample preparation will be determined for the test article during method development.

Test Article/Media Solution. A solution of the test article will be prepared by adding an appropriate volume of the stock solution to 0.2% BSA in Krebs Henseleit buffer equilibrated with 5% $CO_2$ in air. The final concentration will be between 5 µM and 20 µM, and the final assay concentration at initiation of the reactions will be between 1 µM and 10 µM.

Metabolism Controls/Media Solution. A solution of tolbutamide, desipramine and naloxone will be prepared by adding an appropriate volume of each 10 mM stock solution to 0.2% BSA in Krebs Henseleit buffer equilibrated with 5% $CO_2$ in air. The final concentration will be 20 µM for each metabolism control and the final assay concentration will be 10 µM at initiation of the reactions.

Hepatocyte Suspension Solution. The hepatocytes will be thawed and isolated according to the vendor (Invitrotech, Inc.) instructions. During the final step of the procedure, the viability of the cells will be determined using the method of trypan blue exclusion. Then, the hepatocytes will be resuspended with 0.2% BSA in Krebs Henseleit buffer equilibrated with 5% $CO_2$ in air so the final concentration is 0.5 million viable cells/mL. The concentration at the initiation of the reactions will be 0.25 million viable cells/mL.

Initiating Test Article Incubation. Equal volumes of the test article solution prepared in step 2.1.3 will be dispensed into four polypropylene scintillation vials. The vials are pre-warmed for 5-10 minutes at 37° C. with 95% humidity and 5% $CO_2$. Equal volumes of 0.2% BSA in Krebs Henseleit buffer equilibrated with 5% $CO_2$ in air will be added to two of the vials and mixed thoroughly. Immediately after initiating the reaction, a timer is started and a 100 µL sample is removed from each vial and placed into a 1.7-mL centrifuge tube containing a suitable volume of terminating solution. These samples will serve as media controls to check for non-enzymatic degradation and non-specific binding to the vessel.

Equal volumes of the hepatocyte suspension prepared above will be added to two of the vials and mixed thoroughly. Immediately after initiating the reaction, a timer is started and a 100 µL sample is removed from each vial and placed into a 1.7-mL centrifuge tube containing a suitable volume of terminating solution. All vials are placed in an incubator maintained at 37° C., 95% humidity and 5% $CO_2$.

Initiating Metabolism Control Incubation. Equal volumes of the metabolism control solution prepared above will be dispensed into two polypropylene scintillation vials. The vials are pre-warmed for 5-10 minutes at 37° C. with 95% humidity and 5% $CO_2$. Equal volumes of the hepatocyte suspension prepared above will be added to each of the two vials and mixed thoroughly. Immediately after initiating the reaction, a timer is started and a 100 µL sample is removed from each vial and placed into a 1.7-mL centrifuge tube containing an equal volume of terminating solution. All vials are placed in an incubator maintained at 37° C., 95% humidity and 5% $CO_2$.

Sample Collection. The vials will be gently shaken and samples (100 µL) will be removed and placed into a 1.7-mL centrifuge tube containing an appropriate volume of terminating solution according to the following schedule: Test article samples are taken after 5, 10, 15, 30, 60, 90 and 120 minutes; metabolism control samples are taken after 30, 60, 90 and 120 minutes. Immediately after removal of the samples, the vials are placed back in the incubator until the last sample is collected.

Blank Preparation. A sample (100 µL) of the hepatocyte suspension will be added to an equal volume of 0.2% BSA in Krebs Henseleit buffer and mixed thoroughly. A 100 µL sample of this solution will be removed and placed into a 1.7-mL centrifuge tube containing the same volume of terminating solution used for the test article reaction. A sample of the incubation medium (0.2% BSA in Krebs Henseleit buffer) will be placed into a 1.7-mL centrifuge tube containing the same volume of terminating solution used for the test article reaction.

Sample Preparation and Analysis. All vials will be centrifuged at 16,000 g for 3 minutes. The supernatants will be placed into polypropylene autosampler vials and stored at 4° C. (<1 day) or −70° C. (>1 day) until analysis. The test article solutions will be analyzed using HPLC/MS/MS conditions according to standard procedures. In one example, the following HPLC conditions may be used: column (Phenomenex Synergi Hydro-RP, 100.0×2.0 mm, 5 µm); guard column (Phenomenex C18, 4.0×2.0 mm, 5 µm); flow rate (0.3 mL/min); column temperature at 45° C.; injection volume at 10 µL; and ambient autosampler temperature.

EXAMPLE 105

Determination of In Vitro Metabolic Stability in Microsomes

A representative protocol to determine the stability of a new chemical entity in the presence of liver microsomes (human, rat, dog, monkey) in in vitro incubations may be designed as follows. The test article will be incubated with microsomes and suitable media for various times at 37° C. The reaction mixtures will be extracted and analyzed by LC/MS/MS for the parent compound and anticipated metabolites. If applicable, a half-life will be calculated for the consumption of the test article. Metabolism controls will be run for comparison of the half-life values with that obtained for the test article. The metabolism controls are tolbutamide, desipramine and testosterone, and these compounds have defined pharmacokinetics corresponding to low, moderate and high in vivo clearance values, respectively.

Metabolic Stability Study. Generally, six pre-warmed reaction vials with 100 µL of a solution containing 50 mM potassium phosphate, pH 7.4, 2.6 mM NADP+, 6.6 mM glucose 6-phosphate, 0.8 U/mL of glucose 6-phosphate dehydrogenase and 1, 10 or 50 µM of the test compound are prepared. Similar reactions with metabolic controls representing low (tolbutamide), moderate (desipramine), and high (testosterone) clearance compounds are run simultaneously with the same enzyme solution. The reactions are initiated by adding 100 µL of a pre-warmed enzyme solution and incubated at 37° C. The zero time-point reaction is prepared by adding 50 µL of acetonitrile (containing internal standard) to the test compound/cofactor solution prior to adding the enzyme solution. After 15, 30, 60, 90 and 120 minutes, a reaction tube is removed from the water bath and the reaction is terminated with 50 µL of acetonitrile containing internal standard. The reactions are extracted and the samples are analyzed for the parent form of the test compound and one metabolite using a C18 column with MS/MS detection. Each assay is performed in duplicate.

Cofactor/Test compound Solution Concentrations. A stock solution of 10 mM NCE will be prepared in 10% DMSO (v/v). For all assays, a 2, 20 or 100 µM solution of the test article will be prepared in 50 mM potassium phosphate, pH 7.4, 2.6 mM $NADP^+$, 6.6 mM glucose 6-phosphate and 0.8 U/mL of glucose 6-phosphate dehydrogenase (cofactor solution).

Cofactor/Metabolism Control Solution Concentrations. Stock solutions of the metabolism controls (tolbutamide, desipramine, and testosterone) will be used to prepare a 6 µM solution of the metabolism control in cofactor solution described in step Enzyme Solution Concentrations. The enzyme solutions will be prepared by adding liver microsomes to 50 mM potassium phosphate, pH 7.4, to a final concentration of 1 mg/mL. All microsomes were purchased from XenoTech or Invitro-Tech, Inc.

Initiating the Reactions. All the reaction tubes will be prewarmed at 37° C. in a water bath for about 3-5 minutes. The zero time-point control reaction will be prepared for each replicate by adding 50 µL of acetonitrile containing 15.9 µM nebularine (internal standard) to 100 µL of cofactor solution to inactivate the enzymes, and then vortex mixing. The reactions will be initiated by adding 100 µL of the enzyme solution to each of the tubes and vortex mixing. All the tubes, including the zero time-point control, will be incubated in a 37° C. water bath. The final concentrations of all components in the tubes after initiating the reactions are 50 mM potassium phosphate, pH 7.4, 1.3 mM $NADP^+$, 3.3 mM glucose 6-phosphate, 0.4 U/mL of glucose 6-phosphate dehydrogenase, 0.5 mg/mL liver microsomes and 1, 10 or 50 µM test article.

Terminating and Extracting the Reactions. After 15, 30, 60, 90 and 120 minutes at 37° C., the reactions will be terminated by the addition of 150 µL of acetonitrile containing 15.9 µM nebularine (internal standard). The zero time-point control is removed from the water bath after 120 minutes. All vials will be centrifuged at 16,000 g for 3 minutes. The supernatants will be placed into polypropylene autosampler vials and stored at 4° C. (<1 day) or −70° C. (>1 day) until analysis.

Analysis of Test Article Solutions. The test article solutions will be analyzed using HPLC/MS/MS conditions according to standard procedures, such as those described in Example 39.

EXAMPLE 106

Bacterial Mutagenicity Test

This Mutagenicity Assessment assay (Ames Assay) will evaluate the potential of the test article extracts to induce histidine (his) reversion in *S. typhimurium* (his− to his+) or tryptophan (trp) reversion in *E. coli* (trp− to trp+) caused by base changes or frameshift mutations in the genome of tester organisms. Generally, a plate incorporation assay will be conducted with five strains of *Salmonella typhimurium* (TA97a, TA98, TA100, TA102, and TA1535) and one strain of *Escherichia coli* (WP2-uvrA⁻) in the presence and absence of an exogenous mammalian activation system (S9). The test article will be dissolved in 5% dextrose. A series of dilutions will then be prepared in saline just prior to testing. A Range Finding Study will also be conducted for this assay to determine the appropriate doses for definitive mutagenicity assessment.

Test Material Preparation

A stock solution of test article will be prepared at 20.0 mg/mL as follows: 1.0 g test article will be added to 15.0 mL of 0.1 HCl for 1 minute. The test article will be stirred for 15 minutes at room temperature. Next 33.0 mL of deionized water will be added and allowed to stir for 30 minutes. The pH will then be adjusted to 3.53. Lower doses will be prepared by dilution in 5% dextrose from this stock immediately prior to use. To minimize any change of degradation, the test article solutions will be kept on ice after preparation and until just prior to dosing procedures. The test article will be administered in vitro, through a solvent compatible with the test system.

Genotypic Characterization of the Test Strains

Working stocks of test strains will be confirmed for genotypic markers and acceptable spontaneous reversion rates. All working stocks should demonstrate a requirement for histidine or tryptophan (*E. coli* only). Additionally, the following conformations will be made with each assay, as appropriate: sensitivity to crystal violet due to the rfa wall mutation; sensitivity to ultraviolet light due to the deletion of the uvrB gene (uvrA in *E. coli*), resistance to ampicillin due to the presence of the pKM101 plasmid; and resistance to tetracycline due to the presence of the pAQ1 plasmid. Spontaneous reversion rates for the strains will be determined using the negative controls.

Test articles that are water-soluble will be dissolved in isotonic saline or other suitable solvent. Test articles that are not water-soluble will be dissolved in dimethylsulfoxide (DMSO) or other suitable solvent. If DMSO is anticipated to cause adverse reactions with the test article, the test article will be suspended in carboxymethylcellulose. In order to aid in dissolution, heating, vigorous vortexing or alternative solvents may be employed.

Test System

This assay will be conducted in accordance with the plate incorporation methodology originally described by Ames (Ames et al., *Mutation Research* (1975) 31:347-364) and updated by Maron and Ames (Maron et al., *Mutation Research* (1983) 113:173-215). This assay has historically been used to detect mutation in a gene of a histidine requiring strain to produce a histidine independent strain or concordantly, to detect mutation in a gene of a tryptophan requiring strain to produce a tryptophan independent strain. In addition, it has been shown to detect diverse classes of chemical mutagens which produce heritable DNA mutations of a type which are associated with adverse effects.

The *Salmonella typhimurium* strains that may be used in this assay, TA97a, TA98, TA100, and TA102 are described by Maron and Ames, supra; Green et al., *Mutation Research* (1976) 38:33-42); and Brusick et al., *Mutation Research* (1980) 76:169-190)). *S. typhimurium* strain TA1535 and *E. coli* strain Wp2-uvrA⁻ may be obtained from American Type Culture Collection, Manassas, Va. (ATCC numbers: 29629 and 49979, respectively). All working stocks of test strains will be confirmed for genotypic markers and acceptable reversion rates. Working stocks should demonstrate a requirement for histidine or tryptophan (*E. coli* only).

Experimental Methods

Master plates of the tester strains will be prepared from frozen working stocks. To create working cultures for each bacterial strain used in the assay, a single colony will be transferred from the master plate into Oxoid nutrient broth and incubated, with shaking, at 37±2° C. until an optical density (at 650 nm) of 0.6-1.6 is reached. This overnight culture will be used for the mutagenicity test and for genotypic confirmation. Genotype tests will be performed as described in the protocol.

For both the dose range and mutagenicity test, a top agar consisting of 0.6% Difco agar in 0.5% NaCl will be melted and a solution of 0.5 mM L-histidine/0.5 mM biotin or 0.5 mM L-tryptophan will be added to the melted top agar at a ratio of 10 mL per 100 mL agar. The supplemented agar will be aliquotted, 2 mL per tube and held at 45-47° C. To prepare the top agar for treatment, 0.1 mL of the test article or control, 0.1 mL of the bacterial culture and 0.5 mL of phosphate buffered saline will be added to the molten agar. The mixture will be briefly vortexed and poured onto a room temperature minimal glucose agar plate (1.5% Difco agar, 2% glucose, in Vogel-Bonner medium E). Metabolic activation will be provided by adding 0.5 mL of the S9 mix in place of the PBS. The plates will be allowed to harden and then incubated 48-72 hours at 37±2° C. All plates will be counted using an automatic image analysis system. Negative control and test article treated plates will also be examined for the presence of a bacterial lawn.

Exogenous Metabolic Activation

The in vitro metabolic activation system used in this assay is comprised of Sprague Dawley rat liver enzymes and a cofactor pool. The enzymes will be contained in a preparation of liver microsomes (S9 fraction) from rates treated with Arochlor to induce the production of enzymes capable of transforming chemicals to more active forms. Immediately prior to use, the S9 will be thawed and mixed with a cofactor pool to contain 5% S9, 5 mM glucose 6-phosphate, 4 mM β-nicotine-adenine dinucleotide phosphate, 8 mM $MgCl_2$ and 33 mM KCl in a 200 mM phosphate buffer at pH 7.4.

Dose Levels and Replicates

The test article will be tested in triplicate at five dose levels (20.0, 10.0, 5.0, 2.5, and 1.25 mg/mL) along with appropriate vehicle (5% dextrose) and positive controls in the dose range assay. This is equivalent to 2.0, 1.0, 0.5, 0.25, and 0.125 mg/plate.

For the definitive assay, three dose levels will be chosen (10.0, 10.0, and 5.0 mg/mL), which is equivalent to 2.0, 1.0, and 0.5 mg/plate. All treatments, including negative and positive control, will be plated in triplicate against test strains TA97a, TA98, TA100, TA102, TA1535, and WP2-uvrA⁻ in the presence and absence of metabolic activation. These doses will be chosen based on inducing a range of test article toxicity and maximizing the applied dose.

Control Substances

Control substances may be prepared and used in the mutagenicity assay as described in Table 9.

TABLE 9

| Control | Strain | Concentration |
| --- | --- | --- |
| ICR-191 Acridine | TA97a | 1.0 μg/plate |
| 2-nitrofluorene | A98 | 10.0 μg/plate |
| Sodium azide | TA100 and TA1535 | 1.5 μg/plate |
| 1-methyl-3-nitro-1-nitrosognanidine | WP2-uvrA⁻ | 4.0 μg/plate |
| 2-aminoanthracene | all strains (except TA1535) | 10.0 μg/plate |
| 2-aminoanthracene | TA1535 | 1.6 μg/plate |

Negative (Vehicle) Control

Tester strains will be plated with untreated dextrose solution at the corresponding maximum concentration (0.1 mL), with and without S9. These plates serve as the negative controls and provide information regarding background lawn and revertant colony formation.

Dose Range Assay

The initial dose range assay starts at the maximum concentration of 2.0 mg/plate. The four lower doses to be tested will be diluted in a 1:2 dilution series.

Reverse Mutation Assay

Each separate bacterial strain, with and without S9, is considered a separate experiment with its own concurrent positive and vehicle controls. All plates will be scored with an automated colony counter and a printout of the data was made. The positive controls will consist of direct-acting mutagens and mutagens requiring metabolic transformation. A two-fold or greater increase in reversion rates may be observed for all strains with the appropriate positive control. The negative control article reversion rates for each strain should be within or slightly below the expected ranges from laboratory historical data. An induced positive result for any strain would be demonstrated by at least a two-fold increase in the number of revertant colonies per plate over the negative control values.

EXAMPLE 107

In Vitro Chromosome Aberration Assay in CHO Cells

The Chromosomal Aberration Assay may be one of several in vitro tests that can be used to screen materials for their potential genetic toxicity. Chromosome aberrations are mutations which have been associated with carcinogenesis. Therefore, the chromosome aberration assay is relevant for testing potential mutagens and carcinogens (Galloway et al., *Environ. Mut.* (1985) 7:1-51; Galloway et al., *Environ. Mut.* (1987) 10:1-175). This Chromosome Aberration Assay evaluates the potential of the test article extracts to induce damage in Chinese Hamster Ovary Cells (CHO). This test will be conducted in the presence and absence of an exogenous mammalian activation system (S9) over three treatment periods. All negative control treated preparations should demonstrate normal levels of spontaneously occurring aberrations while positive control treated cultures should demonstrate dramatic, dose dependent increases in aberrant chromosomes.

A representative assay to determine whether a test material is clastogenic, i. e., whether it has the capacity to break chromosomes may be designed as follows. Clastogenicity is an important endpoint because it is through chromosomal breakage and inappropriate rejoining that certain oncogenes (e.g., myc) can be activated and certain tumor suppressor genes (e.g., those suppressing retinoblastoma) can be inactivated). In this test, mammalian Chinese Hamster Ovary (CHO) cells will be exposed to the test material and blocked in metaphase using a spindle poison. Visualization of chromosomes will be performed microscopically after hypotonic swelling, fixing and staining the treated CHO cells. Agents found to be capable of inducing chromosome breakage have a high probability of being carcinogens and also have the potential for inducing heritable chromosomal defects.

The CHO-$K_1$ cell line (ATCC number: CCL-61) is a pro-line auxotroph with a modal chromosome number of 20 and a population doubling time of 10-14 hours. This system has been shown to be sensitive to the clastogenic activity of a variety of chemicals (Preston et al., *Mutation Res.* (1981) 87:143-188). CHO cells will be grown and maintained in McCoy's 5A medium supplemented with 10% fetal calf serum, 1% L-glutamine (2 mM), penicillin (100 units/mL), and streptomycin (100 μg/mL). Cultures will be incubated in 5-7% $CO_2$ with loose caps in a humidified incubator at 37±2° C.

Test Procedures

A stock solution will be prepared at 5 mg/mL. Lower doses will be prepared by dilution in 5% dextrose from this stock immediately prior to use. To minimize any chance of degradation, the test article solutions will be kept on ice after preparation and until just prior to dosing procedures. Cells will be seeded at approximately $1-1.5 \times 10^6$ cells per 75 cm$^2$ tissue culture flask in 10 mL fresh medium one day prior to treatment. For treatment, spent medium will be replaced with fresh growth medium and the test article extract, negative or positive control will be added to each flask. Positive controls will be dosed in 0.1 mL volumes to minimize vehicle toxicity. The test article dilutions and negative control will be dosed in 1 mL volumes. Fresh medium will be added to bring the total treatment volume to 10 mL. For the portion of the test with metabolic activation, the S9 activation mix will be added to serum free medium at 1.5%, (v/v) final concentration. All treatments will be carried out in duplicate. The cells will be incubated at 37±2° C. in the presence of the test article extract, the S9 reaction mixture (metabolic activation portion of the study only) and growth medium. The assay will be divided into three treatment periods: 3 hours, 3 hours with S9 activation, and 20 hours.

After the treatment period, all flasks will be evaluated microscopically for gross manifestations of toxicity. i.e., morphological changes in cells or significant cell detachment. All flasks will be washed twice with phosphate buffered saline (PBS). Normal growth medium containing 10% fetal bovine serum (FBS) will be added to the freshly washed cells and the flasks will be returned to the incubator for an additional 14.5-15.5 hours. Microscopic evaluation will be performed immediately prior to harvest. Two hours prior to harvest, 1 μg of colcemid will be added (0.1 μg/mL final concentration) to all flasks to accumulate dividing cells.

The test article extracts will be tested in duplicate at six dose levels (0.5, 0.16, 0.05, 0.016, 0.005, and 0.0016 ml/mL final concentration in culture) along with appropriate vehicle and positive controls.

Metabolic Activation System

The use of a metabolic activation system is an important aspect for evaluation of a test article, as some compounds exist only in a promutagenic state. That is, they become mutagenic only after being acted upon by an outside metabolic source. In vitro test systems lack this ability to metabolize compounds unless an outside system such as S9 is added.

The in vitro metabolic activation system to be used in this assay may comprise Sprague Dawley rat liver enzymes and an energy producing system necessary for their function (NADP and isocitric acid; core reaction mixture). The enzymes will be contained in a preparation of liver microsomes (S9 fraction) from rats treated with Arochlor 1254 to induce enzymes capable of transforming chemicals to more active forms. The S9 may be purchased from Moltox (Boone, N.C.) and retained frozen at less than −70° C. until use. This S9 fraction will be thawed immediately before use and added to the core reaction mixture.

Cell Fixation, Staining and Scoring

Metaphase cells will be collected by mitotic shake off, swollen with 75 mM KCl, fixed in methanol : glacial acetic acid (3:1 v/v). Cells will be pipetted onto glass slides after resuspension in fresh fixative and air dried. The slides will be labeled with a blind code. Three slides will be prepared from each treatment flask. Slides will be stained with Giemsa and permanently mounted. All slides will be read under blind code with the exception of the high dose positive controls, which are evaluated first to ensure the aberration frequency was adequate. Two hundred cells per dose (100 from each of the duplicate flasks) will be read from each of the doses. One hundred cells will be read from each of the high dose positive controls in accordance with the following definitions and were scored as such.

Chromatid Type

TG (Chromatid Gap): "Tid Gap". An achromatic (unstained) region in one chromatid, the size of which is equal to or smaller than the width of a chromatid. These are noted but not usually included in final totals of aberrations, as they may not all be true breaks.

IG (Isochromatid Gap): "Chromosome Gap". The gaps are at the same locus in both sister chromatids. These are noted but not usually included in final totals of aberrations, as they may not all be true breaks.

TB (Chromatid Break): An achromatic region in one chromatid, larger than the width of a chromatid. The associated fragment may be partially or completely displaced, or missing.

ID (Chromatid Deletion): Length of chromatid "cut" from midregion of a chromatid resulting in a small fragment or ring lying beside a shortened chromatid or a gap in the chromatid.

TR (Triradial): An exchange between two chromosomes, which results in a three-armed configuration. May have an associated acentric fragment.

QR (Quadriradial): The same as the triradial, but resulting in a four-armed configuration.

CR (Complex Rearrangement): An exchange among more than two chromosomes which is the result of several breaks and exchanges.

TI (Chromatid Interchange): Exchange within a chromosome involving one or both arms.

Chromosome Type

SB (Chromosome Break): Terminal deletion. Chromosome has a clear break forming an abnormal (deleted) chromosome with an acentric fragment that is dislocated and may remain associated or may appear anywhere in the cell.

DM (Double Minute Fragment): Chromosome interstitial deletion. These appear as small double "dots" or may be paired rings. In some cases, they cannot be distinguished from acentric fragments that result from exchanges or terminal deletions.

D (Dicentric): An exchange between two chromosomes that results in a chromosome with two centromeres. This is often associated with an acentric fragment in which it is classified as Dicentric with Fragment (DF).

MC (Multi-centric Chromosome): An exchange among chromosomes that results in a chromosome with more than two centromeres.

R (Ring): A chromosome that forms a circle containing a centromere. This is often associated with an acentric fragment, in which case it is classified as Ring with Fragment (RF). Acentric rings are also included in this category.

Ab (Abnormal Monocentric Chromosome): This is a chromosome whose morphology is abnormal for the karyotype, and often the result of such things as a translocation or pericentric inversion. Classification used if abnormally cannot be ascribed to, e.g., a reciprocal translocation.

T (Translocation): Obvious transfer of material between two chromosomes resulting in two abnormal chromosomes. When identifiable, scored at "T", not as "2 Ab".

Other

SD (Severely Damaged Cell): A cell with 10 or more aberrations of any type. A heavily damaged cell should be analyzed to identify the type of aberrations and may not have 10 or more, e.g., because of multiple fragments such as those found associated with a tricentric.

PU (Pulverized Chromosome): Despiralized or fragmented chromosome. This may simply be at a different stage of chromosome condensation.

P (+Pulverized Cell): More than one chromosome, up to the whole nucleus, is "pulverized".

PP (Polyploid Cell): A cell containing multiple copies of the haploid number of chromosomes. Polyploid cells are occasionally observed in normal bone marrow or cell culture. These are recorded but are not included in final totals of structural aberrations.

Control Substances

Control substances are prepared and used in this assay as described in published reports. Positive controls which may be used are: cyclophosphamide—High dose 15 μg/mL; cyclophosphamide—Low dose 5 μg/mL; mitomycin C—High dose 1.0 μg/mL; and citomycin C—Low dose 0.25 μg/mL. For negative (vehicle) control, the CHO cells are treated with the 5% dextrose negative controls with and without S9 activation. These treatments provide information regarding background numbers of aberrant cells.

Assay Validity Evaluation and Statistical Analysis

The total number of aberrations (% CA) of the solvent control culture(s) should fall within 1-14%. High dose positive controls should produce a statistically significant increase in the number of aberrations at the 95% confidence level ($p<0.05$) as determined by statistical analysis. Analysis of Variance (ANOVA) may be used to identify significant differences between positive and negative control groups or test article and negative control groups. A difference is considered significant when the p value obtained is less than 0.05.

EXAMPLE 108

Safety and Tolerance Determination in Dogs

A representative study for determining the safety and tolerance of compounds at dose levels administered intravenously once daily to beagle dogs for five consecutive days, for example, may be designed as follows. Safety parameters will be monitored through observation, clinical pathology, and microscopic histopathology assessments.

Experimental Design

Table 10 summarizes a representative study. For example, the study will be conducted using three (3) test article and one (1) control article group. The control article will be the solution (5% dextrose in water) used to dilute the test article prior to administration and will be administered at the same volume as the high dose. The test article dosage levels for this study will be approximately 12, 3.8, and 1.2 mg/kg. Test and control articles will be administered once by intravenous (IV) infusion over approximately a one hour period on five consecutive days.

Blood samples for test article blood level analysis will be taken as follows (i.e., pk/tk sampling). Approximately 1.0 mL of blood will be taken from three male and three female dogs in the low dose group at approximately 20 minutes and 40 minutes from the start of the infusion, and then at the end of infusion (Time 0) and at 5, 10, 15, and 30 minutes, and 1, 2, 4, 8, 12, and 24 hours from the end of the infusion after the first and fifth doses. Also, prior to and immediately after Dose 1 and after Dose 5 for all animals, and for recovery animals prior to necropsy, approximately 5-10 second ECG tracings in a lead II configuration will be obtained. Animals will be terminated one (1) or 15 days after the last dose. Blood for hematology and clinical chemistry analysis will be drawn pre-dose and prior to euthanasia at termination. Following euthanasia, a necropsy will be performed to include collection of major organs for microscopic evaluation.

TABLE 10

| GROUP NO. | ARTICLE[a] | DOSAGE (MG/KG) | PRIMARY NO. ANIMALS (MALE/FEMALE) | RECOVERY (15 DAY) NO. ANIMALS (MALE/FEMALE) |
|---|---|---|---|---|
| 1 | Control | 0.0 | 3/3 | 1/1 |
| 2 | Test Article | 12.0 | 3/3 | 1/1 |
| 3 | Test Article | 3.8 | 3/3 | 1/1 |
| 4 | Test Article | 1.2 | 3/3 | 1/1 |

[a]Delivered as an approximate 1 hour infusion

Test Methods

In a representative study, animals will be assigned to groups as follows: The heaviest dog for a sex will be assigned to Group 1, the next heaviest for that sex will be assigned to Group 2, the next heaviest to Group 3, the next heaviest to Group 4, then continue with Groups 2, 3, 4, and 1, then Groups 3, 4, 1, and 2, continuing with this pattern until each group had a full complement of animals. The test and control article will be administered at each dosing as an intravenous infusion into a cephalic or saphenous vein over approximately one hour.

Animals will be weighed daily prior to dosing and prior to necropsy. All animals will be observed for signs of pharmacological activity, behavioral changes, and toxicity immediately and one hour after dosing. Recovery animals will be also observed once daily during the recovery period. Prior to and immediately after Doses 1 and 5 for all animals, and for recovery animals prior to necropsy, approximately five second ECG tracings in a lead II configuration will be obtained. These tracings will be used to provide data for interpretation of the rhythm and amplitude changes of the QRS-complex and T-wave and to measure QT intervals on a number of segments per tracing (approximately 5-10).

Blood Collection

PK/TK. Blood samples for test article blood level analysis will be taken. Approximately 1 mL of blood will be taken from three males and three females in the low dose group at approximately 20 minutes and 40 minutes from the start of the infusion, and then at the end of infusion (Time 0) and at 5, 10, 15, and 30 minutes, and 1, 2, 4, 8, 12, and 24 hours from the end of the infusion after the first and fifth dose. Plasma (lithium heparin anticoagulant) samples will be prepared for analysis.

Clinical Pathology. After overnight fasting and prior to the first dose (baseline; all animals) and then prior to each necropsy, blood samples will be taken for hematology and clinical chemistry. For hematology assays, blood collected at baseline and prior to necropsy (fasted) are analyzed for erythrocyte count, hematocrit, MCH, leukocyte count, differential WC, MCHC, hemoglobin, MCV, platelet count, PT, and APTT. For clinical chemistry assays, blood collected at baseline and prior to necropsy (fasted) will be tested for: aspartate aminotransferase (ASP), globulin & A/G ratio, Alanine aminotransferase (ALT), sodium, alkaline phosphatase, potassium, gamma glutamyltransferase (GGT), chloride, glucose, calcium, blood urea nitrogen (BUN), total bilirubin, creatinine, inorganic phosphorus, total protein, cholesterol, albumin, and triglycerides.

Necropsy

Following blood sample collection, primary treatment and recovery group animals will be sacrificed at their respective termination times and are necropsied. Major organs will be collected, weighed, and preserved for microscopic evaluation. Necropsy will include examination of the cranial, thoracic, abdominal and pelvic cavities, their viscera, the tissues, organs, and the carcass.

Statistical Methods

Statistical analysis of the clinical chemistry and hematology values and organ and body weight data will be performed to compare the test article groups to the control group. The statistical methods used for the data will be selected as appropriate: parametric data will be analyzed using a one way Analysis of Variance, non-parametric data will be analyzed using the Kurskai-Wallis test. A paired t-test will also be used to compare baseline and post treatment clinical chemistry and hematology values for each animal. Probability (p) values of 0.05 or less will be considered significant for all statistical tests.

EXAMPLE 109

Safety and Tolerance Study in Rats

A representative study to determine the safety and tolerance of a test compound, for example, at three dose levels administered intravenously once daily to rats for five consecutive days may be designed as follows. Safety parameters will be monitored through observation, clinical pathology, and microscopic histopathology assessments. Selected animals will also undergo blood sample collection for pharmacokinetic/toxicokinetic evaluation.

Experimental Methods

Table 11 summarizes a representative study. The study will be conducted using three (3) test and one (1) control article groups. The high and low test article groups and the control group will consist of 28 animals each and will be used to assess tolerance. The medium test article group will consist of 64 animals, of which 28 animals will be used to assess tolerance and 36 animals will be used to determine the level of test article in the blood at various time points after the first and fifth doses in the PK/TK portion of the study. The control article will be the solution (5% dextrose in water; D5W) used to dilute the test article prior to administration and is administered at the same volume as the high dose test article group. The test article dosage levels for this study will be 24, 7.6, and 2.4 mg/kg. Test and control articles will be administered by intravenous (IV) injection into a tail vein over one minute on five consecutive days.

Blood samples for test article blood level analysis will be taken as follows. Approximately 0.3-0.5 mL of blood will be taken from three male and three female rats under anesthesia at each sample time point of pre-dose and at the end of injection (Time 0) and at approximately 0.08, 0.25, 0.5, 1, 2, 4, 8, 12, and 24 hours from the end of the injection after the first and fifth doses. Animals used to assess tolerance will be terminated one day (for the primary group) or 15 days (for the recovery group) after the last dose. At termination of the tolerance test animals, blood for hematology and clinical chemistry analysis will be drawn prior to euthanasia and following euthanasia. A necropsy will be performed to include collection of major organs for microscopic evaluation. The animals used for the pk/tk blood sampling only to determine the level of test article will be euthanized after the final blood sample is collected without any further sampling or observations.

TABLE 11

| GROUP NO. | ARTICLE[a] | DOSAGE (MG/KG) | PRIMARY NO. ANIMALS (MALE/FEMALE) | RECOVERY (15 DAY) NO. ANIMALS (MALE/FEMALE) |
|---|---|---|---|---|
| 1 | Control | 0.0 | 3/3 | 1/1 |
| 2 | Test Article | 12.0 | 3/3 | 1/1 |
| 3 | Test Article | 3.8 | 3/3 | 1/1 |
| 4 | Test Article | 1.2 | 3/3 | 1/1 |

[a]Delivered as an approximate 1 hour infusion

Test Methods

The test and control article will be administered at each dosing as an intravenous infusion into a tail vein over approximately one minute. Animals will be weighed daily prior to dosing and prior to necropsy. All animals will be observed for signs of pharmacological activity, behavioral changes, and toxicity immediately and one hour after dosing. Recovery animals will also be observed once daily during the recovery period. The control animals will be dosed with approximately 6 mL/kg of D5W. The high, mid, and low dose test article animals will be administered dosages of approximately 24 mg/kg, 7.6 mg/kg, and 2.4 mg/kg, respectively.

Blood Collection

PK/TK. Blood samples for test article blood level analysis will be taken. Utilizing 18 male and 18 female medium dose animals, approximately 0.3-0.5 mL of blood will be taken from three male and three female rats under anesthesia at each sampling time point of pre-dose and at the end of injection (Time 0), and at approximately 0.08, 0.25, 0.5, 1, 2, 4, 8, 12, and 24 hours from the end of the injection after the first and fifth dose. Blood sampling will be via retro-orbital bleeding or cardiac puncture bleeding for an animal's terminal sample. Plasma (lithium heparin anticoagulant) samples will be prepared for analysis. General procedures for chemical pathology, necropsy, and histopathology, as well as statistical methods, such as those previously described, will be followed.

EXAMPLE 110

Phosphorylated and Total p53 Assay Protocol

A phosphorylated and total p53 assay protocol may be designed as follows. On Day 1, cells are seeded at $2 \times 10^6$ cells/10 cm dish/10 mL medium. On day two, cells will be treated as follows: control=0.05% DMSO (5µl DMSO stock/10 ml medium); 1 µM test compound (1 µl Stock (10 mM)/10 ml medium); 2 µM test compound (2 µl Stock (10 mM)/10 ml medium); 3 M test compound (3 µl Stock (10 mM)/10 ml medium); 4 µM test compound (4 µl Stock (10 mM)/10 ml medium) and 5 M test compound (5 µl Stock (10 mM)/10 ml medium).

On Day 3, cells will be harvested and attached and floating cells will be collected. Cells will be washed twice with PBS, counted and collected at $4 \times 10^6$ cells/sample. The cell pellet will be frozen at −80° C. until further use. On the same day or on Day 4, cells will be extracted using a cell extraction buffer (3 mL cell extraction buffer, 300 µl protease inhibitor and 10 µL 0.3M PMSF). To each sample will be added 200 µl Buffer, and the solution will be vortexed and set on ice for 30 minutes, and subsequently vortexed after every 10 mins. The solution will be then centrifuged at 13,000 rpm for 10 min, and 100 µl supernatant per tube will be aliquoted and stored at −80° C.

Assay preparation (Day 5). An anti-rabbit IgG HRP solution will be prepared by diluting 10µl of 100× concentrate solution with 1 ml HRP diluent for each 8-well strip. A wash buffer solution will be prepared by diluting the original vial (×25) using distilled water to make a ×1 solution. Dilutions of p53 standard solution or p53 total solution can be prepared as described according to representative parameters of Table 12. To ensure complete reconstitution, standard 1 will be mixed gently and allowed to sit for 10 minutes at room temperature.

TABLE 12

|  | Conc. | Standard Soln. | Dilution Buffer |
|---|---|---|---|
| Standard 1 | 100 Units/ml | Reconstitute 1 Vial worth 0.7 ml of standard Dil. Buffer | |
| Standard 2 | 50 Units/ml | 250 µl of Standard 1 | 250 µl |
| Standard 3 | 25 Units/ml | 250 µl of Standard 2 | 250 µl |
| Standard 4 | 12.5 Units/ml | 250 µl of Standard 3 | 250 µl |
| Standard 5 | 6.25 Units/ml | 250 µl of Standard 4 | 250 µl |
| Standard 6 | 3.12 Units/ml | 250 µl of Standard 5 | 250 µl |
| Standard 7 | 1.6 Units/ml | 250 µl of Standard 6 | 250 µl |
| Standard 8 | 0 |  | 250 µl |

Test Procedure. Allow all solution to reach RT and mix gently before use. Take out and insert 8-well strips. Add 100 µl of standard dilution buffer to standard 8 well (0 ng/ml/well or 0 Units/well). Add nothing to the chromogen blank well. Add 100 µl of standard or diluted sample to the appropriate microtiter wells. Generally, the sample should be diluted with standard dilution buffer at least 1:10 or greater. Each sample will be run in duplicates. Gently tap the side of the plate to thoroughly mix. Cover plate with plate cover and incubate for 2 hours at RT or o/n at 4 C. Wash wells with 400µl working wash buffer 4 times. Let soak for 15-30 sec., and then aspirate the liquid. After washing, the plate will be inverted and tapped dry on absorbance tissue. Add 100 µl of anti-p53 [pS15] or anti-p53 (total) (detection antibody) to each well except chromogen blank. Tap gently to mix; cover plate and incubate 1 hour at RT. Aspirate solution from wells thoroughly.

Wash wells with 400 µl working wash buffer four times. Let soak for 15-30 sec., and then aspirate the liquid. After washing, the plate will be inverted and tapped try on absorbance tissue. Add 100 µl of anti-rabbit IgG HRP working solution. to each well except chromogen blank. Cover plate and incubate 30 min at RT. Wash wells with 400 µl working wash buffer four times. Let soak for 15-30 sec., and then aspirate the liquid. After washing, the plate will be inverted and tapped try on absorbance tissue. Add 100 µl of TMB (stabilized chromogen substrate) to each well and incubate for 30 min. at RT in the dark. The color will change to blue. Add 100 µl Stop soln. Tap plate gently to mix. The color should change to yellow. Read the plate at A450 nm by setting chromogen blank (=100 µl TMB+100 µl Stop soln) as blank. Read absorbance within 2 hours of assay completion.

EXAMPLE 111

Caspase-3/7 Assay Protocol

A representative Caspase-3/7 assay protocol may be designed as follows. On Day 1, seed $0.015 \times 10_6$ HCT-116 cells/50 ul/well. Incubate o/n in 37° C. $CO_2$ incubator. On Day 2, remove 25 ul of medium from wells. Treat HCT-116 cells with 1, 3, and 5 uM test compound. Treat positive control group with Staurosporin 0.01, 0.1, 1 uM. Keep six negative control wells treated with medium only (add 25 ul of diluted sample to appropriate wells). Incubate for 24 h at 37° C. in a $CO_2$ incubator. On Day 3, prepare Apo-ONE Homogeneous Caspase-3/7 assay reagent (Promega) at 10 ul reagent/1 ml buffer. Add 50 ul of diluted reagent. Incubate one hour at room temp. Measure fluorescence at 485/520.

EXAMPLE 112

Annexin V-Alexa 488 Staining Protocol

A representative Annexin V-Alexa 488 staining protocol may be designed as follows. Seed $1.5\text{-}2.0 \times 10^6$ HCT-116 cells/10 cm dish/10 ml medium. Incubate o/n or up to 24 hrs at 37° C. in $CO_2$ incubator. The following day, treat cells with 1, 2, 3, 4 and 5 µM test compound. Keep one or two untreated plates (medium only) as control plates. The following controls are used: untreated samples (no Alexa or propidium iodide), controls treated with propidium iodide or Alexa 488 only, and controls treated with both Alexa 488 and propidium iodide. Harvest cells (collect attached as well as floating cells). Wash cells twice with cold PBS. Re-suspend cells in 1× Annexin binding buffer.

Count cells and dilute in 1× Annexin binding buffer to $1 \times 10^6$ cells/0.1 ml, preparing a sufficient volume to have 100 µl per assay. Add 5 µl of the Annexin V conjugate to each 100 µl of cell suspension. Add 4 µl of propidium iodide solution (stock=1 mg/ml) to each 100 µl of cell suspension. Incubate sample at RT for 15 minutes. Add 400 µl Annexin binding buffer, mix gently and keep samples on ice. Analyze stained cells immediately by flow cytometry.

EXAMPLE 113

DNA Cell Cycle Analysis Protocol

A representative DNA cell cycle analysis protocol will be designed as follows. Seed $1.5\text{-}2.0 \times 10^6$ cells/10 cm dish (seed one extra dish for unstained cells). Incubate cells in 37° C. humidified 5% $CO_2$ incubator for 24 hours. For synchronizing cells in a low growth state to make cells quiescent, remove media and rinse once with serum-free media, add 10 ml of serum-free media to each dish. Incubate the cells for 24 hr in a 37° C. humidified 5% $CO_2$ incubator. Remove media and add treatment (diluted in serum contained media, 10 ml): 1-5 µM test compound plus control. Incubate the cells for 24 hr in a 37° C. humidified 5% $CO_2$ incubator.

To trypsinize/isolate cells, remove treatment. Add 3 ml trypsin/EDTA solution. Keep floating cells and combine with attached cells. Incubate for 5 min in a 37° C. humidified 5% $CO_2$ incubator. Add 3 ml media (containing FBS) to wells and pipette into centrifuge tube. Centrifuge at 1000 rpm for 5 minutes. Decant supernatant and re-suspend pellet in 2-3 ml PBS. Count cells and wash cells once by putting $2 \times 10^6$ cells/tube, adding 2 ml PBS and centrifuging at 1000 rpm for 5 minutes. Re-suspend pelleted cells in 0.3 ml cold PBS.

To fix cells, gently add 0.7 ml ice cold 70% ethanol drop wise to tube containing 0.3 ml of cell suspension in PBS while vortexing. Leave on Ice for one hour (or up to a few days at 4C). Centrifuge at 1000 rpm for 5 minutes. Wash one time with cold PBS (1-2 ml). Centrifuge at 1000 rpm for 5 minutes. Re-suspend cell pellet in 0.25 ml cold PBS, add 5 µl of 10 mg/ml RNAse A (the final concentration being 0.2-0.5 mg/ml). Incubate at 37 C for 1 hour. Add 10 µl of 1 mg/ml of propidium iodide solution in deionized water (the final concentration being 10 µl/ml), and keep in the dark and at 4° C.

until analysis. Analyze on FACS by reading on cytometer at 488 nm. Cells may be stained with propidium iodide on the same day of analysis.

It is understood that the foregoing detailed description and accompanying examples are merely illustrative, and are not to be taken as limitations upon the scope of the invention. Various changes and modifications to the disclosed embodiments will be apparent to those skilled in the art. Such changes and modifications, including without limitation those relating to the chemical structures, substituents, derivatives, intermediates, syntheses, formulations and/or methods of use of the invention, may be made without departing from the spirit and scope thereof. U.S. patents and publications referenced herein are incorporated by reference.

What is claimed is:

1. A compound having formula (1):

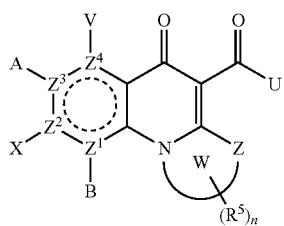

or a pharmaceutically acceptable salt thereof;
wherein A is absent if $Z^3$ is N, and H, halo or $C_{1-10}$ alkyl when $Z^3$ is C;
B is absent if $Z^1$ is N, or is H or halo if $Z^1$ is C;
V is H, halo or $C_{1-10}$ alkyl;
X is an amino substituent selected from an optionally substituted piperidine, pyrrolidine, piperazine, morpholine, or thiomorpholine ring, or is a $C_{1-10}$ thioalkyl group substituted with pyrazine;
$Z^1$ and $Z^3$ are each independently C or N;
$Z^2$ and $Z^4$ are both C;
Z is $NR^1$ or S;
W together with N and Z form a 5-membered ring that is fused to a phenyl ring of the formula

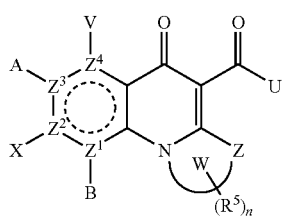

U is $NR^1R^2$ or $NR^1$—$(CR^1{}_2)_n$—$NR^3R^4$;
in each $NR^1R^2$, $R^1$ and $R^2$ together with N form an optionally substituted ring selected from piperidine, pyrrolidine, piperazine, morpholine, and thiomorpholine;
in $NR^3R^4$, $R^3$ and $R^4$ together with N may form an optionally substituted ring selected from piperidine, pyrrolidine, piperazine, morpholine, and thiomorpholine;
$R^1$ and $R^3$ are independently H or $C_{1-6}$ alkyl;
$R^4$ is H, a $C_{1-10}$ alkyl or $C_{2-10}$ alkenyl;
each $R^5$ is independently H, amino, alkoxy, amido, halogen, or cyano; or $R^5$ is $C_{1-6}$ alkyl, $C_{2-6}$ alkenyl, or $C_{2-6}$ alkynyl, each optionally substituted by halo; and
n is 1-6.

2. The compound of claim 1, wherein U is $NR^1R^2$, wherein $R^1$ and $R^2$ together with N form an optionally substituted piperidine, pyrrolidine, piperazine, morpholine, or thiomorpholine ring.

3. The compound of claim 1, wherein U is $NR^1$—$(CR^1{}_2)_n$—$NR^3R^4$; n is 1-4; and $R^3$ and $R^4$ in $NR^3R^4$ together form an optionally substituted piperidine, pyrrolidine, piperazine, morpholine, or thiomorpholine.

4. The compound of claim 1, wherein U is NH—$(CH_2)_n$—$NR^3R^4$ wherein $R^3$ and $R^4$ together with N form an optionally substituted pyrrolidine.

5. The compound of claim 1, wherein U is (2-pyrrolidin-1-yl)ethanamino.

6. The compound of claim 1, wherein A is halo.

7. The compound of claim 1, wherein X is a $C_{1-10}$ thioalkyl group substituted with pyrazine.

8. The compound of claim 1, wherein each of $Z^1$, $Z^2$, $Z^3$ and $Z^4$ are C.

9. The compound of claim 1, wherein three of $Z^1$, $Z^2$, $Z^3$ and $Z^4$ is C, and either $Z^1$ or $Z^3$ is N.

10. The compound of claim 1, wherein $Z^1$ and $Z^3$ are N.

11. The compound of claim 1, wherein $Z^1$ is N.

12. The compound of claim 1, wherein $R^1$ is methyl.

13. The compound of claim 1, wherein at least one of B, A, or V is halo, and the corresponding adjacent $Z^1$, $Z^3$ or $Z^4$ is C.

14. The compound of claim 1, wherein V is H.

15. A pharmaceutical composition comprising the compound of claim 1, and a pharmaceutically acceptable carrier.

16. A compound having the formula

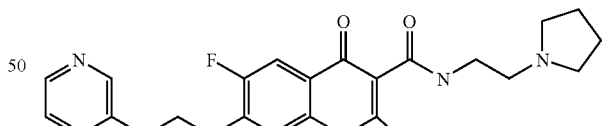

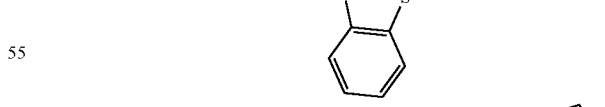

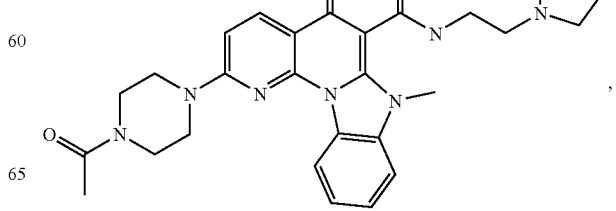

-continued
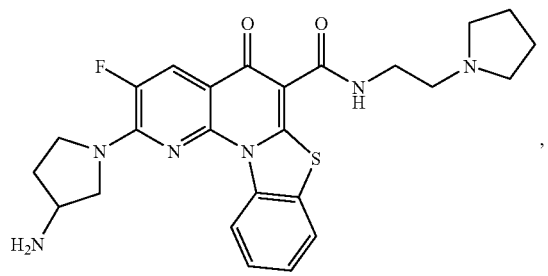,
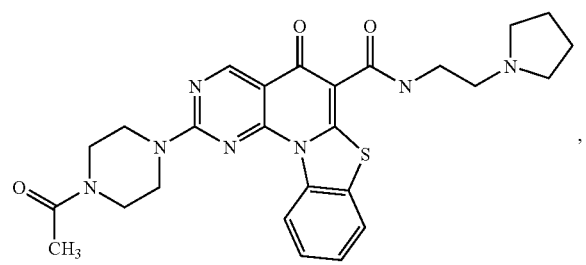,
-continued
or
or a pharmaceutically acceptable salt thereof.
17. A pharmaceutical composition comprising the compound of claim 16, and pharmaceutically acceptable carrier.
* * * * *

```
                          SEQUENCE LISTING

<160> NUMBER OF SEQ ID NOS: 29

<210> SEQ ID NO 1
<211> LENGTH: 27
<212> TYPE: DNA
<213> ORGANISM: Homo sapiens

<400> SEQUENCE: 1
tggggagggt ggggagggtg gggaagg                                          27

<210> SEQ ID NO 2
<211> LENGTH: 37
<212> TYPE: DNA
<213> ORGANISM: Homo sapiens

<400> SEQUENCE: 2
gggggggggg gggcgggggc ggggcgggg gaggggc                                37

<210> SEQ ID NO 3
<211> LENGTH: 57
<212> TYPE: DNA
<213> ORGANISM: Homo sapiens

<400> SEQUENCE: 3 gggggggggac gcgggagctg ggggagggct tggggccagg gcgggcgct taggggg         57

<210> SEQ ID NO 4
<211> LENGTH: 28
<212> TYPE: DNA
<213> ORGANISM: Homo sapiens

<400> SEQUENCE: 4
aggaagggga gggccggggg gaggtggc                                         28

<210> SEQ ID NO 5
<211> LENGTH: 22
<212> TYPE: DNA
<213> ORGANISM: Homo sapiens

<400> SEQUENCE: 5
aggggcgggg cggggcgggg gc                                               22

<210> SEQ ID NO 6
<211> LENGTH: 25
<212> TYPE: DNA
<213> ORGANISM: Homo sapiens

<400> SEQUENCE: 6
gggaggaagg gggcgggagc ggggc                                            25

<210> SEQ ID NO 7
<211> LENGTH: 32
<212> TYPE: DNA
<213> ORGANISM: Homo sapiens
```

```
<400> SEQUENCE: 7 gggggcggg ggcgggcgca gggggagggg gc                              32

<210> SEQ ID NO 8
<211> LENGTH: 23
<212> TYPE: DNA
<213> ORGANISM: Homo sapiens

<400> SEQUENCE: 8
cggggcgggg cggggcggg ggc                                        23

<210> SEQ ID NO 9
<211> LENGTH: 46
<212> TYPE: DNA
<213> ORGANISM: Homo sapiens

<400> SEQUENCE: 9
agaggaggag gaggtcacgg aggaggagga gaaggaggag gaggaa              46

<210> SEQ ID NO 10
<211> LENGTH: 12
<212> TYPE: DNA
<213> ORGANISM: Homo sapiens

<400> SEQUENCE: 10
ggaggaggag ga                                                   12

<210> SEQ ID NO 11
<211> LENGTH: 38
<212> TYPE: DNA
<213> ORGANISM: Homo sapiens

<400> SEQUENCE: 11
agagaagagg ggaggaggag gaggagagga ggaggcgc                       38

<210> SEQ ID NO 12
<211> LENGTH: 13
<212> TYPE: DNA
<213> ORGANISM: Homo sapiens

<400> SEQUENCE: 12 ggaggggggag ggg                                                 13

<210> SEQ ID NO 13
<211> LENGTH: 27
<212> TYPE: DNA
<213> ORGANISM: Homo sapiens

<400> SEQUENCE: 13
aggagaagga ggaggtggag gaggagg                                   27

<210> SEQ ID NO 14
<211> LENGTH: 33
<212> TYPE: DNA
<213> ORGANISM: Homo sapiens

<400> SEQUENCE: 14
aggaggagga gaatgcgagg aggagggagg aga                            33

<210> SEQ ID NO 15
<211> LENGTH: 36
<212> TYPE: DNA
```

```
<213> ORGANISM: Homo sapiens

<400> SEQUENCE: 15
ggggcgggcc gggggcgggg tcccggcggg gcggag                         36

<210> SEQ ID NO 16
<211> LENGTH: 27
<212> TYPE: DNA
<213> ORGANISM: Homo sapiens

<400> SEQUENCE: 16
cgggaggagg aggaaggagg aagcgcg                                   27

<210> SEQ ID NO 17
<211> LENGTH: 45
<212> TYPE: DNA
<213> ORGANISM: Homo sapiens
<220> FEATURE:
<223> OTHER INFORMATION: Primer

<400> SEQUENCE: 17
agtctgactg actgtacgta gctaatacga ctcactatag caatt              45

<210> SEQ ID NO 18
<211> LENGTH: 99
<212> TYPE: DNA
<213> ORGANISM: Homo sapiens
<220> FEATURE:
<223> OTHER INFORMATION: Primer

<400> SEQUENCE: 18
tccaactatg tatactgggg agggtgggga gggtggggaa ggttagcgac acgcaattgc   60
tatagtgagt cgtattagct acgtacagtc agtcagact                      99

<210> SEQ ID NO 19
<211> LENGTH: 15
<212> TYPE: DNA
<213> ORGANISM: Homo sapiens

<400> SEQUENCE: 19
tccaactatg tatac                                                15

<210> SEQ ID NO 20
<211> LENGTH: 35
<212> TYPE: DNA
<213> ORGANISM: Homo sapiens

<400> SEQUENCE: 20
ttagcgacac gcaattgcta tagtgagtcg tatta                          35

<210> SEQ ID NO 21
<211> LENGTH: 80
<212> TYPE: DNA
<213> ORGANISM: Homo sapiens

<400> SEQUENCE: 21
tatacggggt gggggaggga gggattagcg acacgcaatt gctatagtga gtcgtattag   60
ctacgtacag tcagtcagac                                           80

<210> SEQ ID NO 22
<211> LENGTH: 86
<212> TYPE: DNA
<213> ORGANISM: Homo sapiens
```

<400> SEQUENCE: 22
ttataccggg gcggggcggg ggcgggggct tagcgacacg caattgctat agtgagtcgt    60
attagctacg tacagtcagt cagact                                        86

<210> SEQ ID NO 23
<211> LENGTH: 97
<212> TYPE: DNA
<213> ORGANISM: Homo sapiens

<400> SEQUENCE: 23
taggggcggg cgcgggagga aggggcggg agcggggctg ttagcgacac gcaattgcta    60
tagtgagtcg tattagctac gtacagtcag tcagact                            97

<210> SEQ ID NO 24
<211> LENGTH: 97
<212> TYPE: DNA
<213> ORGANISM: Homo sapiens

<400> SEQUENCE: 24
ttagagaaga ggggaggagg aggaggagag gaggaggcgc ttagcgacac gcaattgcta    60
tagtgagtcg tattagctac gtacagtcag tcagact                            97

<210> SEQ ID NO 25
<211> LENGTH: 99
<212> TYPE: DNA
<213> ORGANISM: Homo sapiens

<400> SEQUENCE: 25
tccaactatg tatactgggg agggtgggga gggtggggaa ggttagcgac acgcaattgc    60
tatagtgagt cgtattagct acgtacagtc agtcagact                          99

<210> SEQ ID NO 26
<211> LENGTH: 99
<212> TYPE: DNA
<213> ORGANISM: Homo sapiens

<400> SEQUENCE: 26
tccaactatg tatacccttc cccaccctcc ccaccctccc cattagcgac acgcaattgc    60
tatagtgagt cgtattagct acgtacagtc agtcagact                          99

<210> SEQ ID NO 27
<211> LENGTH: 95
<212> TYPE: DNA
<213> ORGANISM: Homo sapiens

<400> SEQUENCE: 27
tcatatatga ctacttaggg ttagggttag ggttagggtt actgccacgc aattgctata    60
gtgagtcgta ttagctacgt acagtcagtc agact                              95

<210> SEQ ID NO 28
<211> LENGTH: 89
<212> TYPE: DNA
<213> ORGANISM: Homo sapiens

<400> SEQUENCE: 28
atgatcaccg ggaggaggag gaaggaggaa gcgcgctgcc acgcaattgc tatagtgagt    60
cgtattagct acgtacagtc agtcagact                                     89

```
<210> SEQ ID NO 29
<211> LENGTH: 45
<212> TYPE: DNA
<213> ORGANISM: Homo sapiens
<220> FEATURE:
<223> OTHER INFORMATION: Primer

<400> SEQUENCE: 29
agtctgactg actgtacgta gctaatacga ctcactatag caatt          45
```